US011802307B2

(12) United States Patent
Shultzaberger et al.

(10) Patent No.: US 11,802,307 B2
(45) Date of Patent: Oct. 31, 2023

(54) AMPLIFICATION OLIGONUCLEOTIDES

(71) Applicant: Singular Genomics Systems, Inc, San Diego, CA (US)

(72) Inventors: Ryan Shultzaberger, San Diego, CA (US); Allen Lipson, San Diego, CA (US); Daan Witters, San Diego, CA (US)

(73) Assignee: Singular Genomics Systems, Inc., San Diego, CA (US)

( * ) Notice: Subject to any disclaimer, the term of this patent is extended or adjusted under 35 U.S.C. 154(b) by 0 days.

(21) Appl. No.: 18/185,783

(22) Filed: Mar. 17, 2023

(65) Prior Publication Data

US 2023/0212664 A1    Jul. 6, 2023

Related U.S. Application Data

(63) Continuation of application No. PCT/US2022/075843, filed on Sep. 1, 2022.

(60) Provisional application No. 63/331,225, filed on Apr. 14, 2022, provisional application No. 63/245,414, filed on Sep. 17, 2021, provisional application No. 63/240,671, filed on Sep. 3, 2021.

(51) Int. Cl.
C12Q 1/6855 (2018.01)

(52) U.S. Cl.
CPC .................. C12Q 1/6855 (2013.01)

(58) Field of Classification Search
None
See application file for complete search history.

(56) References Cited

U.S. PATENT DOCUMENTS

| | | | |
|---|---|---|---|
| 4,882,245 A | 11/1989 | Gelorme et al. | |
| 4,970,276 A | 11/1990 | Das et al. | |
| 5,034,506 A | 7/1991 | Summerton et al. | |
| 5,235,033 A | 8/1993 | Summerton et al. | |
| 5,763,594 A | 6/1998 | Hiatt et al. | |
| 5,808,045 A | 9/1998 | Hiatt et al. | |
| 5,872,244 A | 2/1999 | Hiatt et al. | |
| 6,232,465 B1 | 5/2001 | Hiatt et al. | |
| 6,703,491 B1 | 3/2004 | Homburger et al. | |
| 6,897,012 B2 | 5/2005 | Hada et al. | |
| 6,991,888 B2 | 1/2006 | Padmanaban et al. | |
| 7,057,026 B2 | 6/2006 | Barnes et al. | |
| 7,467,632 B2 | 12/2008 | Lee et al. | |
| 7,541,444 B2 | 6/2009 | Milton et al. | |
| 10,738,072 B1 | 8/2020 | Graham et al. | |
| 11,236,387 B2 | 2/2022 | Glezer et al. | |
| 11,359,238 B2 | 6/2022 | Glezer et al. | |
| 11,459,602 B2 | 10/2022 | Coll Mulet et al. | |
| 2003/0119018 A1 | 6/2003 | Omura et al. | |
| 2008/0000373 A1 | 1/2008 | Petrucci-Samija et al. | |
| 2010/0160478 A1 | 6/2010 | Nilsson et al. | |
| 2011/0167514 A1 | 7/2011 | Brover et al. | |
| 2013/0012399 A1 | 1/2013 | Myers et al. | |
| 2015/0079351 A1 | 3/2015 | Atasoy et al. | |
| 2016/0017392 A1 | 1/2016 | Arnold et al. | |
| 2021/0047638 A1 | 2/2021 | Chang et al. | |
| 2021/0277461 A1 | 9/2021 | Glezer et al. | |

FOREIGN PATENT DOCUMENTS

| | | |
|---|---|---|
| WO | WO-1996/07669 A1 | 3/1996 |
| WO | WO-2004/018497 A2 | 3/2004 |
| WO | WO-2004/018497 A3 | 6/2004 |
| WO | WO-2018/148723 A1 | 8/2018 |
| WO | WO-2019/183640 A1 | 9/2019 |
| WO | WO-2020/056044 A1 | 3/2020 |
| WO | WO-2021/178893 A2 | 9/2021 |
| WO | WO-2021/178893 A3 | 10/2021 |

OTHER PUBLICATIONS

Bentley, D. R. et al. (Nov. 6, 2008). "Accurate whole human genome sequencing using reversible terminator chemistry," *Nature* 456(7218): 53-59.

Dohm, J. C. et al. (Jul. 26, 2008) "Substantial biases in ultra-short read data sets from high-throughput DNA sequencing," *Nucleic acids research* 36(16): e105.

Feeney, R. et al. (Apr. 1, 1982). "Modification of Proteins," *Advances in Chemistry* 198: 3-55, American Chemical Society, Washington, D.C.

Haas, K-H. et al. (Aug. 30, 1999, e-published Sep. 2, 1999). "Functionalized coating materials based on inorganic-organic polymers," *Thin Solid Films* 351(1-2): 198-203.

International Search report dated Feb. 14, 2023, for PCT application PCT/US2022/075843, filed Sep. 1, 2022, 3 pages.

Johnston, A. D. et al. (Jan. 18, 2019). "PrimerROC: accurate condition-independent dimer prediction using ROC analysis," *Scientific Reports* 9: 209.

Quail, M. A. et al. (Dec. 2008, e-published Nov. 25, 2008). "A large genome center's improvements to the Illumina sequencing system," *Nature methods* 5(12): 1005-1010.

Sayers, E. W. et al. (Jan. 1, 2012, e-published Dec. 2, 2011). "Database resources of the national center for biotechnology information," *Nucleic acids research* 40(D1): D13-D25.

(Continued)

*Primary Examiner* — Angela M. Bertagna

*Assistant Examiner* — Carolyn L Greene

(74) *Attorney, Agent, or Firm* — Mintz, Levin, Cohn, Ferris, Glovsky, Popeo, P.C.; Zachary L. Terranova

(57) ABSTRACT

Disclosed herein, inter alia, are polynucleotides, supports, kits, and methods of use thereof for amplifying, immobilizing, and sequencing polynucleotides.

22 Claims, 6 Drawing Sheets

Specification includes a Sequence Listing.

(56) References Cited

OTHER PUBLICATIONS

Untergasser, A. et al. (Aug. 1, 2012, e-published Jun. 22, 2012). "Primer3—new capabilities and interfaces," *Nucleic acids research* 40(15): e115.
Written Opinion dated Feb. 14, 2023, for PCT application PCT/US2022/075843, filed Sep. 1, 2022, 9 pages.
Zuker, M. (Jul. 1, 2003). "Mfold web server for nucleic acid folding and hybridization prediction," *Nucleic acids research* 31(13): 3406-3415.
U.S. Appl. No. 18/185,785 filed Not yet published, Singular Genomics Systems, Inc.
U.S. Appl. No. 18/185,786 filed Not yet published, Singular Genomics Systems, Inc.
International Search Report and Written Opinion dated Aug. 31, 2021, for PCT application PCT/US2021/021208, filed Mar. 5, 2021, 21 pages.

AMPLIFICATION OLIGONUCLEOTIDES

CROSS-REFERENCES TO RELATED APPLICATIONS

This application is a continuation of International Application No. PCT/US2022/075843, filed Sep. 1, 2022, and which claims the benefit of U.S. Provisional Application No. 63/240,671, filed Sep. 3, 2021, U.S. Provisional Application No. 63/245,414, filed Sep. 17, 2021; and U.S. Provisional Application No. 63/331,225, filed Apr. 14, 2022, each of which are incorporated herein by reference in their entirety and for all purposes.

SEQUENCE LISTING

The instant application contains a Sequence Listing, which has been submitted electronically in ASCII format and is hereby incorporated by reference in its entirety. Said ASCII copy, created on Mar. 7, 2023, is named 051385-558C01US ST26.xml and is 168,717 bytes in size.

BACKGROUND

Genetic analysis is taking on increasing importance in modern society as a diagnostic, prognostic, and as a forensic tool. Next generation sequencing (NGS) methods often rely on the amplification of genomic fragments hybridized to polynucleotide primers on a solid support. Solid-phase nucleic acid amplification techniques generate amplification products that are attached on a solid support in order to form arrays comprised of nucleic acid clusters, referred to as polonies. Each discrete cluster on the array is formed from a first plurality of immobilized polynucleotide primers and a second plurality of immobilized polynucleotide primers. Typically, these immobilized primers include a nucleic acid sequence capable of annealing to library molecules (e.g., template nucleic acids) containing a complementary sequence. As a result, the library capture affinity, amplification factor, the sequencing efficiency and accuracy are at least partially contingent on the nucleic acid sequence of the immobilized primers. Thus, there is a need to obtain effective polynucleotide primers that minimize any negative consequences. Disclosed herein, inter alia, are solutions to these and other problems in the art.

BRIEF SUMMARY

In an aspect is provided a plurality of nucleic acid molecules, wherein each nucleic acid molecule includes a first end, a target sequence, and a second end, wherein the first end includes a sequence selected from SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123, wherein the target sequence of the plurality of nucleic acid molecules are different (e.g., different sequences) from each other.

In an aspect is provided a solid support including a first plurality of immobilized oligonucleotides, and a second plurality of immobilized oligonucleotides, wherein the immobilized oligonucleotides of the first plurality include a sequence selected from SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123, and the immobilized oligonucleotides of the second plurality include a sequence selected from SEQ ID NO:7, SEQ ID NO:30, SEQ ID NO:87, SEQ ID NO:89, SEQ ID NO:91, SEQ ID NO:86, SEQ ID NO:118, SEQ ID NO:120, SEQ ID NO:122, or SEQ ID NO:124.

In an aspect is provided a method of immobilizing a polynucleotide, the method including: contacting a solid support as described herein with a polynucleotide including a primer binding sequence; hybridizing the primer binding sequence to a first immobilized oligonucleotide of the second plurality of immobilized oligonucleotides; and extending the first immobilized oligonucleotide with a polymerase to form a first immobilized polynucleotide.

In another aspect is provided a method of immobilizing a polynucleotide, the method including: contacting the solid support as described herein with a polynucleotide including a primer binding sequence; hybridizing the primer binding sequence to a first immobilized oligonucleotide of the second plurality of immobilized oligonucleotides; and extending the first immobilized oligonucleotide with a polymerase to form a first immobilized polynucleotide. In embodiments, the solid support includes a first plurality of immobilized oligonucleotides, and a second plurality of immobilized oligonucleotides, wherein the immobilized oligonucleotides of the first plurality include a sequence selected from SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123, and the immobilized oligonucleotides of the second plurality include a sequence selected from SEQ ID NO:7, SEQ ID NO:30, SEQ ID NO:87, SEQ ID NO:89, SEQ ID NO:91, SEQ ID NO:86, SEQ ID NO:118, SEQ ID NO:120, SEQ ID NO:122, or SEQ ID NO:124.

In an aspect is provided a plurality of oligonucleotides, wherein each oligonucleotide is capable of hybridizing to SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123. In embodiments, each oligonucleotide is capable of hybridizing to SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123. In embodiments, capable of hybridizing includes 95%, 96%, 97%, 98%, 99%, or 100% complementarity between the oligonucleotide and the hybridizing oligonucleotide (i.e., wherein the nucleic acid molecule capable of hybridizing includes 95% or greater complementary nucleotides which form Watson-Crick hydrogen bonds with the oligonucleotide).

BRIEF DESCRIPTION OF THE DRAWINGS

FIG. 1A shows an embodiment of a Y adapter including (i) a first strand having a 5'-arm and a 3'-portion, and (ii) a second strand having a 5'-portion and a 3'-arm, wherein the 3'-portion of the first strand is substantially complementary to the 5'-portion of the second strand, and the 5'-arm of the first strand is not substantially complementary to the 3'-arm of the second strand. In this embodiment, the complementary portions (i.e., duplex regions) of the Y adapter include a melting temperature (Tm) of about 40-45° C. and a length of about 10 to 15 nucleotides. In embodiments, the complementary portions (i.e., duplex regions) of the Y adapter include a Tm (melting temperature) of about 35-45° C. or 30-45° C. and a length of about 12 bases. FIG. 1B shows an embodiment of a hairpin adapter including a 5'-end, a 5' portion, a loop, a 3' portion and a 3'-end. In this embodiment, a duplex region of the hairpin adapter includes a Tm (melting temperature) of about 40-45° C. and a length of about 10-16 bases. In embodiments, the duplex region of the adapter includes a Tm (melting temperature) of about 35-45° C. or 30-45° C. and a length of about 12 bases. FIG. 1C illustrates an embodiment of a hairpin adapter, which includes a double stranded (stem) region and a loop region. Within the loop region is a priming site (P3) and optionally a unique molecular identifier (UMI). FIG. 1D illustrates the adapters may include different duplex ends. For example, the double-stranded region of a Y adapter (alternatively referred to as a forked adapter) may be blunt-ended (top), have a 3' overhang (middle), or a 5' overhang (bottom). On the right are embodiments of hairpin adapters, each including a 5'-end and a 3'-end. In some embodiments, a hairpin adapter includes a double stranded portion (a double-stranded "stem" region) and a loop, where 5'P refers to a phosphorylated 5' end. A double-stranded stem region of a hairpin adapter may be blunt-ended (top), it may have a 5' overhang (middle), or a 3' overhang (bottom). An overhang may include a single nucleotide or more than one nucleotide.

FIG. 3A shows examples of the P1 adapter sequences. The P1 adapter includes a platform primer 1 (pp1), which is a sequence complementary to a first surface-immobilized primer, an optional index sequence for multiplexing samples, and a region complementary to a first sequencing primer, i.e., a sequencing primer binding site for a first sequencing primer (SP1). Similarly, the P2 adapter contains a platform primer 2 (pp2), which is a sequence complementary to a second surface-immobilized primer, an optional index sequence for multiplexing samples, and a region complementary to a second sequencing primer (SP2). In embodiments, the platform primer sequence is used during amplification reactions (e.g., solid phase amplification). In embodiments, a sequencing primer anneals to the sequencing primer region of the adapter and serves as the initiation point for a sequencing reaction. In embodiments, the platform primer sequence provides complementarity to a sequencing primer. The illustrations depict embodiments of the oligo sequences wherein there are two different platform primer sequences, pp1 and pp2, in combination with two different sequencing primer binding sites: SP1 and SP2. The dashed lines are indicative of regions within the adapter and are included to aid the eye in the different arrangement of the sequences and are not indicative of the overall size or relative length (i.e., the index sequence may not be the same length as the sequencing primer despite the illustration showing the index sequence and sequencing primer as being the same size). It is understood that any P1 adapter depicted in FIG. 3A, or the complement thereof, may be combined with any P2 adapter depicted in FIG. 3B, or complement thereof, when preparing the template nucleic acid sequence. The 5' end of any of the adapters may be covalently attached to a solid surface via a linker (not shown). Suitable sequences for P1 and P2 (and the complements thereof, P1' and P2') are described herein, for example in Table 1.

FIG. 6A illustrates the target polynucleotide (i.e., insert) following fragmentation, size selection, purification, and A-tailing (i.e., adding an dATP to the 3' ends of the insert). This A-tail provides an efficient target to ligate with the 3' T-tail of the universal stem-loop adapter (or universal forked adapter, not shown) illustrated in FIG. 5. Next, the cleavable site in the loop is cleaved, which opens the loops of the adapter resulting in a linear fragment with the SP1 sequence at the 5' end, and the SP2' sequence at the 3' end. Oligonucleotides including SP2 and SP1' complementary sequences are hybridized and extended, thereby adding the platform primer sequence (51) and index 1 at the SP1 end, and platform primer sequence S2 and index 2 at the SP2 end through a limited amplification step (FIG. 6B). Oligonucleotides without indices are used, for example, if no multiplexing is required, as provided in Table 3.

FIG. 7B illustrates the target polynucleotide (i.e., insert) following fragmentation, size selection, purification, and A-tailing (i.e., adding an dATP to the 3' ends of the insert). The stem-loop adapters are ligated to the insert. Next, the cleavable site in the middle of the loop is cleaved, which opens the loops of the adapter resulting in a linear fragment.

DETAILED DESCRIPTION

Figure 1A:
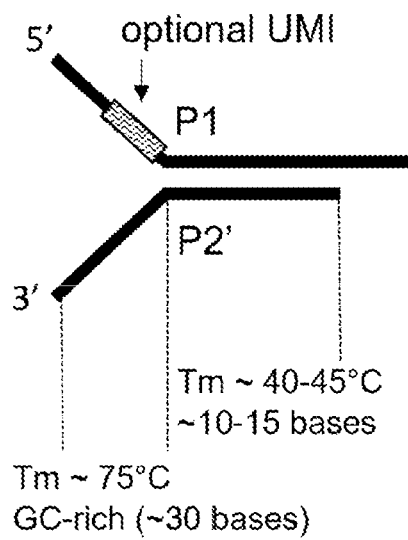
FIGS. 1A-1D show embodiments of adapters.
Figure 1B:
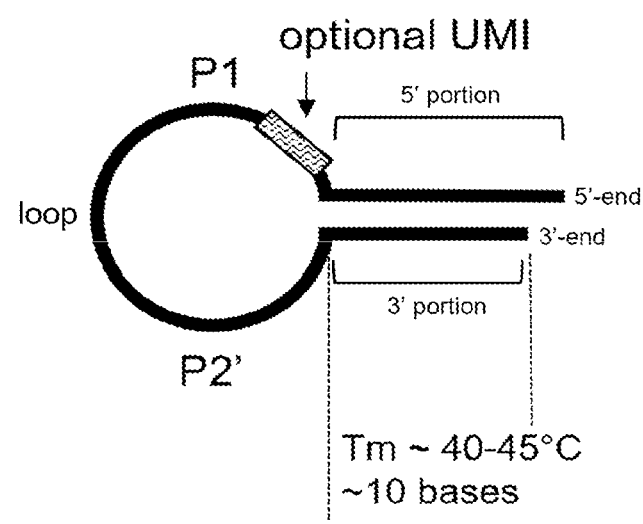
Figure 1C:
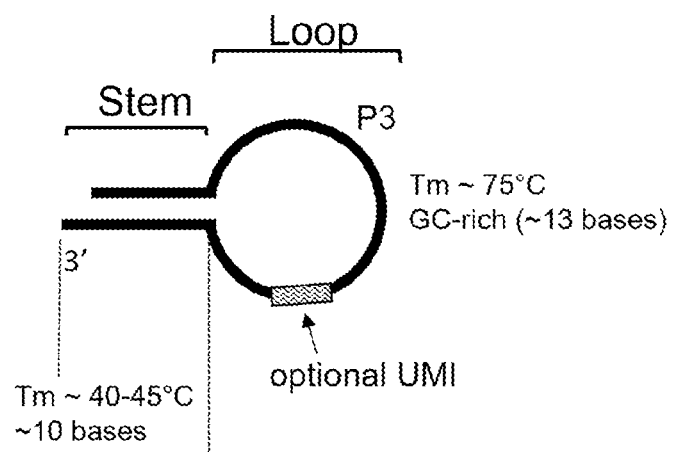
Figure 1D:
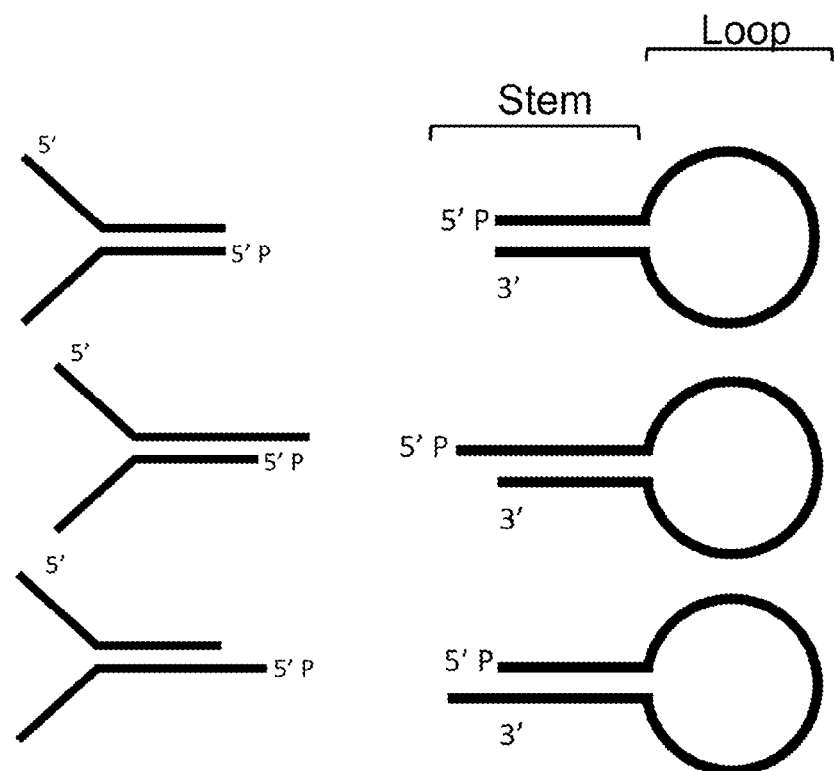

The aspects and embodiments described herein relate to oligonucleotides useful for capturing, amplifying, and/or detecting nucleic acid sequences of interest.

I. Definitions

All patents, patent applications, articles and publications mentioned herein, both supra and infra, are hereby expressly incorporated herein by reference in their entireties. The practice of the technology described herein will employ, unless indicated specifically to the contrary, conventional methods of chemistry, biochemistry, organic chemistry, molecular biology, bioinformatics, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, NY 1994); and Sambrook and Green, Molecular Cloning: A Laboratory Manual, 4th Edition (2012). Methods, devices and materials similar or equivalent to those described herein can be used in the practice of this invention.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

As used herein, the term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

As used herein, the term "complementary" or "substantially complementary" refers to the hybridization, base pairing, or the formation of a duplex between nucleotides or nucleic acids. For example, complementarity exists between the two strands of a double-stranded DNA molecule or between an oligonucleotide primer and a primer binding site on a single-stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed. In embodiments, a first template polynucleotide and a second template polynucleotide of an overlapping cluster are not substantially complementary (e.g., are at least 50%, 75%, 90%, or more non-complementary to each other).

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin or loop structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g. chemical compounds including biomolecules or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, a protein or enzyme (e.g., a DNA polymerase).

As may be used herein, the terms "nucleic acid," "nucleic acid molecule," "nucleic acid sequence," "nucleic acid fragment" and "polynucleotide" are used interchangeably and are intended to include, but are not limited to, a polymeric form of nucleotides covalently linked together that may have various lengths, either deoxyribonucleotides or ribonucleotides, or analogs, derivatives or modifications thereof. Different polynucleotides may have different three-dimensional structures, and may perform various functions, known or unknown. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. As may be used herein, the terms "nucleic acid oligomer" and "oligonucleotide" are used interchangeably and are intended to include, but are not limited to, nucleic acids having a length of 200 nucleotides or less. In some embodiments, an oligonucleotide is a nucleic acid having a length of 2 to 200 nucleotides, 2 to 150 nucleotides, 5 to 150 nucleotides or 5 to 100 nucleotides. The terms "polynucleotide," "oligonucleotide," "oligo" or the like refer, in the usual and customary sense, to a linear sequence of nucleotides. Oligonucleotides are typically from about 5, 6, 7, 8, 9, 10, 12, 15, 25, 30, 40, 50 or more nucleotides in length, up to about 100 nucleotides in length. In some embodiments, an oligonucleotide is a primer configured for extension by a polymerase when the primer is annealed completely or partially to a complementary nucleic acid template. A primer is often a single stranded nucleic acid. In certain embodiments, a primer, or portion thereof, is substantially complementary to a portion of an adapter. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides.

As used herein, the terms "polynucleotide primer" and "primer" refers to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin). Primers (e.g., forward or reverse primers) may be attached to a solid support. A primer can be of any length depending on the particular technique it will be used for. For example, PCR primers are generally between 10 and 40 nucleotides in length. The length and complexity of the nucleic acid fixed onto the nucleic acid template may vary. In some embodiments, a primer has a length of 200 nucleotides or less. In certain embodiments, a primer has a length of 10 to 150 nucleotides, 15 to 150 nucleotides, 5 to 100 nucleotides, 5 to 50 nucleotides or 10 to 50 nucleotides. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template/target DNA to which the primer hybridizes. The addition of a nucleotide residue to the 3' end of a primer by formation of a phosphodiester bond results in a DNA extension product. The addition of a nucleotide residue to the 3' end of the DNA extension product by formation of a phosphodiester bond results in a further DNA extension product. In another embodiment, the primer is an RNA primer. In embodiments, a primer is hybridized to a target polynucleotide. A "primer"

is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the terms "analogue" and "analog", in reference to a chemical compound, refers to compound having a structure similar to that of another one, but differing from it in respect of one or more different atoms, functional groups, or substructures that are replaced with one or more other atoms, functional groups, or substructures. In the context of a nucleotide, a nucleotide analog refers to a compound that, like the nucleotide of which it is an analog, can be incorporated into a nucleic acid molecule (e.g., an extension product) by a suitable polymerase, for example, a DNA polymerase in the context of a nucleotide analogue. The terms also encompass nucleic acids containing known nucleotide analogs or modified backbone residues or linkages, which are synthetic, naturally occurring, or non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphorothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA)), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

The term "nucleoside" refers, in the usual and customary sense, to a glycosylamine including a nucleobase and a five-carbon sugar (ribose or deoxyribose). Non-limiting examples of nucleosides include cytidine, uridine, adenosine, guanosine, thymidine and inosine. Nucleosides may be modified at the base and/or the sugar. The term "nucleotide" refers, in the usual and customary sense, to a single unit of a polynucleotide, i.e., a monomer. Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA. Examples of nucleic acid, e.g., polynucleotides contemplated herein include any types of RNA, e.g., mRNA, siRNA, miRNA, and guide RNA and any types of DNA, genomic DNA, plasmid DNA, and minicircle DNA, and any fragments thereof. The term "duplex" in the context of polynucleotides refers, in the usual and customary sense, to double strandedness.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection (see, e.g., NCBI web site www.ncbi.nlm.nih.gov/BLAST/ or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

In some embodiments, a nucleic acid (e.g., an adapter or a primer) comprises a molecular identifier or a molecular barcode. As used herein, the term "molecular barcode" (which may be referred to as a "tag", a "barcode", an "index" a "molecular identifier", an "identifier sequence" or a "unique molecular identifier" (UMI)) refers to any material (e.g., a nucleotide sequence, a nucleic acid molecule feature) that is capable of distinguishing an individual molecule in a large heterogeneous population of molecules. In embodiments, a barcode is unique in a pool of barcodes that differ from one another in sequence, or is uniquely associated with a particular sample polynucleotide in a pool of sample polynucleotides. In embodiments, every barcode in a pool of adapters is unique, such that sequencing reads comprising the barcode can be identified as originating from a single sample polynucleotide molecule on the basis of the barcode alone. In other embodiments, individual barcode sequences may be used more than once, but adapters comprising the duplicate barcodes are associated with different sequences and/or in different combinations of barcoded adaptors, such that sequence reads may still be uniquely distinguished as originating from a single sample polynucleotide molecule on the basis of a barcode and adjacent sequence information (e.g., sample polynucleotide sequence, and/or one or more adjacent barcodes). In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are about 10 to about 50 nucleotides in length, such as about 15 to about 40 or about 20 to about 30 nucleotides in length. In a pool of different barcodes, barcodes may have the same or different lengths. In general, barcodes are of sufficient length and include sequences that are sufficiently different to allow the identification of sequencing reads that originate from the same sample polynucleotide molecule. In embodiments, each barcode in a plurality of barcodes differs from every other barcode in the plurality by at least three nucleotide positions, such as at least 3, 4, 5, 6, 7, 8, 9, 10, or more nucleotide positions. In some embodiments, substantially degenerate barcodes may be known as random. In some embodiments, a barcode may include a nucleic acid sequence from within a pool of known sequences. In some embodiments, the barcodes may be pre-defined. In embodiments, the index includes about 1 to about 10 nucleotides. In embodiments, the index includes about 3, 4, 5, 6, 7, 8, 9, or about 10 nucleotides. In embodiments, the index includes about 3 nucleotides. In embodiments, the index includes about 5 nucleotides. In embodiments, the index includes about 7 nucleotides. In embodiments, the index includes about 10 nucleotides. In embodiments, the index includes about 6 to about 10 nucleotides.

As used herein, the term "incorporating" or "chemically incorporating," when used in reference to a primer and cognate nucleotide, refers to the process of joining the cognate nucleotide to the primer or extension product thereof by formation of a phosphodiester bond.

As used herein, the term "template polynucleotide" or "template nucleic acid" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. The target sequence may be a portion of a gene, a regulatory sequence, genomic DNA, cDNA, RNA including mRNA, miRNA, rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s). In the context of selective sequencing, "target polynucleotide(s)" refers to the subset of polynucleotide(s) to be sequenced from within a starting population of polynucleotides.

As used herein, the terms "sequencing", "sequence determination", "determining a nucleotide sequence", and the like include determination of a partial or complete sequence information (e.g., a sequence) of a polynucleotide being sequenced, and particularly physical processes for generating such sequence information. That is, the term includes sequence comparisons, consensus sequence determination, contig assembly, fingerprinting, and like levels of information about a target polynucleotide, as well as the express identification and ordering of nucleotides in a target polynucleotide. The term also includes the determination of the identification, ordering, and locations of one, two, or three of the four types of nucleotides within a target polynucleotide. In some embodiments, a sequencing process described herein comprises contacting a template and an annealed primer with a suitable polymerase under conditions suitable for polymerase extension and/or sequencing. The sequencing methods are preferably carried out with the target polynucleotide arrayed on a solid substrate. Multiple target polynucleotides can be immobilized on the solid support through linker molecules, or can be attached to particles, e.g., microspheres, which can also be attached to a solid substrate. In embodiments, the solid substrate is in the form of a chip, a bead, a well, a capillary tube, a slide, a wafer, a filter, a fiber, a porous media, or a column. In embodiments, the solid substrate is gold, quartz, silica, plastic, glass, diamond, silver, metal, or polypropylene. In embodiments, the solid substrate is porous.

As used herein, the term "substrate" refers to a solid support material. The substrate can be non-porous or porous. The substrate can be rigid or flexible. As used herein, the terms "solid support" and "solid surface" refers to discrete solid or semi-solid surface. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. Solid supports in the form of discrete particles may be referred to herein as "beads," which alone does not imply or require any particular shape. A bead can be non-spherical in shape. A solid support may further comprise a polymer or hydrogel on the surface to which the primers are attached (e.g., the primers are covalently attached to the polymer, wherein the polymer is in direct contact with the solid support). Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. The solid supports for some embodiments have at least one surface located within a flow cell.

The solid support, or regions thereof, can be substantially flat. The solid support can have surface features such as wells, pits, channels, ridges, raised regions, pegs, posts or the like. The term solid support is encompassing of a substrate (e.g., a flow cell) having a surface comprising a polymer coating covalently attached thereto. In embodiments, the solid support is a flow cell. The term "flow cell" as used herein refers to a chamber including a solid surface across which one or more fluid reagents can be flowed. Examples of flow cells and related fluidic systems and detection platforms that can be readily used in the methods of the present disclosure are described, for example, in Bentley et al., Nature 456:53-59 (2008). In certain embodiments a substrate comprises a surface (e.g., a surface of a flow cell, a surface of a tube, a surface of a chip), for example a metal surface (e.g. steel, gold, silver, aluminum, silicon and copper). In some embodiments a substrate (e.g., a substrate surface) is coated and/or comprises functional groups and/or inert materials. In certain embodiments a substrate comprises a bead, a chip, a capillary, a plate, a membrane, a wafer (e.g., silicon wafers), a comb, or a pin for example. In some embodiments a substrate comprises a bead and/or a nanoparticle. A substrate can be made of a suitable material, non-limiting examples of which include a plastic or a suitable polymer (e.g., polycarbonate, poly(vinyl alcohol), poly(divinylbenzene), polystyrene, polyamide, polyester, polyvinylidene difluoride (PVDF), polyethylene, polyurethane, polypropylene, and the like), borosilicate, glass, nylon, Wang resin, Merrifield resin, metal (e.g., iron, a metal alloy, sepharose, agarose, polyacrylamide, dextran, cellulose and the like or combinations thereof. In some embodiments a substrate comprises a magnetic material (e.g., iron, nickel, cobalt, platinum, aluminum, and the like). In certain embodiments a substrate comprises a magnetic bead (e.g., DYNABEADS®, hematite, AMPure XP). Magnets can be used to purify and/or capture nucleic acids bound to certain substrates (e.g., substrates comprising a metal or magnetic material).

The term "surface" is intended to mean an external part or external layer of a substrate. The surface can be in contact with another material such as a gas, liquid, gel, polymer, organic polymer, second surface of a similar or different material, metal, or coat. The surface, or regions thereof, can be substantially flat. The substrate and/or the surface can have surface features such as wells, pits, channels, ridges, raised regions, pegs, posts or the like.

The term "well" refers to a discrete concave feature or depression in a substrate having a surface opening that is completely surrounded by interstitial region(s) of the surface. Wells can have any of a variety of shapes at their opening in a surface including but not limited to round, elliptical, square, polygonal, or star shaped (i.e., star shaped with any number of vertices). The cross section of a well taken orthogonally with the surface may be curved, square, polygonal, hyperbolic, conical, or angular. The wells of a microplate may be available in different shapes, for example F-Bottom: flat bottom; C-Bottom: bottom with minimal rounded edges; V-Bottom: V-shaped bottom; or U-Bottom: U-shaped bottom. In embodiments, the well is substantially square. In embodiments, the well is square. In embodiments, the well is F-bottom. In embodiments, the microplate includes 24 substantially round flat bottom wells. In embodiments, the microplate includes 48 substantially round flat bottom wells. In embodiments, the microplate includes 96 substantially round flat bottom wells. In embodiments, the microplate includes 384 substantially square flat bottom wells.

The discrete regions (i.e., features or wells) may have defined locations in a regular array, which may correspond to a rectilinear pattern, circular pattern, hexagonal pattern, or the like. In embodiments, the pattern of wells includes concentric circles of regions, spiral patterns, rectilinear patterns, hexagonal patterns, and the like. In embodiments, the pattern of wells is arranged in a rectilinear or hexagonal pattern A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments, the interstitial region is continuous whereas the features are discrete, for example, as is the case for an array of wells in an otherwise continuous surface. The separation provided by an interstitial region can be partial or full separation. In embodiments, interstitial regions have a surface material that differs from the surface material of the wells (e.g., the interstitial region contains a photoresist and the surface of the well is glass). In embodiments, interstitial regions have a surface material that is the same as the surface material of the wells (e.g., both the surface of the interstitial region and the surface of well contain a passivating polymer or copolymer). In embodiments, interstitial regions have a surface material that is the same as the surface material of the wells (e.g., both the surface of the interstitial region and the surface of well contain a polymer or copolymer).

As used herein, the term "feature" refers a point or area in a pattern that can be distinguished from other points or areas according to its relative location. An individual feature can include one or more polynucleotides. For example, a feature can include a single target nucleic acid molecule having a particular sequence or a feature can include several nucleic acid molecules having the same sequence (and/or complementary sequence, thereof). Different molecules that are at different features of a pattern can be differentiated from each other according to the locations of the features in the pattern. Non-limiting examples of features include wells in a substrate, particles (e.g., beads) in or on a substrate, polymers in or on a substrate, projections from a substrate, ridges on a substrate, or channels in a substrate.

As used herein, the term "sequencing cycle" is used in accordance with its plain and ordinary meaning and refers to incorporating one or more nucleotides (e.g., nucleotide analogues) to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

As used herein, the term "sequencing reaction mixture" is used in accordance with its plain and ordinary meaning and refers to an aqueous mixture that contains the reagents necessary to allow a nucleotide or nucleotide analogue to be added (i.e., incorporated) to a DNA strand by a DNA polymerase. As used herein, the term "invasion-reaction mixture" is used in accordance with its plain and ordinary meaning and refers to an aqueous mixture that contains the reagents necessary to allow a nucleotide or nucleotide analogue to be added to a DNA strand by a DNA polymerase that extends the invasion primer.

As used herein, the term "extension" or "elongation" is used in accordance with their plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) DNA strand.

As used herein, the term "sequencing read" is used in accordance with its plain and ordinary meaning and refers to an inferred sequence of nucleotide bases (or nucleotide base probabilities) corresponding to all or part of a single polynucleotide fragment. A sequencing read may include 10, 20, 30, 40, 50, 60, 70, 80, 90, 100, 150, 200, 250, or more nucleotide bases. In embodiments, a sequencing read includes reading a barcode and a template nucleotide sequence. In embodiments, a sequencing read includes reading a template nucleotide sequence. In embodiments, a sequencing read includes reading a barcode and not a template nucleotide sequence. In embodiments, a sequencing read includes a computationally derived string corresponding to the detected label.

Complementary single stranded nucleic acids and/or substantially complementary single stranded nucleic acids can hybridize to each other under hybridization conditions, thereby forming a nucleic acid that is partially or fully double stranded. All or a portion of a nucleic acid sequence may be substantially complementary to another nucleic acid sequence, in some embodiments. As referred to herein, "substantially complementary" refers to nucleotide sequences that can hybridize with each other under suitable hybridization conditions. Hybridization conditions can be altered to tolerate varying amounts of sequence mismatch within complementary nucleic acids that are substantially complementary. Substantially complementary portions of nucleic acids that can hybridize to each other can be 75% or more, 76% or more, 77% or more, 78% or more, 79% or more, 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more or 99% or more complementary to each other. In some embodiments substantially complementary portions of nucleic acids that can hybridize to each other are 100% complementary. Nucleic acids, or portions thereof, that are configured to hybridize to each other often comprise nucleic acid sequences that are substantially complementary to each other.

"Hybridize" shall mean the annealing of a nucleic acid sequence to another nucleic acid sequence (e.g., one single-stranded nucleic acid (such as a primer) to another nucleic acid) based on the well-understood principle of sequence complementarity. In an embodiment the other nucleic acid is a single-stranded nucleic acid. In some embodiments, one portion of a nucleic acid hybridizes to itself, such as in the formation of a hairpin structure. The propensity for hybridization between nucleic acids depends on the temperature and ionic strength of their milieu, the length of the nucleic acids and the degree of complementarity. The effect of these parameters on hybridization is described in, for example, Sambrook J., Fritsch E. F., Maniatis T., Molecular cloning: a laboratory manual, Cold Spring Harbor Laboratory Press, New York (1989). As used herein, hybridization of a primer, or of a DNA extension product, respectively, is extendable by creation of a phosphodiester bond with an available nucleotide or nucleotide analogue capable of forming a phosphodiester bond, therewith. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence.

As used herein, "specifically hybridizes" refers to preferential hybridization under hybridization conditions where two nucleic acids, or portions thereof, that are substantially complementary, hybridize to each other and not to other nucleic acids that are not substantially complementary to either of the two nucleic acid. For example, specific hybridization includes the hybridization of a primer or capture nucleic acid to a portion of a target nucleic acid (e.g., a template, or adapter portion of a template) that is substantially complementary to the primer or capture nucleic acid. In some embodiments nucleic acids, or portions thereof, that are configured to specifically hybridize are often about 80% or more, 81% or more, 82% or more, 83% or more, 84% or more, 85% or more, 86% or more, 87% or more, 88% or more, 89% or more, 90% or more, 91% or more, 92% or more, 93% or more, 94% or more, 95% or more, 96% or more, 97% or more, 98% or more, 99% or more or 100% complementary to each other over a contiguous portion of nucleic acid sequence. A specific hybridization discriminates over non-specific hybridization interactions (e.g., two nucleic acids that a not configured to specifically hybridize, e.g., two nucleic acids that are 80% or less, 70% or less, 60% or less or 50% or less complementary) by about 2-fold or more, often about 10-fold or more, and sometimes about 100-fold or more, 1000-fold or more, 10,000-fold or more, 100,000-fold or more, or 1,000,000-fold or more. Two nucleic acid strands that are hybridized to each other can form a duplex, which comprises a double stranded portion of nucleic acid.

A nucleic acid can be amplified by any suitable method. The term "amplified" as used herein refers to subjecting a target nucleic acid in a sample to a process that linearly or exponentially generates amplicon nucleic acids having the same or substantially the same (e.g., substantially identical) nucleotide sequence as the target nucleic acid, or segment thereof, and/or a complement thereof. In some embodiments an amplification reaction comprises a suitable thermal stable polymerase. Thermal stable polymerases are known in the art and are stable for prolonged periods of time, at temperature greater than 80° C. when compared to common polymerases found in most mammals. In certain embodiments the term "amplified" refers to a method that comprises a polymerase chain reaction (PCR). Conditions conducive to amplification (i.e., amplification conditions) are well known and often comprise at least a suitable polymerase, a suitable template, a suitable primer or set of primers, suitable nucleotides (e.g., dNTPs), a suitable buffer, and application of suitable annealing, hybridization and/or extension times and temperatures. In certain embodiments an amplified product (e.g., an amplicon) can contain one or more additional and/or different nucleotides than the template sequence, or portion thereof, from which the amplicon was generated (e.g., a primer can contain "extra" nucleotides (such as a 5' portion that does not hybridize to the template), or one or more mismatched bases within a hybridizing portion of the primer).

As used herein, the term "rolling circle amplification (RCA)" refers to a nucleic acid amplification reaction that amplifies a circular nucleic acid template (e.g., single-stranded DNA circles) via a rolling circle mechanism. Rolling circle amplification reaction is initiated by the hybridization of a primer to a circular, often single-stranded, nucleic acid template. The nucleic acid polymerase then extends the primer that is hybridized to the circular nucleic acid template by continuously progressing around the circular nucleic acid template to replicate the sequence of the nucleic acid template over and over again (rolling circle mechanism). The rolling circle amplification typically produces concatemers comprising tandem repeat units of the circular nucleic acid template sequence. The rolling circle amplification may be a linear RCA (LRCA), exhibiting linear amplification kinetics (e.g., RCA using a single specific primer), or may be an exponential RCA (ERCA) exhibiting exponential amplification kinetics. Rolling circle amplification may also be performed using multiple primers (multiply primed rolling circle amplification or MPRCA) leading to hyper-branched concatemers. For example, in a double-primed RCA, one primer may be complementary, as in the linear RCA, to the circular nucleic acid template, whereas the other may be complementary to the tandem repeat unit nucleic acid sequences of the RCA product. Consequently, the double-primed RCA may proceed as a chain reaction with exponential (geometric) amplification kinetics featuring a ramifying cascade of multiple-hybridization, primer-extension, and strand-displacement events involving both the primers. This often generates a discrete set of concatemeric, double-stranded nucleic acid amplification products. The rolling circle amplification may be performed in-vitro under isothermal conditions using a suitable nucleic acid polymerase such as Phi29 DNA polymerase. RCA may be performed by using any of the DNA polymerases that are known in the art (e.g., a Phi29 DNA polymerase, a Bst DNA polymerase, or SD polymerase).

A nucleic acid can be amplified by a thermocycling method or by an isothermal amplification method. In some embodiments, a rolling circle amplification method is used. In some embodiments amplification takes place on a solid support (e.g., within a flow cell) where a nucleic acid, nucleic acid library or portion thereof is immobilized. In certain sequencing methods, a nucleic acid library is added to a flow cell and immobilized by hybridization to anchors under suitable conditions. This type of nucleic acid amplification is often referred to as solid phase amplification. In some embodiments of solid phase amplification, all or a portion of the amplified products are synthesized by an extension initiating from an immobilized primer. Solid phase amplification reactions are analogous to standard solution phase amplifications except that at least one of the amplification oligonucleotides (e.g., primers) is immobilized on a solid support.

In some embodiments, solid phase amplification comprises a nucleic acid amplification reaction comprising only one species of oligonucleotide primer immobilized to a surface or substrate. In certain embodiments solid phase amplification comprises a plurality of different immobilized oligonucleotide primer species. In some embodiments solid phase amplification may comprise a nucleic acid amplification reaction comprising one species of oligonucleotide primer immobilized on a solid surface and a second different oligonucleotide primer species in solution. Multiple different species of immobilized or solution based primers can be used. Non-limiting examples of solid phase nucleic acid amplification reactions include interfacial amplification, bridge PCR amplification, emulsion PCR, WildFire amplification (e.g., US patent publication US20130012399), the like or combinations thereof.

In certain embodiments, a nucleic acid template comprising a complementary forward and reverse stand of a double stranded nucleic acid, a hairpin adapter on one end, and a Y adapter on the other end, is amplified by bridge PCR amplification. The bridge PCR amplification process of a nucleic acid template comprising such a configuration is mechanistically distinct from a bridge amplification that takes place for a single stranded nucleic acid template containing no internal complementary regions. For example, after a denaturation step in bridge PCR of a nucleic acid template comprising such a configuration, amplicons can preferentially form an intramolecular double-stranded region as opposed to staying double-stranded at an intermolecular scale. This enables a free 3' end at the Y-adapter end, which is available for re-priming with additional solid-phase primers.

As used herein, the terms "cluster" and "colony" are used interchangeably to refer to a site (e.g., a discrete site) on a solid support that includes a plurality of immobilized polynucleotides and a plurality of immobilized complementary polynucleotides. In embodiments, the polynucleotides consist of amplicons of a single species (e.g., "monoclonal"), thereby forming a homogenous cluster. However, in preferred embodiments, the polynucleotides at a given site are heterogeneous (e.g., "polyclonal"), such that individual molecules having different sequences are present at the site or feature. In some embodiments, a polyclonal cluster includes template polynucleotides including the same template sequence but containing different adapter sequences compared to other substantially identical template polynucleotides (e.g., the same target polynucleotide sequence from different samples, prepared with the different adapter sequences). The term "clustered array" refers to an array formed from such clusters or colonies. In this context, the term "array" is not to be understood as requiring an ordered arrangement of clusters. The term "array" is used in accordance with its ordinary meaning in the art and refers to a population of different molecules that are attached to one or more solid-phase substrates such that different molecules can be differentiated from each other according to their relative location. An array can include different molecules that are each located at different addressable features on a solid-phase substrate. In some embodiments, an array of sites is provided, wherein each of a plurality of the sites includes a first nucleic acid template and a second nucleic acid template and wherein the first nucleic acid template has a sequence that is different from the sequence of the second nucleic acid template. There can be greater than two different templates (e.g., greater than three different templates, greater than four different templates, etc.) at each of a plurality of sites, in some embodiments. The molecules of the array can be nucleic acid primers, nucleic acid probes, nucleic acid templates, or nucleic acid enzymes such as polymerases or ligases. Arrays useful in embodiments of the invention can have densities that range from about two different features to many millions, billions, or higher. The density of an array can be from two to as many as a billion or more different features per square cm. For example, an array can have at least about 100 features/cm$^2$, at least about 1,000 features/cm$^2$, at least about 10,000 features/cm$^2$, at least about 100,000 features/cm$^2$, at least about 10,000,000 features/cm$^2$, at least about 100,000,000 features/cm$^2$, at least about 1,000,000,000 features/cm$^2$, at least about 2,000,000,000 features/cm$^2$ or higher. In embodiments, the arrays have features at any of a variety of densities including, for example, at least about 10 features/cm$^2$, 100 features/cm$^2$, 500 features/cm$^2$, 1,000 features/cm$^2$, 5,000 features/cm$^2$, 10,000 features/cm$^2$, 50,000 features/cm$^2$, 100,000 features/cm$^2$, 1,000,000 features/cm$^2$, 5,000,000 features/cm$^2$, or higher.

An array of sites (e.g., an array of features) can appear as a grid of spots or patches. The sites can be located in a repeating pattern or in an irregular non-repeating pattern. Particularly useful patterns are hexagonal patterns, rectilinear patterns, grid patterns, patterns having reflective symmetry, patterns having rotational symmetry, or the like. Asymmetric patterns can also be useful; in embodiments, the array of features are present in an asymmetric pattern.

The size of the sites and/or spacing between the sites in an array can vary to achieve high density, medium density, or lower density. High density arrays are characterized as having sites with a pitch that is less than about 15 µm. Medium density arrays have sites with a pitch that is about 15 to 30 µm, while low-density arrays have a pitch that is greater than 30 µm. An array useful in some embodiments can have sites with a pitch that is less than 100 µm, 50 µm, 10 µm, 5 µm, 1 µm, or 0.5 µm. An embodiment of the methods set forth herein can be used to image an array at a resolution sufficient to distinguish sites at the above densities or density ranges. However, the detecting step will typically use a detector having a spatial resolution that is too low to resolve points at a distance equivalent to the spacing between a first template (or first primer extension product hybridized thereto) and a second template (or second primer extension product hybridized thereto) of an overlapping cluster at an individual site. In particular embodiments, sites of an array can each have an area that is larger than about 100 nm$^2$, 250 nm$^2$, 500 nm$^2$, 1 µm$^2$, 2.5 µm$^2$, 5 µm$^2$, 10 µm$^2$, 100 µm$^2$, or 500 µm$^2$. Alternatively or additionally, sites of an array can each have an area that is smaller than about 1 mm$^2$, 500 µm$^2$, 100 µm$^2$, 25 µm$^2$, 10 µm$^2$, 5 µm$^2$, 1 µm$^2$, 500 nm$^2$, or 100 nm$^2$. Indeed, a site can have a size that is in a range between an upper and lower limit selected from those exemplified above.

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol µ DNA polymerase, Pol λ, DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g. Therminator γ, 9° N polymerase (exo-), Therminator II, Therminator III, or Therminator IX). In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044).

The terms "bioconjugate group," "bioconjugate reactive moiety," and "bioconjugate reactive group" refer to a chemical moiety, which participates in a reaction to form a bioconjugate linker (e.g., covalent linker). Non-limiting examples of bioconjugate groups include —NH$_2$, —COOH, —COOCH$_3$, —N-hydroxysuccinimide, —N$_3$, —dibenzylcyclooctyne (DBCO), alkyne, —and/or maleimide. Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |

-continued

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). In embodiments, the first bioconjugate reactive group (e.g., azide moiety) is covalently attached to the second bioconjugate reactive group (e.g., an alkyne moiety) to form a 5-membered heteroatom ring. In embodiments, the first bioconjugate reactive group (e.g., azide moiety) is covalently attached to the second bioconjugate reactive group (e.g., an DBCO moiety) to form a bioconjugate linker.

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or streptavidin to form a avidin-biotin complex or streptavidin-biotin complex.

The methods and kits of the present disclosure may be applied, mutatis mutandis, to the sequencing of RNA, or to determining the identity of a ribonucleotide.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., packaging, buffers, written instructions for performing a method, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

The term "nucleobase" or "base" as used herein refers to a purine or pyrimidine compound, or a derivative thereof, that may be a constituent of nucleic acid (i.e., DNA or RNA, or a derivative thereof). In embodiments, the nucleobase is a divalent purine or pyrimidine, or derivative thereof. In embodiments, the nucleobase is a monovalent purine or pyrimidine, or derivative thereof. In embodiments, the base is a derivative of a naturally occurring DNA or RNA base (e.g., a base analogue). In embodiments, the base is a hybridizing base. In embodiments, the base hybridizes to a complementary base. In embodiments, the base is capable of forming at least one hydrogen bond with a complementary base (e.g., adenine hydrogen bonds with thymine, adenine hydrogen bonds with uracil, guanine pairs with cytosine). Non-limiting examples of a base includes cytosine or a derivative thereof (e.g., cytosine analogue), guanine or a derivative thereof (e.g., guanine analogue), adenine or a derivative thereof (e.g., adenine analogue), thymine or a derivative thereof (e.g., thymine analogue), uracil or a derivative thereof (e.g., uracil analogue), hypoxanthine or a derivative thereof (e.g., hypoxanthine analogue), xanthine or a derivative thereof (e.g., xanthine analogue), 7-methylguanine or a derivative thereof (e.g., 7-methylguanine analogue), deaza-adenine or a derivative thereof (e.g., deaza-adenine analogue), deaza-guanine or a derivative thereof (e.g., deaza-guanine), deaza-hypoxanthine or a derivative thereof, 5,6-dihydrouracil or a derivative thereof (e.g., 5,6-dihydrouracil analogue), 5-methylcytosine or a derivative thereof (e.g., 5-methylcytosine analogue), or 5-hydroxymethylcytosine or a derivative thereof (e.g., 5-hydroxymethylcytosine analogue) moieties. In embodiments, the base is adenine, guanine, uracil, cytosine, thymine, hypoxanthine, xanthine, theobromine, caffeine, uric acid, or isoguanine, which may be optionally substituted or modified. In embodiments, the base is adenine, guanine, hypoxanthine, xanthine, theobromine, caffeine, uric acid, or isoguanine, which may be optionally substituted or modified.

"Synthetic" agents refer to non-naturally occurring agents, such as enzymes or nucleotides. The term "synthetic sequence" as used herein refers to a modified nucleic acid sequence such as those constructed by synthetic methods. In embodiments, a synthetic sequence is artificial or engineered, or derived from or contains an artificial or engineered nucleic acid content (e.g., non-natural or not wild type). For example, a polynucleotide sequence that is inserted or ligated to a target sequence (e.g., genomic DNA) may be referred to as a synthetic sequence. A polynucleotide adapter, as used herein, may be considered as providing a synthetic sequence.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed within the invention. The upper and lower limits of any such smaller range (within a more broadly recited range) may independently be included in the smaller ranges, or as particular values themselves, and are also encompassed within the invention, subject to any specifically excluded limit in the stated range. Where the stated range includes one or both of the limits, ranges excluding either or both of those included limits are also included in the invention.

The term "library" merely refers to a collection or plurality of template nucleic acid molecules which share common sequences at their 5' ends (e.g., the first end) and common sequences at their 3' ends (e.g., the second end). In embodiments, a population of template nucleic acid molecules form a library.

"GC bias" describes the relationship between GC content and read coverage across a genome. For example, a genomic region of a higher GC content tends to have more (or less) sequencing reads covering that region. As described herein, GC bias can be introduced during amplification of library, cluster amplification, and/or the sequencing reactions.

The term "multiplexing" as used herein refers to an analytical method in which the presence and/or amount of multiple targets, e.g., multiple nucleic acid target sequences, can be assayed simultaneously by using the methods and devices as described herein, each of which has at least one different detection characteristic, e.g., fluorescence characteristic (e.g., excitation wavelength, emission wavelength, emission intensity, FWHM (full width at half maximum peak height), or fluorescence lifetime) or a unique nucleic acid sequence characteristic.

The term "adapter" as used herein refers to any linear oligonucleotide that can be ligated to a nucleic acid molecule, thereby generating nucleic acid products that can be sequenced on a sequencing platform (e.g., an Illumina or Singular Genomics sequencing platform). In embodiments, adapters include two reverse complementary oligonucleotides forming a double-stranded structure. In embodiments, an adapter includes two oligonucleotides that are complementary at one portion and mismatched at another portion, forming a Y-shaped or fork-shaped adapter that is double stranded at the complementary portion and has two overhangs at the mismatched portion. Since Y-shaped adapters have a complementary, double-stranded region, they can be considered a special form of double-stranded adapters. When this disclosure contrasts Y-shaped adapters and double stranded adapters, the term "double-stranded adapter" or "blunt-ended" is used to refer to an adapter having two strands that are fully complementary, substantially (e.g., more than 90% or 95%) complementary, or partially complementary. In embodiments, adapters include sequences that bind to sequencing primers. In embodiments, adapters include sequences that bind to immobilized oligonucleotides (e.g., P7 and P5 sequences, or S1 and S2 sequences) or reverse complements thereof. In embodiments, the adapter is substantially non-complementary to the 3' end or the 5' end of any target polynucleotide present in the sample. In embodiments, the adapter can include a sequence that is substantially identical, or substantially complementary, to at least a portion of a primer, for example a universal primer. In embodiments, the adapter can include an index sequence (also referred to as barcode or tag) to assist with downstream error correction, identification or sequencing.

As used herein, "capable of hybridizing" is used in accordance with its ordinary meaning in the art and refers to two oligonucleotides that, under suitable conditions, can form a duplex (e.g., Watson-Crick pairing) which includes a double-stranded portion of nucleic acid. Such conditions, known in the art and described herein, depend upon, for example, the nature of the nucleotide sequence, temperature, and buffer conditions. The stringency of hybridization can be influenced by various parameters, including degree of identity and/or complementarity between the polynucleotides (or any target sequences within the polynucleotides) to be hybridized; melting point of the polynucleotides and/or target sequences to be hybridized, referred to as "Tm"; parameters such as salts, buffers, pH, temperature, GC % content of the polynucleotide and primers, and/or time. Typically, hybridization is favored in lower temperatures and/or increased salt concentrations, as well as reduced concentrations of organic solvents. Some exemplary conditions suitable for hybridization include incubation of the polynucleotides to be hybridized in solutions having sodium salts, such as NaCl, sodium citrate and/or sodium phosphate. In some embodiments, hybridization or wash solutions can include about 10-75% formamide and/or about 0.01-0.7% sodium dodecyl sulfate (SDS). In some embodiments, a hybridization solution can be a stringent hybridization solution which can include any combination of 50% formamide, 5×SSC (0.75 M NaCl, 0.075 M sodium citrate), 50 mM sodium phosphate (pH 6.8), 0.1% sodium pyrophosphate, 5×Denhardt's solution, 0.1% SDS, and/or 10% dextran sulfate. In some embodiments, the hybridization or washing solution can include BSA (bovine serum albumin). In some embodiments, hybridization or washing can be conducted at a temperature range of about 20-25° C., or about 25-30° C., or about 30-35° C., or about 35-40° C., or about 40-45° C., or about 45-50° C., or about 50-55° C., or higher. In some embodiments, hybridization or washing can be conducted for a time range of about 1-10 minutes, or about 10-20 minutes, or about 20-30 minutes, or about 30-40 minutes, or about 40-50 minutes, or about 50-60 minutes, or longer. In some embodiments, hybridization or wash conditions can be conducted at a pH range of about 5-10, or about pH 6-9, or about pH 6.5-8, or about pH 6.5-7.

As used herein, the terms "reversible blocking groups" and "reversible terminators" are used in accordance with their plain and ordinary meanings and refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Non-limiting examples of nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group —OR [reversible terminating (capping) group] is linked to the oxygen atom of the 3'-OH of the pentose, while the label is linked to the base, which acts as a reporter and can be cleaved. The 3'-O-blocked reversible terminators are known in the art, and may be, for instance, a 3'-ONH$_2$ reversible terminator, a 3'-O-allyl reversible terminator, or a 3'-O-azidomethyl reversible terminator. In embodiments, the reversible terminator moiety is attached to the 3'-oxygen of the nucleotide, having the formula:

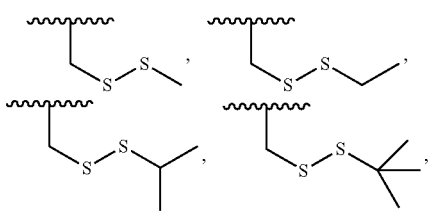

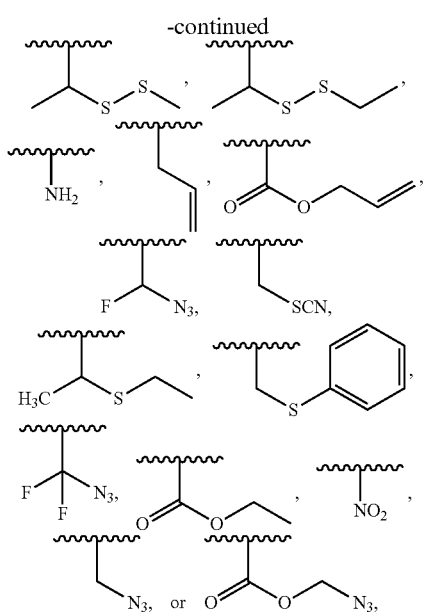

wherein the 3' oxygen of the nucleotide is not shown in the formulae above. The term "allyl" as described herein refers to an unsubstituted methylene attached to a vinyl group (i.e., —CH=CH$_2$), e.g.,

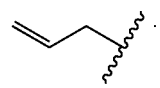

In embodiments, the reversible terminator moiety is

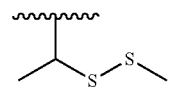

as described in U.S. Pat. No. 10,738,072, which is incorporated herein by reference for all purposes. For example, a nucleotide including a reversible terminator moiety may be represented by the formula:

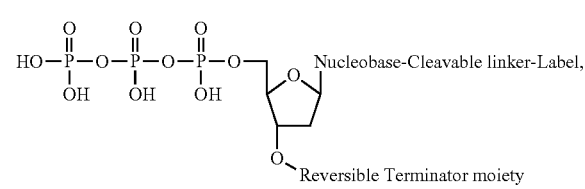

where the nucleobase is adenine or adenine analogue, thymine or thymine analogue, guanine or guanine analogue, or cytosine or cytosine analogue.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent

II. Compositions, Supports, & Kits

In an aspect is provided a solid support including a first plurality of immobilized oligonucleotides, and a second plurality of immobilized oligonucleotides, wherein the immobilized oligonucleotides of the first plurality include a sequence selected from SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123, and the immobilized oligonucleotides of the second plurality include a sequence selected from SEQ ID NO:7, SEQ ID NO:30, SEQ ID NO:87, SEQ ID NO:89, SEQ ID NO:91, SEQ ID NO:86, SEQ ID NO:118, SEQ ID NO:120, SEQ ID NO:122, or SEQ ID NO:124. In embodiments, the immobilized oligonucleotide of the first plurality is SEQ ID NO:5. In embodiments, the immobilized oligonucleotide of the first plurality is SEQ ID NO:9. In embodiments, the immobilized oligonucleotide of the first plurality is SEQ ID NO:85. In embodiments, the immobilized oligonucleotide of the first plurality is SEQ ID NO:92. In embodiments, the immobilized oligonucleotide of the first plurality is SEQ ID NO:90. In embodiments, the immobilized oligonucleotide of the first plurality is SEQ ID NO:88. In embodiments, the immobilized oligonucleotide of the first plurality is SEQ ID NO:117. In embodiments, the immobilized oligonucleotide of the first plurality is SEQ ID NO:119. In embodiments, the immobilized oligonucleotide of the first plurality is SEQ ID NO:121. In embodiments, the immobilized oligonucleotide of the first plurality is SEQ ID NO:123. In embodiments, the immobilized oligonucleotide of the second plurality is SEQ ID NO:7. In embodiments, the immobilized oligonucleotide of the second plurality is SEQ ID NO:30. In embodiments, the immobilized oligonucleotide of the second plurality is SEQ ID NO:87. In embodiments, the immobilized oligonucleotide of the second plurality is SEQ ID NO:89. In embodiments, the immobilized oligonucleotide of the second plurality is SEQ ID NO:91. In embodiments, the immobilized oligonucleotide of the second plurality is SEQ ID NO:86. In embodiments, the immobilized oligonucleotide of the second plurality is SEQ ID NO:118. In embodiments, the immobilized oligonucleotide of the second plurality is SEQ ID NO:120. In embodiments, the immobilized oligonucleotide of the second plurality is SEQ ID NO:122. In embodiments, the immobilized oligonucleotide of the second plurality is SEQ ID NO:124.

In embodiments, the immobilized oligonucleotides of the first plurality are covalently attached to a polymer on the solid support via a first linker. In embodiments, the immobilized oligonucleotides of the second plurality are covalently attached to a polymer on the solid support via a second linker. In embodiments, the first linker, the second linker, or both the first linker and the second linker includes 8 to 16 thymine nucleotides (e.g., consecutive thymine nucleotides, such as a poly-T linker). In embodiments, the first linker and the second linker includes 8 to 16 thymine nucleotides (e.g., consecutive thymine nucleotides, such as a poly-T linker). In embodiments, the linker is at the 5' end of the immobilized oligonucleotides. In embodiments, the first linker, the second linker, or both the first linker and the second linker includes a cleavable site. In embodiments, the first linker and not the second linker includes a cleavable site. In embodiments, the second linker and not the first linker includes a cleavable site. In embodiments, the cleavable site includes one or more deoxyuracil nucleobases (dUs). In embodiments, the first linker, the second linker, or both the first linker and the second linker includes 1 to 5 uracil nucleotides.

Any suitable enzymatic, chemical, or photochemical cleavage reaction may be used to cleave the cleavable site. The cleavage reaction may result in removal of a part or the whole of the strand being cleaved. Suitable cleavage means include, for example, restriction enzyme digestion, in which case the cleavable site is an appropriate restriction site for the enzyme which directs cleavage of one or both strands of a duplex template; RNase digestion or chemical cleavage of a bond between a deoxyribonucleotide and a ribonucleotide, in which case the cleavable site may include one or more ribonucleotides; chemical reduction of a disulfide linkage with a reducing agent (e.g., THPP or TCEP), in which case the cleavable site should include an appropriate disulfide linkage; chemical cleavage of a diol linkage with periodate, in which case the cleavable site should include a diol linkage; generation of an abasic site and subsequent hydrolysis, etc. In embodiments, the cleavable site is included in the surface immobilized primer (e.g., within the polynucleotide sequence of the primer). In embodiments, the linker, the primer, or the template polynucleotide includes a diol linkage which permits cleavage by treatment with periodate (e.g., sodium periodate). It will be appreciated that more than one diol can be included at the cleavable site. One or more diol units may be incorporated into a polynucleotide using standard methods for automated chemical DNA synthesis. Polynucleotide primers including one or more diol linkers can be conveniently prepared by chemical synthesis. The diol linker is cleaved by treatment with any substance, which promotes cleavage of the diol (e.g., a diol-cleaving agent). In embodiments, the diol-cleaving agent is periodate, e.g., aqueous sodium periodate ($NaIO_4$). Following treatment with the diol-cleaving agent (e.g., periodate) to cleave the diol, the cleaved product may be treated with a "capping agent" In order to neutralize reactive species generated in the cleavage reaction. Suitable capping agents for this purpose include amines, e.g., ethanolamine or propanolamine. In embodiments, cleavage may be accomplished by using a modified nucleotide as the cleavable site (e.g., uracil, 8oxoG, 5-mC, 5-hmC) that is removed or nicked via a corresponding DNA glycosylase, endonuclease, or combination thereof.

In embodiments, the cleavable site includes a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent. In embodiments, cleaving the amplicons of a first template polynucleotide includes contacting the cleavable site with a cleaving agent, wherein the cleaving agent includes a reducing agent, sodium periodate, RNase, formamidopyrimidine DNA glycosylase (Fpg), endonuclease, or uracil DNA glycosylase (UDG). In embodiments, the cleaving agent is an endonuclease enzyme such as nuclease P1, AP endonuclease, T7 endonuclease, T4 endonuclease IV, Bal 31 endonuclease, Endonuclease I (endo I), Micrococcal nuclease, Endonuclease II (endo VI, exo III), nuclease BAL-31 or mung bean nuclease. In embodiments, the cleaving agent includes a restriction endonuclease, including, for example a type IIS restriction endonuclease. In embodiments, the cleaving agent is an exonuclease (e.g., RecBCD), restriction nuclease, endoribonuclease, exoribonuclease, or RNase (e.g., RNAse I, II, or III). In embodiments, the cleaving agent is a restriction enzyme. In embodiments, the cleaving agent includes a glycosylase and one or more suitable endonucleases. In embodiments, cleavage is performed under alkaline (e.g., pH greater than 8) buffer conditions at between 40° C. to 80° C.

In embodiments, each of the plurality of immobilized oligonucleotides (e.g., immobilized primers) is about 5 to about 25 nucleotides in length. In embodiments, each of the plurality of immobilized oligonucleotides (e.g., immobilized primers) is about 10 to about 40 nucleotides in length. In embodiments, each of the plurality of immobilized oligonucleotides (e.g., immobilized primers) is about 5 to about 100 nucleotides in length. In embodiments, each of the plurality of immobilized oligonucleotides (e.g., immobilized primers) is about 20 to 200 nucleotides in length. In embodiments, each of the plurality of immobilized oligonucleotides (e.g., immobilized primers) about or at least about 5, 6, 7, 8, 9, 10, 12, 15, 18, 20, 25, 30, 35, 40, 50 or more nucleotides in length.

In embodiments, the solid support is a flow cell, particle, chip, slide, multi-well container, or unpatterned solid support. In embodiments, the solid support is a multi-well container or an unpatterned solid support. In embodiments, the solid support is an unpatterned solid support. The term "unpatterned solid support" as used herein refers to a solid support with a uniform polymer surface including, for example, amplification primers randomly distributed throughout the polymer surface. This is in contrast to a patterned solid support, wherein amplification primers, for example, as localized to specific regions of the surface, such as to wells in an array. In embodiments, an unpatterned solid support does not include organized surface features such as wells, pits, channels, ridges, raised regions, pegs, posts or the like. In embodiments, the surface of an unpatterned solid support does not contain interstitial regions. In embodiments, an unpatterned solid support includes a polymer (e.g., a hydrophilic polymer). In certain embodiments, the unpatterned solid support includes a plurality of oligonucleotides (e.g., primer oligonucleotides) randomly distributed throughout the polymer (e.g., the plurality of primer oligonucleotides are covalently attached to the polymer in a random distribution. In embodiments, the solid support is a glass slide about 75 mm by about 25 mm. In embodiments, the solid support includes a resist (e.g., a photoresist or nanoimprint resist including a crosslinked polymer matrix attached to the solid support).

In embodiments, the solid support includes a polymer, wherein the polymer includes a copolymer of two or more of the following polymerizable monomers, wherein at least one of the polymerizable monomers includes a bioconjugate reactive moiety: polyacrylamide (AAm), poly-N-isopropylacrylamide, poly N-isopropylpolyacrylamide, sulfobetaine acrylate (SBA), carboxybetaine acrylate (CBA), phosphorylcholine acrylate (PCA), sulfobetaine methacrylate (SBMA), carboxybetaine methacrylate (CBMA), phosphorylcholine methacrylate (PCMA), polyethylene glycol acrylate, methacrylate, N-vinyl pyrrolidone, polyethylene glycol (PEG)-thiol/PEG-acrylate, acrylamide/N,N'-bis(acryloyl) cystamine (BACy), PEG/polypropylene oxide (PPO), polyacrylic acid, poly(hydroxyethyl methacrylate) (PHEMA), poly(methyl methacrylate) (PMMA), poly(N-isopropylacrylamide) (PNIPAAm), poly(lactic acid) (PLA), poly(lactic-co-glycolic acid) (PLGA), polycaprolactone (PCL), poly (vinylsulfonic acid) (PVSA), poly(L-aspartic acid), poly(L-glutamic acid), polylysine, agar, agarose, alginate, heparin, alginate sulfate, dextran sulfate, hyaluronan, pectin, carrageenan, gelatin, chitosan, cellulose, collagen, glicydyl methacrylate (GMA), glicydyl methacrylate (GMA) azide, hydroxyethylmethacrylate (HEMA), hydroxyethylacrylate (HEA), hydroxypropylmethacrylate (HPMA), polyethylene glycol methacrylate (PEGMA), polyethylene glycol acrylate (PEGA), and/or isocyanatoethyl methacrylate (IEM). In embodiments, the compositions described herein (e.g., the solid support) do not include poly(N-(5-azidoacetamidylpentyl)acrylamide-co-acrylamide (PAZAM).

In embodiments, the solid support includes two or more wells, wherein each well includes the first plurality of immobilized oligonucleotides and the second plurality of immobilized oligonucleotides. In embodiments, the first plurality of immobilized oligonucleotides and the second plurality of immobilized oligonucleotides are covalently attached to a polymer within the wells (e.g., wherein the polymer is within the well). In embodiments, each well of the solid support is separated by an interstitial region. In embodiments, the interstitial region is substantially free of the polymer.

In embodiments, the solid support includes about 0.2 wells to about 4.0 wells per $\mu m^2$. In embodiments, density of wells on the solid support may be tuned. For example, in embodiments, the multi-well container includes a density of at least about 100 wells per $mm^2$, about 1,000 wells per $mm^2$, about 0.1 million wells per $mm^2$, about 1 million wells per $mm^2$, about 2 million wells per $mm^2$, about 5 million wells per $mm^2$, about 10 million wells per $mm^2$, about 50 million wells per $mm^2$, or more. In embodiments, the multi-well container includes no more than about 50 million wells per $mm^2$, about 10 million wells per $mm^2$, about 5 million wells per $mm^2$, about 2 million wells per $mm^2$, about 1 million wells per $mm^2$, about 0.1 million wells per $mm^2$, about 1,000 wells per $mm^2$, about 100 wells per $mm^2$, or less. In embodiments, the solid support includes about 500, 1,000, 2,500, 5,000, or about 25,000 wells per $mm^2$. In embodiments, the solid support includes about $1 \times 10^6$ to about $1 \times 10^{12}$ wells. In embodiments, the solid support includes about $1 \times 10^7$ to about $1 \times 10^{12}$ wells. In embodiments, the solid support includes about $1 \times 10^8$ to about $1 \times 10^{12}$ wells. In embodiments, the solid support includes about $1 \times 10^6$ to about $1 \times 10^9$ wells. In embodiments, the solid support includes about $1 \times 10^9$ to about $1 \times 10^{10}$ wells. In embodiments, the solid support includes about $1 \times 10^7$ to about $1 \times 10^9$ wells. In embodiments, the solid support includes about $1 \times 10^8$ to about $1 \times 10^8$ wells. In embodiments, the solid support includes about $1 \times 10^6$ to about $1 \times 10^8$ wells. In embodiments, the solid support includes about $1 \times 10^6$, $1 \times 10^7$, $1 \times 10^8$, $1 \times 10^9$, $1 \times 10^{10}$, $1 \times 10^{11}$, $1 \times 10^{12}$, $5 \times 10^{12}$, or more wells. In embodiments, the solid support includes about $1.8 \times 10^9$, $3.7 \times 10^9$, $9.4 \times 10^9$, $1.9 \times 10^{10}$, or about $9.4 \times 10^{10}$ wells. In embodiments, the solid support includes about $1 \times 10^6$ or more wells. In embodiments, the solid support includes about $1 \times 10^7$ or more wells. In embodiments, the solid support includes about $1 \times 10^8$ or more wells. In embodiments, the solid support includes about $1 \times 10^9$ or more wells. In embodiments, the solid support includes about $1 \times 10^{10}$ or more wells. In embodiments, the solid support includes about $1 \times 10^{11}$ or more wells. In embodiments, the solid support includes about $1 \times 10^{12}$ or more wells. In embodiments, the solid support is a glass slide. In embodiments, the solid support is a about 75 mm by about 25 mm. In embodiments, the solid support includes one, two, three, or four channels. In embodiments, each of the wells are separated from each other by about 0.2 $\mu m$ to about 2.0 $\mu m$. In embodiments, the plurality of oligonucleotides is present at a density of about 100 oligonucleotides per $\mu m^2$ to about 1,000,000 oligonucleotides per $\mu m^2$. In embodiments, the plurality of oligonucleotides is present at a density of about 100 oligonucleotides per μm² to about 1,000 oligonucleotides per μm². In embodiments, the plurality of oligonucleotides is present at a density of about 100 oligonucleotides per μm² to about 10,000 oligonucleotides per μm². In embodiments, the plurality of oligonucleotides is present at a density of about 100 oligonucleotides per μm² to about 100,000 oligonucleotides per μm². In embodiments, the plurality of oligonucleotides is present at a density of about 100 oligonucleotides per μm² to about 500,000 oligonucleotides per μm². In embodiments, the plurality of oligonucleotides is present at a density of about 100, 1,000, 10,000, 50,000, 100,000, 250,000, 500,000, 750,000, or 1,000,000 oligonucleotides per μm².

In embodiments, the solid support includes a polymer, resist, and/or hydrogel. In embodiments, the solid support includes a polymer, resist, and hydrogel. In embodiments, the solid support includes a polymer, resist, or hydrogel. In embodiments, the solid support includes a polymer layer. In embodiments, the polymer layer includes polymerized units of alkoxysilyl methacrylate, alkoxysilyl acrylate, alkoxysilyl methylacrylamide, alkoxysilyl methylacrylamide, or a copolymer thereof. In embodiments, the polymer layer includes polymerized units of alkoxysilyl methacrylate. In embodiments, the polymer layer includes polymerized units of alkoxysilyl acrylate. In embodiments, the polymer layer includes polymerized units of alkoxysilyl methylacrylamide. In embodiments, the polymer layer includes polymerized units of alkoxysilyl methylacrylamide. In embodiments, the polymer layer includes glycidyloxypropyl-trimethyloxysilane. In embodiments, the polymer layer includes methacryloxypropyl-trimethoxysilane. In embodiments, the polymer layer includes polymerized units of

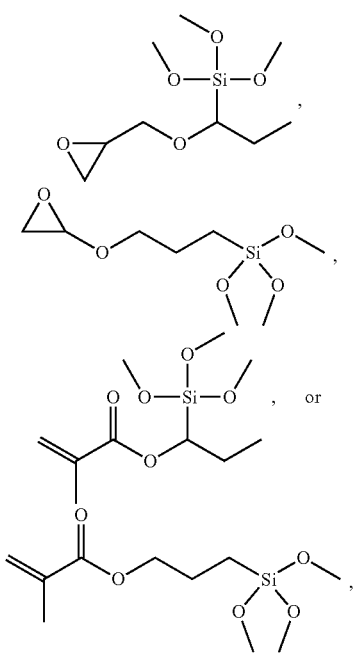

or a copolymer thereof.

In embodiments, the solid support includes a photoresist, alternatively referred to herein as a resist. A "resist" as used herein is used in accordance with its ordinary meaning in the art of lithography and refers to a polymer matrix (e.g., a polymer network). In embodiments, the photoresist is a silsesquioxane resist, an epoxy-based polymer resist, poly (vinylpyrrolidone-vinyl acrylic acid) copolymer resist, an Off-stoichiometry thiol-enes (OSTE) resist, amorphous fluoropolymer resist, a crystalline fluoropolymer resist, polysiloxane resist, or a organically modified ceramic polymer resist. In embodiments, the photoresist is a silsesquioxane resist. In embodiments, the photoresist is an epoxy-based polymer resist. In embodiments, the photoresist is a poly(vinylpyrrolidone-vinyl acrylic acid) copolymer resist. In embodiments, the photoresist is an Off-stoichiometry thiol-enes (OSTE) resist. In embodiments, the photoresist is an amorphous fluoropolymer resist. In embodiments, the photoresist is a crystalline fluoropolymer resist. In embodiments, the photoresist is a polysiloxane resist. In embodiments, the photoresist is an organically modified ceramic polymer resist. In embodiments, the photoresist includes polymerized alkoxysilyl methacrylate polymers and metal oxides (e.g., $SiO_2$, ZrO, MgO, $Al_2O_3$, $TiO_2$ or $Ta_2O_5$). In embodiments, the photoresist includes polymerized alkoxysilyl acrylate polymers and metal oxides (e.g., $SiO_2$, ZrO, MgO, $Al_2O_3$, $TiO_2$ or $Ta_2O_5$). In embodiments, the photoresist includes metal atoms, such as Si, Zr, Mg, Al, Ti, or Ta atoms.

In embodiments, the solid support is a multiwell container or an unpatterned solid support (e.g., an unpatterned surface). In embodiments, the solid support is a multiwell container. In embodiments, the solid support is an unpatterned solid support. In embodiments, the solid support includes a photoresist. A photoresist is a light-sensitive polymer material used to form a patterned coating on a surface. The process begins by coating a substrate (e.g., a glass substrate) with a light-sensitive organic material. A mask with the desired pattern is used to block light so that only unmasked regions of the material will be exposed to light. In the case of a positive photoresist, the photosensitive material is degraded by light and a suitable solvent will dissolve away the regions that were exposed to light, leaving behind a coating where the mask was placed. In the case of a negative photoresist, the photosensitive material is strengthened (either polymerized or cross-linked) by light, and a suitable solvent will dissolve away only the regions that were not exposed to light, leaving behind a coating in areas where the mask was not placed. In embodiments, the solid support includes an epoxy-based photoresist (e.g., SU-8, SU-8 2000, SU-8 3000, SU-8 GLM2060). In embodiments, the solid support includes a negative photoresist. Negative refers to a photoresist whereby the parts exposed to UV become cross-linked (i.e., immobilized), while the remainder of the polymer remains soluble and can be washed away during development. In embodiments, the solid support includes an Off-stoichiometry thiol-enes (OSTE) polymer (e.g., an OSTE resist). In embodiments, the solid support includes an Hydrogen Silsesquioxane (HSQ) polymer (e.g., HSQ resist). In embodiments, the solid support includes a crosslinked polymer matrix on the surface of the wells and the interstitial regions.

In embodiments, the solid support includes a nanoimprint resist (e.g., an etch mask for pattern transfer into various substrates, typically including cross-linked polymers that are resistant to many conventional solvents and other wet etches). In embodiments, the solid support includes a photoresist and polymer layer, wherein the photoresist is between the solid support and the polymer layer. In embodiments, the photoresist is on the interstitial areas and not the surface of the wells. Suitable photoresist compositions are known in the art, such as, for example the compositions and resins described in U.S. Pat. Nos. 6,897,012; 6,991,888; 4,882,245; 7,467,632; 4,970,276, each of which is incorporated herein by reference in their entirety. In embodiments, the solid support includes a photoresist and polymer layer, wherein the photoresist is covalently attached to the solid support and covalently attached to the polymer layer. In embodiments, the resist is an amorphous (non-crystalline) fluoropolymer (e.g., CYTOP® from Bellex), a crystalline fluoropolymer, or a fluoropolymer having both amorphous and crystalline domains. In embodiments, the resist is a suitable polysiloxane, such as polydimethylsiloxane (PDMS). In embodiments, the solid support includes a resist (e.g., a nanoimprint lithography (NIL) resist). Nanoimprint resists can include thermal curable materials (e.g., thermoplastic polymers), and/or UV-curable polymers. In embodiments, the solid support is generated by pressing a transparent mold possessing the pattern of interest (e.g., the pattern of wells) into photo-curable liquid film, followed by solidifying the liquid materials via a UV light irradiation. Typical UV-curable resists have low viscosity, low surface tension, and suitable adhesion to the glass substrate. For example, the solid support surface, but not the surface of the wells, is coated in an organically modified ceramic polymer (ORMOCER®, registered trademark of Fraunhofer-Gesellschaft zur Förderung der angewandten Forschung e. V. in Germany). Organically modified ceramics contain organic side chains attached to an inorganic siloxane backbone. Several ORMOCER® polymers are now provided under names such as "Ormocore", "Ormoclad" and "Ormocomp" by Micro Resist Technology GmbH. In embodiments, the solid support includes a resist as described in Haas et al Volume 351, Issues 1-2, 30 Aug. 1999, Pages 198-203, US 2015/0079351A1, US 2008/0000373, or US 2010/0160478, each of which is incorporated herein by reference. In embodiments, the solid support surface, and the surface of the wells, is coated in an organically modified ceramic polymer (ORMOCER®, registered trademark of Fraunhofer-Gesellschaft zur Förderung der angewandten Forschung e. V. in Germany). In embodiments, the resist (e.g., the organically modified ceramic polymer) is not removed prior to particle deposition. In embodiments, the wells are within the resist polymer and not the solid support.

In embodiments, the wells are separated from each other by interstitial regions including a polymer layer as described herein (e.g., an amphiphilic copolymer). In embodiments, the solid support further includes a photoresist, wherein the photoresist does not contact the bottom of the well. In embodiments, the polymer layer is substantially free of overlapping amplification clusters. In embodiments, the solid support does not include a polymer (e.g., the solid support is a patterned glass slide). In embodiments, the wells do not include a polymer (e.g., an amphiphilic polymer as described herein). In embodiments, the solid support further includes a photoresist, wherein the photoresist is in contact the bottom of the well and the interstitial space. In embodiments, the wells include a polymer (e.g., a polymer and/or resist as described herein).

In embodiments, well includes a plurality of oligonucleotide moieties covalently attached to the well via a polymeric bioconjugate linker. In embodiments, the polymeric bioconjugate linker is formed through a reaction between a particle polymer (e.g., a polymer covalently attached to the surface of the particle) including a first bioconjugate reactive moiety and an oligonucleotide including a second bioconjugate reactive moiety. In embodiments, the polymeric bioconjugate linker is formed through a reaction between a surface polymer (e.g., a polymer covalently attached to the surface of the well) including a first bioconjugate reactive moiety (e.g., an azide) and an oligonucleotide including a second bioconjugate reactive moiety (e.g., DBCO). In embodiments, the polymeric bioconjugate linker is a polymer including a subunit of formula Ia, Ib, II, or III as described in U.S. Pat. No. 11,236,387, which is incorporated herein by reference in its entirety. In embodiments, each oligonucleotide moiety includes a DBCO bioconjugate reactive moiety that reacts with an azide bioconjugate reactive moiety on the solid support and forms a bioconjugate linker that covalently links the oligonucleotide moiety to the solid support, for example according to the following scheme:

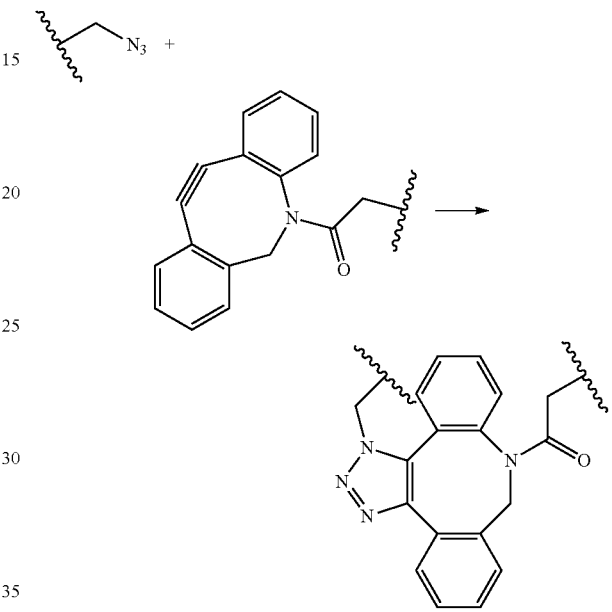

Scheme 1. An example mechanism of the bioconjugate covalent linker formed by reacting a DBCO containing oligonucleotide with a solid support containing an azide moiety (or vice versa). The symbol "⁓" refers to the attachment point to the oligonucleotide moiety and the solid support polymer, respectively.

In an aspect is provided a plurality of oligonucleotides, wherein each oligonucleotide is capable of hybridizing (e.g., via specific hybridization) to SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123. In embodiments, each oligonucleotide is capable of hybridizing to SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123. In embodiments, each oligonucleotide is capable of hybridizing to SEQ ID NO:5. In embodiments, each oligonucleotide is capable of hybridizing to SEQ ID NO:9. In embodiments, each oligonucleotide is capable of hybridizing to SEQ ID NO:85. In embodiments, each oligonucleotide is capable of hybridizing to SEQ ID NO:92. In embodiments, each oligonucleotide is capable of hybridizing to SEQ ID NO:90. In embodiments, each oligonucleotide is capable of hybridizing to SEQ ID NO:88. In embodiments, each oligonucleotide is capable of hybridizing to SEQ ID NO:117. In embodiments, each oligonucleotide is capable of hybridizing to SEQ ID NO:119. In embodiments, each oligonucleotide is capable of hybridizing to SEQ ID NO:121. In embodiments, each oligonucleotide is capable of hybridizing to SEQ ID NO:123. In embodiments, capable of hybridizing includes 95%, 96%, 97%, 98%, 99%, or 100% complementarity (i.e., wherein the oligonucleotide includes 95% or greater complementary nucleotides which form Watson-Crick hydrogen bonds with the hybridizing oligonucleotide). In embodiments, each oligonucleotide includes the sequence of SEQ ID NO:2, SEQ ID NO:28, SEQ ID NO:109, SEQ ID NO:111, SEQ ID NO:113, SEQ ID NO:115, SEQ ID NO:141, SEQ ID NO:143, SEQ ID NO: 145, SEQ ID NO:147, or a sequence greater than 90% homologous thereto. In embodiments, each oligonucleotide includes SEQ ID NO:2. In embodiments, each oligonucleotide includes SEQ ID NO:28. In embodiments, each oligonucleotide includes SEQ ID NO:109. In embodiments, each oligonucleotide includes SEQ ID NO:111. In embodiments, each oligonucleotide includes SEQ ID NO:113. In embodiments, each oligonucleotide includes SEQ ID NO:115. In embodiments, each oligonucleotide includes SEQ ID NO:141. In embodiments, each oligonucleotide includes SEQ ID NO:143. In embodiments, each oligonucleotide includes SEQ ID NO: 145. In embodiments, each oligonucleotide includes SEQ ID NO:147. Exemplary hybridization conditions may include hybridization in a buffer of 40% formamide, 1 M NaCl, 1% SDS at 37° C., and a wash in 1×SSC at 45° C. In embodiments, capable of hybridizing includes hybridization at 5×SSC and 40° C. In embodiments, hybridization occurs when the two oligonucleotides are 100% complementary. In embodiments, hybridization occurs when the two oligonucleotides are greater than 99% complementary. In embodiments, hybridization occurs when the two oligonucleotides are greater than 98% complementary. In embodiments, hybridization occurs when the two oligonucleotides are 99% complementary. In embodiments, hybridization occurs when the two oligonucleotides are 98% complementary. In embodiments, capable of hybridizing includes hybridization in a buffer including 20-200 mM KCl or NaCl, 0.5-12 mM $Mg^{2+}$, about 1-3M betaine, and about 0-10% DMSO.

In an aspect is provided a plurality of oligonucleotides, wherein each oligonucleotide is capable of hybridizing (e.g., via specific hybridization) to SEQ ID NO:7, SEQ ID NO:30, SEQ ID NO:87, SEQ ID NO:89, SEQ ID NO:91, SEQ ID NO:86, SEQ ID NO:118, SEQ ID NO:120, SEQ ID NO:122, or SEQ ID NO:124. In embodiments, each oligonucleotide is capable of specifically hybridizing to SEQ ID NO:7, SEQ ID NO:30, SEQ ID NO:87, SEQ ID NO:89, SEQ ID NO:91, SEQ ID NO:86, SEQ ID NO:118, SEQ ID NO:120, SEQ ID NO:122, or SEQ ID NO:124. In embodiments, each oligonucleotide is capable of hybridizing to SEQ ID NO:7. In embodiments, each oligonucleotide is capable of hybridizing to SEQ ID NO:30. In embodiments, each oligonucleotide is capable of hybridizing to SEQ ID NO:87. In embodiments, each oligonucleotide is capable of hybridizing to SEQ ID NO:89. In embodiments, each oligonucleotide is capable of hybridizing to SEQ ID NO:91. In embodiments, each oligonucleotide is capable of hybridizing to SEQ ID NO:86. In embodiments, each oligonucleotide is capable of hybridizing to SEQ ID NO:118. In embodiments, each oligonucleotide is capable of hybridizing to SEQ ID NO:120. In embodiments, each oligonucleotide is capable of hybridizing to SEQ ID NO:122. In embodiments, each oligonucleotide is capable of hybridizing to SEQ ID NO:124. In embodiments, each oligonucleotide includes the sequence of SEQ ID NO:6, SEQ ID NO:11, SEQ ID NO:110, SEQ ID NO:112, SEQ ID NO:114, SEQ ID NO:116, SEQ ID NO:142, SEQ ID NO:144, SEQ ID NO:146, or SEQ ID NO:148. In embodiments, each oligonucleotide is SEQ ID NO:6. In embodiments, each oligonucleotide is SEQ ID NO:11. In embodiments, each oligonucleotide is SEQ ID NO:110. In embodiments, each oligonucleotide is SEQ ID NO:112. In embodiments, each oligonucleotide is SEQ ID NO:114. In embodiments, each oligonucleotide is SEQ ID NO:116. In embodiments, each oligonucleotide is SEQ ID NO:142. In embodiments, each oligonucleotide is SEQ ID NO:144. In embodiments, each oligonucleotide is SEQ ID NO:146. In embodiments, each oligonucleotide is SEQ ID NO:148. In embodiments, capable of hybridizing includes 95%, 96%, 97%, 98%, 99%, or 100% complementarity (i.e., wherein the nucleic acid molecule capable of hybridizing includes 95% or greater nucleotides which form Watson-Crick hydrogen bonds with the oligonucleotide). Exemplary hybridization conditions may include hybridization in a buffer of 40% formamide, 1 M NaCl, 1% SDS at 37° C., and a wash in 1×SSC at 45° C. In embodiments, capable of hybridizing includes hybridization at 5×SSC and 40° C. In embodiments, hybridization occurs when the two oligonucleotides are 100% complementary. In embodiments, hybridization occurs when the two oligonucleotides are greater than 99% complementary. In embodiments, hybridization occurs when the two oligonucleotides are greater than 98% complementary. In embodiments, hybridization occurs when the two oligonucleotides are 99% complementary. In embodiments, hybridization occurs when the two oligonucleotides are 98% complementary. In embodiments, capable of hybridizing includes hybridization in a buffer including 20-200 mM KCl or NaCl, 0.5-12 mM $Mg^{2+}$, about 1-3M betaine, and about 0-10% DMSO.

In embodiments, capable of hybridizing includes hybridization at 5×SSC and 40° C. For example, hybridization can be performed at a temperature ranging from 15° C. to 95° C. In some embodiments, the hybridization is performed at a temperature of about 20° C., about 25° C., about 30° C., about 35° C., about 40° C., about 45° C., about 50° C., about 55° C., about 60° C., about 65° C., about 70° C., about 75° C., about 80° C., about 85° C., about 90° C., or about 95° C. In other embodiments, the stringency of the hybridization can be further altered by the addition or removal of components of the buffered solution. In embodiments, hybridization may occur in a hybridization solution which can include any combination of 50% formamide, 5×SSC (0.75 M NaCl, 0.075 M sodium citrate), 50 mM sodium phosphate (pH 6.8), 0.1% sodium pyrophosphate, 5×Denhardt's solution, 0.1% SDS, and/or 10% dextran sulfate. Exemplary hybridization conditions may include hybridization in a buffer of 40% formamide, 1 M NaCl, 1% SDS at 37° C., and a wash in 1×SSC at 45° C. In embodiments, capable of hybridizing includes hybridization at 5×SSC and 40° C. In embodiments, hybridization occurs when the two oligonucleotides are 100% complementary. In embodiments, hybridization occurs when the two oligonucleotides are greater than 99% complementary. In embodiments, hybridization occurs when the two oligonucleotides are greater than 98% complementary. In embodiments, hybridization occurs when the two oligonucleotides are 99% complementary. In embodiments, hybridization occurs when the two oligonucleotides are 98% complementary. In embodiments, capable of hybridizing includes hybridization in a buffer including 20-200 mM KCl or NaCl, 0.5-12 mM Mg2+, about 1-3M betaine, and about 0-10% DMSO.

In embodiments, the oligonucleotide is a linear oligonucleotide including a 5' end and a 3' end. In embodiments, the oligonucleotide includes a primer binding sequence. In embodiments, the oligonucleotide is a circular oligonucleotide.

In an aspect is provided a plurality of nucleic acid molecules, wherein each nucleic acid molecule includes a first end, a target sequence, and a second end, wherein the first end includes a sequence selected from SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123, wherein the target sequence of the plurality of nucleic acid molecules are different from each other. In embodiments, the second end includes a sequence selected from SEQ ID NO:4, SEQ ID NO:102, SEQ ID NO:104, SEQ ID NO:106, SEQ ID NO:108, SEQ ID NO:134, SEQ ID NO:136, SEQ ID NO:138, or SEQ ID NO:140. In embodiments, the target sequence includes genomic DNA. In embodiments, the target sequence includes cancer-associated gene, or fragment thereof. In embodiments, the cancer-associated gene is a AKT1, AKT2, AKT3, ALK, AR, ARAF, ARID1A, ATM, ATR, ATRX, AXL, BAP1, BRAF, BRCA1, BRCA2, BTK, CBL, CCND1, CCND2, CCND3, CCNE1, CDK12, CDK2, CDK4, CDK6, CDKN1B, CDKN2A, CDKN2B, CHEK1, CHEK2, CREBBP, CSF1R, CTNNB1, DDR2, EGFR, ERBB2, ERBB3, ERBB4, ERCC2, ERG, ESR1, ETV1, ETV4, ETV5, EZH2, FANCA, FANCD2, FANCI, FBXW7, FGF19, FGF3, FGFR1, FGFR2, FGFR3, FGFR4, FGR, FLT3, FOXL2, GATA2, GNA11, GNAQ, GNAS, H3F3A, HIST1H3B, HNF1A, HRAS, IDH1, IDH2, IGF1R, JAK1, JAK2, JAK3, KDR, KIT, KNSTRN, KRAS, MAGOH, MAP2K1, MAP2K2, MAP2K4, MAPK1, MAX, MDM2, MDM4, MED12, MET, MLH1, MRE11A, MSH2, MSH6, MTOR, MYB, MYBL1, MYC, MYCL, MYCN, MYD88, NBN, NF1, NF2, NFE2L2, NOTCH1, NOTCH2, NOTCH3, NOTCH4, NRAS, NRG1, NTRK1, NTRK2, NTRK3, NUTM1, PALB2, PDGFRA, PDGFRB, PIK3CA, PIK3CB, PIK3R1, PMS2, POLE, PPARG, PPP2R1A, PRKACA, PRKACB, PTCH1, PTEN, PTPN11, RAC1, RAD50, RAD51, RAD51B, RAD51C, RAD51D, RAF1, RB1, RELA, RET, RHEB, RHOA, RICTOR, RNF43, ROS1, RSPO2, RSPO3, SETD2, SF3B1, SLX4, SMAD4, SMARCA4, SMARCB1, SMO, SPOP, SRC, STAT3, STK11, TERT, TOP1, TP53, TSC1, TSC2, U2AF1, or XPO1 gene. In embodiments, the cancer-associated gene is a ABL1, AKT1, ALK, APC, ATM, BRAF, CDH1, CDKN2A, CSF1R, CTNNB1, EGFR, ERBB2, ERBB4, EZH2, FBXW7, FGFR1, FGFR2, FGFR3, FLT3, GNA11, GNAQ, GNAS, HNF1A, HRAS, IDH1, IDH2, JAK2, JAK3, KDR, KIT, KRAS, MET, MLH1, MPL, NOTCH1, NPM1, NRAS, PDGFRA, PIK3CA, PTEN, PTPN11, RB1, RET, SMAD4, SMARCB1, SMO, SRC, STK11, TP53, or VHL gene.

Figure 2:
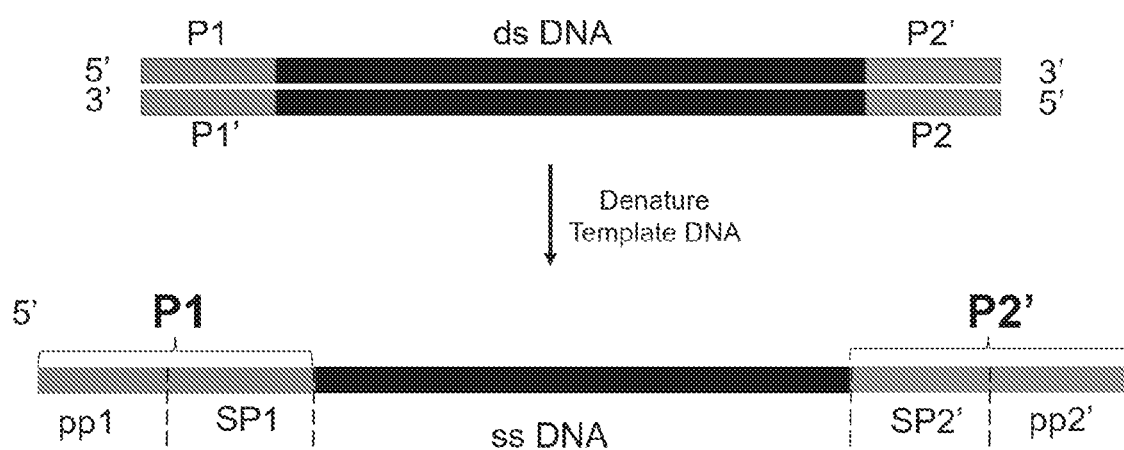
FIG. 2 illustrates a double-stranded template nucleic acid prepared according to standard library prep methods (e.g., fragmenting, polishing, A-tailing, etc.). Adapters P1 and P2', or alternatively P1' and P2 are ligated to each of the ends of the template. For clarity, the ssDNA is depicted showing an embodiment of the P1 and P2' adapters, wherein each adapter includes a platform priming sequence, referred to as pp1 or pp2', and a sequencing primer sequence, referred to as SP1 or SP2', for P1 and P2', respectively.
Figure 3A:
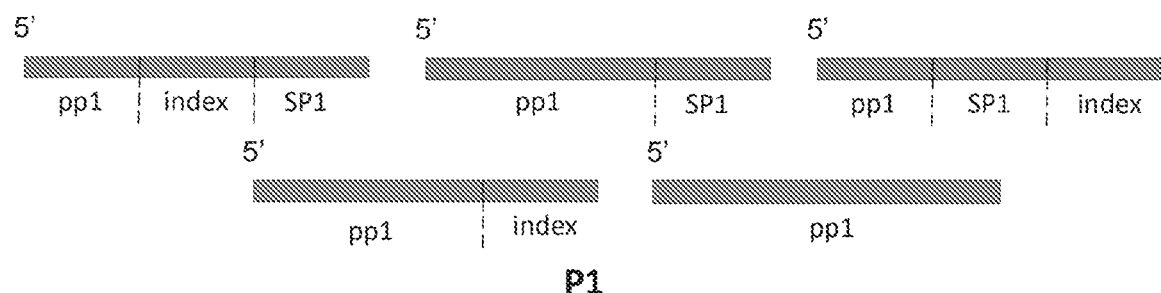
FIGS. 3A-3B is a schematic of the adapter sequences used in some embodiments described herein.
Figure 3B:
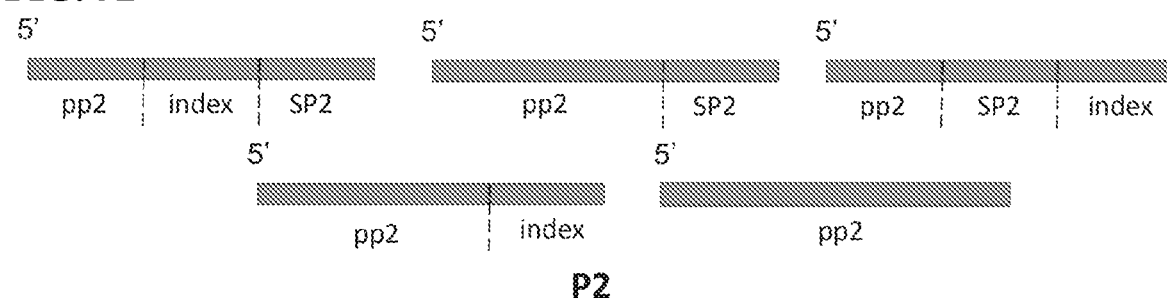
Figure 4:
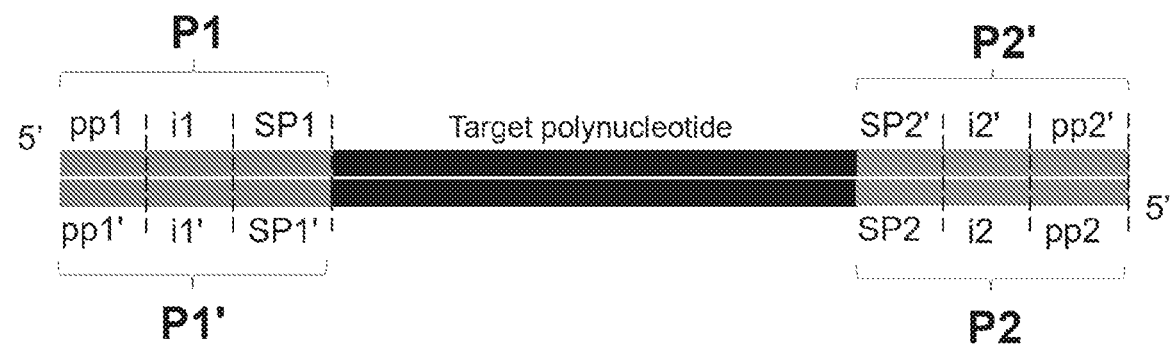
FIG. 4. Adapters used during library preparation may add several functional synthetic sequences to each end of the inserts, thereby forming a target polynucleotide. On the 5' ends of the target polynucleotide (also referred to herein as an insert) the P1 and P2 adapters are attached as anchors for the formation of clusters on the flow cell. The P1 adapter includes a first platform primer sequence, an optional index (i1), and a primer binding site for a first sequencing primer (SP1). The P2 adapter includes a second platform primer sequence, an optional index (i2), and a primer binding site for a second sequencing primer (SP2). The complements P1' and P2' are shown on the 3' end of the target polynucleotide. When constructing libraries for multiplexed reads, index 1 and index 2 sequences may be placed in between pp1 and SP1, and pp2 and SP2 respectively. The inserts and indices may be sequenced using the primers described in Table 2 as a non-limiting example.
Figure 5:
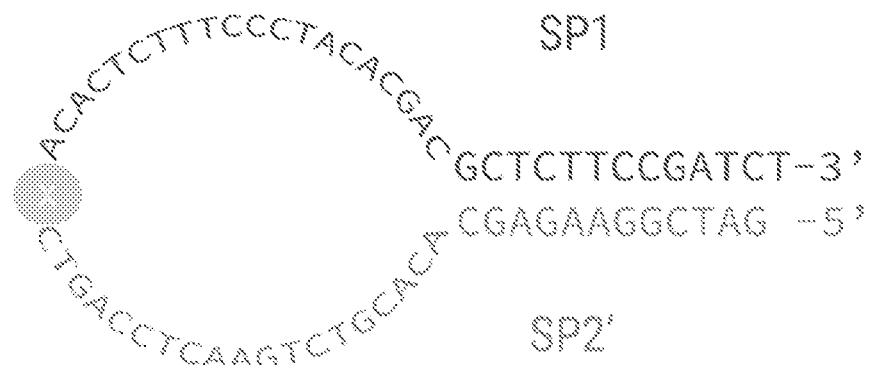
FIG. 5. Illustrated in FIG. 5 is a universal stem-loop adapter used during library preparation to introduce the sequences necessary for cluster generation and sequencing. The stem-loop adapter includes short complementary sequences at the 5' and 3' ends (i.e., a stem), a non-complementary segment in the center with one or more cleavable sites in the middle, indicated by an 'X', and a T-overhang at the 3' end. In embodiments, the 3' half of the loop and the 3' end of the stem contain the SP1 sequence (i.e., 5'-ACACTCTTTCCCTACACG ACGCTCTTCC-GATCT (SEQ ID NO:152), and the 5' half of the loop and the 5' end of the stem (i.e., a portion) are complementary to the SP2 sequencing primer (SP2') (i.e., 5'-GATCG-GAAGAGCACACGTCTGAACTCCAGTC (SEQ ID NO:178), optionally without an adenine (dATP) at the 5' end as depicted in FIG. 5. Example sequences of SP1 and SP2 sequencing primers are provided in Table 2.
Figure 6A:
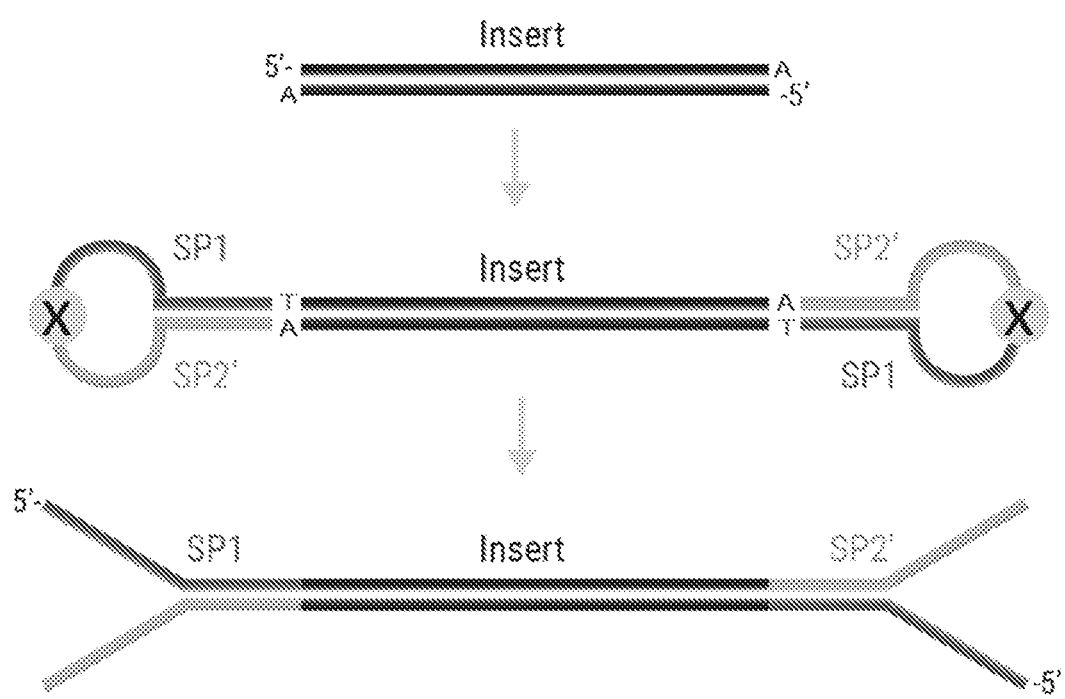
FIGS. 6A-6B. Generalized library prep protocol. Adding the necessary sequences for amplification and sequencing to a library is performed using standard methods known in the art, as described briefly herein.
Figure 6B:
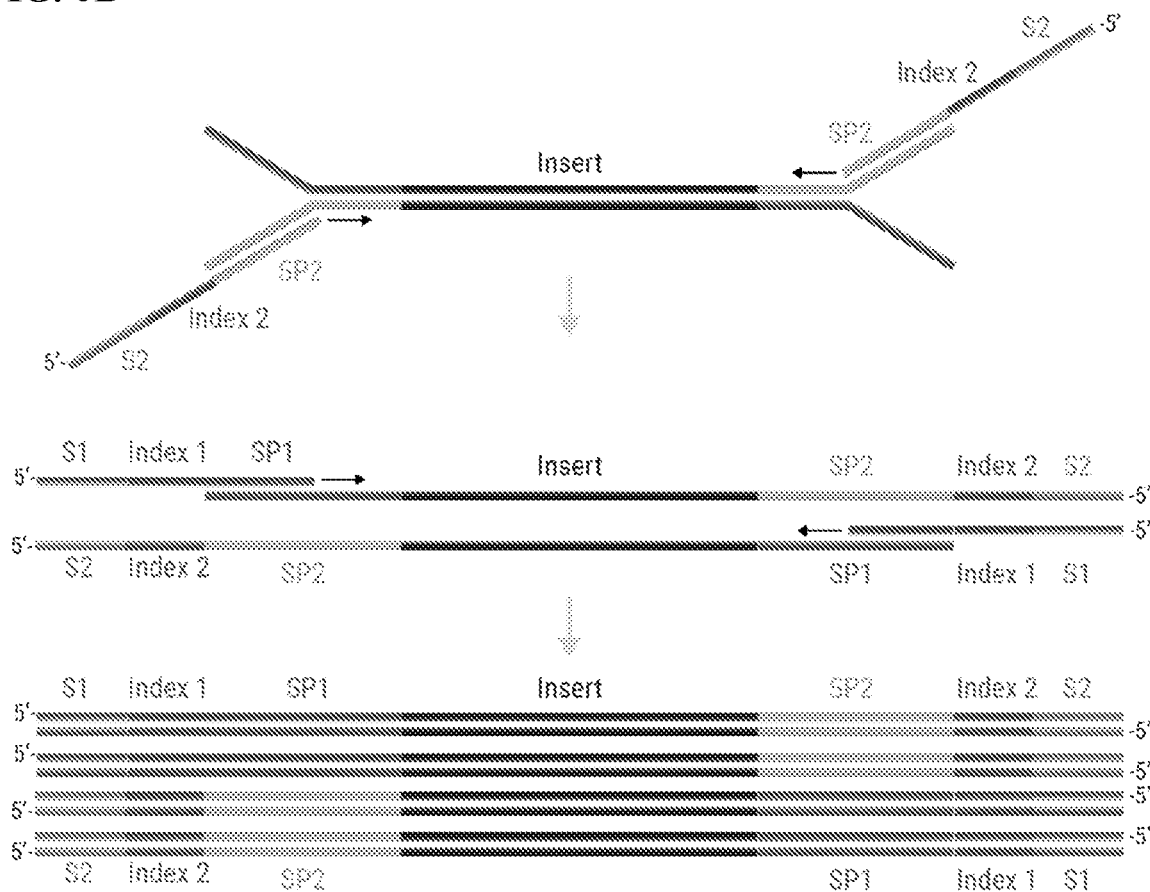
Figure 7A:
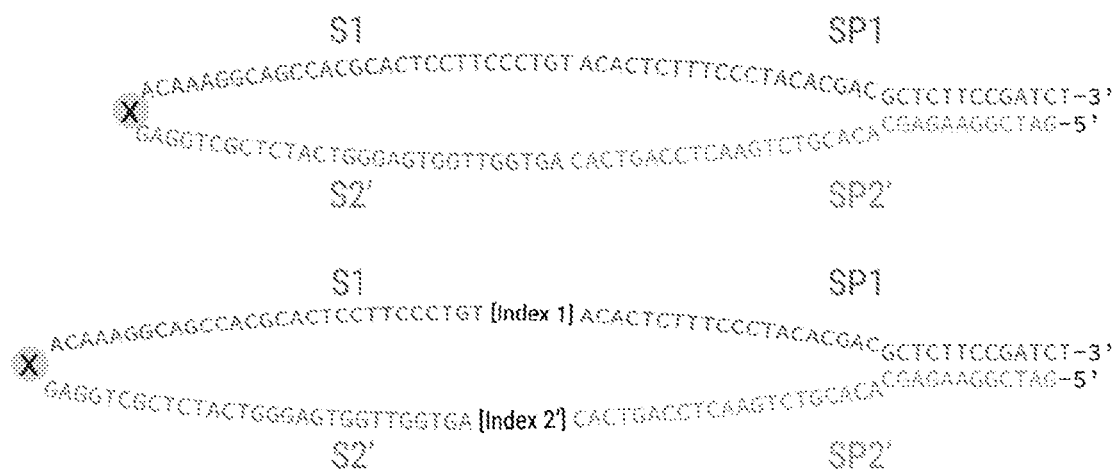
FIG. 7A. Illustrated in FIG. 7A is a stem-loop adapter used during library preparation to introduce the sequences necessary for cluster generation and sequencing on a sequencing device (e.g., the G4™ sequencing platform). The stem-loop adapter includes short complementary sequences at the 5' and 3' ends (i.e., a stem), a non-complementary segment in the center with one or more cleavable sites in the middle, such as a uracil nucleotide, indicated by an 'X', and a T-overhang at the 3' end. In embodiments, the stem-loop includes from 5'-3', a sequencing primer binding sequence (SP2'), an optional index (index 2'), a platform primer binding sequence (S2'), a cleavable site (X), a platform primer sequence (S1), an optional index (index 1), and a sequencing primer sequence (SP1). The sequences illustrated in FIG. 7A include SP2': 5'-GATCG- GAAGAGCACACGTCTGAACTCCAGTC (SEQ ID NO:178), S2': 5'-AGTGGTTGGTGAGGGTCATCTCGCTGGAG (SEQ ID NO:179), S1: 5'-ACAAAGGCAGCCACGCACTCCTTCCCTGT (SEQ ID NO:176), and SP1: ACACTCTTTCCCTACACGACGCTCTTCCGATCT (SEQ ID NO:152).
Figure 7B:
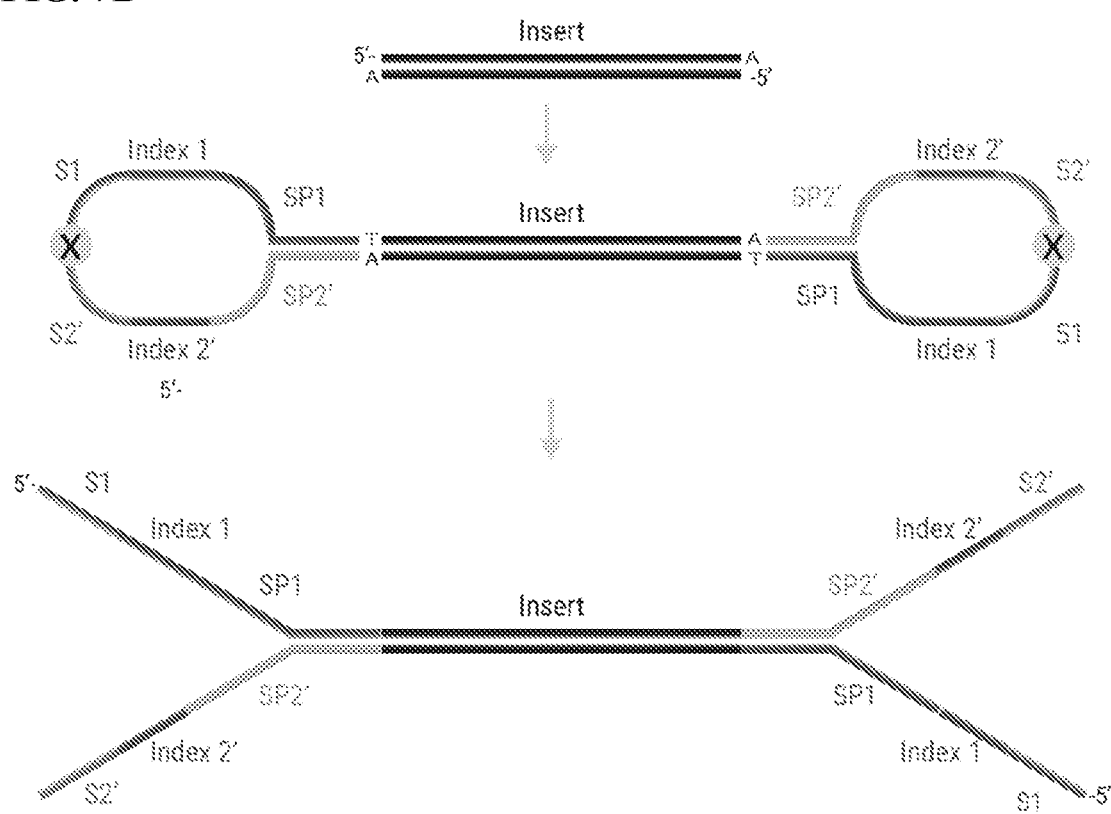
FIG. 7B. PCR-free library preparation has certain advantages, including reducing PCR bias and a simplified workflow. For PCR-free sequencing, the stem-loop adapters that include platform primer sequences (or complements thereof) are included in the stem-loop adapter. In addition to the cleavable site and SP1 and SP2' sequences, the PCR-free stem-loop adapter also contains the S1 sequence and the complementary sequence to S2, S2', (as illustrated in FIG. 7A, upper). For indexed applications, dual indices are embedded within the adapter design (FIG. 7A, lower).

In reference to a "first end" and/or a "second end" of a nucleic acid molecule, it is understood that the "end" is in reference to the sequence of nucleotides at or near the terminus of the molecule. The first end and/or the second end may include nucleotides at the immediate 3' and/or 5', and thus the first end if on the 5' portion of the nucleic acid molecule may include a terminal nucleotide, which includes a 5' phosphate group attached to the fifth carbon in the sugar-ring of the deoxyribose sugar ring. Alternatively, if the first end (or second end) is on the 3' portion of the nucleic acid molecule, the first end may include a terminal hydroxyl (—OH) chemical group attached to the third carbon in the sugar ring. As illustrated in FIG. 2, the first end may include all or a portion the pp1 sequence and/or all or a portion of the SP1 sequence. In embodiments, the first end includes a portion of the full pp1 sequence, or a complement thereof. Similarly, in embodiments, the second end includes a portion of the pp2 sequence, or a complement thereof. In embodiments, the first end is the 5' end and the second end is the 3' end. In embodiments, the first end includes a 5' phosphate moiety. In embodiments, the second end includes a 3'-OH (i.e., a 3'-hydroxyl) moiety. In embodiments, the first end and/or the second end includes the sequence as provided herein, in addition to one or more spacer nucleotides.

In an aspect is provided a plurality of template nucleic acids, wherein each template nucleic acid includes a first end, and a second end capable of hybridizing (e.g., via specific hybridization) to any one of the sequences of SEQ ID NO:1 to SEQ ID NO:148, wherein a portion of the plurality of template nucleic acids are different (e.g., different sequences) from each other. In embodiments, the template nucleic acid includes, from 5' to 3', a first adapter, a target sequence, and a second adapter. In embodiments more than 50%, or more than 60%, or more than 70%, or more than 80%, or more than 90%, of the plurality of template nucleic acids include different target sequences, wherein substantially all of the template nucleic acids share a common adapter sequence at each end. In embodiments, the first adapter includes a sequence described herein (e.g., a sequence provided in Table 1). In embodiments, the second adapter includes a sequence described herein (e.g., a sequence provided in Table 1), provided the second adapter and first adapter include different sequences.

In embodiments, the second end is capable of hybridizing to any one of the sequences of SEQ ID NO:1, SEQ ID NO:2, SEQ ID NO:3, SEQ ID NO:4, SEQ ID NO:5, SEQ ID NO:6, SEQ ID NO:7, or SEQ ID NO:8. In embodiments, the second end is capable of hybridizing to SEQ ID NO:1. In embodiments, the second end is capable of hybridizing to SEQ ID NO:2. In embodiments, the second end is capable of hybridizing to SEQ ID NO:3. In embodiments, the second end is capable of hybridizing to SEQ ID NO:4. In embodiments, the second end is capable of hybridizing to SEQ ID NO:5. In embodiments, the second end is capable of hybridizing to SEQ ID NO:6. In embodiments, the second end is capable of hybridizing to SEQ ID NO:7. In embodiments, the second end is capable of hybridizing to SEQ ID NO:8. In embodiments, the second end is capable of hybridizing to SEQ ID NO:2 and the first end is capable of hybridizing to SEQ ID NO:6.

In embodiments, the second end is capable of hybridizing to SEQ ID NO:85. In embodiments, the second end is capable of hybridizing to SEQ ID NO:86. In embodiments, the second end is capable of hybridizing to SEQ ID NO:87. In embodiments, the second end is capable of hybridizing to SEQ ID NO:88. In embodiments, the second end is capable of hybridizing to SEQ ID NO:89. In embodiments, the second end is capable of hybridizing to SEQ ID NO:90. In embodiments, the second end is capable of hybridizing to SEQ ID NO:91. In embodiments, the second end is capable of hybridizing to SEQ ID NO:92. In embodiments, the second end is capable of hybridizing to SEQ ID NO:93. In embodiments, the second end is capable of hybridizing to SEQ ID NO:94. In embodiments, the second end is capable of hybridizing to SEQ ID NO:95. In embodiments, the second end is capable of hybridizing to SEQ ID NO:96. In embodiments, the second end is capable of hybridizing to SEQ ID NO:97. In embodiments, the second end is capable of hybridizing to SEQ ID NO:98. In embodiments, the second end is capable of hybridizing to SEQ ID NO:99. In embodiments, the second end is capable of hybridizing to SEQ ID NO:100. In embodiments, the second end is capable of hybridizing to SEQ ID NO:101. In embodiments, the second end is capable of hybridizing to SEQ ID NO:102. In embodiments, the second end is capable of hybridizing to SEQ ID NO:103. In embodiments, the second end is capable of hybridizing to SEQ ID NO:104. In embodiments, the second end is capable of hybridizing to SEQ ID NO:105. In embodiments, the second end is capable of hybridizing to SEQ ID NO:106. In embodiments, the second end is capable of hybridizing to SEQ ID NO:107. In embodiments, the second end is capable of hybridizing to SEQ ID NO:108. In embodiments, the second end is capable of hybridizing to SEQ ID NO:109. SEQ ID NO:110. In embodiments, the second end is capable of hybridizing to SEQ ID NO:111. In embodiments, the second end is capable of hybridizing to SEQ ID NO:112. In embodiments, the second end is capable of hybridizing to SEQ ID NO:113. In embodiments, the second end is capable of hybridizing to SEQ ID NO:114. In embodiments, the second end is capable of hybridizing to SEQ ID NO:115. In embodiments, the second end is capable of hybridizing to SEQ ID NO:116. In embodiments, the second end is capable of hybridizing to SEQ ID NO:117. In embodiments, the second end is capable of hybridizing to SEQ ID NO:118. In embodiments, the second end is capable of hybridizing to SEQ ID NO:119. In embodiments, the second end is capable of hybridizing to SEQ ID NO:120. In embodiments, the second end is capable of hybridizing to SEQ ID NO:121. In embodiments, the second end is capable of hybridizing to SEQ ID NO:122. In embodiments, the second end is capable of hybridizing to SEQ ID NO:123. In embodiments, the second end is capable of hybridizing to SEQ ID NO:124. In embodiments, the second end is capable of hybridizing to SEQ ID NO:125. In embodiments, the second end is capable of hybridizing to SEQ ID NO:126. In embodiments, the second end is capable of hybridizing to SEQ ID NO:127. In embodiments, the second end is capable of hybridizing to SEQ ID NO:128. In embodiments, the second end is capable of hybridizing to SEQ ID NO:129. In embodiments, the second end is capable of hybridizing to SEQ ID NO:130. In embodiments, the second end is capable of hybridizing to SEQ ID NO:131. In embodiments, the second end is capable of hybridizing to SEQ ID NO:132. In embodiments, the second end is capable of hybridizing to SEQ ID NO:133. In embodiments, the second end is capable of hybridizing to SEQ ID NO:134. In embodiments, the second end is capable of hybridizing to SEQ ID NO:135. In embodiments, the second end is capable of hybridizing to SEQ ID NO:136. In embodiments, the second end is capable of hybridizing to SEQ ID NO:137. In embodiments, the second end is capable of hybridizing to SEQ ID NO:138. In embodiments, the second end is capable of hybridizing to SEQ ID NO:139. In embodiments, the second end is capable of hybridizing to SEQ ID NO:140. In embodiments, the second end is capable of hybridizing to SEQ ID NO:141. In embodiments, the second end is capable of hybridizing to SEQ ID NO:142. In embodiments, the second end is capable of hybridizing to SEQ ID NO:143. In embodiments, the second end is capable of hybridizing to SEQ ID NO:144. In embodiments, the second end is capable of hybridizing to SEQ ID NO:145. In embodiments, the second end is capable of hybridizing to SEQ ID NO:146. In embodiments, the second end is capable of hybridizing to SEQ ID NO:147. In embodiments, the second end is capable of hybridizing to SEQ ID NO:148.

In embodiments, the second end is capable of hybridizing to any one of the sequences of SEQ ID NO:7, SEQ ID NO:11, SEQ ID NO:30, SEQ ID NO:87, SEQ ID NO:89, SEQ ID NO:91, SEQ ID NO:86, SEQ ID NO:118, SEQ ID NO:120, SEQ ID NO:122, or SEQ ID NO:124. In embodiments, the second end is capable of hybridizing to SEQ ID NO:7. In embodiments, the second end is capable of hybridizing to SEQ ID NO:11. In embodiments, the second end is capable of hybridizing to SEQ ID NO:30. In embodiments, the second end is capable of hybridizing to SEQ ID NO:87. In embodiments, the second end is capable of hybridizing to SEQ ID NO:89. In embodiments, the second end is capable of hybridizing to SEQ ID NO:91. In embodiments, the second end is capable of hybridizing to SEQ ID NO:86. In embodiments, the second end is capable of hybridizing to SEQ ID NO:118. In embodiments, the second end is capable of hybridizing to SEQ ID NO:120. In embodiments, the second end is capable of hybridizing to SEQ ID NO:122. In embodiments, the second end is capable of hybridizing to SEQ ID NO:124.

In embodiments, the second end includes SEQ ID NO:1, SEQ ID NO:2, SEQ ID NO:3, SEQ ID NO:4, SEQ ID NO:5, SEQ ID NO:6, SEQ ID NO:7, or SEQ ID NO:8. In embodiments, the second end includes SEQ ID NO:1. In embodiments, the second end includes SEQ ID NO:2. In embodiments, the second end includes SEQ ID NO:3. In embodiments, the second end includes SEQ ID NO:4. In embodiments, the second end includes SEQ ID NO:5. In embodiments, the second end includes SEQ ID NO:6. In embodiments, the second end includes SEQ ID NO:7. In embodiments, the second end includes SEQ ID NO:8.

In embodiments, the second end includes SEQ ID NO:85. In embodiments, the second end includes SEQ ID NO:86. In embodiments, the second end includes SEQ ID NO:87. In embodiments, the second end includes SEQ ID NO:88. In embodiments, the second end includes SEQ ID NO:89. In embodiments, the second end includes SEQ ID NO:90. In embodiments, the second end includes SEQ ID NO:91. In embodiments, the second end includes SEQ ID NO:92. In embodiments, the second end includes SEQ ID NO:93. In embodiments, the second end includes SEQ ID NO:94. In embodiments, the second end includes SEQ ID NO:95. In embodiments, the second end includes SEQ ID NO:96. In embodiments, the second end includes SEQ ID NO:97. In embodiments, the second end includes SEQ ID NO:98. In embodiments, the second end includes SEQ ID NO:99. In embodiments, the second end includes SEQ ID NO:100. In embodiments, the second end includes SEQ ID NO:101. In embodiments, the second end includes SEQ ID NO:102. In embodiments, the second end includes SEQ ID NO:103. In embodiments, the second end includes SEQ ID NO:104. In embodiments, the second end includes SEQ ID NO:105. In embodiments, the second end includes SEQ ID NO:106. In embodiments, the second end includes SEQ ID NO:107. In embodiments, the second end includes SEQ ID NO:108. In embodiments, the second end includes SEQ ID NO:109. In embodiments, the second end includes SEQ ID NO:110. In embodiments, the second end includes SEQ ID NO:111. In embodiments, the second end includes SEQ ID NO:112. In embodiments, the second end includes SEQ ID NO:113. In embodiments, the second end includes SEQ ID NO:114. In embodiments, the second end includes SEQ ID NO:115. In embodiments, the second end includes SEQ ID NO:116. In embodiments, the second end includes SEQ ID NO:117. In embodiments, the second end includes SEQ ID NO:118. In embodiments, the second end includes SEQ ID NO:119. In embodiments, the second end includes SEQ ID NO:120. In embodiments, the second end includes SEQ ID NO:121. In embodiments, the second end includes SEQ ID NO:122. In embodiments, the second end includes SEQ ID NO:123. In embodiments, the second end includes SEQ ID NO:124. In embodiments, the second end includes SEQ ID NO:125. In embodiments, the second end includes SEQ ID NO:126. In embodiments, the second end includes SEQ ID NO:127. In embodiments, the second end includes SEQ ID NO:128. In embodiments, the second end includes SEQ ID NO:129. In embodiments, the second end includes SEQ ID NO:130. In embodiments, the second end includes SEQ ID NO:131. In embodiments, the second end includes SEQ ID NO:132. In embodiments, the second end includes SEQ ID NO:133. In embodiments, the second end includes SEQ ID NO:134. In embodiments, the second end includes SEQ ID NO:135. In embodiments, the second end includes SEQ ID NO:136. In embodiments, the second end includes SEQ ID NO:137. In embodiments, the second end includes SEQ ID NO:138. In embodiments, the second end includes SEQ ID NO:139. In embodiments, the second end includes SEQ ID NO:140. In embodiments, the second end includes SEQ ID NO:141. In embodiments, the second end includes SEQ ID NO:142. In embodiments, the second end includes SEQ ID NO:143. In embodiments, the second end includes SEQ ID NO:144. In embodiments, the second end includes SEQ ID NO:145. In embodiments, the second end includes SEQ ID NO:146. In embodiments, the second end includes SEQ ID NO:147. In embodiments, the second end includes SEQ ID NO:148.

In embodiments, the second end includes SEQ ID NO:6, SEQ ID NO:11, SEQ ID NO:110, SEQ ID NO:112, SEQ ID NO:114, SEQ ID NO:116, SEQ ID NO:142, SEQ ID NO:144, SEQ ID NO:146, or SEQ ID NO:148. In embodiments, the second end includes SEQ ID NO:6. In embodiments, the second end includes SEQ ID NO:11. In embodiments, the second end includes SEQ ID NO:110. In embodiments, the second end includes SEQ ID NO:112. In embodiments, the second end includes SEQ ID NO:114. In embodiments, the second end includes SEQ ID NO:116. In embodiments, the second end includes SEQ ID NO:142. In embodiments, the second end includes SEQ ID NO:144. In embodiments, the second end includes SEQ ID NO:146. In embodiments, the second end includes SEQ ID NO:148.

In embodiments, the second end includes SEQ ID NO:1. In embodiments, the second end includes SEQ ID NO:2. In embodiments, the second end includes SEQ ID NO:3. In embodiments, the second end includes SEQ ID NO:4. In embodiments, the second end includes SEQ ID NO:5. In embodiments, the second end includes SEQ ID NO:6. In embodiments, the second end includes SEQ ID NO:7. In embodiments, the second end includes SEQ ID NO:8. In embodiments, the second end includes SEQ ID NO:9. In embodiments, the second end includes SEQ ID NO:10. In embodiments, the second end includes SEQ ID NO:11. In embodiments, the second end includes SEQ ID NO:12. In embodiments, the second end includes SEQ ID NO:13. In embodiments, the second end includes SEQ ID NO:14. In embodiments, the second end includes SEQ ID NO:15. In embodiments, the second end includes SEQ ID NO:16. In embodiments, the second end includes SEQ ID NO:17. In embodiments, the second end includes SEQ ID NO:18. In embodiments, the second end includes SEQ ID NO:19. In embodiments, the second end includes SEQ ID NO:20. In embodiments, the second end includes SEQ ID NO:21. In embodiments, the second end includes SEQ ID NO:22. In embodiments, the second end includes SEQ ID NO:23. In embodiments, the second end includes SEQ ID NO:24. In embodiments, the second end includes SEQ ID NO:25. In embodiments, the second end includes SEQ ID NO:26. In embodiments, the second end includes SEQ ID NO:27. In embodiments, the second end includes SEQ ID NO:28. In embodiments, the second end includes SEQ ID NO:29. In embodiments, the second end includes SEQ ID NO:30. In embodiments, the second end includes SEQ ID NO:31. In embodiments, the second end includes SEQ ID NO:32. In embodiments, the second end includes SEQ ID NO:33. In embodiments, the second end includes SEQ ID NO:34. In embodiments, the second end includes SEQ ID NO:35. In embodiments, the second end includes SEQ ID NO:36. In embodiments, the second end includes SEQ ID NO:37. In embodiments, the second end includes SEQ ID NO:38. In embodiments, the second end includes SEQ ID NO:39. In embodiments, the second end includes SEQ ID NO:40. In embodiments, the second end includes SEQ ID NO:41. In embodiments, the second end includes SEQ ID NO:42. In embodiments, the second end includes SEQ ID NO:43. In embodiments, the second end includes SEQ ID NO:44. In embodiments, the second end includes SEQ ID NO:45. In embodiments, the second end includes SEQ ID NO:46. In embodiments, the second end includes SEQ ID NO:47. In embodiments, the second end includes SEQ ID NO:48. In embodiments, the second end includes SEQ ID NO:49. In embodiments, the second end includes SEQ ID NO:50. In embodiments, the second end includes SEQ ID NO:51. In embodiments, the second end includes SEQ ID NO:52. In embodiments, the second end includes SEQ ID NO:53. In embodiments, the second end includes SEQ ID NO:54. In embodiments, the second end includes SEQ ID NO:55. In embodiments, the second end includes SEQ ID NO:56. In embodiments, the second end includes SEQ ID NO:57. In embodiments, the second end includes SEQ ID NO:58. In embodiments, the second end includes SEQ ID NO:59. In embodiments, the second end includes SEQ ID NO:60. In embodiments, the second end includes SEQ ID NO:61. In embodiments, the second end includes SEQ ID NO:62. In embodiments, the second end includes SEQ ID NO:63. In embodiments, the second end includes SEQ ID NO:64. In embodiments, the second end includes SEQ ID NO:65. In embodiments, the second end includes SEQ ID NO:66. In embodiments, the second end includes SEQ ID NO:67. In embodiments, the second end includes SEQ ID NO:68. In embodiments, the second end includes SEQ ID NO:69. In embodiments, the second end includes SEQ ID NO:70. In embodiments, the second end includes SEQ ID NO:71. In embodiments, the second end includes SEQ ID NO:72. In embodiments, the second end includes SEQ ID NO:73. In embodiments, the second end includes SEQ ID NO:74. In embodiments, the second end includes SEQ ID NO:75. In embodiments, the second end includes SEQ ID NO:76. In embodiments, the second end includes SEQ ID NO:77. In embodiments, the second end includes SEQ ID NO:78. In embodiments, the second end includes SEQ ID NO:79. In embodiments, the second end includes SEQ ID NO:80. In embodiments, the second end includes SEQ ID NO:81. In embodiments, the second end includes SEQ ID NO:82. In embodiments, the second end includes SEQ ID NO:83. In embodiments, the second end includes SEQ ID NO:84. In embodiments, the second end includes SEQ ID NO:85. In embodiments, the second end includes SEQ ID NO:86. In embodiments, the second end includes SEQ ID NO:87. In embodiments, the second end includes SEQ ID NO:88. In embodiments, the second end includes SEQ ID NO:89. In embodiments, the second end includes SEQ ID NO:90. In embodiments, the second end includes SEQ ID NO:91. In embodiments, the second end includes SEQ ID NO:92. In embodiments, the second end includes SEQ ID NO:93. In embodiments, the second end includes SEQ ID NO:94. In embodiments, the second end includes SEQ ID NO:95. In embodiments, the second end includes SEQ ID NO:96. In embodiments, the second end includes SEQ ID NO:97. In embodiments, the second end includes SEQ ID NO:98. In embodiments, the second end includes SEQ ID NO:99. In embodiments, the second end includes SEQ ID NO:100. In embodiments, the second end includes SEQ ID NO:101. In embodiments, the second end includes SEQ ID NO:102. In embodiments, the second end includes SEQ ID NO:103. In embodiments, the second end includes SEQ ID NO:104. In embodiments, the second end includes SEQ ID NO:105. In embodiments, the second end includes SEQ ID NO:106. In embodiments, the second end includes SEQ ID NO:107. In embodiments, the second end includes SEQ ID NO:108. In embodiments, the second end includes SEQ ID NO:109. In embodiments, the second end includes SEQ ID NO:110. In embodiments, the second end includes SEQ ID NO:111. In embodiments, the second end includes SEQ ID NO:112. In embodiments, the second end includes SEQ ID NO:113. In embodiments, the second end includes SEQ ID NO:114. In embodiments, the second end includes SEQ ID NO:115. In embodiments, the second end includes SEQ ID NO:116. In embodiments, the second end includes SEQ ID NO:117. In embodiments, the second end includes SEQ ID NO:118. In embodiments, the second end includes SEQ ID NO:119. In embodiments, the second end includes SEQ ID NO:120. In embodiments, the second end includes SEQ ID NO:121. In embodiments, the second end includes SEQ ID NO:122. In embodiments, the second end includes SEQ ID NO:123. In embodiments, the second end includes SEQ ID NO:124. In embodiments, the second end includes SEQ ID NO:125. In embodiments, the second end includes SEQ ID NO:126. In embodiments, the second end includes SEQ ID NO:127. In embodiments, the second end includes SEQ ID NO:128. In embodiments, the second end includes SEQ ID NO:129. In embodiments, the second end includes SEQ ID NO:130. In embodiments, the second end includes SEQ ID NO:131. In embodiments, the second end includes SEQ ID NO:132. In embodiments, the second end includes SEQ ID NO:133. In embodiments, the second end includes SEQ ID NO:134. In embodiments, the second end includes SEQ ID NO:135. In embodiments, the second end includes SEQ ID NO:136. In embodiments, the second end includes SEQ ID NO:137. In embodiments, the second end includes SEQ ID NO:138. In embodiments, the second end includes SEQ ID NO:139. In embodiments, the second end includes SEQ ID NO:140. In embodiments, the second end includes SEQ ID NO:141. In embodiments, the second end includes SEQ ID NO:142. In embodiments, the second end includes SEQ ID NO:143. In embodiments, the second end includes SEQ ID NO:144. In embodiments, the second end includes SEQ ID NO:145. In embodiments, the second end includes SEQ ID NO:146. In embodiments, the second end includes SEQ ID NO:147. In embodiments, the second end includes SEQ ID NO:148.

In embodiments, the first end is capable of hybridizing to any one of the sequences of SEQ ID NO:1, SEQ ID NO:47, SEQ ID NO:101, SEQ ID NO:103, SEQ ID NO:105, SEQ ID NO:107, SEQ ID NO:133, SEQ ID NO:135, SEQ ID NO:137, or SEQ ID NO:139. In embodiments, the first end is capable of hybridizing to SEQ ID NO:1. In embodiments, the first end is capable of hybridizing to SEQ ID NO:47. In embodiments, the first end is capable of hybridizing to SEQ ID NO:101. In embodiments, the first end is capable of hybridizing to SEQ ID NO:103. In embodiments, the first end is capable of hybridizing to SEQ ID NO:105. In embodiments, the first end is capable of hybridizing to SEQ ID NO:107. In embodiments, the first end is capable of hybridizing to SEQ ID NO:133. In embodiments, the first end is capable of hybridizing to SEQ ID NO:135. In embodiments, the first end is capable of hybridizing to SEQ ID NO:137. In embodiments, the first end is capable of hybridizing to SEQ ID NO:139. In embodiments, the first end is capable of hybridizing to SEQ ID NO:2.

In embodiments, the first end includes SEQ ID NO:1, SEQ ID NO:2, SEQ ID NO:3, SEQ ID NO:4, SEQ ID NO:5, SEQ ID NO:6, SEQ ID NO:7, or SEQ ID NO:8, wherein the second end and first end are different. In embodiments, the first end includes SEQ ID NO:1, wherein the second end and first end are different. In embodiments, the first end includes SEQ ID NO:2, wherein the second end and first end are different. In embodiments, the first end includes SEQ ID NO:3, wherein the second end and first end are different. In embodiments, the first end includes SEQ ID NO:4, wherein the second end and first end are different. In embodiments, the first end includes SEQ ID NO:5, wherein the second end and first end are different. In embodiments, the first end includes SEQ ID NO:6, wherein the second end and first end are different. In embodiments, the first end includes SEQ ID NO:7, wherein the second end and first end are different. In embodiments, the first end includes SEQ ID NO:8, wherein the second end and first end are different. For example, when the second end and first end are different, it is understood the second end and first end are different sequences (i.e., having a different SEQ ID NO).

In embodiments, the first end includes SEQ ID NO:85, wherein the second end and first end are different. In embodiments, the first end includes SEQ ID NO:86, wherein the second end and first end are different. In embodiments, the first end includes SEQ ID NO:87, wherein the second end and first end are different. In embodiments, the first end includes SEQ ID NO:88, wherein the second end and first end are different. In embodiments, the first end includes SEQ ID NO:89, wherein the second end and first end are different. In embodiments, the first end includes SEQ ID NO:90, wherein the second end and first end are different. In embodiments, the first end includes SEQ ID NO:91, wherein the second end and first end are different. In embodiments, the first end includes SEQ ID NO:92, wherein the second end and first end are different. In embodiments, the first end includes SEQ ID NO:93, wherein the second end and first end are different. In embodiments, the first end includes SEQ ID NO:94, wherein the second end and first end are different. In embodiments, the first end includes SEQ ID NO:95, wherein the second end and first end are different. In embodiments, the first end includes SEQ ID NO:96, wherein the second end and first end are different. In embodiments, the first end includes SEQ ID NO:97, wherein the second end and first end are different. In embodiments, the first end includes SEQ ID NO:98, wherein the second end and first end are different. In embodiments, the first end includes SEQ ID NO:99, wherein the second end and first end are different. In embodiments, the first end includes SEQ ID NO:100, wherein the second end and first end are different. In embodiments, the first end includes SEQ ID NO:101, wherein the second end and first end are different. In embodiments, the first end includes SEQ ID NO:102, wherein the second end and first end are different. In embodiments, the first end includes SEQ ID NO:103, wherein the second end and first end are different. In embodiments, the first end includes SEQ ID NO:104, wherein the second end and first end are different. In embodiments, the first end includes SEQ ID NO:105, wherein the second end and first end are different. In embodiments, the first end includes SEQ ID NO:106, wherein the second end and first end are different. In embodiments, the first end includes SEQ ID NO:107, wherein the second end and first end are different. In embodiments, the first end includes SEQ ID NO:108, wherein the second end and first end are different. In embodiments, the first end includes SEQ ID NO:109 SEQ ID NO:110, wherein the second end and first end are different. In embodiments, the first end includes SEQ ID NO:111, wherein the second end and first end are different. In embodiments, the first end includes SEQ ID NO:112, wherein the second end and first end are different. In embodiments, the first end includes SEQ ID NO:113, wherein the second end and first end are different. In embodiments, the first end includes SEQ ID NO:114, wherein the second end and first end are different. In embodiments, the first end includes SEQ ID NO:115, wherein the second end and first end are different. In embodiments, the first end includes SEQ ID NO:116, wherein the second end and first end are different. In embodiments, the first end includes SEQ ID NO:117, wherein the second end and first end are different. In embodiments, the first end includes SEQ ID NO:118, wherein the second end and first end are different. In embodiments, the first end includes SEQ ID NO:119, wherein the second end and first end are different. In embodiments, the first end includes SEQ ID NO:120, wherein the second end and first end are different. In embodiments, the first end includes SEQ ID NO:121, wherein the second end and first end are different. In embodiments, the first end includes SEQ ID NO:122, wherein the second end and first end are different. In embodiments, the first end includes SEQ ID NO:123, wherein the second end and first end are different. In embodiments, the first end includes SEQ ID NO:124, wherein the second end and first end are different. In embodiments, the first end includes SEQ ID NO:125, wherein the second end and first end are different. In embodiments, the first end includes SEQ ID NO:126, wherein the second end and first end are different. In embodiments, the first end includes SEQ ID NO:127, wherein the second end and first end are different. In embodiments, the first end includes SEQ ID NO:128, wherein the second end and first end are different. In embodiments, the first end includes SEQ ID NO:129, wherein the second end and first end are different. In embodiments, the first end includes SEQ ID NO:130, wherein the second end and first end are different. In embodiments, the first end includes SEQ ID NO:131, wherein the second end and first end are different. In embodiments, the first end includes SEQ ID NO:132, wherein the second end and first end are different. In embodiments, the first end includes SEQ ID NO:133, wherein the second end and first end are different. In embodiments, the first end includes SEQ ID NO:134, wherein the second end and first end are different. In embodiments, the first end includes SEQ ID NO:135, wherein the second end and first end are different. In embodiments, the first end includes SEQ ID NO:136, wherein the second end and first end are different. In embodiments, the first end includes SEQ ID NO:137, wherein the second end and first end are different. In embodiments, the first end includes SEQ ID NO:138, wherein the second end and first end are different. In embodiments, the first end includes SEQ ID NO:139, wherein the second end and first end are different. In embodiments, the first end includes SEQ ID NO:140, wherein the second end and first end are different. In embodiments, the first end includes SEQ ID NO:141, wherein the second end and first end are different. In embodiments, the first end includes SEQ ID NO:142, wherein the second end and first end are different. In embodiments, the first end includes SEQ ID NO:143, wherein the second end and first end are different. In embodiments, the first end includes SEQ ID NO:144, wherein the second end and first end are different. In embodiments, the first end includes SEQ ID NO:145, wherein the second end and first end are different. In embodiments, the first end includes SEQ ID NO:146, wherein the second end and first end are different. In embodiments, the first end includes SEQ ID NO:147, wherein the second end and first end are different. In embodiments, the first end includes SEQ ID NO:148, wherein the second end and first end are different.

In embodiments, the first end includes SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123. In embodiments, the first end includes SEQ ID NO:5. In embodiments, the first end includes SEQ ID NO:9. In embodiments, the first end includes SEQ ID NO:85. In embodiments, the first end includes SEQ ID NO:92. In embodiments, the first end includes SEQ ID NO:90. In embodiments, the first end includes SEQ ID NO:88. In embodiments, the first end includes SEQ ID NO:117. In embodiments, the first end includes SEQ ID NO:119. In embodiments, the first end includes SEQ ID NO:121. In embodiments, the first end includes SEQ ID NO:123.

In embodiments, the first end includes SEQ ID NO:1, wherein the first end and the second end are different. In embodiments, the first end includes SEQ ID NO:2, wherein the first end and the second end are different. In embodiments, the first end includes SEQ ID NO:3, wherein the first end and the second end are different. In embodiments, the first end includes SEQ ID NO:4, wherein the first end and the second end are different. In embodiments, the first end includes SEQ ID NO:5, wherein the first end and the second end are different. In embodiments, the first end includes SEQ ID NO:6, wherein the first end and the second end are different. In embodiments, the first end includes SEQ ID NO:7, wherein the first end and the second end are different. In embodiments, the first end includes SEQ ID NO:8, wherein the first end and the second end are different. In embodiments, the first end includes SEQ ID NO:9, wherein the first end and the second end are different. In embodiments, the first end includes SEQ ID NO:10, wherein the first end and the second end are different. In embodiments, the first end includes SEQ ID NO:11, wherein the first end and the second end are different. In embodiments, the first end includes SEQ ID NO:12, wherein the first end and the second end are different. In embodiments, the first end includes SEQ ID NO:13, wherein the first end and the second end are different. In embodiments, the first end includes SEQ ID NO:14, wherein the first end and the second end are different. In embodiments, the first end includes SEQ ID NO:15, wherein the first end and the second end are different. In embodiments, the first end includes SEQ ID NO:16, wherein the first end and the second end are different. In embodiments, the first end includes SEQ ID NO:17, wherein the first end and the second end are different. In embodiments, the first end includes SEQ ID NO:18, wherein the first end and the second end are different. In embodiments, the first end includes SEQ ID NO:19, wherein the first end and the second end are different. In embodiments, the first end includes SEQ ID NO:20, wherein the first end and the second end are different. In embodiments, the first end includes SEQ ID NO:21, wherein the first end and the second end are different. In embodiments, the first end includes SEQ ID NO:22, wherein the first end and the second end are different. In embodiments, the first end includes SEQ ID NO:23, wherein the first end and the second end are different. In embodiments, the first end includes SEQ ID NO:24, wherein the first end and the second end are different. In embodiments, the first end includes SEQ ID NO:25, wherein the first end and the second end are different. In embodiments, the first end includes SEQ ID NO:26, wherein the first end and the second end are different. In embodiments, the first end includes SEQ ID NO:27, wherein the first end and the second end are different. In embodiments, the first end includes SEQ ID NO:28, wherein the first end and the second end are different. In embodiments, the first end includes SEQ ID NO:29, wherein the first end and the second end are different. In embodiments, the first end includes SEQ ID NO:30, wherein the first end and the second end are different. In embodiments, the first end includes SEQ ID NO:31, wherein the first end and the second end are different. In embodiments, the first end includes SEQ ID NO:32, wherein the first end and the second end are different. In embodiments, the first end includes SEQ ID NO:33, wherein the first end and the second end are different. In embodiments, the first end includes SEQ ID NO:34, wherein the first end and the second end are different. In embodiments, the first end includes SEQ ID NO:35, wherein the first end and the second end are different. In embodiments, the first end includes SEQ ID NO:36, wherein the first end and the second end are different. In embodiments, the first end includes SEQ ID NO:37, wherein the first end and the second end are different. In embodiments, the first end includes SEQ ID NO:38, wherein the first end and the second end are different. In embodiments, the first end includes SEQ ID NO:39, wherein the first end and the second end are different. In embodiments, the first end includes SEQ ID NO:40, wherein the first end and the second end are different. In embodiments, the first end includes SEQ ID NO:41, wherein the first end and the second end are different. In embodiments, the first end includes SEQ ID NO:42, wherein the first end and the second end are different. In embodiments, the first end includes SEQ ID NO:43, wherein the first end and the second end are different. In embodiments, the first end includes SEQ ID NO:44, wherein the first end and the second end are different. In embodiments, the first end includes SEQ ID NO:45, wherein the first end and the second end are different. In embodiments, the first end includes SEQ ID NO:46, wherein the first end and the second end are different. In embodiments, the first end includes SEQ ID NO:47, wherein the first end and the second end are different. In embodiments, the first end includes SEQ ID NO:48, wherein the first end and the second end are different. In embodiments, the first end includes SEQ ID NO:49, wherein the first end and the second end are different. In embodiments, the first end includes SEQ ID NO:50, wherein the first end and the second end are different. In embodiments, the first end includes SEQ ID NO:51, wherein the first end and the second end are different. In embodiments, the first end includes SEQ ID NO:52, wherein the first end and the second end are different. In embodiments, the first end includes SEQ ID NO:53, wherein the first end and the second end are different. In embodiments, the first end includes SEQ ID NO:54, wherein the first end and the second end are different. In embodiments, the first end includes SEQ ID NO:55, wherein the first end and the second end are different. In embodiments, the first end includes SEQ ID NO:56, wherein the first end and the second end are different. In embodiments, the first end includes SEQ ID NO:57, wherein the first end and the second end are different. In embodiments, the first end includes SEQ ID NO:58, wherein the first end and the second end are different. In embodiments, the first end includes SEQ ID NO:59, wherein the first end and the second end are different. In embodiments, the first end includes SEQ ID NO:60, wherein the first end and the second end are different. In embodiments, the first end includes SEQ ID NO:61, wherein the first end and the second end are different. In embodiments, the first end includes SEQ ID NO:62, wherein the first end and the second end are different. In embodiments, the first end includes SEQ ID NO:63, wherein the first end and the second end are different. In embodiments, the first end includes SEQ ID NO:64, wherein the first end and the second end are different. In embodiments, the first end includes SEQ ID NO:65, wherein the first end and the second end are different. In embodiments, the first end includes SEQ ID NO:66, wherein the first end and the second end are different. In embodiments, the first end includes SEQ ID NO:67, wherein the first end and the second end are different. In embodiments, the first end includes SEQ ID NO:68, wherein the first end and the second end are different. In embodiments, the first end includes SEQ ID NO:69, wherein the first end and the second end are different. In embodiments, the first end includes SEQ ID NO:70, wherein the first end and the second end are different. In embodiments, the first end includes SEQ ID NO:71, wherein the first end and the second end are different. In embodiments, the first end includes SEQ ID NO:72, wherein the first end and the second end are different. In embodiments, the first end includes SEQ ID NO:73, wherein the first end and the second end are different. In embodiments, the first end includes SEQ ID NO:74, wherein the first end and the second end are different. In embodiments, the first end includes SEQ ID NO:75, wherein the first end and the second end are different. In embodiments, the first end includes SEQ ID NO:76, wherein the first end and the second end are different. In embodiments, the first end includes SEQ ID NO:77, wherein the first end and the second end are different. In embodiments, the first end includes SEQ ID NO:78, wherein the first end and the second end are different. In embodiments, the first end includes SEQ ID NO:79, wherein the first end and the second end are different. In embodiments, the first end includes SEQ ID NO:80, wherein the first end and the second end are different. In embodiments, the first end includes SEQ ID NO:81, wherein the first end and the second end are different. In embodiments, the first end includes SEQ ID NO:82, wherein the first end and the second end are different. In embodiments, the first end includes SEQ ID NO:83, wherein the first end and the second end are different. In embodiments, the first end includes SEQ ID NO:84, wherein the first end and the second end are different. In embodiments, the first end includes SEQ ID NO:85, wherein the first end and the second end are different. In embodiments, the first end includes SEQ ID NO:86, wherein the first end and the second end are different. In embodiments, the first end includes SEQ ID NO:87, wherein the first end and the second end are different. In embodiments, the first end includes SEQ ID NO:88, wherein the first end and the second end are different. In embodiments, the first end includes SEQ ID NO:89, wherein the first end and the second end are different. In embodiments, the first end includes SEQ ID NO:90, wherein the first end and the second end are different. In embodiments, the first end includes SEQ ID NO:91, wherein the first end and the second end are different. In embodiments, the first end includes SEQ ID NO:92, wherein the first end and the second end are different. In embodiments, the first end includes SEQ ID NO:93, wherein the first end and the second end are different. In embodiments, the first end includes SEQ ID NO:94, wherein the first end and the second end are different. In embodiments, the first end includes SEQ ID NO:95, wherein the first end and the second end are different. In embodiments, the first end includes SEQ ID NO:96, wherein the first end and the second end are different. In embodiments, the first end includes SEQ ID NO:97, wherein the first end and the second end are different. In embodiments, the first end includes SEQ ID NO:98, wherein the first end and the second end are different. In embodiments, the first end includes SEQ ID NO:99, wherein the first end and the second end are different. In embodiments, the first end includes SEQ ID NO:100, wherein the first end and the second end are different. In embodiments, the first end includes SEQ ID NO:101, wherein the first end and the second end are different. In embodiments, the first end includes SEQ ID NO:102, wherein the first end and the second end are different. In embodiments, the first end includes SEQ ID NO:103, wherein the first end and the second end are different. In embodiments, the first end includes SEQ ID NO:104, wherein the first end and the second end are different. In embodiments, the first end includes SEQ ID NO:105, wherein the first end and the second end are different. In embodiments, the first end includes SEQ ID NO:106, wherein the first end and the second end are different. In embodiments, the first end includes SEQ ID NO:107, wherein the first end and the second end are different. In embodiments, the first end includes SEQ ID NO:108, wherein the first end and the second end are different. In embodiments, the first end includes SEQ ID NO:109, wherein the first end and the second end are different. In embodiments, the first end includes SEQ ID NO:110, wherein the first end and the second end are different. In embodiments, the first end includes SEQ ID NO:111, wherein the first end and the second end are different. In embodiments, the first end includes SEQ ID NO:112, wherein the first end and the second end are different. In embodiments, the first end includes SEQ ID NO:113, wherein the first end and the second end are different. In embodiments, the first end includes SEQ ID NO:114, wherein the first end and the second end are different. In embodiments, the first end includes SEQ ID NO:115, wherein the first end and the second end are different. In embodiments, the first end includes SEQ ID NO:116, wherein the first end and the second end are different. In embodiments, the first end includes SEQ ID NO:117, wherein the first end and second end are different. In embodiments, the first end includes SEQ ID NO:118, wherein the first end and second end are different. In embodiments, the first end includes SEQ ID NO:119, wherein the first end and second end are different. In embodiments, the first end includes SEQ ID NO:120, wherein the first end and second end are different. In embodiments, the first end includes SEQ ID NO:121, wherein the first end and second end are different. In embodiments, the first end includes SEQ ID NO:122, wherein the first end and second end are different. In embodiments, the first end includes SEQ ID NO:123, wherein the first end and second end are different. In embodiments, the first end includes SEQ ID NO:124, wherein the first end and second end are different. In embodiments, the first end includes SEQ ID NO:125, wherein the first end and second end are different. In embodiments, the first end includes SEQ ID NO:126, wherein the first end and second end are different. In embodiments, the first end includes SEQ ID NO:127, wherein the first end and second end are different. In embodiments, the first end includes SEQ ID NO:128, wherein the first end and second end are different. In embodiments, the first end includes SEQ ID NO:129, wherein the first end and second end are different. In embodiments, the first end includes SEQ ID NO:130, wherein the first end and second end are different. In embodiments, the first end includes SEQ ID NO:131, wherein the first end and second end are different. In embodiments, the first end includes SEQ ID NO:132, wherein the first end and second end are different. In embodiments, the first end includes SEQ ID NO:133, wherein the first end and second end are different. In embodiments, the first end includes SEQ ID NO:134, wherein the first end and second end are different. In embodiments, the first end includes SEQ ID NO:135, wherein the first end and second end are different. In embodiments, the first end includes SEQ ID NO:136, wherein the first end and second end are different. In embodiments, the first end includes SEQ ID NO:137, wherein the first end and second end are different. In embodiments, the first end includes SEQ ID NO:138, wherein the first end and second end are different. In embodiments, the first end includes SEQ ID NO:139, wherein the first end and second end are different. In embodiments, the first end includes SEQ ID NO:140, wherein the first end and second end are different. In embodiments, the first end includes SEQ ID NO:141, wherein the first end and second end are different. In embodiments, the first end includes SEQ ID NO:142, wherein the first end and second end are different. In embodiments, the first end includes SEQ ID NO:143, wherein the first end and second end are different. In embodiments, the first end includes SEQ ID NO:144, wherein the first end and second end are different. In embodiments, the first end includes SEQ ID NO:145, wherein the first end and second end are different. In embodiments, the first end includes SEQ ID NO:146, wherein the first end and second end are different. In embodiments, the first end includes SEQ ID NO:147, wherein the first end and second end are different. In embodiments, the first end includes SEQ ID NO:148, wherein the first end and second end are different.

In embodiments, the first end includes SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and the second end includes SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132. In embodiments, a template nucleic acid is between the first and second end. In embodiments, the first end includes SEQ ID NO:5 and the second end includes SEQ ID NO:7. In embodiments, the first end includes SEQ ID NO:5 and the second end includes SEQ ID NO:87. In embodiments, the first end includes SEQ ID NO:5 and the second end includes SEQ ID NO:89. In embodiments, the first end includes SEQ ID NO:5 and the second end includes SEQ ID NO:91. In embodiments, the first end includes SEQ ID NO:5 and the second end includes SEQ ID NO:86. In embodiments, the first end includes SEQ ID NO:5 and the second end includes SEQ ID NO:118. In embodiments, the first end includes SEQ ID NO:5 and the second end includes SEQ ID NO:120. In embodiments, the first end includes SEQ ID NO:5 and the second end includes SEQ ID NO:122. In embodiments, the first end includes SEQ ID NO:5 and the second end includes SEQ ID NO:124. In embodiments, the first end includes SEQ ID NO:85 and the second end includes SEQ ID NO:7. In embodiments, the first end includes SEQ ID NO:85 and the second end includes SEQ ID NO:87. In embodiments, the first end includes SEQ ID NO:85 and the second end includes SEQ ID NO:89. In embodiments, the first end includes SEQ ID NO:85 and the second end includes SEQ ID NO:91. In embodiments, the first end includes SEQ ID NO:85 and the second end includes SEQ ID NO:86. In embodiments, the first end includes SEQ ID NO:85 and the second end includes SEQ ID NO:118. In embodiments, the first end includes SEQ ID NO:85 and the second end includes SEQ ID NO:120. In embodiments, the first end includes SEQ ID NO:85 and the second end includes SEQ ID NO:122. In embodiments, the first end includes SEQ ID NO:85 and the second end includes SEQ ID NO:124. In embodiments, the first end includes SEQ ID NO:92 and the second end includes SEQ ID NO:7. In embodiments, the first end includes SEQ ID NO:92 and the second end includes SEQ ID NO:87. In embodiments, the first end includes SEQ ID NO:92 and the second end includes SEQ ID NO:89. In embodiments, the first end includes SEQ ID NO:92 and the second end includes SEQ ID NO:91. In embodiments, the first end includes SEQ ID NO:92 and the second end includes SEQ ID NO:86. In embodiments, the first end includes SEQ ID NO:92 and the second end includes SEQ ID NO:118. In embodiments, the first end includes SEQ ID NO:92 and the second end includes SEQ ID NO:120. In embodiments, the first end includes SEQ ID NO:92 and the second end includes SEQ ID NO:122. In embodiments, the first end includes SEQ ID NO:92 and the second end includes SEQ ID NO:124. In embodiments, the first end includes SEQ ID NO:90 and the second end includes SEQ ID NO:7. In embodiments, the first end includes SEQ ID NO:90 and the second end includes SEQ ID NO:87. In embodiments, the first end includes SEQ ID NO:90 and the second end includes SEQ ID NO:89. In embodiments, the first end includes SEQ ID NO:90 and the second end includes SEQ ID NO:91. In embodiments, the first end includes SEQ ID NO:90 and the second end includes SEQ ID NO:86. In embodiments, the first end includes SEQ ID NO:90 and the second end includes SEQ ID NO:118. In embodiments, the first end includes SEQ ID NO:90 and the second end includes SEQ ID NO:120. In embodiments, the first end includes SEQ ID NO:90 and the second end includes SEQ ID NO:122. In embodiments, the first end includes SEQ ID NO:90 and the second end includes SEQ ID NO:124. In embodiments, the first end includes SEQ ID NO:88 and the second end includes SEQ ID NO:7. In embodiments, the first end includes SEQ ID NO:88 and the second end includes SEQ ID NO:87. In embodiments, the first end includes SEQ ID NO:88 and the second end includes SEQ ID NO:89. In embodiments, the first end includes SEQ ID NO:88 and the second end includes SEQ ID NO:91. In embodiments, the first end includes SEQ ID NO:88 and the second end includes SEQ ID NO:86. In embodiments, the first end includes SEQ ID NO:88 and the second end includes SEQ ID NO:118. In embodiments, the first end includes SEQ ID NO:88 and the second end includes SEQ ID NO:120. In embodiments, the first end includes SEQ ID NO:88 and the second end includes SEQ ID NO:122. In embodiments, the first end includes SEQ ID NO:88 and the second end includes SEQ ID NO:124. In embodiments, the first end includes SEQ ID NO:117 and the second end includes SEQ ID NO:7. In embodiments, the first end includes SEQ ID NO:117 and the second end includes SEQ ID NO:87. In embodiments, the first end includes SEQ ID NO:117 and the second end includes SEQ ID NO:89. In embodiments, the first end includes SEQ ID NO:117 and the second end includes SEQ ID NO:91. In embodiments, the first end includes SEQ ID NO:117 and the second end includes SEQ ID NO:86. In embodiments, the first end includes SEQ ID NO:117 and the second end includes SEQ ID NO:118. In embodiments, the first end includes SEQ ID NO:117 and the second end includes SEQ ID NO:120. In embodiments, the first end includes SEQ ID NO:117 and the second end includes SEQ ID NO:122. In embodiments, the first end includes SEQ ID NO:117 and the second end includes SEQ ID NO:124. In embodiments, the first end includes SEQ ID NO:119 and the second end includes SEQ ID NO:7. In embodiments, the first end includes SEQ ID NO:119 and the second end includes SEQ ID NO:87. In embodiments, the first end includes SEQ ID NO:119 and the second end includes SEQ ID NO:89. In embodiments, the first end includes SEQ ID NO:119 and the second end includes SEQ ID NO:91. In embodiments, the first end includes SEQ ID NO:119 and the second end includes SEQ ID NO:86. In embodiments, the first end includes SEQ ID NO:119 and the second end includes SEQ ID NO:118. In embodiments, the first end includes SEQ ID NO:119 and the second end includes SEQ ID NO:120. In embodiments, the first end includes SEQ ID NO:119 and the second end includes SEQ ID NO:122. In embodiments, the first end includes SEQ ID NO:119 and the second end includes SEQ ID NO:124. In embodiments, the first end includes SEQ ID NO:121 and the second end includes SEQ ID NO:7. In embodiments, the first end includes SEQ ID NO:121 and the second end includes SEQ ID NO:87. In embodiments, the first end includes SEQ ID NO:121 and the second end includes SEQ ID NO:89. In embodiments, the first end includes SEQ ID NO:121 and the second end includes SEQ ID NO:91. In embodiments, the first end includes SEQ ID NO:121 and the second end includes SEQ ID NO:86. In embodiments, the first end includes SEQ ID NO:121 and the second end includes SEQ ID NO:118. In embodiments, the first end includes SEQ ID NO:121 and the second end includes SEQ ID NO:120. In embodiments, the first end includes SEQ ID NO:121 and the second end includes SEQ ID NO:122. In embodiments, the first end includes SEQ ID NO:121 and the second end includes SEQ ID NO:124. In embodiments, the first end includes SEQ ID NO:123 and the second end includes SEQ ID NO:7. In embodiments, the first end includes SEQ ID NO:123 and the second end includes SEQ ID NO:87. In embodiments, the first end includes SEQ ID NO:123 and the second end includes SEQ ID NO:89. In embodiments, the first end includes SEQ ID NO:123 and the second end includes SEQ ID NO:91. In embodiments, the first end includes SEQ ID NO:123 and the second end includes SEQ ID NO:86. In embodiments, the first end includes SEQ ID NO:123 and the second end includes SEQ ID NO:118. In embodiments, the first end includes SEQ ID NO:123 and the second end includes SEQ ID NO:120. In embodiments, the first end includes SEQ ID NO:123 and the second end includes SEQ ID NO:122. In embodiments, the first end includes SEQ ID NO:123 and the second end includes SEQ ID NO:124.

In embodiments, the first end includes SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and the second end includes SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132. In embodiments, a template nucleic acid is between the first and second end. In embodiments, the first end includes SEQ ID NO:2 and the second end includes SEQ ID NO:7. In embodiments, the first end includes SEQ ID NO:2 and the second end includes SEQ ID NO:87. In embodiments, the first end includes SEQ ID NO:2 and the second end includes SEQ ID NO:89. In embodiments, the first end includes SEQ ID NO:2 and the second end includes SEQ ID NO:91. In embodiments, the first end includes SEQ ID NO:2 and the second end includes SEQ ID NO:86. In embodiments, the first end includes SEQ ID NO:2 and the second end includes SEQ ID NO:118. In embodiments, the first end includes SEQ ID NO:2 and the second end includes SEQ ID NO:120. In embodiments, the first end includes SEQ ID NO:2 and the second end includes SEQ ID NO:122. In embodiments, the first end includes SEQ ID NO:2 and the second end includes SEQ ID NO:124. In embodiments, the first end includes SEQ ID NO:109 and the second end includes SEQ ID NO:7. In embodiments, the first end includes SEQ ID NO:109 and the second end includes SEQ ID NO:87. In embodiments, the first end includes SEQ ID NO:109 and the second end includes SEQ ID NO:89. In embodiments, the first end includes SEQ ID NO:109 and the second end includes SEQ ID NO:91. In embodiments, the first end includes SEQ ID NO:109 and the second end includes SEQ ID NO:86. In embodiments, the first end includes SEQ ID NO:109 and the second end includes SEQ ID NO:118. In embodiments, the first end includes SEQ ID NO:109 and the second end includes SEQ ID NO:120. In embodiments, the first end includes SEQ ID NO:109 and the second end includes SEQ ID NO:122. In embodiments, the first end includes SEQ ID NO:109 and the second end includes SEQ ID NO:124. In embodiments, the first end includes SEQ ID NO:111 and the second end includes SEQ ID NO:7. In embodiments, the first end includes SEQ ID NO:111 and the second end includes SEQ ID NO:87. In embodiments, the first end includes SEQ ID NO:111 and the second end includes SEQ ID NO:89. In embodiments, the first end includes SEQ ID NO:111 and the second end includes SEQ ID NO:91. In embodiments, the first end includes SEQ ID NO:111 and the second end includes SEQ ID NO:86. In embodiments, the first end includes SEQ ID NO:111 and the second end includes SEQ ID NO:118. In embodiments, the first end includes SEQ ID NO:111 and the second end includes SEQ ID NO:120. In embodiments, the first end includes SEQ ID NO:111 and the second end includes SEQ ID NO:122. In embodiments, the first end includes SEQ ID NO:111 and the second end includes SEQ ID NO:124. In embodiments, the first end includes SEQ ID NO:113 and the second end includes SEQ ID NO:7. In embodiments, the first end includes SEQ ID NO:113 and the second end includes SEQ ID NO:87. In embodiments, the first end includes SEQ ID NO:113 and the second end includes SEQ ID NO:89. In embodiments, the first end includes SEQ ID NO:113 and the second end includes SEQ ID NO:91. In embodiments, the first end includes SEQ ID NO:113 and the second end includes SEQ ID NO:86. In embodiments, the first end includes SEQ ID NO:113 and the second end includes SEQ ID NO:118. In embodiments, the first end includes SEQ ID NO:113 and the second end includes SEQ ID NO:120. In embodiments, the first end includes SEQ ID NO:113 and the second end includes SEQ ID NO:122. In embodiments, the first end includes SEQ ID NO:113 and the second end includes SEQ ID NO:124. In embodiments, the first end includes SEQ ID NO:115 and the second end includes SEQ ID NO:7. In embodiments, the first end includes SEQ ID NO:115 and the second end includes SEQ ID NO:87. In embodiments, the first end includes SEQ ID NO:115 and the second end includes SEQ ID NO:89. In embodiments, the first end includes SEQ ID NO:115 and the second end includes SEQ ID NO:91. In embodiments, the first end includes SEQ ID NO:115 and the second end includes SEQ ID NO:86. In embodiments, the first end includes SEQ ID NO:115 and the second end includes SEQ ID NO:118. In embodiments, the first end includes SEQ ID NO:115 and the second end includes SEQ ID NO:120. In embodiments, the first end includes SEQ ID NO:115 and the second end includes SEQ ID NO:122. In embodiments, the first end includes SEQ ID NO:115 and the second end includes SEQ ID NO:124. In embodiments, the first end includes SEQ ID NO:141 and the second end includes SEQ ID NO:7. In embodiments, the first end includes SEQ ID NO:141 and the second end includes SEQ ID NO:87. In embodiments, the first end includes SEQ ID NO:141 and the second end includes SEQ ID NO:89. In embodiments, the first end includes SEQ ID NO:141 and the second end includes SEQ ID NO:91. In embodiments, the first end includes SEQ ID NO:141 and the second end includes SEQ ID NO:86. In embodiments, the first end includes SEQ ID NO:141 and the second end includes SEQ ID NO:118. In embodiments, the first end includes SEQ ID NO:141 and the second end includes SEQ ID NO:120. In embodiments, the first end includes SEQ ID NO:141 and the second end includes SEQ ID NO:122. In embodiments, the first end includes SEQ ID NO:141 and the second end includes SEQ ID NO:124. In embodiments, the first end includes SEQ ID NO:143 and the second end includes SEQ ID NO:7. In embodiments, the first end includes SEQ ID NO:143 and the second end includes SEQ ID NO:87. In embodiments, the first end includes SEQ ID NO:143 and the second end includes SEQ ID NO:89. In embodiments, the first end includes SEQ ID NO:143 and the second end includes SEQ ID NO:91. In embodiments, the first end includes SEQ ID NO:143 and the second end includes SEQ ID NO:86. In embodiments, the first end includes SEQ ID NO:143 and the second end includes SEQ ID NO:118. In embodiments, the first end includes SEQ ID NO:143 and the second end includes SEQ ID NO:120. In embodiments, the first end includes SEQ ID NO:143 and the second end includes SEQ ID NO:122. In embodiments, the first end includes SEQ ID NO:143 and the second end includes SEQ ID NO:124. In embodiments, the first end includes SEQ ID NO:145 and the second end includes SEQ ID NO:7. In embodiments, the first end includes SEQ ID NO:145 and the second end includes SEQ ID NO:87. In embodiments, the first end includes SEQ ID NO:145 and the second end includes SEQ ID NO:89. In embodiments, the first end includes SEQ ID NO:145 and the second end includes SEQ ID NO:91. In embodiments, the first end includes SEQ ID NO:145 and the second end includes SEQ ID NO:86. In embodiments, the first end includes SEQ ID NO:145 and the second end includes SEQ ID NO:118. In embodiments, the first end includes SEQ ID NO:145 and the second end includes SEQ ID NO:120. In embodiments, the first end includes SEQ ID NO:145 and the second end includes SEQ ID NO:122. In embodiments, the first end includes SEQ ID NO:145 and the second end includes SEQ ID NO:124. In embodiments, the first end includes SEQ ID NO:147 and the second end includes SEQ ID NO:7. In embodiments, the first end includes SEQ ID NO:147 and the second end includes SEQ ID NO:87. In embodiments, the first end includes SEQ ID NO:147 and the second end includes SEQ ID NO:89. In embodiments, the first end includes SEQ ID NO:147 and the second end includes SEQ ID NO:91. In embodiments, the first end includes SEQ ID NO:147 and the second end includes SEQ ID NO:86. In embodiments, the first end includes SEQ ID NO:147 and the second end includes SEQ ID NO:118. In embodiments, the first end includes SEQ ID NO:147 and the second end includes SEQ ID NO:120. In embodiments, the first end includes SEQ ID NO:147 and the second end includes SEQ ID NO:122. In embodiments, the first end includes SEQ ID NO:147 and the second end includes SEQ ID NO:124.

In embodiments, the first end includes SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and the second end includes SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148. In embodiments, a template nucleic acid is between the first and second end. In embodiments, the first end includes SEQ ID NO:5 and the second end includes SEQ ID NO:6. In embodiments, the first end includes SEQ ID NO:5 and the second end includes SEQ ID NO:110. In embodiments, the first end includes SEQ ID NO:5 and the second end includes SEQ ID NO:112. In embodiments, the first end includes SEQ ID NO:5 and the second end includes SEQ ID NO:114. In embodiments, the first end includes SEQ ID NO:5 and the second end includes SEQ ID NO:116. In embodiments, the first end includes SEQ ID NO:5 and the second end includes SEQ ID NO:142. In embodiments, the first end includes SEQ ID NO:5 and the second end includes SEQ ID NO:144. In embodiments, the first end includes SEQ ID NO:5 and the second end includes SEQ ID NO:146. In embodiments, the first end includes SEQ ID NO:5 and the second end includes SEQ ID NO:148. In embodiments, the first end includes SEQ ID NO:85 and the second end includes SEQ ID NO:6. In embodiments, the first end includes SEQ ID NO:85 and the second end includes SEQ ID NO:110. In embodiments, the first end includes SEQ ID NO:85 and the second end includes SEQ ID NO:112. In embodiments, the first end includes SEQ ID NO:85 and the second end includes SEQ ID NO:114. In embodiments, the first end includes SEQ ID NO:85 and the second end includes SEQ ID NO:116. In embodiments, the first end includes SEQ ID NO:85 and the second end includes SEQ ID NO:142. In embodiments, the first end includes SEQ ID NO:85 and the second end includes SEQ ID NO:144. In embodiments, the first end includes SEQ ID NO:85 and the second end includes SEQ ID NO:146. In embodiments, the first end includes SEQ ID NO:85 and the second end includes SEQ ID NO:148. In embodiments, the first end includes SEQ ID NO:92 and the second end includes SEQ ID NO:6. In embodiments, the first end includes SEQ ID NO:92 and the second end includes SEQ ID NO:110. In embodiments, the first end includes SEQ ID NO:92 and the second end includes SEQ ID NO:112. In embodiments, the first end includes SEQ ID NO:92 and the second end includes SEQ ID NO:114. In embodiments, the first end includes SEQ ID NO:92 and the second end includes SEQ ID NO:116. In embodiments, the first end includes SEQ ID NO:92 and the second end includes SEQ ID NO:142. In embodiments, the first end includes SEQ ID NO:92 and the second end includes SEQ ID NO:144. In embodiments, the first end includes SEQ ID NO:92 and the second end includes SEQ ID NO:146. In embodiments, the first end includes SEQ ID NO:92 and the second end includes SEQ ID NO:148. In embodiments, the first end includes SEQ ID NO:90 and the second end includes SEQ ID NO:6. In embodiments, the first end includes SEQ ID NO:90 and the second end includes SEQ ID NO:110. In embodiments, the first end includes SEQ ID NO:90 and the second end includes SEQ ID NO:112. In embodiments, the first end includes SEQ ID NO:90 and the second end includes SEQ ID NO:114. In embodiments, the first end includes SEQ ID NO:90 and the second end includes SEQ ID NO:116. In embodiments, the first end includes SEQ ID NO:90 and the second end includes SEQ ID NO:142. In embodiments, the first end includes SEQ ID NO:90 and the second end includes SEQ ID NO:144. In embodiments, the first end includes SEQ ID NO:90 and the second end includes SEQ ID NO:146. In embodiments, the first end includes SEQ ID NO:90 and the second end includes SEQ ID NO:148. In embodiments, the first end includes SEQ ID NO:88 and the second end includes SEQ ID NO:6. In embodiments, the first end includes SEQ ID NO:88 and the second end includes SEQ ID NO:110. In embodiments, the first end includes SEQ ID NO:88 and the second end includes SEQ ID NO:112. In embodiments, the first end includes SEQ ID NO:88 and the second end includes SEQ ID NO:114. In embodiments, the first end includes SEQ ID NO:88 and the second end includes SEQ ID NO:116. In embodiments, the first end includes SEQ ID NO:88 and the second end includes SEQ ID NO:142. In embodiments, the first end includes SEQ ID NO:88 and the second end includes SEQ ID NO:144. In embodiments, the first end includes SEQ ID NO:88 and the second end includes SEQ ID NO:146. In embodiments, the first end includes SEQ ID NO:88 and the second end includes SEQ ID NO:148. In embodiments, the first end includes SEQ ID NO:117 and the second end includes SEQ ID NO:6. In embodiments, the first end includes SEQ ID NO:117 and the second end includes SEQ ID NO:110. In embodiments, the first end includes SEQ ID NO:117 and the second end includes SEQ ID NO:112. In embodiments, the first end includes SEQ ID NO:117 and the second end includes SEQ ID NO:114. In embodiments, the first end includes SEQ ID NO:117 and the second end includes SEQ ID NO:116. In embodiments, the first end includes SEQ ID NO:117 and the second end includes SEQ ID NO:142. In embodiments, the first end includes SEQ ID NO:117 and the second end includes SEQ ID NO:144. In embodiments, the first end includes SEQ ID NO:117 and the second end includes SEQ ID NO:146. In embodiments, the first end includes SEQ ID NO:117 and the second end includes SEQ ID NO:148. In embodiments, the first end includes SEQ ID NO:119 and the second end includes SEQ ID NO:6. In embodiments, the first end includes SEQ ID NO:119 and the second end includes SEQ ID NO:110. In embodiments, the first end includes SEQ ID NO:119 and the second end includes SEQ ID NO:112. In embodiments, the first end includes SEQ ID NO:119 and the second end includes SEQ ID NO:114. In embodiments, the first end includes SEQ ID NO:119 and the second end includes SEQ ID NO:116. In embodiments, the first end includes SEQ ID NO:119 and the second end includes SEQ ID NO:142. In embodiments, the first end includes SEQ ID NO:119 and the second end includes SEQ ID NO:144. In embodiments, the first end includes SEQ ID NO:119 and the second end includes SEQ ID NO:146. In embodiments, the first end includes SEQ ID NO:119 and the second end includes SEQ ID NO:148. In embodiments, the first end includes SEQ ID NO:121 and the second end includes SEQ ID NO:6. In embodiments, the first end includes SEQ ID NO:121 and the second end includes SEQ ID NO:110. In embodiments, the first end includes SEQ ID NO:121 and the second end includes SEQ ID NO:112. In embodiments, the first end includes SEQ ID NO:121 and the second end includes SEQ ID NO:114. In embodiments, the first end includes SEQ ID NO:121 and the second end includes SEQ ID NO:116. In embodiments, the first end includes SEQ ID NO:121 and the second end includes SEQ ID NO:142. In embodiments, the first end includes SEQ ID NO:121 and the second end includes SEQ ID NO:144. In embodiments, the first end includes SEQ ID NO:121 and the second end includes SEQ ID NO:146. In embodiments, the first end includes SEQ ID NO:121 and the second end includes SEQ ID NO:148. In embodiments, the first end includes SEQ ID NO:123 and the second end includes SEQ ID NO:6. In embodiments, the first end includes SEQ ID NO:123 and the second end includes SEQ ID NO:110. In embodiments, the first end includes SEQ ID NO:123 and the second end includes SEQ ID NO:112. In embodiments, the first end includes SEQ ID NO:123 and the second end includes SEQ ID NO:114. In embodiments, the first end includes SEQ ID NO:123 and the second end includes SEQ ID NO:116. In embodiments, the first end includes SEQ ID NO:123 and the second end includes SEQ ID NO:142. In embodiments, the first end includes SEQ ID NO:123 and the second end includes SEQ ID NO:144. In embodiments, the first end includes SEQ ID NO:123 and the second end includes SEQ ID NO:146. In embodiments, the first end includes SEQ ID NO:123 and the second end includes SEQ ID NO:148.

In embodiments, the first end includes, SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and the second end includes SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148. In embodiments, a template nucleic acid is between the first and second end. In embodiments, the first end includes SEQ ID NO:2 and the second end includes SEQ ID NO:6. In embodiments, the first end includes SEQ ID NO:2 and the second end includes SEQ ID NO:110. In embodiments, the first end includes SEQ ID NO:2 and the second end includes SEQ ID NO:112. In embodiments, the first end includes SEQ ID NO:2 and the second end includes SEQ ID NO:114. In embodiments, the first end includes SEQ ID NO:2 and the second end includes SEQ ID NO:116. In embodiments, the first end includes SEQ ID NO:2 and the second end includes SEQ ID NO:142. In embodiments, the first end includes SEQ ID NO:2 and the second end includes SEQ ID NO:144. In embodiments, the first end includes SEQ ID NO:2 and the second end includes SEQ ID NO:146. In embodiments, the first end includes SEQ ID NO:2 and the second end includes SEQ ID NO:148. In embodiments, the first end includes SEQ ID NO:109 and the second end includes SEQ ID NO:6. In embodiments, the first end includes SEQ ID NO:109 and the second end includes SEQ ID NO:110. In embodiments, the first end includes SEQ ID NO:109 and the second end includes SEQ ID NO:112. In embodiments, the first end includes SEQ ID NO:109 and the second end includes SEQ ID NO:114. In embodiments, the first end includes SEQ ID NO:109 and the second end includes SEQ ID NO:116. In embodiments, the first end includes SEQ ID NO:109 and the second end includes SEQ ID NO:142. In embodiments, the first end includes SEQ ID NO:109 and the second end includes SEQ ID NO:144. In embodiments, the first end includes SEQ ID NO:109 and the second end includes SEQ ID NO:146. In embodiments, the first end includes SEQ ID NO:109 and the second end includes SEQ ID NO:148. In embodiments, the first end includes SEQ ID NO:111 and the second end includes SEQ ID NO:6. In embodiments, the first end includes SEQ ID NO:111 and the second end includes SEQ ID NO:110. In embodiments, the first end includes SEQ ID NO:111 and the second end includes SEQ ID NO:112. In embodiments, the first end includes SEQ ID NO:111 and the second end includes SEQ ID NO:114. In embodiments, the first end includes SEQ ID NO:111 and the second end includes SEQ ID NO:116. In embodiments, the first end includes SEQ ID NO:111 and the second end includes SEQ ID NO:142. In embodiments, the first end includes SEQ ID NO:111 and the second end includes SEQ ID NO:144. In embodiments, the first end includes SEQ ID NO:111 and the second end includes SEQ ID NO:146. In embodiments, the first end includes SEQ ID NO:111 and the second end includes SEQ ID NO:148. In embodiments, the first end includes SEQ ID NO:113 and the second end includes SEQ ID NO:6. In embodiments, the first end includes SEQ ID NO:113 and the second end includes SEQ ID NO:110. In embodiments, the first end includes SEQ ID NO:113 and the second end includes SEQ ID NO:112. In embodiments, the first end includes SEQ ID NO:113 and the second end includes SEQ ID NO:114. In embodiments, the first end includes SEQ ID NO:113 and the second end includes SEQ ID NO:116. In embodiments, the first end includes SEQ ID NO:113 and the second end includes SEQ ID NO:142. In embodiments, the first end includes SEQ ID NO:113 and the second end includes SEQ ID NO:144. In embodiments, the first end includes SEQ ID NO:113 and the second end includes SEQ ID NO:146. In embodiments, the first end includes SEQ ID NO:113 and the second end includes SEQ ID NO:148. In embodiments, the first end includes SEQ ID NO:115 and the second end includes SEQ ID NO:6. In embodiments, the first end includes SEQ ID NO:115 and the second end includes SEQ ID NO:110. In embodiments, the first end includes SEQ ID NO:115 and the second end includes SEQ ID NO:112. In embodiments, the first end includes SEQ ID NO:115 and the second end includes SEQ ID NO:114. In embodiments, the first end includes SEQ ID NO:115 and the second end includes SEQ ID NO:116. In embodiments, the first end includes SEQ ID NO:115 and the second end includes SEQ ID NO:142. In embodiments, the first end includes SEQ ID NO:115 and the second end includes SEQ ID NO:144. In embodiments, the first end includes SEQ ID NO:115 and the second end includes SEQ ID NO:146. In embodiments, the first end includes SEQ ID NO:115 and the second end includes SEQ ID NO:148. In embodiments, the first end includes SEQ ID NO:141 and the second end includes SEQ ID NO:6. In embodiments, the first end includes SEQ ID NO:141 and the second end includes SEQ ID NO:110. In embodiments, the first end includes SEQ ID NO:141 and the second end includes SEQ ID NO:112. In embodiments, the first end includes SEQ ID NO:141 and the second end includes SEQ ID NO:114. In embodiments, the first end includes SEQ ID NO:141 and the second end includes SEQ ID NO:116. In embodiments, the first end includes SEQ ID NO:141 and the second end includes SEQ ID NO:142. In embodiments, the first end includes SEQ ID NO:141 and the second end includes SEQ ID NO:144. In embodiments, the first end includes SEQ ID NO:141 and the second end includes SEQ ID NO:146. In embodiments, the first end includes SEQ ID NO:141 and the second end includes SEQ ID NO:148. In embodiments, the first end includes SEQ ID NO:143 and the second end includes SEQ ID NO:6. In embodiments, the first end includes SEQ ID NO:143 and the second end includes SEQ ID NO:110. In embodiments, the first end includes SEQ ID NO:143 and the second end includes SEQ ID NO:112. In embodiments, the first end includes SEQ ID NO:143 and the second end includes SEQ ID NO:114. In embodiments, the first end includes SEQ ID NO:143 and the second end includes SEQ ID NO:116. In embodiments, the first end includes SEQ ID NO:143 and the second end includes SEQ ID NO:142. In embodiments, the first end includes SEQ ID NO:143 and the second end includes SEQ ID NO:144. In embodiments, the first end includes SEQ ID NO:143 and the second end includes SEQ ID NO:146. In embodiments, the first end includes SEQ ID NO:143 and the second end includes SEQ ID NO:148. In embodiments, the first end includes SEQ ID NO:145 and the second end includes SEQ ID NO:6. In embodiments, the first end includes SEQ ID NO:145 and the second end includes SEQ ID NO:110. In embodiments, the first end includes SEQ ID NO:145 and the second end includes SEQ ID NO:112. In embodiments, the first end includes SEQ ID NO:145 and the second end includes SEQ ID NO:114. In embodiments, the first end includes SEQ ID NO:145 and the second end includes SEQ ID NO:116. In embodiments, the first end includes SEQ ID NO:145 and the second end includes SEQ ID NO:142. In embodiments, the first end includes SEQ ID NO:145 and the second end includes SEQ ID NO:144. In embodiments, the first end includes SEQ ID NO:145 and the second end includes SEQ ID NO:146. In embodiments, the first end includes SEQ ID NO:145 and the second end includes SEQ ID NO:148. In embodiments, the first end includes SEQ ID NO:147 and the second end includes SEQ ID NO:6. In embodiments, the first end includes SEQ ID NO:147 and the second end includes SEQ ID NO:110. In embodiments, the first end includes SEQ ID NO:147 and the second end includes SEQ ID NO:112. In embodiments, the first end includes SEQ ID NO:147 and the second end includes SEQ ID NO:114. In embodiments, the first end includes SEQ ID NO:147 and the second end includes SEQ ID NO:116. In embodiments, the first end includes SEQ ID NO:147 and the second end includes SEQ ID NO:142. In embodiments, the first end includes SEQ ID NO:147 and the second end includes SEQ ID NO:144. In embodiments, the first end includes SEQ ID NO:147 and the second end includes SEQ ID NO:146. In embodiments, the first end includes SEQ ID NO:147 and the second end includes SEQ ID NO:148.

In embodiments, the second end includes SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and the first end includes SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132. In embodiments, a template nucleic acid is between the first and second end.

In embodiments, the second end includes SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and the first end includes SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132. In embodiments, a template nucleic acid is between the first and second end.

In embodiments, the second end includes SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and the first end includes SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148. In embodiments, a template nucleic acid is between the first and second end.

In embodiments, the second end includes SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and the first end includes SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148. In embodiments, a template nucleic acid is between the first and second end.

In embodiments, the template nucleic acids include genomic DNA. In embodiments, the template polynucleotide includes genomic DNA, complementary DNA (cDNA), cell-free DNA (cfDNA), messenger RNA (mRNA), transfer RNA (tRNA), ribosomal RNA (rRNA), cell-free RNA (cfRNA), or noncoding RNA (ncRNA).

In embodiments, the template polynucleotide (also referred to herein as a nucleic acid molecule) is about 100 to 1000 nucleotides in length. In embodiments, the template polynucleotide is about 350 nucleotides in length. In embodiments, the template polynucleotide is about 10, 20, 50, 100, 150, 200, 300, or 500 nucleotides in length. The template polynucleotide molecules can vary length, such as about 100-300 nucleotides long, about 300-500 nucleotides long, or about 500-1000 nucleotides long. In embodiments, the template polynucleotide is about 100-1000 nucleotides, about 150-950 nucleotides, about 200-900 nucleotides, about 250-850 nucleotides, about 300-800 nucleotides, about 350-750 nucleotides, about 400-700 nucleotides, or about 450-650 nucleotides. In embodiments, the template polynucleotide is about 150 nucleotides. In embodiments, the template polynucleotide is about 100-1000 nucleotides long. In embodiments, the template polynucleotide is about 100-300 nucleotides long. In embodiments, the template polynucleotide is about 300-500 nucleotides long. In embodiments, the template polynucleotide is about 500-1000 nucleotides long. In embodiments, the template polynucleotide is about 100 nucleotides. In embodiments, the template polynucleotide is about 300 nucleotides. In embodiments, the template polynucleotide is about 500 nucleotides. In embodiments, the template polynucleotide is about 1000 nucleotides. In embodiments, the nucleic acid molecule includes 50 to 1000 nucleotides. In embodiments, the nucleic acid molecule includes 100 to 500 nucleotides. In embodiments, the nucleic acid molecule consists of 50 to 1000 nucleotides.

In embodiments, the template polynucleotide (e.g., genomic template DNA) is first treated to form single-stranded linear fragments (e.g., ranging in length from about 50 to about 600 nucleotides). Treatment typically entails fragmentation, such as by chemical fragmentation, enzymatic fragmentation, or mechanical fragmentation, followed by denaturation to produce single-stranded DNA fragments. In embodiments, the template polynucleotide includes an adapter. The adaptor may have other functional elements including tagging sequences (i.e., a barcode), attachment sequences, palindromic sequences, restriction sites, sequencing primer binding sites, functionalization sequences, and the like. Barcodes can be of any of a variety of lengths. In embodiments, the primer includes a barcode that is 10-50, 20-30, or 4-12 nucleotides in length. In embodiments, the adapter includes a primer binding sequence that is complementary to at least a portion of a primer (e.g., a sequencing primer). Primer binding sites can be of any suitable length. In embodiments, a primer binding site is about or at least about 10, 15, 20, 25, 30, or more nucleotides in length. In embodiments, a primer binding site is 10-50, 15-30, or 20-25 nucleotides in length. The primer binding site may be selected such that the primer (e.g., sequencing primer) has the following properties, for example having a length of about 20-30 nucleotides; approximately 50% GC content, and a Tm of about 55° C. to about 65° C.

In embodiments, the first end or second end is capable of hybridizing under stringent hybridization conditions. The phrase "stringent hybridization conditions" refers to conditions under which a primer will hybridize to its complementary subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. In embodiments, the first end or second end is capable of hybridizing at 5×SSC and 40° C. In embodiments, the first end or second end is capable of hybridizing at 5×SSC and in the presence of ethylene glycol. Methods for generating SSC buffers (sodium chloride and sodium citrate solutions) are known in the art; for example, a 1×SSC buffer includes 150 mM NaCl and 15 mM sodium citrate. A 20×SSC solution includes 3 M sodium chloride and 0.3 M sodium citrate. Nucleic acids that do not hybridize to each other under stringent conditions are still substantially identical if the polypeptides, which they encode, are substantially identical. This occurs, for example, when a copy of a nucleic acid is created using the maximum codon degeneracy permitted by the genetic code. In such cases, the nucleic acids typically hybridize under moderately stringent hybridization conditions. In embodiments, the first end or second end is capable of hybridizing under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. For example, a positive hybridization is at least twice background. Those of ordinary skill will readily recognize that alternative hybridization and wash conditions can be utilized to provide conditions of similar stringency. Additional guidelines for determining hybridization parameters are provided in numerous references (see, e.g., *Current Protocols in Molecular Biology* (Ausubel et al., eds. 1995 supplement)).

In another aspect is provided a composition including the plurality of template nucleic acids as described herein, including embodiments, hybridized to a plurality of first oligonucleotides via the first ends of the template nucleic acids, wherein the first oligonucleotides are immobilized on a solid support (e.g., a particle or a flow cell). In embodiments, each of the first oligonucleotides are covalently attached to a polymer on the solid support. In embodiments, the composition further includes a plurality of second oligonucleotides immobilized on the solid support.

In an aspect is provided a composition including a solid support and a first plurality of immobilized oligonucleotides, wherein the oligonucleotides in the plurality each include a sequence described herein (e.g., a sequence in Table 1). In embodiments, the sequence is selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109 SEQ ID NO:110, SEQ ID NO:111, SEQ ID NO:112, SEQ ID NO:113, SEQ ID NO:114 SEQ ID NO:115 SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, or SEQ ID NO:148. In embodiments, the composition further includes a second plurality of immobilized oligonucleotides, wherein the oligonucleotides in the plurality each include a sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109 SEQ ID NO:110, SEQ ID NO:111, SEQ ID NO:112, SEQ ID NO:113, SEQ ID NO:114 SEQ ID NO:115 SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, or SEQ ID NO:148, provided the second plurality of oligonucleotides is different than the first plurality of oligonucleotides.

In embodiments, the oligonucleotides in the first or second plurality each include a sequence selected from SEQ ID NO:5, SEQ ID NO:9, SEQ ID NO:85, SEQ ID NO:92, SEQ ID NO:90, SEQ ID NO:88, SEQ ID NO:7, SEQ ID NO:11, SEQ ID NO:30, SEQ ID NO:87, SEQ ID NO:89, SEQ ID NO:91, SEQ ID NO:86, SEQ ID NO:117, SEQ ID NO:118, SEQ ID NO:119, SEQ ID NO:120, SEQ ID NO:121, SEQ ID NO:122, SEQ ID NO:123, or SEQ ID NO:124, provided the second plurality of oligonucleotides is different than the first plurality of oligonucleotides.

In embodiments, the oligonucleotides in the first plurality each include a sequence selected from SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and the oligonucleotides in the second plurality each include a sequence selected from SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132. In embodiments, the oligonucleotides in the first plurality each include SEQ ID NO:5 and the oligonucleotides in the second plurality each include SEQ ID NO:7. In embodiments, the oligonucleotides in the first plurality each include SEQ ID NO:5 and the oligonucleotides in the second plurality each include SEQ ID NO:87. In embodiments, the oligonucleotides in the first plurality each include SEQ ID NO:5 and the oligonucleotides in the second plurality each include SEQ ID NO:89. In embodiments, the oligonucleotides in the first plurality each include SEQ ID NO:5 and the oligonucleotides in the second plurality each include SEQ ID NO:91. In embodiments, the oligonucleotides in the first plurality each include SEQ ID NO:5 and the oligonucleotides in the second plurality each include SEQ ID NO:86. In embodiments, the oligonucleotides in the first plurality each include SEQ ID NO:5 and the oligonucleotides in the second plurality each include SEQ ID NO:118. In embodiments, the oligonucleotides in the first plurality each include SEQ ID NO:5 and the oligonucleotides in the second plurality each include SEQ ID NO:120. In embodiments, the oligonucleotides in the first plurality each include SEQ ID NO:5 and the oligonucleotides in the second plurality each include SEQ ID NO:122. In embodiments, the oligonucleotides in the first plurality each include SEQ ID NO:5 and the oligonucleotides in the second plurality each include SEQ ID NO:124. In embodiments, the oligonucleotides in the first plurality each include SEQ ID NO:85 and the oligonucleotides in the second plurality each include SEQ ID NO:7. In embodiments, the oligonucleotides in the first plurality each include SEQ ID NO:85 and the oligonucleotides in the second plurality each include SEQ ID NO:87. In embodiments, the oligonucleotides in the first plurality each include SEQ ID NO:85 and the oligonucleotides in the second plurality each include SEQ ID NO:89. In embodiments, the oligonucleotides in the first plurality each include SEQ ID NO:85 and the oligonucleotides in the second plurality each include SEQ ID NO:91. In embodiments, the oligonucleotides in the first plurality each include SEQ ID NO:85 and the oligonucleotides in the second plurality each include SEQ ID NO:86. In embodiments, the oligonucleotides in the first plurality each include SEQ ID NO:85 and the oligonucleotides in the second plurality each include SEQ ID NO:118. In embodiments, the oligonucleotides in the first plurality each include SEQ ID NO:85 and the oligonucleotides in the second plurality each include SEQ ID NO:120. In embodiments, the oligonucleotides in the first plurality each include SEQ ID NO:85 and the oligonucleotides in the second plurality each include SEQ ID NO:122. In embodiments, the oligonucleotides in the first plurality each include SEQ ID NO:85 and the oligonucleotides in the second plurality each include SEQ ID NO:124. In embodiments, the oligonucleotides in the first plurality each include SEQ ID NO:92 and the oligonucleotides in the second plurality each include SEQ ID NO:7. In embodiments, the oligonucleotides in the first plurality each include SEQ ID NO:92 and the oligonucleotides in the second plurality each include SEQ ID NO:87. In embodiments, the oligonucleotides in the first plurality each include SEQ ID NO:92 and the oligonucleotides in the second plurality each include SEQ ID NO:89. In embodiments, the oligonucleotides in the first plurality each include SEQ ID NO:92 and the oligonucleotides in the second plurality each include SEQ ID NO:91. In embodiments, the oligonucleotides in the first plurality each include SEQ ID NO:92 and the oligonucleotides in the second plurality each include SEQ ID NO:86. In embodiments, the oligonucleotides in the first plurality each include SEQ ID NO:92 and the oligonucleotides in the second plurality each include SEQ ID NO:118. In embodiments, the oligonucleotides in the first plurality each include SEQ ID NO:92 and the oligonucleotides in the second plurality each include SEQ ID NO:120. In embodiments, the oligonucleotides in the first plurality each include SEQ ID NO:92 and the oligonucleotides in the second plurality each include SEQ ID NO:122. In embodiments, the oligonucleotides in the first plurality each include SEQ ID NO:92 and the oligonucleotides in the second plurality each include SEQ ID NO:124. In embodiments, the oligonucleotides in the first plurality each include SEQ ID NO:90 and the oligonucleotides in the second plurality each include SEQ ID NO:7. In embodiments, the oligonucleotides in the first plurality each include SEQ ID NO:90 and the oligonucleotides in the second plurality each include SEQ ID NO:87. In embodiments, the oligonucleotides in the first plurality each include SEQ ID NO:90 and the oligonucleotides in the second plurality each include SEQ ID NO:89. In embodiments, the oligonucleotides in the first plurality each include SEQ ID NO:90 and the oligonucleotides in the second plurality each include SEQ ID NO:91. In embodiments, the oligonucleotides in the first plurality each include SEQ ID NO:90 and the oligonucleotides in the second plurality each include SEQ ID NO:86. In embodiments, the oligonucleotides in the first plurality each include SEQ ID NO:90 and the oligonucleotides in the second plurality each include SEQ ID NO:118. In embodiments, the oligonucleotides in the first plurality each include SEQ ID NO:90 and the oligonucleotides in the second plurality each include SEQ ID NO:120. In embodiments, the oligonucleotides in the first plurality each include SEQ ID NO:90 and the oligonucleotides in the second plurality each include SEQ ID NO:122. In embodiments, the oligonucleotides in the first plurality each include SEQ ID NO:90 and the oligonucleotides in the second plurality each include SEQ ID NO:124. In embodiments, the oligonucleotides in the first plurality each include SEQ ID NO:88 and the oligonucleotides in the second plurality each include SEQ ID NO:7. In embodiments, the oligonucleotides in the first plurality each include SEQ ID NO:88 and the oligonucleotides in the second plurality each include SEQ ID NO:87. In embodiments, the oligonucleotides in the first plurality each include SEQ ID NO:88 and the oligonucleotides in the second plurality each include SEQ ID NO:89. In embodiments, the oligonucleotides in the first plurality each include SEQ ID NO:88 and the oligonucleotides in the second plurality each include SEQ ID NO:91. In embodiments, the oligonucleotides in the first plurality each include SEQ ID NO:88 and the oligonucleotides in the second plurality each include SEQ ID NO:86. In embodiments, the oligonucleotides in the first plurality each include SEQ ID NO:88 and the oligonucleotides in the second plurality each include SEQ ID NO:118. In embodiments, the oligonucleotides in the first plurality each include SEQ ID NO:88 and the oligonucleotides in the second plurality each include SEQ ID NO:120. In embodiments, the oligonucleotides in the first plurality each include SEQ ID NO:88 and the oligonucleotides in the second plurality each include SEQ ID NO:122. In embodiments, the oligonucleotides in the first plurality each include SEQ ID NO:88 and the oligonucleotides in the second plurality each include SEQ ID NO:124. In embodiments, the oligonucleotides in the first plurality each include SEQ ID NO:117 and the oligonucleotides in the second plurality each include SEQ ID NO:7. In embodiments, the first plurality each include SEQ ID NO:117 and the oligonucleotides in the second plurality each include SEQ ID NO:87. In embodiments, the oligonucleotides in the first plurality each include SEQ ID NO:117 and the oligonucleotides in the second plurality each include SEQ ID NO:89. In embodiments, the oligonucleotides in the first plurality each include SEQ ID NO:117 and the oligonucleotides in the second plurality each include SEQ ID NO:91. In embodiments, the oligonucleotides in the first plurality each include SEQ ID NO:117 and the oligonucleotides in the second plurality each include SEQ ID NO:86. In embodiments, the oligonucleotides in the first plurality each include SEQ ID NO:117 and the oligonucleotides in the second plurality each include SEQ ID NO:118. In embodiments, the oligonucleotides in the first plurality each include SEQ ID NO:117 and the oligonucleotides in the second plurality each include SEQ ID NO:120. In embodiments, the oligonucleotides in the first plurality each include SEQ ID NO:117 and the oligonucleotides in the second plurality each include SEQ ID NO:122. In embodiments, the oligonucleotides in the first plurality each include SEQ ID NO:117 and the oligonucleotides in the second plurality each include SEQ ID NO:124. In embodiments, the oligonucleotides in the first plurality each include SEQ ID NO:119 and the oligonucleotides in the second plurality each include SEQ ID NO:7. In embodiments, the oligonucleotides in the first plurality each include SEQ ID NO:119 and the oligonucleotides in the second plurality each include SEQ ID NO:87. In embodiments, the oligonucleotides in the first plurality each include SEQ ID NO:119 and the oligonucleotides in the second plurality each include SEQ ID NO:89. In embodiments, the oligonucleotides in the first plurality each include SEQ ID NO:119 and the oligonucleotides in the second plurality each include SEQ ID NO:91. In embodiments, the oligonucleotides in the first plurality each include SEQ ID NO:119 and the oligonucleotides in the second plurality each include SEQ ID NO:86. In embodiments, the oligonucleotides in the first plurality each include SEQ ID NO:119 and the oligonucleotides in the second plurality each include SEQ ID NO:118. In embodiments, the oligonucleotides in the first plurality each include SEQ ID NO:119 and the oligonucleotides in the second plurality each include SEQ ID NO:120. In embodiments, the oligonucleotides in the first plurality each include SEQ ID NO:119 and the oligonucleotides in the second plurality each include SEQ ID NO:122. In embodiments, the oligonucleotides in the first plurality each include SEQ ID NO:119 and the oligonucleotides in the second plurality each include SEQ ID NO:124. In embodiments, the oligonucleotides in the first plurality each include SEQ ID NO:121 and the oligonucleotides in the second plurality each include SEQ ID NO:7. In embodiments, the oligonucleotides in the first plurality each include SEQ ID NO:121 and the oligonucleotides in the second plurality each include SEQ ID NO:87. In embodiments, the oligonucleotides in the first plurality each include SEQ ID NO:121 and the oligonucleotides in the second plurality each include SEQ ID NO:89. In embodiments, the oligonucleotides in the first plurality each include SEQ ID NO:121 and the oligonucleotides in the second plurality each include SEQ ID NO:91. In embodiments, the oligonucleotides in the first plurality each include SEQ ID NO:121 and the oligonucleotides in the second plurality each include SEQ ID NO:86. In embodiments, the oligonucleotides in the first plurality each include SEQ ID NO:121 and the oligonucleotides in the second plurality each include SEQ ID NO:118. In embodiments, the oligonucleotides in the first plurality each include SEQ ID NO:121 and the oligonucleotides in the second plurality each include SEQ ID NO:120. In embodiments, the oligonucleotides in the first plurality each include SEQ ID NO:121 and the oligonucleotides in the second plurality each include SEQ ID NO:122. In embodiments, the oligonucleotides in the first plurality each include SEQ ID NO:121 and the oligonucleotides in the second plurality each include SEQ ID NO:124. In embodiments, the oligonucleotides in the first plurality each include SEQ ID NO:123 and the oligonucleotides in the second plurality each include SEQ ID NO:7. In embodiments, the oligonucleotides in the first plurality each include SEQ ID NO:123 and the oligonucleotides in the second plurality each include SEQ ID NO:87. In embodiments, the oligonucleotides in the first plurality each include SEQ ID NO:123 and the oligonucleotides in the second plurality each include SEQ ID NO:89. In embodiments, the oligonucleotides in the first plurality each include SEQ ID NO:123 and the oligonucleotides in the second plurality each include SEQ ID NO:91. In embodiments, the oligonucleotides in the first plurality each include SEQ ID NO:123 and the oligonucleotides in the second plurality each include SEQ ID NO:86. In embodiments, the oligonucleotides in the first plurality each include SEQ ID NO:123 and the oligonucleotides in the second plurality each include SEQ ID NO:118. In embodiments, the oligonucleotides in the first plurality each include SEQ ID NO:123 and the oligonucleotides in the second plurality each include SEQ ID NO:120. In embodiments, the oligonucleotides in the first plurality each include SEQ ID NO:123 and the oligonucleotides in the second plurality each include SEQ ID NO:122. In embodiments, the oligonucleotides in the first plurality each include SEQ ID NO:123 and the oligonucleotides in the second plurality each include SEQ ID NO:124.

In embodiments, the oligonucleotides in the first plurality each include a sequence selected from SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and the oligonucleotides in the second plurality each include a sequence selected from SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132.

In embodiments, the oligonucleotides in the first plurality each include a sequence selected from SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and the oligonucleotides in the second plurality each include a sequence selected from SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148.

In embodiments, the oligonucleotides in the first plurality each include a sequence selected from SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, the oligonucleotides in the first plurality each include a sequence selected from SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148.

In embodiments, each of the plurality of immobilized oligonucleotides (e.g., immobilized primers) is about 15 to about 35 nucleotides in length. In embodiments, each of the plurality of immobilized oligonucleotides (e.g., immobilized primers) is about 10 to about 40 nucleotides in length. In embodiments, each of the plurality of immobilized oligonucleotides (e.g., immobilized primers) is about 5 to about 100 nucleotides in length. In embodiments, each of the plurality of immobilized oligonucleotides (e.g., immobilized primers) is about 20 to 200 nucleotides in length. In embodiments, each of the plurality of immobilized oligonucleotides (e.g., immobilized primers) about or at least about 5, 6, 7, 8, 9, 10, 12, 15, 18, 20, 25, 30, 35, 40, 50 or more nucleotides in length. In embodiments, one or more immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, the 3' modification is a 3'-phosphate modification, including a 3' phosphate moiety, which is removed by a PNK enzyme or a phosphatase enzyme. Alternatively, abasic site cleavage with certain endonucleases (e.g., Endo IV) results in a 3'-OH at the cleavable site from the 3'-diesterase activity.

In embodiments, the immobilized oligonucleotides include one or more phosphorothioate nucleotides. In embodiments, the immobilized oligonucleotides include a plurality of phosphorothioate nucleotides. In embodiments, about or at least about 20%, 30%, 40%, 50%, 60%, 70%, 80%, 90%, or about 100% of the nucleotides in the immobilized oligonucleotides are phosphorothioate nucleotides. In embodiments, most of the nucleotides in the immobilized oligonucleotides are phosphorothioate nucleotides. In embodiments, all of the nucleotides in the immobilized oligonucleotides are phosphorothioate nucleotides. In embodiments, none of the nucleotides in the immobilized oligonucleotides are phosphorothioate nucleotides. In embodiments, the 5' end of the immobilized oligonucleotide includes one or more phosphorothioate nucleotides. In embodiments, the 5' end of the immobilized oligonucleotide includes between one and five phosphorothioate nucleotides.

In embodiments, the first and second polynucleotides are each attached to the solid support (i.e., immobilized on the surface of a solid support). The polynucleotide molecules can be fixed to surface by a variety of techniques, including covalent attachment and non-covalent attachment. In embodiments, the polynucleotides are confined to an area of a discrete region (referred to as a cluster or feature). The discrete regions may have defined locations in a regular array, which may correspond to a rectilinear pattern, circular pattern, hexagonal pattern, or the like. A regular array of such regions is advantageous for detection and data analysis of signals collected from the arrays during an analysis. These discrete regions are separated by interstitial regions. As used herein, the term "interstitial region" refers to an area in a substrate or on a surface that separates other areas of the substrate or surface. For example, an interstitial region can separate one concave feature of an array from another concave feature of the array. The two regions that are separated from each other can be discrete, lacking contact with each other. In another example, an interstitial region can separate a first portion of a feature from a second portion of a feature. In embodiments, the interstitial region is continuous whereas the features are discrete, for example, as is the case for an array of wells in an otherwise continuous surface. The separation provided by an interstitial region can be partial or full separation. Interstitial regions will typically have a surface material that differs from the surface material of the features on the surface. For example, features of an array can have polynucleotides that exceeds the amount or concentration present at the interstitial regions. In some embodiments, the polynucleotides and/or primers may not be present at the interstitial regions. In embodiments, at least two different primers are attached to the solid support (e.g., a forward and a reverse primer), which facilitates generating multiple amplification products from the first extension product or a complement thereof In embodiments, the immobilized oligonucleotides are covalently attached to the solid support via a linker. The linkers may also include spacer nucleotides. Including spacer nucleotides in the linker puts the polynucleotide in an environment having a greater resemblance to free solution. This can be beneficial, for example, in enzyme-mediated reactions such as sequencing-by-synthesis. It is believed that such reactions suffer less steric hindrance issues that can occur when the polynucleotide is directly attached to the solid support or is attached through a very short linker (e.g., a linker comprising about 1 to 3 carbon atoms). Spacer nucleotides form part of the polynucleotide but do not participate in any reaction carried out on or with the polynucleotide (e.g. a hybridization or amplification reaction). In embodiments, the spacer nucleotides include 1 to 20 nucleotides. In embodiments, the linker includes 6 spacer nucleotides. In embodiments, the linker includes 7 spacer nucleotides. In embodiments, the linker includes 8 spacer nucleotides. In embodiments, the linker includes 10 spacer nucleotides. In embodiments, the linker includes 12 spacer nucleotides. In embodiments, the linker includes 15 spacer nucleotides. It is preferred to use poly-T spacers, although other nucleotides and combinations thereof can be used. In embodiments, the linker includes 10, 11, 12, 13, 14, or 15 T spacer nucleotides. In embodiments, the linker includes 12 T spacer nucleotides. Spacer nucleotides are typically included at the 5' ends of polynucleotides, which are attached to a suitable support. Attachment can be achieved via a phosphorothioate present at the 5' end of the polynucleotide, an azide moiety, a dibenzocyclooctyne (DBCO) moiety, or any other bioconjugate reactive moiety. In embodiments, the linker includes 6 to 16 thymine nucleotides, and wherein the linker is at the 5' end of the immobilized oligonucleotides. In embodiments, the linker includes 12 to 16 thymine nucleotides, and wherein the linker is at the 5' end of the immobilized oligonucleotides. In embodiments, the linker includes one or more uracil nucleotides, wherein the linker is at the 5' end of the immobilized oligonucleotides. In embodiments, the linker includes 1 to 5 uracil nucleotides, wherein the linker is at the 5' end of the immobilized oligonucleotides. In embodiments, the linker includes 5 uracil nucleotides, wherein the linker is at the 5' end of the immobilized oligonucleotides. In embodiments, the linker includes 6 to 16 thymine nucleotides and 1 to 5 uracil nucleotides, wherein the linker is at the 5' end of the immobilized oligonucleotides. In embodiments, the linker includes 12 to 16 thymine nucleotides and 1 to 5 uracil nucleotides, wherein the linker is at the 5' end of the immobilized oligonucleotides.

In an aspect is provided a nucleic acid polymerase complex including a nucleic acid polymerase, wherein the nucleic acid polymerase is bound (e.g., non-covalently bound) to an oligonucleotide described herein, including embodiments. In embodiments, the complex includes a polymerase bound to a sequence as described herein (e.g., a sequence within Table 1). In embodiments, the nucleic acid polymerase is a mutant polymerase. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044). In embodiments, the oligonucleotide is immobilized to a solid support. In embodiments, the oligonucleotide is immobilized to a polymer attached to a solid support. In embodiments, the oligonucleotide is immobilized to a bead. In embodiments, the oligonucleotide is immobilized to a polymer, wherein the polymer is attached to a bead. In embodiments, the solid support includes a polymer layer (alternatively referred to as a polymer coating). In some embodiments, the solid support includes a hydrophilic polymer layer. In some embodiments, the hydrophilic polymer is a silane-functionalized polymer. In some embodiments, the silane-functionalized polymer is a silane functionalized polyethylene glycol (Si-PEG) polymer or a silane functionalized poly(acrylamide) (Si-PAm).

In an aspect is provided an array, including: a solid support including a surface, the surface comprising a plurality of wells separated from each other by interstitial regions on the surface, wherein one or more wells includes a particle, wherein the particle includes a plurality of bioconjugate reactive moieties, a plurality of oligonucleotide moieties, or a combination thereof. In embodiments, the oligonucleotide moiety includes one or more sequences described herein, for example, in Table 1. In embodiments, the 5' end of the oligonucleotide moiety includes one or more uracil nucleotides. In embodiments, the sequence is SEQ ID NO:1. In embodiments, the sequence is SEQ ID NO:2. In embodiments, the sequence is SEQ ID NO:3. In embodiments, the sequence is SEQ ID NO:4. In embodiments, the sequence is SEQ ID NO:5. In embodiments, the sequence is SEQ ID NO:6. In embodiments, the sequence is SEQ ID NO:7. In embodiments, the sequence is SEQ ID NO:8. In embodiments, the sequence is SEQ ID NO:9. In embodiments, the sequence is SEQ ID NO:10. In embodiments, the sequence is SEQ ID NO:11. In embodiments, the sequence is SEQ ID NO:12. In embodiments, the sequence is SEQ ID NO:13. In embodiments, the sequence is SEQ ID NO:14. In embodiments, the sequence is SEQ ID NO:15. In embodiments, the sequence is SEQ ID NO:16. In embodiments, the sequence is SEQ ID NO:17. In embodiments, the sequence is SEQ ID NO:18. In embodiments, the sequence is SEQ ID NO:19. In embodiments, the sequence is SEQ ID NO:20. In embodiments, the sequence is SEQ ID NO:21. In embodiments, the sequence is SEQ ID NO:22. In embodiments, the sequence is SEQ ID NO:23. In embodiments, the sequence is SEQ ID NO:24. In embodiments, the sequence is SEQ ID NO:25. In embodiments, the sequence is SEQ ID NO:26. In embodiments, the sequence is SEQ ID NO:27. In embodiments, the sequence is SEQ ID NO:28. In embodiments, the sequence is SEQ ID NO:29. In embodiments, the sequence is SEQ ID NO:30. In embodiments, the sequence is SEQ ID NO:31. In embodiments, the sequence is SEQ ID NO:32. In embodiments, the sequence is SEQ ID NO:33. In embodiments, the sequence is SEQ ID NO:34. In embodiments, the sequence is SEQ ID NO:35. In embodiments, the sequence is SEQ ID NO:36. In embodiments, the sequence is SEQ ID NO:37. In embodiments, the sequence is SEQ ID NO:38. In embodiments, the sequence is SEQ ID NO:39. In embodiments, the sequence is SEQ ID NO:40. In embodiments, the sequence is SEQ ID NO:41. In embodiments, the sequence is SEQ ID NO:42. In embodiments, the sequence is SEQ ID NO:43. In embodiments, the sequence is SEQ ID NO:44. In embodiments, the sequence is SEQ ID NO:45. In embodiments, the sequence is SEQ ID NO:46. In embodiments, the sequence is SEQ ID NO:47. In embodiments, the sequence is SEQ ID NO:48. In embodiments, the sequence is SEQ ID NO:49. In embodiments, the sequence is SEQ ID NO:50. In embodiments, the sequence is SEQ ID NO:51. In embodiments, the sequence is SEQ ID NO:52. In embodiments, the sequence is SEQ ID NO:53. In embodiments, the sequence is SEQ ID NO:54. In embodiments, the sequence is SEQ ID NO:55. In embodiments, the sequence is SEQ ID NO:56. In embodiments, the sequence is SEQ ID NO:57. In embodiments, the sequence is SEQ ID NO:58. In embodiments, the sequence is SEQ ID NO:59. In embodiments, the sequence is SEQ ID NO:60. In embodiments, the sequence is SEQ ID NO:61. In embodiments, the sequence is SEQ ID NO:62. In embodiments, the sequence is SEQ ID NO:63. In embodiments, the sequence is SEQ ID NO:64. In embodiments, the sequence is SEQ ID NO:65. In embodiments, the sequence is SEQ ID NO:66. In embodiments, the sequence is SEQ ID NO:67. In embodiments, the sequence is SEQ ID NO:68. In embodiments, the sequence is SEQ ID NO:69. In embodiments, the sequence is SEQ ID NO:70. In embodiments, the sequence is SEQ ID NO:71. In embodiments, the sequence is SEQ ID NO:72. In embodiments, the sequence is SEQ ID NO:73. In embodiments, the sequence is SEQ ID NO:74. In embodiments, the sequence is SEQ ID NO:75. In embodiments, the sequence is SEQ ID NO:76. In embodiments, the sequence is SEQ ID NO:77. In embodiments, the sequence is SEQ ID NO:78. In embodiments, the sequence is SEQ ID NO:79. In embodiments, the sequence is SEQ ID NO:80. In embodiments, the sequence is SEQ ID NO:81. In embodiments, the sequence is SEQ ID NO:82. In embodiments, the sequence is SEQ ID NO:83. In embodiments, the sequence is SEQ ID NO:84. In embodiments, the sequence is SEQ ID NO:85. In embodiments, the sequence is SEQ ID NO:86. In embodiments, the sequence is SEQ ID NO:87. In embodiments, the sequence is SEQ ID NO:88. In embodiments, the sequence is SEQ ID NO:89. In embodiments, the sequence is SEQ ID NO:90. In embodiments, the sequence is SEQ ID NO:91. In embodiments, the sequence is SEQ ID NO:92. In embodiments, the sequence is SEQ ID NO:93. In embodiments, the sequence is SEQ ID NO:94. In embodiments, the sequence is SEQ ID NO:95. In embodiments, the sequence is SEQ ID NO:96. In embodiments, the sequence is SEQ ID NO:97. In embodiments, the sequence is SEQ ID NO:98. In embodiments, the sequence is SEQ ID NO:99. In embodiments, the sequence is SEQ ID NO:100. In embodiments, the sequence is SEQ ID NO:101. In embodiments, the sequence is SEQ ID NO:102. In embodiments, the sequence is SEQ ID NO:103. In embodiments, the sequence is SEQ ID NO:104. In embodiments, the sequence is SEQ ID NO:105. In embodiments, the sequence is SEQ ID NO:106. In embodiments, the sequence is SEQ ID NO:107. In embodiments, the sequence is SEQ ID NO:108. In embodiments, the sequence is SEQ ID NO:109. In embodiments, the sequence is SEQ ID NO:110. In embodiments, the sequence is SEQ ID NO:111. In embodiments, the sequence is SEQ ID NO:112. In embodiments, the sequence is SEQ ID NO:113. In embodiments, the sequence is SEQ ID NO:114. In embodiments, the sequence is SEQ ID NO:115. In embodiments, the sequence is SEQ ID NO:116. In embodiments, the sequence is SEQ ID NO:117. In embodiments, the sequence is SEQ ID NO:118. In embodiments, the sequence is SEQ ID NO:119. In embodiments, the sequence is SEQ ID NO:120. In embodiments, the sequence is SEQ ID NO:121. In embodiments, the sequence is SEQ ID NO:122. In embodiments, the sequence is SEQ ID NO:123. In embodiments, the sequence is SEQ ID NO:124. In embodiments, the sequence is SEQ ID NO:125. In embodiments, the sequence is SEQ ID NO:126. In embodiments, the sequence is SEQ ID NO:127. In embodiments, the sequence is SEQ ID NO:128. In embodiments, the sequence is SEQ ID NO:129. In embodiments, the sequence is SEQ ID NO:130. In embodiments, the sequence is SEQ ID NO:131. In embodiments, the sequence is SEQ ID NO:132. In embodiments, the sequence is SEQ ID NO:133. In embodiments, the sequence is SEQ ID NO:134. In embodiments, the sequence is SEQ ID NO:135. In embodiments, the sequence is SEQ ID NO:136. In embodiments, the sequence is SEQ ID NO:137. In embodiments, the sequence is SEQ ID NO:138. In embodiments, the sequence is SEQ ID NO:139. In embodiments, the sequence is SEQ ID NO:140. In embodiments, the sequence is SEQ ID NO:141. In embodiments, the sequence is SEQ ID NO:142. In embodiments, the sequence is SEQ ID NO:143. In embodiments, the sequence is SEQ ID NO:144. In embodiments, the sequence is SEQ ID NO:145. In embodiments, the sequence is SEQ ID NO:146. In embodiments, the sequence is SEQ ID NO:147. In embodiments, the sequence is SEQ ID NO:148.

In embodiments, the array includes SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132.

In embodiments, the array includes SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132.

In embodiments, the array includes SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148.

In embodiments, the array includes SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148.

In embodiments, the array includes a first immobilized oligonucleotide including SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and a second immobilized oligonucleotide including SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132.

In embodiments, the array includes a first immobilized oligonucleotide including SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and a second immobilized oligonucleotide including SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132.

In embodiments, the array includes a first immobilized oligonucleotide including SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and a second immobilized oligonucleotide including SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148.

In embodiments, the array includes a first immobilized oligonucleotide including SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and a second immobilized oligonucleotide including SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148.

In embodiments, the oligonucleotide moiety (alternatively referred to herein as primer or polynucleotide primer) is covalently attached to the polymer. In embodiments, the 5' end of the oligonucleotide moiety contains a functional group that is tethered to the polymer (i.e., the particle shell polymer or the polymer particle). Non-limiting examples of covalent attachment include amine-modified oligonucleotide moieties reacting with epoxy or isothiocyanate groups on the polymer, succinylated oligonucleotide moieties reacting with aminophenyl or aminopropyl functional groups on the polymer, dibenzocyclooctyne-modified oligonucleotide moieties reacting with azide functional groups on the polymer (or vice versa), trans-cyclooctyne-modified oligonucleotide moieties reacting with tetrazine or methyl tetrazine groups on the polymer (or vice versa), disulfide modified oligonucleotide moieties reacting with mercapto-functional groups on the polymer, amine-functionalized oligonucleotide moieties reacting with carboxylic acid groups on the polymer via 1-ethyl-3-(3-dimethylaminopropyl)-carbodiimide hydrochloride (EDC) chemistry, thiol-modified oligonucleotide moieties attaching to a polymer via a disulfide bond or maleimide linkage, alkyne-modified oligonucleotide moieties attaching to a polymer via copper-catalyzed click reactions to azide functional groups on the polymer, and acrydite-modified oligonucleotide moieties polymerizing with free acrylic acid monomers on the polymer to form polyacrylamide or reacting with thiol groups on the polymer. In embodiments, the oligonucleotide moiety is attached to the polymer through electrostatic binding. For example, the negatively charged phosphate backbone of the primer may be bound electrostatically to positively charged monomers in the polymer.

In embodiments, the one or more oligonucleotide moieties include at least two different primers attached to the polymer (e.g., a forward and a reverse primer), each of which may be present in multiple copies. In embodiments, about or at most at most about 50%, 40%, 30%, 25%, 20%, 15%, 10%, 5%, or less of the monomers in the polymer of each particle are attached to a copy of the oligonucleotide moiety. In embodiments, about 1-25%, about 2-20%, about 3-15%, about 4-14%, or about 5-12% of the monomers in the polymer of each particle are attached to a copy of the oligonucleotide moiety, or a number or a range between any two of these values. In embodiments, about 5-10% of the monomers in the polymer of each particle are attached to a copy of the oligonucleotide moiety. In embodiments, two different oligonucleotide moieties are attached to the particle (e.g., a forward and a reverse primer), which facilitates generating multiple amplification products from the first extension product or a complement thereof.

In some embodiments, the oligonucleotide moiety is about 5 to about 50 nucleotides in length. In some embodiments, the oligonucleotide moiety is about 5 to about 40 nucleotides in length. In some embodiments, the oligonucleotide moiety is about 10 to about 45 nucleotides in length. In some embodiments, the oligonucleotide moiety is about 15 to about 40 nucleotides in length. In some embodiments, the oligonucleotide moiety is about 20 to about 35 nucleotides in length. In some embodiments, the oligonucleotide moiety is about 20 to about 30 nucleotides in length. In some embodiments, the oligonucleotide moiety is about 25 to about 30 nucleotides in length.

In embodiments, the oligonucleotide moiety includes spacer nucleotides. Including spacer nucleotides in the linker puts the target polynucleotide in an environment having a greater resemblance to free solution. This can be beneficial, for example, in enzyme-mediated reactions such as sequencing-by-synthesis. It is believed that such reactions suffer less steric hindrance issues that can occur when the polynucleotide is directly attached to the particle or is attached through a very short linker (e.g., a linker comprising about 1 to 3 carbon atoms). Spacer nucleotides form part of the oligonucleotide moiety but do not participate in any reaction carried out on or with the oligonucleotide (e.g., a hybridization or amplification reaction). In embodiments, the spacer nucleotides include 1 to 20 nucleotides. In embodiments, the linker includes 10 spacer nucleotides. In embodiments, the linker includes 12 spacer nucleotides. In embodiments, the linker includes 15 spacer nucleotides. It is preferred to use poly-T spacers, although other nucleotides and combinations thereof can be used. In embodiments, the linker includes 10, 11, 12, 13, 14, or 15 T spacer nucleotides. In embodiments, the linker includes 12 T spacer nucleotides. Spacer nucleotides are typically included at the 5' ends of oligonucleotide, which are attached to the particle. Attachment can be achieved via a phosphorothioate present at the 5' end of the oligonucleotide, an azide moiety, a dibenzocyclooctyne (DBCO) moiety, or any other bioconjugate reactive moiety. The linker may be a carbon-containing chain such as those of formula $—(CH_2)n—$ wherein "n" is from 1 to about 1000. However, a variety of other linkers may be used so long as the linkers are stable under conditions used in DNA sequencing. In embodiments, the linker includes polyethylene glycol (PEG) having a general formula of $—(CH_2—CH_2—O)m-$, wherein m is from about 1 to 500.

In embodiments, the linker, adapter (e.g., hairpin) or the oligonucleotides (e.g., primers) include a cleavable site. A cleavage site is a site, which allows controlled cleavage of the immobilized polynucleotide strand (e.g., the linker, the primer, or the polynucleotide) by chemical, enzymatic or photochemical means. Any suitable enzymatic, chemical, or photochemical cleavage reaction may be used to cleave the cleavage site. The cleavage reaction may result in removal of a part or the whole of the strand being cleaved. Suitable cleavage means include, for example, restriction enzyme digestion, in which case the cleavage site is an appropriate restriction site for the enzyme which directs cleavage of one or both strands of a duplex template; RNase digestion or chemical cleavage of a bond between a deoxyribonucleotide and a ribonucleotide, in which case the cleavage site may include one or more ribonucleotides; chemical reduction of a disulfide linkage with a reducing agent (e.g., THPP or TCEP), in which case the cleavage site should include an appropriate disulfide linkage; chemical cleavage of a diol linkage with periodate, in which case the cleavage site should include a diol linkage; generation of an abasic site and subsequent hydrolysis, etc. In embodiments, the cleavage site is included in the oligonucleotide (e.g., within the oligonucleotide sequence of the primer). In embodiments, the linker or the oligonucleotide includes a diol linkage which permits cleavage by treatment with periodate (e.g., sodium periodate). It will be appreciated that more than one diol can be included at the cleavage site. One or more diol units may be incorporated into a polynucleotide using standard methods for automated chemical DNA synthesis. Oligonucleotide nucleotide primers including one or more diol linkers can be conveniently prepared by chemical synthesis. The diol linker is cleaved by treatment with any substance, which promotes cleavage of the diol (e.g., a diol-cleaving agent). In embodiments, the diol-cleaving agent is periodate, e.g., aqueous sodium periodate ($NaIO_4$). Following treatment with the diol-cleaving agent (e.g., periodate) to cleave the diol, the cleaved product may be treated with a "capping agent" in order to neutralize reactive species generated in the cleavage reaction. Suitable capping agents for this purpose include amines, e.g., ethanolamine or propanolamine. In embodiments, cleavage may be accomplished by using a modified nucleotide as the cleavable site (e.g., uracil, 8oxoG, 5-mC, 5-hmC) that is removed or nicked via a corresponding DNA glycosylase, endonuclease, or combination thereof.

In embodiments, cleavage of a surface-immobilized oligonucleotide including a modified nucleotide, for example, including one or more uracils, may be accomplished using a cleavage mixture including about 150 mM to about 300 mM glycine-KOH, about 5 mM to about 15 mM MgCl2, about 0.05% to about 0.15% Triton X-100, and about 0.05 U/uL to about 0.2 U/uL uracil DNA glycosylase (UDG). In embodiments, the cleavage mixture can have a pH greater than pH 8.0, greater than pH 8.5, greater than pH 9.0, greater than pH 9.5, or greater than pH 10.0. In other embodiments, the cleavage mixture can have a pH ranging, for example, from about pH 8.0 to about pH 10.0, from about pH 8.5 to about pH 10.0, or from about pH 9.0 to about pH 10.0. For example, the cleavage mixture is applied to an immobilized oligonucleotide including one or more uracils, incubated at about 37° C. to about 42° C. for 10 min, and then incubated at about 65° C. to about 72° C. for 30 min. Following cleavage, the surface is washed with wash buffer, followed by subsequent washes with about 0.05M NaOH to about 0.15M NaOH, and another wash with wash buffer.

In embodiments, the oligonucleotide moiety includes one or more phosphorothioate nucleotides. In embodiments, the oligonucleotide moiety includes a plurality of phosphorothioate nucleotides. In embodiments, about or at least about 20%, 30%, 40%, 50%, 60%, 70%, 80%, 90%, or about 100% of the nucleotides in the oligonucleotide moiety are phosphorothioate nucleotides. In embodiments, most of the nucleotides in the oligonucleotide moiety are phosphorothioate nucleotides. In embodiments, all of the nucleotides in the oligonucleotide moiety are phosphorothioate nucleotides. In embodiments, none of the nucleotides in the oligonucleotide moiety are phosphorothioate nucleotides. In embodiments, only the last, or last and penultimate, phosphodiester bonds at both the 3' and 5' ends of the oligonucleotides will be substituted with phosphorothioate bonds.

In some embodiments, the oligonucleotide moiety is capable of hybridizing to a complementary sequence of a template nucleic acid. In embodiments, the oligonucleotide moiety includes DNA. In embodiments, the oligonucleotide moiety includes RNA. In embodiments, the oligonucleotide moiety is DNA. In embodiments, the oligonucleotide moiety is RNA. In embodiments, the oligonucleotide moiety includes a single-stranded DNA. In embodiments, the oligonucleotide moiety includes a single-stranded RNA. In embodiments, the oligonucleotide moiety is a single-stranded DNA. In embodiments, the oligonucleotide moiety is a single-stranded RNA. In embodiments, the oligonucleotide moiety is a nucleic acid sequence complementary to a target polynucleotide (e.g., complementary to a common adapter sequence of the target polynucleotide).

In some embodiments, the particle includes a plurality of bioconjugate reactive moieties. In embodiments, the particle includes a plurality of azide moieties, alkyne moieties, dibenzocyclooctyne (DBCO) moieties, epoxy moieties, or isocyanate moieties. In some embodiments, the particle includes a plurality of oligonucleotide moieties (e.g., ssDNA moieties).

In another aspect is provided a polynucleotide adapter, including a first strand including a first binding sequence and a first tail sequence; and a second strand including a second binding sequence and a second tail sequence, wherein at least a portion of the first binding sequence is hybridized to a portion of the second binding sequence; wherein the first tail sequence includes SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123 and the second tail sequence includes SEQ ID NO:4, SEQ ID NO:102, SEQ ID NO:104, SEQ ID NO:106, SEQ ID NO:108, SEQ ID NO:134, SEQ ID NO:136, SEQ ID NO:138, or SEQ ID NO:140, and the first binding sequence includes SEQ ID NO:152 and the second binding sequence includes SEQ ID NO:178. In embodiments, the polynucleotide adapter is a Y polynucleotide adapter. In embodiments, the polynucleotide adapter is a hairpin adapter. In embodiments, the hairpin adapter includes a cleavable site (e.g., a cleavable site as described herein). In embodiments, the first tail sequence is ligated (e.g., covalently attached together) to the second tail sequence.

In an aspect is provided a polynucleotide adapter formed by annealing of partially complementary first and second polynucleotide strands, wherein at least one of the strands includes a polynucleotide sequence complementary to the sequence of any one of the sequences of SEQ ID NO:1 to SEQ ID NO:148. In embodiments, the polynucleotide adapter is a Y polynucleotide adapter. In embodiments, the polynucleotide adapter is a hairpin adapter. In embodiments, the hairpin adapter includes a cleavable site. In embodiments, the polynucleotide adapter further includes a sequencing primer binding sequence (e.g., 5'-AGATCGGAAGAGCACACGTCTGAACTCCAGTCA (SEQ ID NO:149), 5'-AGATCGGAAGAGCGTCGTGTAGGGAAAGAGTGT (SEQ ID NO:150), 5'-GCCTTGGCACCCGAGAATTCCA (SEQ ID NO:151), 5'-ACACTCTTTCCCTACACGACGCTCTTCCGATCT (SEQ ID NO:152), 5'-CACTCTTTCCCTACACGACGCTCTTCCGATCT (SEQ ID NO:153), 5'-CGGTCTCGGCATTCCTGCTGAACCGCTCTTCCGATCT (SEQ ID NO:154), 5'-ACTCTTTCCCTACACGACGCTCTTCCGATCT (SEQ ID NO:155), 5'-GTGACTGGAGTTCAGACGTGTGCTCTTCCGATCT (SEQ ID NO:156), 5'-CAAGCAGAAGACGGCATACGA (SEQ ID NO:157), 5'-CGACTCACTATAGGGAGAGCGGC (SEQ ID NO:158), 5'-AAGAACATCGATTTTCCATGGCAG (SEQ ID NO:159), 5'-AACGCCAAACCTACGGCTTTACTTCCTGTGGCT (SEQ ID NO:160), 5'-TCTTGAGTCATTCGCAGGGCATGTGCCAGACCT (SEQ ID NO:161), 5'-TCGGCGTTGTCTGCTATCGTTCTTGGCACTCCT (SEQ ID NO:162), 5'-GGAGCAATAACCATAAGGCCGTTGACAAGCCCT (SEQ ID NO:163), 5'-GGCGTATTGCCTTGGTTCTGGCAGCCTCATTGT (SEQ ID NO:164), 5'-CAGCAGAGGGAACGATTTCAACTTCCTGTGGCT (SEQ ID NO:165), 5'-CTACTGCAAGGGTGTCTAGAATGTGCCAGACCT (SEQ ID NO:166), 5'-GACCGACTCGTGAAACGTAATCTTGGCACTCCT (SEQ ID NO:167), 5'-ACACATTCTTTGCGCCCAGAGTTGACAAGCCCT (SEQ ID NO:168), 5'-ATTTCATTCGACACCCGGTCGCAGCCTCATTGT (SEQ ID NO:169), or a complement thereof). In embodiments, the polynucleotide adapter further includes an index sequence (e.g., a barcode or UMI, as depicted in FIGS. 1A-1C and FIGS. 3A-3B). In embodiments, the index sequence includes 1, 2, 3, 4, 5, 6, 7, 8, 9, 10, 11, or 12 nucleotides. In embodiments, the index sequence is 5 nucleotides. In embodiments, the index sequence is 6 nucleotides. In embodiments, the index sequence is 8 nucleotides. In embodiments, the index sequence is 12 nucleotides.

In an aspect is provided a kit. In embodiments, the kit includes the compositions, solid supports, and/or adapters (e.g., the oligonucleotides) as described herein. Generally, the kit includes one or more containers providing a composition and one or more additional reagents (e.g., a buffer suitable for polynucleotide extension). In embodiments, the kit includes a solid support (e.g., a patterned substrate), wherein the support includes a plurality of immobilized oligonucleotides. When the solid support includes an array of discrete sites of immobilized oligonucleotides, it may be referred to as an array. The kit may also include a template nucleic acid (DNA and/or RNA), one or more primer polynucleotides, nucleoside triphosphates (including, e.g., deoxyribonucleotides, ribonucleotides, particles, labeled nucleotides, and/or modified nucleotides), buffers, salts, and/or labels (e.g., fluorophores). In embodiments, the kit includes an array with particles (e.g., particles including immobilized oligonucleotides) already loaded into the wells. In embodiments, the array is filled with a buffered solution. Alternatively, in embodiments, the array is not filled with a buffered solution. In embodiments, the array is dry. In embodiments, the array with particles already loaded into the wells is filled with a buffered solution. In embodiments, the particles are in a container. In embodiments, the particles are in aqueous suspension or as a powder within the container. The container may be a storage device or other readily usable vessel capable of storing and protecting the particles. In embodiments, the kit includes a first polynucleotide adapter including the sequence of SEQ ID NO:1 to SEQ ID NO:148. In embodiments, the kit further includes a second polynucleotide adapter including the sequence of SEQ ID NO:1 to SEQ ID NO:148, wherein the first polynucleotide adapter and the second polynucleotide adapter are different (e.g., the first polynucleotide adapter and the second polynucleotide adapter include different sequences). In embodiments, the kit includes a polymerase and a plurality of deoxynucleotides (dNTPs).

In embodiments, the kit includes a first polynucleotide adapter including the sequence of SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and includes a second polynucleotide adapter including the sequence of SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132.

In embodiments, the kit includes a first polynucleotide adapter including the sequence of SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and includes a second polynucleotide adapter including the sequence of SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132.

In embodiments, the kit includes a first polynucleotide adapter including the sequence of SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and includes a second polynucleotide adapter including the sequence of SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148.

In embodiments, the kit includes a first polynucleotide adapter include the sequence of SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and includes a second polynucleotide adapter including the sequence of SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148.

In an aspect is provided a kit including an oligonucleotide, wherein the oligonucleotide includes a first sequencing primer sequence, a platform primer sequence, a platform primer binding sequence, and a second sequencing primer binding sequence, wherein the platform primer sequence includes a sequence selected from SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123; and the platform primer binding sequence includes a sequence selected from SEQ ID NO:4, SEQ ID NO:102, SEQ ID NO:104, SEQ ID NO:106, SEQ ID NO:108, SEQ ID NO:134, SEQ ID NO:136, SEQ ID NO:138, or SEQ ID NO:140. In embodiments, the kit includes a plurality of oligonucleotides (e.g., the oligonucleotide as described herein), wherein the oligonucleotides of the plurality include the same platform primer sequence. In embodiments, the oligonucleotides of the plurality of oligonucleotides include an index sequence.

In an aspect is provided a kit including a first oligonucleotide including a first sequencing primer sequence and a second sequencing primer binding sequence; a second oligonucleotide including from 5' to 3', a first platform primer sequence and a sequence complementary to the first sequencing primer sequence (e.g., complementary to the SP1 or SP2 sequence, as described herein); a third oligonucleotide including from 5' to 3', a second platform primer sequence and a sequence complementary to the second sequencing primer binding sequence (e.g., complementary to the SP1 or SP2 sequence, as described herein); wherein the first platform primer sequence includes a sequence selected from SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123; and the second platform primer sequence include a sequence selected from SEQ ID NO:7, SEQ ID NO:30, SEQ ID NO:87, SEQ ID NO:89, SEQ ID NO:91, SEQ ID NO:86, SEQ ID NO:118, SEQ ID NO:120, SEQ ID NO:122, or SEQ ID NO:124.

In embodiments, the kit includes a sequencing polymerase, and one or more amplification polymerases (e.g., Bst Lf, BSU, Bst 2.0, or Bst 3.0). In embodiments, the sequencing polymerase is capable of incorporating modified nucleotides. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ, DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol υ DNA polymerase, or a thermophilic nucleic acid polymerase (e.g., Therminator γ, 9° N polymerase (exo-), Therminator II, Therminator III, or Therminator IX). In embodiments, the DNA polymerase is a thermophilic nucleic acid polymerase. In embodiments, the DNA polymerase is a modified archaeal DNA polymerase. In embodiments, the polymerase is a reverse transcriptase. In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes). In embodiments, the kit includes a strand-displacing polymerase. In embodiments, the kit includes a strand-displacing polymerase, such as a phi29 polymerase, phi29 mutant polymerase, or a thermostable phi29 mutant polymerase.

In embodiments, the kit includes a buffered solution. Typically, the buffered solutions contemplated herein are made from a weak acid and its conjugate base or a weak base and its conjugate acid. For example, sodium acetate and acetic acid are buffer agents that can be used to form an acetate buffer. Other examples of buffer agents that can be used to make buffered solutions include, but are not limited to, Tris, bicine, tricine, HEPES, TES, MOPS, MOPSO and PIPES. Additionally, other buffer agents that can be used in enzyme reactions, hybridization reactions, and detection reactions are known in the art. In embodiments, the buffered solution can include Tris. With respect to the embodiments described herein, the pH of the buffered solution can be modulated to permit any of the described reactions. In some embodiments, the buffered solution can have a pH greater than pH 7.0, greater than pH 7.5, greater than pH 8.0, greater than pH 8.5, greater than pH 9.0, greater than pH 9.5, greater than pH 10, greater than pH 10.5, greater than pH 11.0, or greater than pH 11.5. In other embodiments, the buffered solution can have a pH ranging, for example, from about pH 6 to about pH 9, from about pH 8 to about pH 10, or from about pH 7 to about pH 9. In embodiments, the buffered solution can comprise one or more divalent cations. Examples of divalent cations can include, but are not limited to, $Mg^{2+}$, $Mn^{2+}$, $Zn^{2+}$, and $Ca^{2+}$. In embodiments, the buffered solution can contain one or more divalent cations at a concentration sufficient to permit hybridization of a nucleic acid. In embodiments, the buffered solution includes about 10 mM Tris, about 20 mM Tris, about 30 mM Tris, about 40 mM Tris, or about 50 mM Tris. In embodiments the buffered solution includes about 50 mM NaCl, about 75 mM NaCl, about 100 mM NaCl, about 125 mM NaCl, about 150 mM NaCl, about 200 mM NaCl, about 300 mM NaCl, about 400 mM NaCl, or about 500 mM NaCl. In embodiments, the buffered solution includes about 0.05 mM EDTA, about 0.1 mM EDTA, about 0.25 mM EDTA, about 0.5 mM EDTA, about 1.0 mM EDTA, about 1.5 mM EDTA or about 2.0 mM EDTA. In embodiments, the buffered solution includes about 0.01% Triton X-100, about 0.025% Triton X-100, about 0.05% Triton X-100, about 0.1% Triton X-100, or about 0.5% Triton X-100. In embodiments, the buffered solution includes 20 mM Tris pH 8.0, 100 mM NaCl, 0.1 mM EDTA, 0.025% Triton X-100. In embodiments, the buffered solution includes 20 mM Tris pH 8.0, 150 mM NaCl, 0.1 mM EDTA, 0.025% Triton X-100. In embodiments, the buffered solution includes 20 mM Tris pH 8.0, 300 mM NaCl, 0.1 mM EDTA, 0.025% Triton X-100. In embodiments, the buffered solution includes 20 mM Tris pH 8.0, 400 mM NaCl, 0.1 mM EDTA, 0.025% Triton X-100. In embodiments, the buffered solution includes 20 mM Tris pH 8.0, 500 mM NaCl, 0.1 mM EDTA, 0.025% Triton X-100.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits. In embodiments, the kit includes, without limitation, nucleic acid primers, probes, adapters, enzymes, and the like, and are each packaged in a container, such as, without limitation, a vial, tube or bottle, in a package suitable for commercial distribution, such as, without limitation, a box, a sealed pouch, a blister pack and a carton. The package typically contains a label or packaging insert indicating the uses of the packaged materials. As used herein, "packaging materials" includes any article used in the packaging for distribution of reagents in a kit, including without limitation containers, vials, tubes, bottles, pouches, blister packaging, labels, tags, instruction sheets and package inserts.

Adapters and/or primers may be supplied in the kits ready for use, as concentrates-requiring dilution before use, or in a lyophilized or dried form requiring reconstitution prior to use. If required, the kits may further include a supply of a suitable diluent for dilution or reconstitution of the primers and/or adapters. Optionally, the kits may further include supplies of reagents, buffers, enzymes, and dNTPs for use in carrying out nucleic acid amplification and/or sequencing. Further components, which may optionally be supplied in the kit, include sequencing primers suitable for sequencing templates prepared using the methods described herein.

In embodiments, the kit includes an end repair mix, or an enzymatic fragmentation solution and end repair mix, the adapters as described herein, including a ligase, primers, enzymes, and a plurality of dNTPs.

In an aspect is provided an oligonucleotide, wherein the oligonucleotide includes any one of the sequences of SEQ ID NO:1 to SEQ ID NO:169. In embodiments, the oligonucleotide includes two or more sequences selected from SEQ ID NO:1 to SEQ ID NO:169. In embodiments, the oligonucleotide includes a sequencing primer binding sequence (e.g., 5'-AGATCGGAAGAGCACACGTCT-GAACTCCAGTCA (SEQ ID NO:149), 5'-AGATCG-GAAGAGCGTCGTGTAGGGAAAGAGTGT (SEQ ID NO:150), 5'-GCCTTGGCACCCGAGAATTCCA (SEQ ID NO:151), 5'-ACACTCTTTCCCTACACGACGCTCTTCC-GATCT (SEQ ID NO:152), 5'-CACTCTTTCCCTA-CACGACGCTCTTCCGATCT (SEQ ID NO:153), 5'-CGGTCTCGGCATTCCTGCTGAACCGCTCTTCC-GATCT (SEQ ID NO:154), 5'-ACTCTTTCCCTA-CACGACGCTCTTCCGATCT (SEQ ID NO:155), 5'-GTGACTGGAGTTCAGACGTGTGCTCTTCCGATCT (SEQ ID NO:156), 5'-CAAGCAGAAGACGGCATACGA (SEQ ID NO:157), 5'-CGACTCACTATAGG-GAGAGCGGC (SEQ ID NO:158), 5'-AAGAACATCGAT-TTTCCATGGCAG (SEQ ID NO:159), 5'-AACGC-CAAACCTACGGCTTTACTTCCTGTGGCT (SEQ ID NO:160), 5'-TCTTGAGTCATTCGCAGGG-CATGTGCCAGACCT (SEQ ID NO:161), 5'-TCGGCGTTGTCTGCTATCGTTCTTGGCACTCCT (SEQ ID NO:162), 5'-GGAGCAATAACCAT-AAGGCCGTTGACAAGCCCT (SEQ ID NO:163), 5'-GGCGTATTGCCTTGGTTCTGGCAGCCTCATTGT (SEQ ID NO:164), 5'-CAGCAGAGGGAACGATTT-CAACTTCCTGTGGCT (SEQ ID NO:165), 5'-CTACTGCAAGGGTGTCTAGAATGTGCCAGACCT (SEQ ID NO:166), 5'-GACCGACTCGT-GAAACGTAATCTTGGCACTCCT (SEQ ID NO:167), 5'-ACACATTCTTTGCGCCCAGAGTTGACAAGCCCT (SEQ ID NO:168), 5'-ATTTCAT-TCGACACCCGGTCGCAGCCTCATTGT (SEQ ID NO:169), or a complement thereof). In embodiments, the oligonucleotide further includes an index sequence (e.g., a barcode or UMI, as depicted in FIGS. 1A-1C and FIGS. 3A-3B). In embodiments, the index sequence includes 1, 2, 3, 4, 5, 6, 7, 8, 9, 10, 11, or 12 nucleotides. In embodiments, the index sequence is 5 nucleotides. In embodiments, the index sequence is 6 nucleotides. In embodiments, the index sequence is 8 nucleotides. In embodiments, the index sequence is 12 nucleotides. In general, the index is of sufficient length and includes sequences that are sufficiently different to allow the identification of associated features or nucleic acid sequences based on barcodes with which they are associated.

In embodiments, the kit includes a first oligonucleotide (e.g., a first adapter) including any one of the sequences of SEQ ID NO:1 to SEQ ID NO:169. In embodiments, the oligonucleotide includes two or more sequences selected from SEQ ID NO:1 to SEQ ID NO:169. In embodiments, the kit further includes a second oligonucleotide (e.g., a second adapter) including any one of the sequences of SEQ ID NO:1 to SEQ ID NO:148. In embodiments, the first adapter and the second adapter sequences are different (i.e., the first adapter and the second adapter sequences include different sequences described in Table 1, having different SEQ ID NOs). In embodiments, the first and/or second adapter further includes a sequencing primer binding sequence (e.g., 5'-AGATCGGAAGAGCACACGTCTGAACTCCAGTCA (SEQ ID NO:149), 5'-AGATCG-GAAGAGCGTCGTGTAGGGAAAGAGTGT (SEQ ID NO:150), 5'-GCCTTGGCACCCGAGAATTCCA (SEQ ID NO:151), 5'-ACACTCTTTCCCTACACGACGCTCTTCCGATCT (SEQ ID NO:152), 5'-CACTCTTTCCCTACACGACGCTCTTCCGATCT (SEQ ID NO:153), 5'-CGGTCTCGGCATTCCTGCTGAACCGCTCTTCCGATCT (SEQ ID NO:154), 5'-ACTCTTTCCCTACACGACGCTCTTCCGATCT (SEQ ID NO:155), 5'-GTGACTGGAGTTCAGACGTGTGCTCTTCCGATCT (SEQ ID NO:156), 5'-CAAGCAGAAGACGGCATACGA (SEQ ID NO:157), 5'-CGACTCACTATAGGGAGAGCGGC (SEQ ID NO:158), 5'-AAGAACATCGATTTTCCATGGCAG (SEQ ID NO:159), 5'-AACGCCAAACCTACGGCTTTACTTCCTGTGGCT (SEQ ID NO:160), 5'-TCTTGAGTCATTCGCAGGGCATGTGCCAGACCT (SEQ ID NO:161), 5'-TCGGCGTTGTCTGCTATCGTTCTTGGCACTCCT (SEQ ID NO:162), 5'-GGAGCAATAACCATAAGGCCGTTGACAAGCCCT (SEQ ID NO:163), 5'-GGCGTATTGCCTTGGTTCTGGCAGCCTCATTGT (SEQ ID NO:164), 5'-CAGCAGAGGGAACGATTTCAACTTCCTGTGGCT (SEQ ID NO:165), 5'-CTACTGCAAGGGTGTCTAGAATGTGCCAGACCT (SEQ ID NO:166), 5'-GACCGACTCGTGAAACGTAATCTTGGCACTCCT (SEQ ID NO:167), 5'-ACACATTCTTTGCGCCCAGAGTTGACAAGCCCT (SEQ ID NO:168), 5'-ATTTCATTCGACACCCGGTCGCAGCCTCATTGT (SEQ ID NO:169), or a complement thereof). In embodiments, the polynucleotide adapter further includes an index sequence (e.g., a barcode or UMI, as depicted in FIGS. 1A-1C and FIGS. 3A-3B).

In embodiments, each index in a plurality of indices differs from every other index in the plurality by at least three nucleotide positions, such as at least 3, 4, 5, 6, 7, 8, 9, 10, or more nucleotide positions. In embodiments, the indices are selected to form a known set of indices, e.g., the set of indices may be distinguished by a particular Hamming distance. An index may include a unique sequence (e.g., an index sequence) that gives the oligonucleotide its identifying functionality. The unique sequence may be random or non-random. In embodiments, the index is known (i.e., the nucleic sequence is known before sequencing) and is sorted into a basis-set according to their Hamming distance.

In embodiments, the index is taken from a "pool" or "set" or "basis-set" of potential index sequences. The set of indices may be selected using any suitable technique, e.g., randomly, or such that the sequences allow for error detection and/or correction, or having a particular feature, such as by being separated by a certain distance (e.g., Hamming distance). In embodiments, the method includes selecting a basis-set of indices having a specified Hamming distance (e.g., a Hamming distance of 10; a Hamming distance of 5). The pool may have any number of potential index sequences, e.g., at least 100, at least 300, at least 500, at least 1,000, at least 3,000, at least 5,000, at least 10,000, at least 30,000, at least 50,000, at least 100,000, at least 300,000, at least 500,000, or at least 1,000,000 barcode sequences. In embodiments, the index is at least 5, 6, 7, 8, 9, 10, 11, 12, 13, 14, or 15 nucleotides in length. In embodiments, the index sequence includes 1, 2, 3, 4, 5, 6, 7, 8, 9, 10, 11, or 12 nucleotides. In embodiments, the index sequence is 5 nucleotides. In embodiments, the index sequence is 6 nucleotides. In embodiments, the index sequence is 8 nucleotides. In embodiments, the index sequence is 12 nucleotides.

In an aspect is provided a nucleic acid sequencing device, including: a stage configured to hold the solid support (e.g., an array) as described herein; an array as described herein, including embodiments; and a detector for obtaining sequencing data. In some embodiments, the detector is an imaging detector, such as a CCD, EMCCD, or s-CMOS detector.

In an aspect is provided a nucleic acid sequencing device, including: a stage configured to hold an array or solid support as described herein, including embodiments; an array or solid support as described herein, including embodiments; and a detector for obtaining sequencing data. In some embodiments, the detector is an imaging detector, such as a CCD, EMCCD, or s-CMOS detector.

In an aspect is provided a microfluidic device including the solid support as described herein. For example, a microfluidic device may be a nucleic acid sequencing device. The term "nucleic acid sequencing device" and the like means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, for the purpose of determining the nucleic acid sequence of a template polynucleotide. Nucleic acid sequencing devices may further include valves, pumps, and specialized functional coatings on interior walls. Nucleic acid sequencing devices may include a receiving unit, or platen, that orients the flow cell such that a maximal surface area of the flow cell is available to be exposed to an optical lens. Other nucleic acid sequencing devices include those provided by Singular Genomics™ (e.g., the G4™ system), Illumina™ (e.g., HiSeq™, MiSeq™, NextSeq™, or NovaSeg™ systems), Life Technologies™ (e.g., ABI PRISM™, or SOLiD™ systems), Pacific Biosciences (e.g., systems using SMRT™ Technology such as the Sequel™ or RS II™ systems), or Qiagen (e.g., Genereader™ system). Nucleic acid sequencing devices may further include fluidic reservoirs (e.g., bottles), valves, pressure sources, pumps, sensors, control systems, valves, pumps, and specialized functional coatings on interior walls. In embodiments, the device includes a plurality of a sequencing reagent reservoirs and a plurality of clustering reagent reservoirs. In embodiments, the clustering reagent reservoir includes amplification reagents (e.g., an aqueous buffer containing enzymes, salts, and nucleotides, denaturants, crowding agents, etc.) In embodiments, the reservoirs include sequencing reagents (such as an aqueous buffer containing enzymes, salts, and nucleotides); a wash solution (an aqueous buffer); a cleave solution (an aqueous buffer containing a cleaving agent, such as a reducing agent); or a cleaning solution (a dilute bleach solution, dilute NaOH solution, dilute HCl solution, dilute antibacterial solution, or water). The fluid of each of the reservoirs can vary. The fluid can be, for example, an aqueous solution which may contain buffers (e.g., saline-sodium citrate (SSC), ascorbic acid, tris(hydroxymethyl)aminomethane or "Tris"), aqueous salts (e.g., KCl or $(NH_4)_2SO_4$), nucleotides, polymerases, cleaving agent (e.g., tri-n-butyl-phosphine, triphenyl phosphine and its sulfonated versions (i.e., tris(3-sulfophenyl)-phosphine, TPPTS), and tri(carboxyethyl)phosphine (TCEP) and its salts, cleaving agent scavenger compounds (e.g., 2'-Dithiobisethanamine or 11-Azido-3,6,9-trioxaundecane-1-amine), chelating agents (e.g., EDTA), detergents, surfactants, crowding agents, or stabilizers (e.g., PEG, Tween, BSA). Non-limited examples of reservoirs include cartridges, pouches, vials, containers, and eppendorf tubes. In embodiments, the device is configured to perform fluorescent imaging. In embodiments, the device includes one or more light sources (e.g., one or more lasers). In embodiments, the illuminator or light source is a radiation source (i.e., an origin or generator of propagated electromagnetic energy) providing incident light to the sample. A radiation source can include an illumination source producing electromagnetic radiation in the ultraviolet (UV) range (about 200 to 390 nm), visible (VIS) range (about 390 to 770 nm), or infrared (IR) range (about 0.77 to 25 microns), or other range of the electromagnetic spectrum. In embodiments, the illuminator or light source is a lamp such as an arc lamp or quartz halogen lamp. In embodiments, the illuminator or light source is a coherent light source. In embodiments, the light source is a laser, LED (light emitting diode), a mercury or tungsten lamp, or a super-continuous diode. In embodiments, the light source provides excitation beams having a wavelength between 200 nm to 1500 nm. In embodiments, the laser provides excitation beams having a wavelength of 405 nm, 470 nm, 488 nm, 514 nm, 520 nm, 532 nm, 561 nm, 633 nm, 639 nm, 640 nm, 800 nm, 808 nm, 912 nm, 1024 nm, or 1500 nm. In embodiments, the illuminator or light source is a light-emitting diode (LED). The LED can be, for example, an Organic Light Emitting Diode (OLED), a Thin Film Electroluminescent Device (TFELD), or a Quantum dot based inorganic organic LED. The LED can include a phosphorescent OLED (PHOLED). In embodiments, the nucleic acid sequencing device includes an imaging system (e.g., an imaging system as described herein). The imaging system capable of exciting one or more of the identifiable labels (e.g., a fluorescent label) linked to a nucleotide and thereafter obtain image data for the identifiable labels. The image data (e.g., detection data) may be analyzed by another component within the device. The imaging system may include a system described herein and may include a fluorescence spectrophotometer including an objective lens and/or a solid-state imaging device. The solid-state imaging device may include a charge coupled device (CCD) and/or a complementary metal oxide semiconductor (CMOS). The system may also include circuitry and processors, including systems using microcontrollers, reduced instruction set computers (RISC), application specific integrated circuits (ASICs), field programmable gate array (FPGAs), logic circuits, and any other circuit or processor capable of executing functions described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. In embodiments, the device includes a thermal control assembly useful to control the temperature of the reagents.

III. Methods

In an aspect is provided a method of immobilizing a polynucleotide, the method including: contacting the solid support as described herein with a polynucleotide including a primer binding sequence (e.g., a sequence complementary to an immobilized oligonucleotide); hybridizing the primer binding sequence to a first immobilized oligonucleotide of the second plurality of immobilized oligonucleotides; and extending the first immobilized oligonucleotide with a polymerase to form a first immobilized polynucleotide. In embodiments, the solid support includes a first plurality of immobilized oligonucleotides, and a second plurality of immobilized oligonucleotides, wherein the immobilized oligonucleotides of the first plurality include a sequence selected from SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123, and the immobilized oligonucleotides of the second plurality include a sequence selected from SEQ ID NO:7, SEQ ID NO:30, SEQ ID NO:87, SEQ ID NO:89, SEQ ID NO:91, SEQ ID NO:86, SEQ ID NO:118, SEQ ID NO:120, SEQ ID NO:122, or SEQ ID NO:124.

In embodiments, the polynucleotide further includes a primer sequence, and the immobilized polynucleotide includes a complement of the primer sequence. In embodiments, the method includes hybridizing the complement of the primer sequence to a second immobilized oligonucleotide of the first plurality of immobilized oligonucleotides and extending the second immobilized oligonucleotide with a polymerase to form a second immobilized polynucleotide. In embodiments, the method further includes amplifying the first and second immobilized polynucleotides to form amplification products.

In embodiments, the polynucleotide further includes a primer sequence, and extending the immobilized oligonucleotide includes forming a first immobilized polynucleotide including a complement of the primer sequence. In embodiments, the method includes hybridizing the complement of the primer sequence to a second immobilized primer of the first plurality of immobilized oligonucleotides, and extending the second immobilized primer with a polymerase to form a second immobilized polynucleotide. In embodiments, the method includes amplifying the first and second immobilized polynucleotides to form amplification products.

In embodiments of the methods provided herein, the contacting step is performed under non-hybridizing conditions. In embodiments of the methods provided herein, the contacting step is performed under non-hybridizing conditions initially, then the conditions are changed to hybridizing conditions. In embodiments of the methods provided herein, the contacting step is performed under hybridizing conditions initially, then the conditions are changed to non-hybridizing conditions. In general, contacting the sample under non-hybridizing conditions can facilitate distribution of target polynucleotides within a polymeric particle prior to subsequent steps (e.g., amplification). Examples of non-hybridizing conditions include but are not limited to low salt, high temperature, and/or presence of additives such as formamide. The precise nature of non-hybridizing conditions (e.g., the temperature, or the amounts of salt or formamide) will vary with factors such as the length, GC-content, or melting temperature (Tm) of primers (or the target-hybridizing portion thereof) present in the reaction. In embodiments, primers are designed to have Tm's within 15, 10, 5, 3 or fewer degrees of one another. In embodiments, non-hybridizing conditions comprises a temperature that is about or at least about 5, 10, 15, 20, or more degrees above the average Tm of primers in the reaction.

In embodiments, amplifying includes 1 to 100 bridge-PCR amplification cycles. In embodiments, amplifying includes 5 to 50 bridge-PCR amplification cycles. In embodiments, amplifying includes 20 to 40 bridge-PCR amplification cycles. In embodiments, amplifying includes about 5 minutes to about 4 hours of solid-phase rolling circle amplification (RCA), solid-phase exponential rolling circle amplification (eRCA), solid-phase recombinase polymerase amplification (RPA), solid-phase helicase dependent amplification (HDA), or template walking amplification. In embodiments, amplifying includes about 30 minutes to about 2 hours of solid-phase rolling circle amplification (RCA).

In embodiments, the method includes sequencing the amplification product(s). Sequencing includes, for example, detecting a sequence of signals within the particle. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the readout is accomplished by epifluorescence imaging. A variety of sequencing chemistries are available, non-limiting examples of which are described herein In embodiments, sequencing includes hybridizing a sequencing primer (e.g., a sequencing primer as described herein, for example SEQ ID NO:152) to the amplification product, or a complement thereof, and contacting the sequencing primer with a sequencing solution including one or more modified nucleotides including a reversible terminator, and monitoring the sequential incorporation of complementary nucleotides to generate one or more sequencing reads, wherein the reversible terminator is removed prior to the introduction of the next complementary nucleotide.

In an aspect is provided a method of sequencing a template polynucleotide. In embodiments, the method includes contacting a solid support (e.g., a solid support as described herein) with a sample including a template polynucleotide. In embodiments, the method include hybridizing the template polynucleotide to the oligonucleotide moiety. In embodiments, the method includes extending the oligonucleotide moiety to generate a complement of the template polynucleotide immobilized to the particle. In embodiments, the method includes forming a plurality of amplification products by subjecting the solid support to suitable amplification conditions (e.g., as described herein). In embodiments, the method includes contacting the immobilized template polynucleotide, or complement thereof, with a sequencing primer, and with a polymerase, incorporating one or more nucleotides into an extension strand. In embodiments, the method includes detecting the one or more nucleotides incorporated into the extension strand.

In embodiments, sequencing includes hybridizing a sequencing primer to an amplification product, or a complement thereof, incorporating one or more modified nucleotides into the sequencing primer with a polymerase to create an extension strand, and detecting the one or more incorporated nucleotides.

In embodiments, the first immobilized oligonucleotide includes a cleavable site. In embodiments, the second immobilized oligonucleotide includes a cleavable site. In embodiments, the method includes cleaving the cleavable site (e.g., contacting the cleavable site with a cleaving agent) and removing the immobilized polynucleotide from the solid support. In embodiments, cleaving the cleavable site includes contacting the cleavable site with a cleaving agent. In embodiments, the cleaving agent is selected from sodium periodate, RNase, formamidopyrimidine DNA glycosylase (Fpg), endonuclease, uracil DNA glycosylase (UDG), TCEP, THPP, sodium dithionite ($Na_2S_2O_4$), hydrazine ($N_2H_4$), Pd(0), or ultraviolet radiation.

In an aspect is provided a method of immobilizing a template nucleic acid on a solid support, the method including: a) contacting the composition (e.g., the solid support) as described herein with a template polynucleotide, wherein the template nucleic acid includes a sequence complementary to a first immobilized polynucleotide; b) extending the first immobilized polynucleotide with a polymerase to generate an immobilized complement of the template nucleic acid; c) removing the template polynucleotide and annealing the immobilized complement of the template nucleic acid to a second immobilized polynucleotide; d) extending the second immobilized polynucleotide with a polymerase to generate an immobilized template nucleic acid.

In embodiments, removing the template polynucleotide includes denaturing the duplex, including thermal or chemical denaturation (e.g., chemical denaturation in 100 mM sodium hydroxide solution). In embodiments, removing includes denaturing the duplex with a formamide solution.

In an aspect is provided a method of amplifying template nucleic acid molecules, the method including i) fragmenting a polynucleotide sample to generate a plurality of polynucleotide fragments each having a first end and a second end; ii) ligating a first adapter polynucleotide to the first end of each the polynucleotide fragments (e.g., using a suitable ligase enzyme, such as a T4 DNA ligase); iii) ligating a second adapter polynucleotide to the second end of each the polynucleotide fragments; iv) annealing an amplification primer to the first adapter, the second adapter, or both the first and the second adapter, and extending the amplification primer with an enzyme to generate amplification products, wherein the amplification products include a plurality template nucleic acid molecules, each including a first adapter polynucleotide or a complement thereof and a second adapter polynucleotide or a complement thereof, wherein the first adapter polynucleotide and the second adapter polynucleotide each independently include as described herein (e.g., a sequence of SEQ ID NO:1 to SEQ ID NO:148). In embodiments, the method further includes sequencing the amplification products.

In embodiments, the sequencing includes sequencing-by-synthesis, sequencing by ligation, or pyrosequencing. In embodiments, generating a first sequencing read or a second sequencing read includes a sequencing by synthesis process. In embodiments, generating a sequencing read includes executing a plurality of sequencing cycles, each cycle including extending the sequencing primer by incorporating a nucleotide or nucleotide analogue using a polymerase and detecting a characteristic signature indicating that the nucleotide or nucleotide analogue has been incorporated. In embodiments, the method includes sequencing the first and/or the second strand of a double-stranded amplification product by extending a sequencing primer hybridized thereto. A variety of sequencing methodologies can be used such as sequencing-by-synthesis (SBS), pyrosequencing, sequencing by ligation (SBL), or sequencing by hybridization (SBH). In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. A plurality of different nucleic acid fragments that have been attached at different locations of an array can be subjected to an SBS technique under conditions where events occurring for different templates can be distinguished due to their location in the array. In embodiments, the sequencing step includes annealing and extending a sequencing primer to incorporate a detectable label that indicates the identity of a nucleotide in the target polynucleotide, detecting the detectable label, and repeating the extending and detecting steps. In embodiments, the methods include sequencing one or more bases of a target nucleic acid by extending a sequencing primer hybridized to a target nucleic acid (e.g., an amplification product produced by the amplification methods described herein). In embodiments, the sequencing step may be accomplished by a sequencing-by-synthesis (SBS) process. In embodiments, sequencing comprises a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 10,738,072, 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' block may be removed to allow addition of the next successive nucleotide. By ordering the products derived using these modified nucleotides it is possible to deduce the DNA sequence of the DNA template.

Sequencing includes, for example, detecting a sequence of signals. In embodiments, sequencing includes detecting a sequence of signals and generating one or more sequencing reads. Examples of sequencing include, but are not limited to, sequencing by synthesis (SBS) processes in which reversibly terminated nucleotides carrying fluorescent dyes are incorporated into a growing strand, complementary to the target strand being sequenced. In embodiments, the nucleotides are labeled with up to four unique fluorescent dyes. In embodiments, the nucleotides are labeled with at least two unique fluorescent dyes. In embodiments, the readout is accomplished by epifluorescence imaging. A variety of sequencing chemistries are available, non-limiting examples of which are described herein.

In embodiments, generating amplification products includes bridge polymerase chain reaction (bPCR) amplification, solid-phase rolling circle amplification (RCA), solid-phase exponential rolling circle amplification (eRCA), solid-phase recombinase polymerase amplification (RPA), solid-phase helicase dependent amplification (HDA), template walking amplification, or emulsion PCR on particles, or combinations of the methods. In embodiments, generating amplification products includes a bridge polymerase chain reaction amplification. In embodiments, generating amplification products includes a thermal bridge polymerase chain reaction (t-bPCR) amplification. In embodiments, generating amplification products includes a chemical bridge polymerase chain reaction (c-bPCR) amplification. Chemical bridge polymerase chain reactions include fluidically cycling a denaturant (e.g., formamide) and maintaining the temperature within a narrow temperature range (e.g., +/−5° C.). In contrast, thermal bridge polymerase chain reactions include thermally cycling between high temperatures (e.g., 85° C.-95° C.) and low temperatures (e.g., 60° C.-70° C.). Thermal bridge polymerase chain reactions may also include a denaturant, typically at a much lower concentration than traditional chemical bridge polymerase chain reactions. In embodiments, amplifying includes a plurality of cycles of strand denaturation, primer hybridization, and primer extension. Although each cycle will include each of these three events (denaturation, hybridization, and extension), events within a cycle may or may not be discrete.

Methods for fragmenting a polynucleotide sample are known in the art. Three approaches available to fragment nucleic acid chains may include: physical, enzymatic, and chemical. DNA fragmentation is typically done by physical methods (i.e., nebulization, acoustic shearing, and sonication) or enzymatic methods (i.e., non-specific endonuclease cocktails and transposase tagmentation reactions). Fragmented DNA may be blunt-ended by a number of methods known to those skilled in the art. Following fragmentation, the DNA fragments are end repaired or end polished. Typical polishing mixtures contain T4 DNA polymerase and T4 polynucleotide kinase. These enzymes excise 3' overhangs, fill in 3' recessed ends, and remove any potentially damaged nucleotides thereby generating blunt ends on the nucleic acid fragments. The T4 polynucleotide kinase used in the polishing mix adds a phosphate to the 5' ends of DNA fragments that can be lacking such, thus making them ligation-compatible to NGS adapters. Generally, a single adenine base is added to form an overhang via an A-tailing reaction. This "A" overhang allows adapters containing a single thymine overhanging base to base pair with the DNA fragments. Additional sequences such as adapters or primers may then be added using conventional means to permit platform specific sequences or to provide a binding site for sequencing primers. Following adapter ligation, the nucleic acid templates may be purified, amplified, or sequenced using methods known to those skilled in the art.

In an aspect is provided a method of forming a library of template nucleic acid molecules, the method including i) fragmenting a polynucleotide sample to generate a plurality of polynucleotide fragments each having a first end and a second end; ii) ligating a first adapter polynucleotide to the first end of each the polynucleotide fragments (e.g., using a suitable ligase enzyme, such as a T4 DNA ligase); and iii) ligating a second adapter polynucleotide to the second end of each the polynucleotide fragments. In embodiments, the first adapter and second adapter includes a sequence of SEQ ID NO:1 to SEQ ID NO:148. In embodiments, the first adapter includes SEQ ID NO:5 and the second adapter includes SEQ ID NO:6. In embodiments, the first adapter includes SEQ ID NO:5. In embodiments, the first adapter includes SEQ ID NO:9. In embodiments, the first adapter includes SEQ ID NO:85. In embodiments, the first adapter includes SEQ ID NO:92. In embodiments, the first adapter includes SEQ ID NO:90. In embodiments, the first adapter includes SEQ ID NO:88. In embodiments, the first adapter includes SEQ ID NO:117. In embodiments, the first adapter includes SEQ ID NO:119. In embodiments, the first adapter includes SEQ ID NO:121. In embodiments, the first adapter includes SEQ ID NO:123. In embodiments, the second adapter includes SEQ ID NO:6. In embodiments, the second adapter includes SEQ ID NO:11. In embodiments, the second adapter includes SEQ ID NO:110. In embodiments, the second adapter includes SEQ ID NO:112. In embodiments, the second adapter includes SEQ ID NO:114. In embodiments, the second adapter includes SEQ ID NO:116. In embodiments, the second adapter includes SEQ ID NO:142. In embodiments, the second adapter includes SEQ ID NO:144. In embodiments, the second adapter includes SEQ ID NO:146. In embodiments, the second adapter includes SEQ ID NO:148. In embodiments, the method further includes amplifying the library of template nucleic acid molecules to form amplification products. In embodiments, the method further includes sequencing the amplification products (e.g., hybridizing a sequencing primer to the amplification product (or a complement thereof) incorporating one or more nucleotides into the sequencing primer with a polymerase to create an extension strand; and detecting the one or more incorporated nucleotides so as to identify each incorporated nucleotide in said extension strand.

EXAMPLES

Example 1. Experimenting to Arrive at Effective Polynucleotide Primers

Genetic analysis is taking on increasing importance in modern society as a diagnostic, prognostic, and as a forensic tool. Next generation sequencing (NGS) methods often rely on the amplification of genomic fragments hybridized to polynucleotide primers on a solid support. Solid-phase nucleic acid amplification techniques, generate amplification products that are attached on a solid support in order to form arrays comprised of nucleic acid clusters, referred to as polonies. Each discrete cluster on the array is formed from a first plurality of immobilized polynucleotide primers and a second plurality of immobilized polynucleotide primers, wherein each plurality is different. Typically, these immobilized primers include a nucleic acid sequence capable of annealing to library molecules (e.g., template nucleic acids) containing a complementary sequence. As a result, the library capture affinity, amplification factor, the sequencing efficiency and accuracy are at least partially contingent on the nucleic acid sequence of the immobilized primers. For example, a primer sharing complementarity to a portion of the genome will generate undesired amplification products.

Solution phase polymerase chain reaction (PCR) amplification methods is a standard molecular biology technique with a multiplicity of uses (e.g., DNA cloning, functional analysis of genes, diagnosis of diseases, genotyping and discovery of genetic variants). Reliable primer design is crucial for successful PCR, and given the diversity of applications, the design of PCR primers requires flexibility in the approach. Thus, a number of primer design tools exist, for example PrimerSelect (Plasterer TN. PRIMERSELECT. Primer and probe design, Methods Mol. Biol., 1997, vol. 70 (pg. 291-302)), Primer Express (Applied BiosystemsPrimer Express® Software Version 3.0 Getting Started Guide, 2004), OLIGO 7 (Rychlik W. OLIGO 7 primer analysis software, Methods Mol. Biol., 2007, vol. 402 (pg. 35-60)) and Primer3 (Untergasser, A. et al. Primer3-new capabilities and interfaces. Nucleic Acids Res 40, e115 (2012)). Additional online tools, for example the OligoAnalyzer™ Tool provided by Integrated DNA Technologies (accessible at www.sg.idtdna.com/pages/tools/oligoanalyzer) or Primer-ROC (Johnston, A. D., Lu, J., Ru, Kl. et al. Sci Rep 9, 209 (2019)) sheds additional insight into the secondary structure of the primers and the amplicon, as well as the self- and heterodimerization tendencies of each primer set. Primer-BLAST is another web service that supports the selection of effective primers by considering opportunities for mispriming across an entire genome or transcriptome (Sayers E W et al., Nucleic Acids Res., 2012, vol. 40 (pg. D13-D25)) These tools are useful starting points for generating effective primers.

A goal of effective primer design is to maximize product yield and minimize off-target amplification, without introducing any biases (e.g., skewing the amplification products to over- or under-represent portions). Primer pairs should have melting temps (Tms) within 5° C. of each other. Prevention of primer-primer interaction artefacts (i.e., primer-dimers) formed by primer-primer binding and subsequent elongation is one way to avoid any deleterious effects. Primer-primer interactions can competitively inhibit binding to target DNA, remove primers from the reaction pool, and exhaust dNTPs, which results in reduced amplification efficiency and suboptimal product yields. Primer formulations should be desalted or HPLC purified to avoid oligo manufacturing byproducts that can reduce PCR efficiency.

Primer3 allows for the selection of the primer on the basis of melting temperature (Tm), primer length, and 3'-end stability, which was considered when designing each primer set. Calculating the melting temperature and performing thermodynamic modelling for estimating the propensity of primers to hybridize with other primers or to hybridize at unintended sites in the template offer an accurate approach for predicting the energetic stability of DNA structures. For example, because of electronic effects of nucleobase stacking, the stability of 5'-CT-3' hybridized to 3'-GA-5' is different from that of 5'-CA-3' hybridized to 3'-GT-5', despite the base pairings C:G and T:A are the same. It is recommended to perform primer analysis with sophisticated modelling capabilities to capture such electronic effects. Additionally, in silico validation of primer and amplicon sequences was performed. The online software OligoAnalyzer™ Tool provides information on amplicon secondary structure and the possibility of self- or heterodimer formation by the primer sequence itself by calculating the Gibbs free energy ($\Delta G$).

While software and online tools can provide an initial set of primer sequences, proper confirmatory validation occurs ex silico. We performed a series of experiments varying amplification conditions (e.g., temperature, additives, incubation duration) and sequencing the resulting amplicons to derive an optimized primer sequence. The measured metrics include amplification efficiency (e.g., reported as cluster signal brightness following hybridization of a fluorescently-labelled probe), and sequencing quality indicators, such as a quality score, accuracy, GC bias, and overall percent perfect reads per sequencing cycle.

When generating sequencing reads it is advantageous to obtain as broad a representation of the genome as possible. It is known that PCR amplification can introduce artifacts into sequencing libraries. In addition to nucleotide misincorporation, PCR amplification tends to be uneven, so that some sequence species become overrepresented in the resulting library. This situation is exacerbated by templates with GC-biased compositions. It is well known that extreme base compositions, i.e., GC-poor or GC-rich sequences, lead to uneven coverage or even no coverage of reads across the entirety of genome (see, for example Quail et al. Nat Methods. 2008 December; 5(12):1005-10). For example, read coverage of sequenced regions may be biased depending on the GC content of the library, when it was found the highest read density was found in intervals with elevated GC content (Dohm et al. Nucleic Acids Res. 2008 September; 36(16):e105). This GC bias can be introduced during PCR amplification of the library, cluster amplification, and the sequencing reactions. New experimental designs and optimized amplification protocols have been developed to reduce GC bias, and so it is preferable that sequencing reactions do not introduce any GC bias. High GC primers can bind non-specifically to off target templates. Secondary structures are more likely in high GC content target DNA and can cause inefficient primer binding.

The oligonucleotides described herein include a "primer-binding" sequence, which enable specific hybridization of amplification primers when the templates are in used in a solid-phase amplification reaction. The primer-binding sequences are thus determined by the sequence of the primers to be ultimately used for solid-phase amplification. The sequence of these primers is advantageously selected to ideally avoid, or at least minimize, binding of the primers to the target sequences of the templates within the library. By way of example, if the target portions of the templates are derived from human genomic DNA, then the sequences of the oligonucleotides to be used in solid phase amplification were selected to minimize non-specific binding to any human genomic sequence.

First, to generate effective primer sequences, we generated 5,000,000 random primer pairs with a target GC content of approximately 50-55% GC having a length of 35 bp. Next, to ensure the target GC content remains within 50-55% for smaller sizes (e.g., less than 35 bp), we selected for pairs that had 50-55% GC over the range of 1-25 bp, 1-30 bp, 1-35 bp. This ensures that if using a truncated version on the surface, the GC content will remain in the range of approximately 50-55%. To this set, we calculated the maximum melting temperature (Tm) and the maximum number of consecutive base matches for RY1 and RY2 homo and hetero-dimers. For the heterodimer calculation, we compared RY1 relative to RY2-SP1 construct and RY2 to RY1-SP1 construct, wherein SP1 and SP2 refer to a sequence primer binding sequence. Next, we modeled each primer sequence through mFold (Mfold web server for nucleic acid folding and hybridization prediction. Nucleic Acids Res. 31 (13), 3406-15, (2003)) and determined minimum ΔG of all potential secondary structures.

We filtered pairs to retain primer sequences with i) limited sequence overlap (i.e., minimal overlap so as not to form primer-dimers) and ii) minimal secondary structure. From this filtered set we manually modified individual bases to further reduce overlap, followed by a BLAST alignment to determine the % identity against all available sequences in Genbank and removed primers with any significant matches (e.g., removed sequences with greater than 1% identity to a known sequence). Preferred melting temperatures are about 55° C. to about 75° C. (e.g., in 100 mM NaCl buffer). In embodiments, the melting temperature is about 60° C. to about 73° C. In embodiments, the melting temperature is about 68° C. to about 73° C. The resulting sequences are provided in Table 1, absent any linking spacer nucleotides or cleavable sites. In embodiments, it is preferred to use poly-T (i.e., two or more consecutive thymine nucleotides) spacers, although other nucleotides and combinations thereof can be used. In embodiments, the linker includes 10, 11, 12, 13, 14, or 15 T spacer nucleotides. In embodiments, the linker includes 12 T spacer nucleotides. In embodiments, the linker attaching the primer to the solid support includes one or more cleavable site(s).

TABLE 1

Effective primer sequences. It is understood that white space, line breaks, and text formatting are not indicative of separate sequences or structural implications.

| Internal Ref Name | Sequence | SEQ ID Num. |
| --- | --- | --- |
| RY1 | 5'-CAGGGAAGGAGTGCGTGGCTGCCTTTGT | SEQ ID NO: 1 |
| RY2 | 5'-TGTTTCCGTCGGTGCGTGAGGAAGGGAC | SEQ ID NO: 2 |
| RY3 | 5'-GTCCCTTCCTCACGCACCGACGGAAACA | SEQ ID NO: 3 |
| RY4 | 5'-GTGGTTGGTGAGGGTCATCTCGCTGGAG | SEQ ID NO: 4 |
| RY5 | 5'-ACAAAGGCAGCCACGCACTCCTTCCCTG | SEQ ID NO: 5 |
| RY6 | 5'-GAGGTCGCTCTACTGGGAGTGGTTGGTG | SEQ ID NO: 6 |
| RY7 | 5'-CTCCAGCGAGATGACCCTCACCAACCAC | SEQ ID NO: 7 |
| RY8 | 5'-CACCAACCACTCCCAGTAGAGCGACCTC | SEQ ID NO: 8 |
| RY9 | 5'-ACAAAGGCAGCCACGCACTCCTTCCCTGAAGGCCGGAATCT | SEQ ID NO: 9 |
| RY10 | 5'-GCTGCCGCCACTAGCCATCTTACTGCTGAGGACTCTTCGCT | SEQ ID NO: 10 |
| RY11 | 5'-GATTCCGGCCTTGTGGTTGGTGAGGGTCATCTCGCTGGAG | SEQ ID NO: 11 |
| RY12 | 5'-GCGAAGAGTCCTGGAGTGCCGCCAATGTATGCGAGGGTGA | SEQ ID NO: 12 |

TABLE 1-continued

Effective primer sequences. It is understood that white space, line breaks, and text formatting are not indicative of separate sequences or structural implications.

| Internal Ref Name | Sequence | SEQ ID Num. |
|---|---|---|
| RY13 | 5'-GCGCGCG TTT TTT TT GCTTGCGTCTCCTGCCAGCCATATCCGGTCTACGTGATCC TTT TTT TT CGCGCGCT | SEQ ID NO: 13 |
| RY14 | 5'-GCGCGCG TTT TTT TTT TTT TT GCTTGCGTCTCCTGCCAGCCATATCCGGTCTACGTGATCC TTT TTT TTT TTT TT CGCGCGCT | SEQ ID NO: 14 |
| RY15 | 5'-GGATCACGTAGATTTTGCTTGCGTCTCCTGCCAGCCATATCC GGTTTTTCTACGTGATTCCT | SEQ ID NO: 15 |
| RY16 | 5'-GCGAAGAGTCCT GGAGTGCCGCCAATGTATGCGAGGGTGA GCTGCCGCCACTAGCCATCTTACTGCTG AGGACTCTTCGCT | SEQ ID NO: 16 |
| RY17 | 5'-GCGAAGAGTCCT TTT TTT GGAGTGCCGCCAATGTATGCGAGGGTGA GCTGCCGCCACTAGCCATCTTACTGCTG TTT TTT AGGACTCTTCGCT | SEQ ID NO: 17 |
| RY18 | 5'-GCGAAGAGTCCT TTT TTT GGAGTGCCGCCAATGTATGCGAGGGTGA TTT TTTT GCTGCCGCCACTAGCCATCTTACTGCTG TTT TTT AGGACTCTTCGCT | SEQ ID NO: 18 |
| RY19 | 5'-GATTCCGGCCTT GTGGTTGGTGAGGGTCATCTCGCTGGAGACAAAGGCAGC CACGCACTCCTTCCCTGAAGGCCGGAATCT | SEQ ID NO: 19 |
| RY20 | 5'-GATTCCGGCCTT TTT TTT GTGGTTGGTGAGGGTCATCTCGCTGGAGACAAAGGCAGCCACGCACTCCTTCCCT G TTTTTT AAGGCCGGAATCT | SEQ ID NO: 20 |
| RY21 | 5'-GATTCCGGCCTT TTT TTT GTGGTTGGTGAGGGTCATCTCGCTGGAGTTT TTT TACAAAGGCAGCCACGCACTCCTTCCCTG TTT TTT AAGGCCGGAATCT | SEQ ID NO: 21 |
| RY22 | 5'-GGATCACGTAGATTTTGCTTGCGTCTCCTGCCAGCCATAT CCGGTTTTTCTACGTGATCCT | SEQ ID NO: 22 |
| RY23 | 5'-GG ATC ACG TAG ATT TTT TTT TTT TGC TTG CGT CTC CTG CCA GCC ATA TCC GGT TTT TTT TTT TTT CTA CGT GAT CCT | SEQ ID NO: 23 |
| RY24 | 5'-GG ATC ACG TAG ATT TTT TTT TTT TTT TTT TTT TTT TGC TTG CGT CTC CTG CCA GCC ATA TCC GGT TTT TTT TTT TTT TTT TTT TTT TTT CTA CGT GAT CCT | SEQ ID NO: 24 |
| RY25 | 5'-GG ATC ACG TAG ATT TTT TTT TTT TTT TTT TTT TTT TTT TTT TTT TTG CTT GCG TCT CCT GCC AGC CAT ATC CGG TTT TTT TTT TTC TAC GTG ATC CT | SEQ ID NO: 25 |
| RY26 | 5'-GGA TCA CGT AGA TTT TAG ATC TGC TTG CGT CTC CTG CCA GCC ATA TCC GGT TTT TCT ACG TGA TCC T | SEQ ID NO: 26 |
| RY27 | 5'-GGA TCA CGT AGA TTTTTTTTTTT AGA TCT GCT TGC GTC TCC TGC CAG CCA TAT CCG GTTTTTTTTTTTC TAC GTG ATC CT | SEQ ID NO: 27 |
| RY28 | 5'-TGTTTCCGTCGGTGCGTGAGGAAGGGACTTCCGGCCTTAGA | SEQ ID NO: 28 |
| RY29 | 5'-CGACGGCGGTGATCGGTAGAATGACGACTCCTGAGAAGCGA | SEQ ID NO: 29 |
| RY30 | 5'-CTAAGGCCGGAACACCAACCACTCCCAGTAGAGCGACCTC | SEQ ID NO: 30 |
| RY31 | 5'-CGCTTCTCAGGACCTCACGGCGGTTACATACGCTCCCACT | SEQ ID NO: 31 |
| RY32 | 5'-CGCGCGCAAAAAAAACGAACGCAGAGGACG GTCGGTATAGGCCAGATGCACTAGGAAAAAAAAGCGCGCGA | SEQ ID NO: 32 |
| RY33 | 5'-CGCGCGCAAAAAAAAAAAAAACGAACGCAG AGGACGGTCGGTATAGGCCAGATGCACTAGGAAAAAAAAAAAAAAAGCGCGCGA | SEQ ID NO: 33 |
| RY34 | 5'-CCTAGTGCATCTAAAACGAACGCAGAGGAC GGTCGGTATAGGCCAAAAAGATGCACTAAGGA | SEQ ID NO: 34 |
| RY35 | 5'-CGCTTCTCAGGACCTCACGGCGGTTACATACG CTCCCACTCGACGGCGGTGATCGGTAGAATGACGACTCCTGAGAAGCGA | SEQ ID NO: 35 |

TABLE 1-continued

Effective primer sequences. It is understood that white space, line breaks, and text formatting are not indicative of separate sequences or structural implications.

| Internal Ref Name | Sequence | SEQ ID Num. |
|---|---|---|
| RY36 | 5'-CGCTTCTCAGGAAAAAAACCTCACGGCGGT TACATACGCTCCCACTCGACGGCGGTGATCGGTAGAATGAC GACAAAAAATCCTGAGAAGCGA | SEQ ID NO: 36 |
| RY37 | 5'-CGCTTCTCAGGAAAAAAACCTCACGGCGGTTACATACGCTCCCAC TAAAAAAACGACGGCGGTGATCGGTAGAATGACGACAAAAAATCCTGAGAAGC GA | SEQ ID NO: 37 |
| RY38 | 5'-CTAAGGCCGGAACACCAACCACTCCCAGTAGAGCGACCTCTGTTTCC GTCGGTGCGTGAGGAAGGGACTTCCGGCCTTAGA | SEQ ID NO: 38 |
| RY39 | 5'-CTAAGGCCGGAAAAAAAACACCAACCACTCCCAGTAGAGCGACCTC TGTTTCCGTCGGTGCGTGAGGAAGGGACAAAAAATTCCGGCCTTAGA | SEQ ID NO: 39 |
| RY40 | 5'-CTAAGGCCGGAAAAAAAACACCAACCACTCCCAGTAGAGCGACCTCAA AAAAATGTTTCCGTCGGTGCGTGAGGAAGGGACAAAAAATTCCGGCCTTAGA | SEQ ID NO: 40 |
| RY41 | 5'-CCTAGTGCATCTAAAACGAACGCAGAGGACGGTCGGTATAGGCCAAA AAGATGCACTAGGA | SEQ ID NO: 41 |
| RY42 | 5'-CCTAGTGCATCTAAAAAAAAAAACGAACGCAGAGGACGGTCGGTAT AGGCCAAAAAAAAAAAAAGATGCACTAGGA | SEQ ID NO: 42 |
| RY43 | 5'-CCTAGTGCATCTAAAAAAAAAAAAAAAAA AAAAACGAACGCAGAGGACGGTCGGTATAGGCCAAAAAAAAAA AAAAAAAAAAAAAGATGCACTAGGA | SEQ ID NO: 43 |
| RY44 | 5'-CCTAGTGCATCTAAAAAAAAAAAAAAAAAAA AAAAAAAAAAAAAAACGAACGCAGAGGACGGTCGGTATAGGCCA AAAAAAAAAAGATGCACTAGGA | SEQ ID NO: 44 |
| RY45 | 5'-CCTAGTGCATCTAAAATCTAGACGAACGCAGAGGACGGTCGGTA TAGGCCAAAAGATGCACTAGGA | SEQ ID NO: 45 |
| RY46 | 5'-CCTAGTGCATCTAAAAAAAAAAATCTAGACGAACGCAGAGGACG GTCGGTATAGGCCAAAAAAAAAAAGATGCACTAGGA | SEQ ID NO: 46 |
| RY47 | 5'-AGATTCCGGCCTTCAGGGAAGGAGTGCGTGGCTGCCTTTGT | SEQ ID NO: 47 |
| RY48 | 5-AGCGAAGAGTCCTCAGCAGTAAGATGGCTAGTGGCGGCAGC | SEQ ID NO: 48 |
| RY49 | 5'-TCACCCTCGCATACATTGGCGGCACTCCAGGACTCTTCGC | SEQ ID NO: 49 |
| RY50 | 5'-CTCCAGCGAGATGACCCTCACCAACCACAAGGCCGGAATC | SEQ ID NO: 50 |
| RY51 | 5'- AGCGCGCGAAAAAAAAGGATCACGTAGACCGGATATGGCTGGCAGGAGACGCA AGCAAAAAAAACGCGCGC | SEQ ID NO: 51 |
| RY52 | 5'-AGGAATCACGTAGAAAAACCGGATATGGCTGGCAGGAG ACGCAAGCAAAATCTACGTGATCC | SEQ ID NO: 52 |
| RY53 | 5'-AGCGCGCGAAAAAAAAAAAAAGGATCACGTAGACCG GATATGGCTGGCAGGAGACGCAAGCAAAAAAAAAAAAACGCGCGC | SEQ ID NO: 53 |
| RY54 | 5'-AGCGAAGAGTCCTCAGCAGTAAGATGGCTAGTGGCGGC AGCTCACCCTCGCATACATTGGCGGCACTCCAGGACTCTTCGC | SEQ ID NO: 54 |
| RY55 | 5'-AGCGAAGAGTCCTAAAAAACAGCAGTAAGATGGCTAG TGGCGGCAGCTCACCCTCGCATACATTGGCGGCACTCCAAAAAAAGGACTCTTCG C | SEQ ID NO: 55 |
| RY56 | 5'-AGCGAAGAGTCCTAAAAAACAGCAGTAAGATGGCTAGTGGCGGC AGCAAAAAAATCACCCTCGCATACATTGGCGGCACTCCAAAAAAAGGACTCTTCG C | SEQ ID NO: 56 |
| RY57 | 5'-AGATTCCGGCCTTCAGGGAAGGAGTGCGTGGCTGCCTTTGTCTC CAGCGAGATGACCCTCACCAACCACAAGGCCGGAATC | SEQ ID NO: 57 |

TABLE 1-continued

Effective primer sequences. It is understood that white space, line breaks, and text formatting are not indicative of separate sequences or structural implications.

| Internal Ref Name | Sequence | SEQ ID Num. |
| --- | --- | --- |
| RY58 | 5'-AGATTCCGGCCTTAAAAAACAGGGAAGGAGTGCGTGGCTGCCTTT GTCTCCAGCGAGATGACCCTCACCAACCACAAAAAAAAGGCCGGAATC | SEQ ID NO: 58 |
| RY59 | 5'-AGATTCCGGCCTTAAAAAACAGGGAAGGAGTGCGTGGCTGCCTT TGTAAAAAAACTCCAGCGAGATGACCCTCACCAACCACAAAAAAAAGGCCGGAA TC | SEQ ID NO: 59 |
| RY60 | 5'-AGGATCACGTAGAAAAACCGGATATGGCTGGCAGGAGACGCAAGC AAAATCTACGTGATCC | SEQ ID NO: 60 |
| RY61 | 5'-AGGATCACGTAGAAAAAAAAAAAAACCGGATATGGCTGGCAGGA GACGCAAGCAAAAAAAAAAAAATCTACGTGATCC | SEQ ID NO: 61 |
| RY62 | 5'-AGGATCACGTAGAAAAAAAAAAAAAAAAAAAAAAAACCGGATAT GGCTGGCAGGAGACGCAAGCAAAAAAAAAAAAAAAAAAAAAAATCTACGTGA TCC | SEQ ID NO: 62 |
| RY63 | 5'-AGGATCACGTAGAAAAAAAAAAACCGGATATGGCTGGCAGGAGAC GCAAGCAGATCTAAAAAAAAAAATCTACGTGATCC | SEQ ID NO: 63 |
| RY64 | 5'-AGGATCACGTAGAAAAACCGGATATGGCTGGCAGGAGACGCAAGCA GATCTAAAATCTACGTGATCC | SEQ ID NO: 64 |
| RY65 | 5'-AGGATCACGTAGAAAAAAAAAAACCGGATATGGCTGGCAGGAGACGC AAGCAAAAAAAAAAAAAAAAAAAAAAAAAAAAAAAATCTACGTGA TCC | SEQ ID NO: 65 |
| RY66 | 5'-AGTGGGAGCGTATGTAACCGCCGTGAGGTCCTGAGAAGCG | SEQ ID NO: 66 |
| RY67 | 5'-GAGGTCGCTCTACTGGGAGTGGTTGGTGTTCCGGCCTTAG | SEQ ID NO: 67 |
| RY68 | 5'-TCGCTTCTCAGGAGTCGTCATTCTACCGATCACCGCCGTCG | SEQ ID NO: 68 |
| RY69 | 5'-TCTAAGGCCGGAAGTCCCTTCCTCACGCACCGACGGAAACA | SEQ ID NO: 69 |
| RY70 | 5'-TCCTTAGTGCATCTTTTTTGGCCTATACCGACCGTCCTCTGCGTTCGT TTTAGATGCACTAGG | SEQ ID NO: 70 |
| RY71 | 5'-TCGCGCGCTTTTTTTTTTTTCCTAGTGCATCTGGCCTATACCGACC GTCCTCTGCGTTCGTTTTTTTTTTTTTTGCGCGCG | SEQ ID NO: 71 |
| RY72 | 5'-TCGCGCGCTTTTTTTTCCTAGTGCATCTGGCCTATACCGACCGTCCT CTGCGTTCGTTTTTTTTGCGCGCG | SEQ ID NO: 72 |
| RY73 | 5'-TCGCTTCTCAGGAGTCGTCATTCTACCGATCACCGCCGTCGAGTGG GAGCGTATGTAACCGCCGTGAGGTCCTGAGAAGCG | SEQ ID NO: 73 |
| RY74 | 5'-TCGCTTCTCAGGATTTTTTGTCGTCATTCTACCGATCACCGCCGTCG TTTTTTTAGTGGGAGCGTATGTAACCGCCGTGAGGTTTTTTTCCTGAGAAGCG | SEQ ID NO: 74 |
| RY75 | 5'-TCGCTTCTCAGGATTTTTTGTCGTCATTCTACCGATCACCGCCGTCGAG TGGGAGCGTATGTAACCGCCGTGAGGTTTTTTTCCTGAGAAGCG | SEQ ID NO: 75 |
| RY76 | 5'-TCTAAGGCCGGAATTTTTTGTCCCTTCCTCACGCACCGACGGAAACAT TTTTTTGAGGTCGCTCTACTGGGAGTGGTTGGTGTTTTTTTTCCGGCCTTAG | SEQ ID NO: 76 |
| RY77 | 5'-TCTAAGGCCGGAATTTTTTGTCCCTTCCTCACGCACCGACGGAAACAG AGGTCGCTCTACTGGGAGTGGTTGGTGTTTTTTTTCCGGCCTTAG | SEQ ID NO: 77 |
| RY78 | 5'-TCTAAGGCCGGAAGTCCCTTCCTCACGCACCGACGGAAACAGAGGT CGCTCTACTGGGAGTGGTTGGTGTTCCGGCCTTAG | SEQ ID NO: 78 |
| RY79 | 5'-TCCTAGTGCATCTTTTTTTTTTTTTTTTTTTTGGCCTATACCGACC GTCCTCTGCGTTCGTTTTTTTTTTTTTTTTTTTTTAGATGCACTAGG | SEQ ID NO: 79 |
| RY80 | 5'-TCCTAGTGCATCTTTTTTTTTTTGGCCTATACCGACCGTCCTCTGCG TTCGTTTTTTTTTTTTTAGATGCACTAGG | SEQ ID NO: 80 |

TABLE 1-continued

Effective primer sequences. It is understood that white space, line breaks, and text formatting are not indicative of separate sequences or structural implications.

| Internal Ref Name | Sequence | SEQ ID Num. |
|---|---|---|
| RY81 | 5'-TCCTAGTGCATCTTTTTGGCCTATACCGACCGTCCTCTGCGTTCGT TTTAGATGCACTAGG | SEQ ID NO: 81 |
| RY82 | 5'-TCCTAGTGCATUTTTTTTTTTTGGCCTATACCGACCGTCCTCTGC GTTCGTCTAGATTTTTTTTTTAGATGCACTAGG | SEQ ID NO: 82 |
| RY83 | 5'-TCCTAGTGCATCTTTTTGGCCTATACCGACCGTCCTCTGCGTTCGTC TAGATTTTAGATGCACTAGG | SEQ ID NO: 83 |
| RY84 | 5'-TCCTAGTGCATCTTTTTTTTTTGGCCTATACCGACCGTCCTCTGCG TTCGTTTTTTTTTTTTTTTTTTTTTTTTTTTTTTTTTAGATGCACTAGG | SEQ ID NO: 84 |
| RY85 | 5'-ACAAAGGCAGCCACGCACTCCTTCC | SEQ ID NO: 85 |
| RY86 | 5'-CTCCAGCGAGATGACC | SEQ ID NO: 86 |
| RY87 | 5'-CTCCAGCGAGATGACCCTCACCAAC | SEQ ID NO: 87 |
| RY88 | 5'-ACAAAGGCAGCCACGC | SEQ ID NO: 88 |
| RY89 | 5'-CTCCAGCGAGATGACCCTCACC | SEQ ID NO: 89 |
| RY90 | 5'-ACAAAGGCAGCCACGCACT | SEQ ID NO: 90 |
| RY91 | 5'-CTCCAGCGAGATGACCCTC | SEQ ID NO: 91 |
| RY92 | 5'-ACAAAGGCAGCCACGCACTCCT | SEQ ID NO: 92 |
| RY93 | 5'-CCTTCCTCACGCACCGACGGAAACA | SEQ ID NO: 93 |
| RY94 | 5'-CAACCACTCCCAGTAGAGCGACCTC | SEQ ID NO: 94 |
| RY95 | 5'-TCCTCACGCACCGACGGAAACA | SEQ ID NO: 95 |
| RY96 | 5'-CCACTCCCAGTAGAGCGACCTC | SEQ ID NO: 96 |
| RY97 | 5'-TCACGCACCGACGGAAACA | SEQ ID NO: 97 |
| RY98 | 5'-CTCCCAGTAGAGCGACCTC | SEQ ID NO: 98 |
| RY99 | 5'-CGCACCGACGGAAACA | SEQ ID NO: 99 |
| RY100 | 5'-CCAGTAGAGCGACCTC | SEQ ID NO: 100 |
| RY101 | 5'-GGAAGGAGTGCGTGGCTGCCTTTGT | SEQ ID NO: 101 |
| RY102 | 5'-GTTGGTGAGGGTCATCTCGCTGGAG | SEQ ID NO: 102 |
| RY103 | 5'-AGGAGTGCGTGGCTGCCTTTGT | SEQ ID NO: 103 |
| RY104 | 5'-GGTGAGGGTCATCTCGCTGGAG | SEQ ID NO: 104 |

TABLE 1-continued

Effective primer sequences. It is understood that white space, line breaks, and text formatting are not indicative of separate sequences or structural implications.

| Internal Ref Name | Sequence | SEQ ID Num. |
|---|---|---|
| RY105 | 5'-AGTGCGTGGCTGCCTTTGT | SEQ ID NO: 105 |
| RY106 | 5'-GAGGGTCATCTCGCTGGAG | SEQ ID NO: 106 |
| RY107 | 5'-GCGTGGCTGCCTTTGT | SEQ ID NO: 107 |
| RY108 | 5'-GGTCATCTCGCTGGAG | SEQ ID NO: 108 |
| RY109 | 5'-TGTTTCCGTCGGTGCGTGAGGAAGG | SEQ ID NO: 109 |
| RY110 | 5'-GAGGTCGCTCTACTGGGAGTGGTTG | SEQ ID NO: 110 |
| RY111 | 5'-TGTTTCCGTCGGTGCGTGAGGA | SEQ ID NO: 111 |
| RY112 | 5'-GAGGTCGCTCTACTGGGAGTGG | SEQ ID NO: 112 |
| RY113 | 5'-TGTTTCCGTCGGTGCGTGA | SEQ ID NO: 113 |
| RY114 | 5'-GAGGTCGCTCTACTGGGAG | SEQ ID NO: 114 |
| RY115 | 5'-TGTTTCCGTCGGTGCG | SEQ ID NO: 115 |
| RY116 | 5'-GAGGTCGCTCTACTGG | SEQ ID NO: 116 |
| RY117 | 5'-AAGGCAGCCACGCACTCCTTCCCTG | SEQ ID NO: 117 |
| RY118 | 5'-CAGCGAGATGACCCTCACCAACCAC | SEQ ID NO: 118 |
| RY119 | 5'-GCAGCCACGCACTCCTTCCCTG | SEQ ID NO: 119 |
| RY120 | 5'-CGAGATGACCCTCACCAACCAC | SEQ ID NO: 120 |
| RY121 | 5'-GCCACGCACTCCTTCCCTG | SEQ ID NO: 121 |
| RY122 | 5'-GATGACCCTCACCAACCAC | SEQ ID NO: 122 |
| RY123 | 5'-ACGCACTCCTTCCCTG | SEQ ID NO: 123 |
| RY124 | 5'-GACCCTCACCAACCAC | SEQ ID NO: 124 |
| RY125 | 5'-GTCCCTTCCTCACGCACCGACGGAA | SEQ ID NO: 125 |
| RY126 | 5'-CACCAACCACTCCCAGTAGAGCGAC | SEQ ID NO: 126 |
| RY127 | 5'-GTCCCTTCCTCACGCACCGACG | SEQ ID NO: 127 |
| RY128 | 5'-CACCAACCACTCCCAGTAGAGC | SEQ ID NO: 128 |

TABLE 1-continued

Effective primer sequences. It is understood that white space, line breaks, and text formatting are not indicative of separate sequences or structural implications.

| Internal Ref Name | Sequence | SEQ ID Num. |
|---|---|---|
| RY129 | 5'-GTCCCTTCCTCACGCACCG | SEQ ID NO: 129 |
| RY130 | 5'-CACCAACCACTCCCAGTAG | SEQ ID NO: 130 |
| RY131 | 5'-GTCCCTTCCTCACGCA | SEQ ID NO: 131 |
| RY132 | 5'-CACCAACCACTCCCAG | SEQ ID NO: 132 |
| RY133 | 5'-CAGGGAAGGAGTGCGTGGCTGCCTT | SEQ ID NO: 133 |
| RY134 | 5'-GTGGTTGGTGAGGGTCATCTCGCTG | SEQ ID NO: 134 |
| RY135 | 5'-CAGGGAAGGAGTGCGTGGCTGC | SEQ ID NO: 135 |
| RY136 | 5'-GTGGTTGGTGAGGGTCATCTCG | SEQ ID NO: 136 |
| RY137 | 5'-CAGGGAAGGAGTGCGTGGC | SEQ ID NO: 137 |
| RY138 | 5'-GTGGTTGGTGAGGGTCATC | SEQ ID NO: 138 |
| RY139 | 5'-CAGGGAAGGAGTGCGT | SEQ ID NO: 139 |
| RY140 | 5'-GTGGTTGGTGAGGGTC | SEQ ID NO: 140 |
| RY141 | 5'-TTCCGTCGGTGCGTGAGGAAGGGAC | SEQ ID NO: 141 |
| RY142 | 5'-GTCGCTCTACTGGGAGTGGTTGGTG | SEQ ID NO: 142 |
| RY143 | 5'-CGTCGGTGCGTGAGGAAGGGAC | SEQ ID NO: 143 |
| RY144 | 5'-GCTCTACTGGGAGTGGTTGGTG | SEQ ID NO: 144 |
| RY145 | 5'-CGGTGCGTGAGGAAGGGAC | SEQ ID NO: 145 |
| RY146 | 5'-CTACTGGGAGTGGTTGGTG | SEQ ID NO: 146 |
| RY147 | 5'-TGCGTGAGGAAGGGAC | SEQ ID NO: 147 |
| RY148 | 5'-CTGGGAGTGGTTGGTG | SEQ ID NO: 148 |
| RY149 | 5'-ACG ACC TTC TTG TAG TCC TTA CGG C | SEQ ID NO: 170 |
| RY150 | 5'-ACA GTT AGG TCA CAC TCT CCA CCA C | SEQ ID NO: 171 |
| RY151 | 5'-TGA TAG CTG AAA CTA GCC TCA CCG C | SEQ ID NO: 172 |
| RY152 | 5'-ACC CAT ATC GAG GAG TCA AGT TGG C | SEQ ID NO: 173 |

TABLE 1-continued

Effective primer sequences. It is understood that white space, line breaks, and text formatting are not indicative of separate sequences or structural implications.

| Internal Ref Name | Sequence | SEQ ID Num. |
|---|---|---|
| RY153 | 5'-ATG GGC TGC CTA TGC CGT AAT ATC C | SEQ ID NO: 174 |
| RY154 | 5'-AGT AAT GAA CAG CGC GTG GTC ACA C | SEQ ID NO: 175 |

The primer sequences were synthesized and immobilized to a solid support using a poly-T spacer (e.g., 12 consecutive dTTPs). A library of nucleic acid molecules was prepared and amplified. Out of the initial 5,000,000 random primer pairs, only a selection of sequences satisfied the selection criteria (e.g., melting temps, GC content, secondary structure, etc.), set 1: (SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123) and set 2: (SEQ ID NO:7, SEQ ID NO:30, SEQ ID NO:87, SEQ ID NO:89, SEQ ID NO:91, SEQ ID NO:86, SEQ ID NO:118, SEQ ID NO:120, SEQ ID NO:122, or SEQ ID NO:124) and performed well during initial studies, resulting in the greatest amount of amplifiable clusters and highest quality scores during sequencing experiments under the tested conditions, relative to SEQ ID NO:170, SEQ ID NO:171, SEQ ID NO:172, SEQ ID NO:173, SEQ ID NO:174, and SEQ ID NO:175 (nucleotide primer length 25 bp). Further optimization may be performed to maximize the amount of primers available for amplifying, minimize unintended biases introduced during library formation, melting temperature modulation, and normalizing the brightness for all four dyes used during sequencing. It is understood that the complementary and reverse complementary sequences of set 1 and set 2 perform equally as well.

For example, the following protocol is then followed to prepare a template nucleic acid strand for amplifying and sequencing on next generation sequencing devices. The input DNA is fragmented to make small DNA molecules with a modal size of about 100 to about 400 base pairs with random ends. This is done by sonication, chemical fragmentation, or enzymatic fragmentation. The resulting DNA fragments generated by sonication are end polished to produce a library of DNA fragments with blunt, 5'-phosphorylated ends that are ready for ligation. The end polishing is accomplished by using the T4 DNA polymerase, which can fill in 5' overhangs via its polymerase activity and recess 3' overhangs via its 3'—>5' exonuclease activity. The phosphorylation of 5' ends is accomplished by T4 polynucleotide kinase.

Adapter ligation: Ligation of double-stranded DNA adapters is accomplished by use of T4 DNA ligase; the adapter includes sequences, or complements thereof, provided in Table 1. Depending on the adapter, some double-stranded adapters may not have 5' phosphates and contain a 5' overhang on one end to prevent ligation in the incorrect orientation.

Now the adapter-ligated library may be size-selected (e.g., selecting for approximately 200-250 base pair size range). By doing this, unligated adapters and adapter dimers are removed, and the optimal size-range for subsequent PCR and sequencing is selected. Adapter dimers are the result of self-ligation of the adapters without an insert sequence. These dimers form clusters very efficiently and consume valuable space on the flow cell without generating any useful data. Thus, known cleanup methods may be used, such as magnetic bead-based clean up, or purification on agarose gels.

The resultant strand is then subjected to immobilization, amplification, and a nucleic acid sequencing reaction using any available sequencing technology. Once data is available from the sequencing reaction, initial processing (often termed "pre-processing") of the sequences is typically employed prior to annotation. Pre-processing includes filtering out low-quality sequences, sequence trimming to remove continuous low-quality nucleotides, merging paired-end sequences, or identifying and filtering out PCR repeats using known techniques in the art.

TABLE 2

The target polynucleotide and indices may be sequenced using primers with the sequences identified in this table. In embodiments, one or more of the nucleotides are LNA nucleotides, e.g., nucleotides at the 5' end, to modulate the melting temperature.

| Primer name | Sequenced Segment | Sequence of Primer | SEQ ID Num. |
|---|---|---|---|
| S1 | Index 1 | 5'-ACAAAGGCAGCCACG CACTCCTTCCCTGT | SEQ ID NO: 176 |
| SP1 | Read 1 Insert | 5'-ACACTCTTTCCCTACAC GACGCTCTTCCGATCT | SEQ ID NO: 152 |
| S2 | Index 2 | 5'-CTCCAGCGAGATGACC CTCACCAACCACT | SEQ ID NO: 177 |
| SP2 | Read 2 Insert | 5'-GTGACTGGAGTTCAGA CGTGTGCTCTTCCGATCT | SEQ ID NO: 156 |

TABLE 3

Oligonucleotides useful for introducing amplification sequences (e.g., platform primer sequences) with or without indices on generic libraries. The '*' is indicative of an optional phosphorothioate bond between the two nucleotides. The consecutive "N" nucleotides indicate the position of Index 1 and Index 2, which may include an 8-12 random nucleotide index sequence subject to certain criteria (e.g., Hamming distance, GC content, etc.).

| Primer | Sequence of Oligonucleotide |
|---|---|
| S1-Index12-SP1 | 5'-ACAAAGGCAGCCACGCACTCCTTCCCTGTNNN NNNNNNNNNACACTCTTTCCCTACACGACG*C (SEQ ID NO: 180) |
| S2-Index12-SP2 | 5'-CTCCAGCGAGATGACCCTCACCAACCACTNNNN NNNNNNNNGTGACTGGAGTTCAGACGTG*T (SEQ ID NO: 181) |
| S1-SP1 | 5'-ACAAAGGCAGCCACGCACTCCTTCCCTGTA CACTCTTTCCCTACACGACG*C (SEQ ID NO: 182) |
| S2-SP2 | 5'-CTCCAGCGAGATGACCCTCACCAACCACTG TGACTGGAGTTCAGACGTG*T (SEQ ID NO: 183) |
| S1-Index8-SP1 | 5'-ACAAAGGCAGCCACGCACTCCTTCCCTGTNNNN NNNNACACTCTTTCCCTACACGACG*C (SEQ ID NO: 184) |
| S2-Index8-SP2 | 5'-CTCCAGCGAGATGACCCTCACCAACCACTNN NNNNNNGTGACTGGAGTTCAGACGTG*T (SEQ ID NO: 185) |

P-Embodiments

The present disclosure provides the following illustrative embodiments.

Embodiment P1. A plurality of template nucleic acids, wherein each template nucleic acid comprises a first end, and a second end capable of hybridizing to any one of the sequences of SEQ ID NO:1 to SEQ ID NO:116, wherein a portion of the plurality of template nucleic acids are different from each other.

Embodiment P2. The plurality of Embodiment P1, wherein the second end is capable of hybridizing to any one of the sequences of SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

Embodiment P3. The plurality of Embodiment P1, wherein the second end is capable of hybridizing to any one of the sequences of SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109 SEQ ID NO:110, SEQ ID NO:111, SEQ ID NO:112, SEQ ID NO:113, SEQ ID NO:114, SEQ ID NO:115 or SEQ ID NO:116.

Embodiment P4. The plurality of Embodiment P1, wherein the second end is capable of hybridizing to any one of the sequences of SEQ ID NO:7, SEQ ID NO:11, SEQ ID NO:30, SEQ ID NO:87, SEQ ID NO:89, SEQ ID NO:91, or SEQ ID NO:86.

Embodiment P5. The plurality of Embodiment P1, wherein the second end comprises SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

Embodiment P6. The plurality of Embodiment P1, wherein the second end comprises SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109 SEQ ID NO:110, SEQ ID NO:111, SEQ ID NO:112, SEQ ID NO:113, SEQ ID NO:114, SEQ ID NO:115 or SEQ ID NO:116.

Embodiment P7. The plurality of Embodiment P1, wherein the second end comprises SEQ ID NO:6, SEQ ID NO:11, SEQ ID NO:110, SEQ ID NO:112, SEQ ID NO:114, or SEQ ID NO:116.

Embodiment P8. The plurality of any one of Embodiment P1 to Embodiment P7, wherein the first end is capable of hybridizing to any one of the sequences of SEQ ID NO:1, SEQ ID NO:47, SEQ ID NO:101, SEQ ID NO:103, SEQ ID NO:105, or SEQ ID NO:107.

Embodiment P9. The plurality of any one of Embodiment P1 to Embodiment P7, wherein the first end comprises SEQ ID NO:1, SEQ ID NO:2, SEQ ID NO:3, SEQ ID NO:4, SEQ ID NO:5, SEQ ID NO:6, SEQ ID NO:7, or SEQ ID NO:8, wherein the second end and first end are different.

Embodiment P10. The plurality of any one of Embodiment P1 to Embodiment P7, wherein the first end comprises SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109 SEQ ID NO:110, SEQ ID NO:111, SEQ ID NO:112, SEQ ID NO:113, SEQ ID NO:114, SEQ ID NO:115 or SEQ ID NO:116, wherein the second end and first end are different.

Embodiment P11. The plurality of any one of Embodiment P1 to Embodiment P7, wherein the first end comprises SEQ ID NO:5, SEQ ID NO:9, SEQ ID NO:85, SEQ ID NO:92, SEQ ID NO:90, or SEQ ID NO:88.

Embodiment P12. The plurality of any one of Embodiment P1 to Embodiment P11, wherein the template nucleic acids comprise genomic DNA.

Embodiment P13. The plurality of any one of Embodiment P1 to Embodiment P12, wherein the first end or second end is capable of hybridizing at 5×SSC and 40° C.

Embodiment P14. A composition comprising the plurality of template nucleic acids of Embodiment P1 to Embodiment P13 hybridized to a plurality of first oligonucleotides via the first ends of the template nucleic acids, wherein the first oligonucleotides are immobilized on a solid support.

Embodiment P15. The composition of Embodiment P14, wherein each of the first oligonucleotides are covalently attached to a polymer on the solid support.

Embodiment P16. A composition comprising a solid support and a plurality of immobilized oligonucleotides, wherein the oligonucleotides in the plurality each comprise a sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109 SEQ ID NO:110, SEQ ID NO:111, SEQ ID NO:112, SEQ ID NO:113, SEQ ID NO:114 SEQ ID NO:115 or SEQ ID NO:116.

Embodiment P17. The composition of Embodiment P16, wherein the oligonucleotides in the plurality each comprise a sequence selected from SEQ ID NO:5, SEQ ID NO:9, SEQ ID NO:85, SEQ ID NO:92, SEQ ID NO:90, SEQ ID NO:88, SEQ ID NO:7, SEQ ID NO:11, SEQ ID NO:30, SEQ ID NO:87, SEQ ID NO:89, SEQ ID NO:91, or SEQ ID NO:86.

Embodiment P18. The composition of any one of Embodiment P14 to Embodiment P16, wherein the immobilized oligonucleotides are covalently attached to the solid support via a linker.

Embodiment P19. The composition of Embodiment P18, wherein the linker comprises 8 to 16 thymine nucleotides, and wherein the linker is at the 5' end of the immobilized oligonucleotides.

Embodiment P20. A method of immobilizing a template nucleic acid on a solid support, said method comprising: a) contacting the composition of any one of Embodiment P16 to Embodiment P19 with a template polynucleotide, wherein the template nucleic acid comprises a sequence complementary to a first immobilized polynucleotide; b) extending the first immobilized polynucleotide with a polymerase to generate an immobilized complement of the template nucleic acid; c) removing the template polynucleotide and annealing the immobilized complement of the template nucleic acid to a second immobilized polynucleotide; d) extending the second immobilized polynucleotide with a polymerase to generate an immobilized template nucleic acid.

Embodiment P21. A method of amplifying template nucleic acid molecules, the method comprising i) fragmenting a polynucleotide sample to generate a plurality of polynucleotide fragments each having a first end and a second end; ii) ligating a first adapter polynucleotide to the first end of each the polynucleotide fragments; iii) ligating a second adapter polynucleotide to the second end of each the polynucleotide fragments; iv) annealing an amplification primer to the first adapter, the second adapter, or both the first and the second adapter, and extending the amplification primer to generate amplification products, wherein the amplification products comprise a plurality template nucleic acid molecules, each comprising a first adapter polynucleotide or a complement thereof and a second adapter polynucleotide or a complement thereof, wherein the first adapter polynucleotide and the second adapter polynucleotide each independently comprise a sequence of SEQ ID NO:1 to SEQ ID NO:116.

Embodiment P22. A polynucleotide adapter formed by annealing of partially complementary first and second polynucleotide strands, wherein at least one of the strands comprises a polynucleotide sequence complementary to the sequence of any one of the sequences of SEQ ID NO:1 to SEQ ID NO:116.

Embodiment P23. The polynucleotide adapter of Embodiment P22, wherein the polynucleotide adapter is a Y polynucleotide adapter.

Embodiment P24. The polynucleotide adapter of Embodiment P22, wherein the polynucleotide adapter is a hairpin adapter.

Embodiment P25. The polynucleotide adapter of Embodiment P24, wherein the hairpin adapter comprises a cleavable site.

Embodiment P26. A kit comprising a first polynucleotide adapter comprising the sequence of SEQ ID NO:1 to SEQ ID NO:116.

Embodiment P27. The kit of Embodiment P26, further comprising a second polynucleotide adapter comprising the sequence of SEQ ID NO:1 to SEQ ID NO:116, wherein the first polynucleotide adapter and the second polynucleotide adapter are different.

Embodiment P28. A plurality of template nucleic acids, wherein each template nucleic acid comprises a first end, and a second end capable of hybridizing to any one of the sequences of SEQ ID NO:1 to SEQ ID NO:148, wherein a portion of the plurality of template nucleic acids are different from each other.

Embodiment P29. The plurality of Embodiment P28, wherein the second end is capable of hybridizing to any one of the sequences of SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

Embodiment P30. The plurality of Embodiment P28, wherein the second end is capable of hybridizing to any one of the sequences of SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109 SEQ ID NO:110, SEQ ID NO:111, SEQ ID NO:112, SEQ ID NO:113, SEQ ID NO:114 SEQ ID NO:115 SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, or SEQ ID NO:148.

Embodiment P31. The plurality of Embodiment P28, wherein the second end is capable of hybridizing to any one of the sequences of SEQ ID NO:7, SEQ ID NO:11, SEQ ID NO:30, SEQ ID NO:87, SEQ ID NO:89, SEQ ID NO:91, SEQ ID NO:86, SEQ ID NO:118, SEQ ID NO:120, SEQ ID NO:122, or SEQ ID NO:124.

Embodiment P32. The plurality of Embodiment P28, wherein the second end comprises SEQ ID NO:1, SEQ ID NO:2, SEQ ID NO:3, SEQ ID NO:4, SEQ ID NO:5, SEQ ID NO:6, SEQ ID NO:7, or SEQ ID NO:8.

Embodiment P33. The plurality of Embodiment P28, wherein the second end comprises SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109 SEQ ID NO:110, SEQ ID NO:111, SEQ ID NO:112, SEQ ID NO:113, SEQ ID NO:114 SEQ ID NO:115 SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, or SEQ ID NO:148.

Embodiment P34. The plurality of Embodiment P28, wherein the second end comprises SEQ ID NO:6, SEQ ID NO:11, SEQ ID NO:110, SEQ ID NO:112, SEQ ID NO:114, SEQ ID NO:116, SEQ ID NO:142, SEQ ID NO:144, SEQ ID NO:146, or SEQ ID NO:148.

Embodiment P35. The plurality of Embodiment P28, wherein the first end comprises SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and the second end comprises SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132.

Embodiment P36. The plurality of Embodiment P28, wherein the first end comprises SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and the second end comprises SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132.

Embodiment P37. The plurality of Embodiment P28, wherein the first end comprises SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and the second end comprises SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148.

Embodiment P38. The plurality of Embodiment P28, wherein the first end comprises, SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and the second end comprises SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148.

Embodiment P39. The plurality of any one of Embodiment P28 to Embodiment P38, wherein the first end is capable of hybridizing to any one of the sequences of SEQ ID NO:1, SEQ ID NO:47, SEQ ID NO:101, SEQ ID NO:103, SEQ ID NO:105, SEQ ID NO:107, SEQ ID NO:133, SEQ ID NO:135, SEQ ID NO:137, or SEQ ID NO:139.

Embodiment P40. The plurality of any one of Embodiment P28 to Embodiment P38, wherein the first end comprises SEQ ID NO:1, SEQ ID NO:2, SEQ ID NO:3, SEQ ID NO:4, SEQ ID NO:5, SEQ ID NO:6, SEQ ID NO:7, or SEQ ID NO:8, wherein the second end and first end are different.

Embodiment P41. The plurality of any one of Embodiment P28 to P38, wherein the first end comprises SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109 SEQ ID NO:110, SEQ ID NO:111, SEQ ID NO:112, SEQ ID NO:113, SEQ ID NO:114 SEQ ID NO:115 SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, or SEQ ID NO:148, wherein the second end and first end are different.

Embodiment P42. The plurality of any one of Embodiment P28 to Embodiment P38, wherein the first end comprises SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123.

Embodiment P43. The plurality of any one of Embodiment P28 to Embodiment P42, wherein the template nucleic acids comprise genomic DNA.

Embodiment P44. The plurality of any one of Embodiment P28 to Embodiment P43, wherein the first end or second end is capable of hybridizing at 5×SSC and 40° C.

Embodiment P45. A composition comprising the plurality of template nucleic acids of any one of Embodiment P28 to Embodiment P44 hybridized to a plurality of first oligonucleotides via the first ends of the template nucleic acids, wherein the first oligonucleotides are immobilized on a solid support.

Embodiment P46. A composition comprising the plurality of template nucleic acids of any one of Embodiment P28 to Embodiment P44 hybridized to a plurality of second oligonucleotides via the second ends of the template nucleic acids, wherein the second oligonucleotides are immobilized on a solid support.

Embodiment P47. The composition of Embodiment P45 or Embodiment P46, wherein each of the first oligonucleotides are covalently attached to a polymer on the solid support.

Embodiment P48. The composition of Embodiment P46 or Embodiment P47, wherein each of the second oligonucleotides are covalently attached to a polymer on the solid support.

Embodiment P49. A composition comprising a solid support and a first plurality of immobilized oligonucleotides, wherein the oligonucleotides in the plurality each comprise a sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109 SEQ ID NO:110, SEQ ID NO:111, SEQ ID NO:112, SEQ ID NO:113, SEQ ID NO:114 SEQ ID NO:115 SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, or SEQ ID NO:148.

Embodiment P50. The composition of Embodiment P49, further comprising a second plurality of immobilized oligonucleotides, wherein the oligonucleotides in the plurality each include a sequence selected from SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:103, SEQ ID NO:104, SEQ ID NO:105, SEQ ID NO:106, SEQ ID NO:107, SEQ ID NO:108, SEQ ID NO:109 SEQ ID NO:110, SEQ ID NO:111, SEQ ID NO:112, SEQ ID NO:113, SEQ ID NO:114 SEQ ID NO:115 or SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, SEQ ID NO:129, SEQ ID NO:130, SEQ ID NO:131, SEQ ID NO:132, SEQ ID NO:133, SEQ ID NO:134, SEQ ID NO:135, SEQ ID NO:136, SEQ ID NO:137, SEQ ID NO:138, SEQ ID NO:139, SEQ ID NO:140, SEQ ID NO:141, SEQ ID NO:142, SEQ ID NO:143, SEQ ID NO:144, SEQ ID NO:145, SEQ ID NO:146, SEQ ID NO:147, or SEQ ID NO:148, provided the second plurality of oligonucleotides is different than the first plurality of oligonucleotides.

Embodiment P51. The composition of Embodiment P49 or Embodiment P50, wherein the oligonucleotides in the first or second plurality each comprise a sequence selected from SEQ ID NO:5, SEQ ID NO:9, SEQ ID NO:85, SEQ ID NO:92, SEQ ID NO:90, SEQ ID NO:88, SEQ ID NO:7, SEQ ID NO:11, SEQ ID NO:30, SEQ ID NO:87, SEQ ID NO:89, SEQ ID NO:91, SEQ ID NO:86, SEQ ID NO:117, SEQ ID NO:118, SEQ ID NO:119, SEQ ID NO:120, SEQ ID NO:121, SEQ ID NO:122, SEQ ID NO:123, or SEQ ID NO:124, provided the second plurality of oligonucleotides is different that the first plurality of oligonucleotides.

Embodiment P52. The composition of any one of Embodiment P45 to Embodiment P50, wherein the immobilized oligonucleotides are covalently attached to the solid support via a linker.

Embodiment P53. The composition of Embodiment P52, wherein the linker comprises 8 to 16 thymine nucleotides, and wherein the linker is at the 5' end of the immobilized oligonucleotides.

Embodiment P54. The composition of Embodiment P52 or Embodiment P53, wherein the linker comprises 1 to 5 uracil nucleotides, and wherein the linker is at the 5' end of the immobilized oligonucleotides.

Embodiment P55. A method of immobilizing a template nucleic acid on a solid support, said method comprising: a) contacting the composition of any one of Embodiment P49 to Embodiment P54 with a template polynucleotide, wherein the template nucleic acid comprises a sequence complementary to a first immobilized polynucleotide; b) extending the first immobilized polynucleotide with a polymerase to generate an immobilized complement of the template nucleic acid; c) removing the template polynucleotide and annealing the immobilized complement of the template nucleic acid to a second immobilized polynucleotide; d) extending the second immobilized polynucleotide with a polymerase to generate an immobilized template nucleic acid.

Embodiment P56. A method of amplifying template nucleic acid molecules, the method comprising i) fragmenting a polynucleotide sample to generate a plurality of polynucleotide fragments each having a first end and a second end; ii) ligating a first adapter polynucleotide to the first end of each of the polynucleotide fragments; iii) ligating a second adapter polynucleotide to the second end of each of the polynucleotide fragments; iv) annealing an amplification primer to the first adapter, the second adapter, or both the first and the second adapter, and extending the amplification primer to generate amplification products, wherein the amplification products comprise a plurality of template nucleic acid molecules, each comprising a first adapter polynucleotide or a complement thereof and a second adapter polynucleotide or a complement thereof, wherein the first adapter polynucleotide and the second adapter polynucleotide each independently comprise a sequence of SEQ ID NO:1 to SEQ ID NO:148.

Embodiment P57. A polynucleotide adapter formed by annealing of partially complementary first and second polynucleotide strands, wherein at least one of the strands comprises a polynucleotide sequence complementary to the sequence of any one of the sequences of SEQ ID NO:1 to SEQ ID NO:148.

Embodiment P58. The polynucleotide adapter of Embodiment P57, wherein the polynucleotide adapter is a Y polynucleotide adapter.

Embodiment P59. The polynucleotide adapter of Embodiment P57, wherein the polynucleotide adapter is a hairpin adapter.

Embodiment P60. The polynucleotide adapter of Embodiment P59, wherein the hairpin adapter comprises a cleavable site.

Embodiment P61. A kit comprising a first polynucleotide adapter comprising the sequence of SEQ ID NO:1 to SEQ ID NO:148.

Embodiment P62. The kit of Embodiment P61, further comprising a second polynucleotide adapter comprising the sequence of SEQ ID NO:1 to SEQ ID NO:148, wherein the first polynucleotide adapter and the second polynucleotide adapter are different.

Embodiment P63. The kit of Embodiment P61 or Embodiment P62, wherein the first polynucleotide adapter comprises the sequence of SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and wherein the second polynucleotide adapter comprises the sequence of SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132.

Embodiment P64. The kit of Embodiment P61 or Embodiment P62, wherein the first polynucleotide adapter comprises the sequence of SEQ ID NO:1, SEQ ID NO:2, SEQ ID NO:101, SEQ ID NO:103, SEQ ID NO:105, SEQ ID NO:107, SEQ ID NO:109, SEQ ID NO:111, SEQ ID NO:113, SEQ ID NO:115, SEQ ID NO:133, SEQ ID NO:135, SEQ ID NO:137, SEQ ID NO:139, SEQ ID NO:141, SEQ ID NO:143, SEQ ID NO:145, or SEQ ID NO:147, and wherein the second polynucleotide adapter comprises the sequence of SEQ ID NO:7, SEQ ID NO:8, SEQ ID NO:87, SEQ ID NO:89, SEQ ID NO:91, SEQ ID NO:86, SEQ ID NO:94, SEQ ID NO:96, SEQ ID NO:98, SEQ ID NO:100, SEQ ID NO:118, SEQ ID NO:120, SEQ ID NO:122, SEQ ID NO:124, SEQ ID NO:126, SEQ ID NO:128, SEQ ID NO:130, or SEQ ID NO:132.

Embodiment P65. The kit of Embodiment P61 or Embodiment P62, wherein the first polynucleotide adapter comprises the sequence of SEQ ID NO:3, SEQ ID NO:5, SEQ ID NO:85, SEQ ID NO:92, SEQ ID NO:90, SEQ ID NO:88, SEQ ID NO:93, SEQ ID NO:95, SEQ ID NO:97, SEQ ID NO:99, SEQ ID NO:117, SEQ ID NO:119, SEQ ID NO:121, SEQ ID NO:123, SEQ ID NO:125, SEQ ID NO:127, SEQ ID NO:129, or SEQ ID NO:131, and wherein the second polynucleotide adapter comprises the sequence of SEQ ID NO:4, SEQ ID NO:6, SEQ ID NO:102, SEQ ID NO:104, SEQ ID NO:106, SEQ ID NO:108, SEQ ID NO:110, SEQ ID NO:112, SEQ ID NO:114, SEQ ID NO:116, SEQ ID NO:134, SEQ ID NO:136, SEQ ID NO:138, SEQ ID NO:140, SEQ ID NO:142, SEQ ID NO:144, SEQ ID NO:146, or SEQ ID NO:148.

ADDITIONAL EMBODIMENTS

The present disclosure provides the following additional illustrative embodiments.

Embodiment 1. A plurality of template nucleic acids, wherein each template nucleic acid comprises a first end, and a second end capable of hybridizing to any one of the sequences of SEQ ID NO:2, SEQ ID NO:5, SEQ ID NO:6, SEQ ID NO:7, SEQ ID NO:9, SEQ ID NO:11, SEQ ID NO:28, SEQ ID NO:30, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:141, SEQ ID NO:142, SEQ ID NO:143, SEQ ID NO:144, SEQ ID NO:145, SEQ ID NO:146, SEQ ID NO:147, or SEQ ID NO:148, wherein a portion of the plurality of template nucleic acids are different from each other.

Embodiment 2. The plurality of Embodiment 1, wherein the second end is capable of hybridizing to any one of the sequences of SEQ ID NO:2, SEQ ID NO:5, SEQ ID NO:6, SEQ ID NO:7, SEQ ID NO:11, SEQ ID NO:30, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:109 SEQ ID NO:110, SEQ ID NO:111, SEQ ID NO:112, SEQ ID NO:113, SEQ ID NO:114 SEQ ID NO:115 SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:141, SEQ ID NO:142, SEQ ID NO:143, SEQ ID NO:144, SEQ ID NO:145, SEQ ID NO:146, SEQ ID NO:147, or SEQ ID NO:148.

Embodiment 3. The plurality of Embodiment 1, wherein the second end comprises SEQ ID NO:2, SEQ ID NO:5, SEQ ID NO:6, SEQ ID NO:7, SEQ ID NO:11, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:109 SEQ ID NO:110, SEQ ID NO:111, SEQ ID NO:112, SEQ ID NO:113, SEQ ID NO:114 SEQ ID NO:115 SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:141, SEQ ID NO:142, SEQ ID NO:143, SEQ ID NO:144, SEQ ID NO:145, SEQ ID NO:146, SEQ ID NO:147, or SEQ ID NO:148.

Embodiment 4. The plurality of Embodiment 1, wherein the first end comprises SEQ ID NO:5, SEQ ID NO:85, SEQ ID NO:88, SEQ ID NO:90, SEQ ID NO:92, SEQ ID NO:117, SEQ ID NO:119, SEQ ID NO:121, or SEQ ID NO:123, and the second end comprises SEQ ID NO:7, SEQ ID NO:86, SEQ ID NO:87, SEQ ID NO:89, SEQ ID NO:91, SEQ ID NO:118, SEQ ID NO:120, SEQ ID NO:122, or SEQ ID NO:124.

Embodiment 5. The plurality of Embodiment 1, wherein the first end comprises SEQ ID NO:2, SEQ ID NO:109, SEQ ID NO:111, SEQ ID NO:113, SEQ ID NO:115, SEQ ID NO:141, SEQ ID NO:143, SEQ ID NO:145, or SEQ ID NO:147, and the second end comprises SEQ ID NO:7, SEQ ID NO:86, SEQ ID NO:87, SEQ ID NO:89, SEQ ID NO:91, SEQ ID NO:118, SEQ ID NO:120, SEQ ID NO:122, or SEQ ID NO:124.

Embodiment 6. The plurality of Embodiment 1, wherein the first end comprises SEQ ID NO:5, SEQ ID NO:85, SEQ ID NO:88, SEQ ID NO:90, SEQ ID NO:92, SEQ ID NO:117, SEQ ID NO:119, SEQ ID NO:121, or SEQ ID NO:123, and the second end comprises SEQ ID NO:6, SEQ ID NO:110, SEQ ID NO:112, SEQ ID NO:114, SEQ ID NO:116, SEQ ID NO:142, SEQ ID NO:144, SEQ ID NO:146, or SEQ ID NO:148.

Embodiment 7. The plurality of Embodiment 1, wherein the first end comprises, SEQ ID NO:2, SEQ ID NO:109, SEQ ID NO:111, SEQ ID NO:113, SEQ ID NO:115, SEQ ID NO:141, SEQ ID NO:143, SEQ ID NO:145, or SEQ ID NO:147, and the second end comprises SEQ ID NO:6, SEQ ID NO:110, SEQ ID NO:112, SEQ ID NO:114, SEQ ID NO:116, SEQ ID NO:142, SEQ ID NO:144, SEQ ID NO:146, or SEQ ID NO:148.

Embodiment 8. The plurality of any one of Embodiments 1 to 7, wherein the first end comprises SEQ ID NO:2, SEQ ID NO:5, SEQ ID NO:6, SEQ ID NO:7, SEQ ID NO:9, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:109 SEQ ID NO:110, SEQ ID NO:111 SEQ ID NO:112, SEQ ID NO:113, SEQ ID NO:114, SEQ ID NO:115 SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:141, SEQ ID NO:142, SEQ ID NO:143, SEQ ID NO:144, SEQ ID NO:145, SEQ ID NO:146, SEQ ID NO:147, or SEQ ID NO:148, wherein the second end and first end are different.

Embodiment 9. The plurality of any one of Embodiments 1 to 8, wherein the template nucleic acids comprise genomic DNA.

Embodiment 10. The plurality of any one of Embodiments 1 to 9, wherein the first end or second end is capable of hybridizing at 5×SSC and 40° C.

Embodiment 11. A composition comprising the plurality of template nucleic acids of any one of Embodiments 1 to 10 hybridized to a plurality of first oligonucleotides via the first ends of the template nucleic acids, wherein the first oligonucleotides are immobilized on a solid support.

Embodiment 12. A composition comprising the plurality of template nucleic acids of any one of Embodiments 1 to 11 hybridized to a plurality of second oligonucleotides via the second ends of the template nucleic acids, wherein the second oligonucleotides are immobilized on a solid support.

Embodiment 13. The composition of Embodiment 11 or 12, wherein each of the first oligonucleotides are covalently attached to a polymer on the solid support.

Embodiment 14. The composition of Embodiment 12 or 13, wherein each of the second oligonucleotides are covalently attached to a polymer on the solid support.

Embodiment 15. A composition comprising a solid support and a first plurality of immobilized oligonucleotides, wherein the oligonucleotides in the plurality each comprise a sequence selected from SEQ ID NO:2, SEQ ID NO:5, SEQ ID NO:6, SEQ ID NO:7, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:109 SEQ ID NO:110, SEQ ID NO:111 SEQ ID NO:112, SEQ ID NO:113, SEQ ID NO:114, SEQ ID NO:115 SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:141, SEQ ID NO:142, SEQ ID NO:143, SEQ ID NO:144, SEQ ID NO:145, SEQ ID NO:146, SEQ ID NO:147, or SEQ ID NO:148.

Embodiment 16. The composition of Embodiment 15, further comprising a second plurality of immobilized oligonucleotides, wherein the oligonucleotides in the plurality each comprise a sequence selected from SEQ ID NO:2, SEQ ID NO:5, SEQ ID NO:6, SEQ ID NO:7, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:109 SEQ ID NO:110, SEQ ID NO:111, SEQ ID NO:112, SEQ ID NO:113, SEQ ID NO:114, SEQ ID NO:115 SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:141, SEQ ID NO:142, SEQ ID NO:143, SEQ ID NO:144, SEQ ID NO:145, SEQ ID NO:146, SEQ ID NO:147, or SEQ ID NO:148, provided the second plurality of oligonucleotides is different than the first plurality of oligonucleotides.

Embodiment 17. The composition of Embodiment 15, wherein the oligonucleotides in the first or second plurality each comprise a sequence selected from SEQ ID NO:5, SEQ ID NO:7, SEQ ID NO:9, SEQ ID NO:11, SEQ ID NO:30, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:117, SEQ ID NO:118, SEQ ID NO:119, SEQ ID NO:120, SEQ ID NO:121, SEQ ID NO:122, SEQ ID NO:123, or SEQ ID NO:124, provided the second plurality of oligonucleotides is different that the first plurality of oligonucleotides.

Embodiment 18. The composition of any one of Embodiments 11 to 15, wherein the immobilized oligonucleotides are covalently attached to the solid support via a linker.

Embodiment 19. The composition of Embodiment 18, wherein the linker comprises 8 to 16 thymine nucleotides, and wherein the linker is at the 5' end of the immobilized oligonucleotides.

Embodiment 20. The composition of Embodiment 18 or 19, wherein the linker comprises 1 to 5 uracil nucleotides, and wherein the linker is at the 5' end of the immobilized oligonucleotides.

Embodiment 21. A method of amplifying template nucleic acid molecules, the method comprising i) fragmenting a polynucleotide sample to generate a plurality of polynucleotide fragments each having a first end and a second end; ii) ligating a first adapter polynucleotide to the first end of each of the polynucleotide fragments; iii) ligating a second adapter polynucleotide to the second end of each of the polynucleotide fragments; iv) annealing an amplification primer to the first adapter, the second adapter, or both the first and the second adapter, and extending the amplification primer to generate amplification products, wherein the amplification products comprise a plurality of template nucleic acid molecules, each comprising a first adapter polynucleotide or a complement thereof and a second adapter polynucleotide or a complement thereof, wherein the first adapter polynucleotide and the second adapter polynucleotide each independently comprise a sequence of SEQ ID NO:2, SEQ ID NO:5, SEQ ID NO:6, SEQ ID NO:7, SEQ ID NO:9, SEQ ID NO:11, SEQ ID NO:28, SEQ ID NO:30, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:141, SEQ ID NO:142, SEQ ID NO:143, SEQ ID NO:144, SEQ ID NO:145, SEQ ID NO:146, SEQ ID NO:147, or SEQ ID NO:148.

Embodiment 22. A polynucleotide adapter formed by annealing of partially complementary first and second polynucleotide strands, wherein at least one of the strands comprises a polynucleotide sequence complementary to the sequence of any one of the sequences of SEQ ID NO:2, SEQ ID NO:5, SEQ ID NO:6, SEQ ID NO:7, SEQ ID NO:9, SEQ ID NO:11, SEQ ID NO:28, SEQ ID NO:30, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:141, SEQ ID NO:142, SEQ ID NO:143, SEQ ID NO:144, SEQ ID NO:145, SEQ ID NO:146, SEQ ID NO:147, or SEQ ID NO:148.

Embodiment 23. The polynucleotide adapter of Embodiment 22, wherein the polynucleotide adapter is a Y polynucleotide adapter.

Embodiment 24. The polynucleotide adapter of Embodiment 22, wherein the polynucleotide adapter is a hairpin adapter.

Embodiment 25. The polynucleotide adapter of Embodiment 24, wherein the hairpin adapter comprises a cleavable site.

Embodiment 26. A kit comprising a first polynucleotide adapter comprising the sequence of SEQ ID NO:2, SEQ ID NO:5, SEQ ID NO:6, SEQ ID NO:7, SEQ ID NO:9, SEQ ID NO:11, SEQ ID NO:28, SEQ ID NO:30, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:141, SEQ ID NO:142, SEQ ID NO:143, SEQ ID NO:144, SEQ ID NO:145, SEQ ID NO:146, SEQ ID NO:147, or SEQ ID NO:148.

Embodiment 27. The kit of Embodiment 26, further comprising a second polynucleotide adapter comprising the sequence of SEQ ID NO:2, SEQ ID NO:5, SEQ ID NO:6, SEQ ID NO:7, SEQ ID NO:9, SEQ ID NO:11, SEQ ID NO:28, SEQ ID NO:30, SEQ ID NO:85, SEQ ID NO:86, SEQ ID NO:87, SEQ ID NO:88, SEQ ID NO:89, SEQ ID NO:90, SEQ ID NO:91, SEQ ID NO:92, SEQ ID NO:109, SEQ ID NO:110, SEQ ID NO:111, SEQ ID NO:112, SEQ ID NO:113, SEQ ID NO:114, SEQ ID NO:115, SEQ ID NO:116, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:141, SEQ ID NO:142, SEQ ID NO:143, SEQ ID NO:144, SEQ ID NO:145, SEQ ID NO:146, SEQ ID NO:147, or SEQ ID NO:148, wherein the first polynucleotide adapter and the second polynucleotide adapter are different.

Embodiment 28. The kit of Embodiment 26 or 27, wherein the first polynucleotide adapter comprises the sequence of SEQ ID NO:5, SEQ ID NO:85, SEQ ID NO:88, SEQ ID NO:90, SEQ ID NO:92, SEQ ID NO:117, SEQ ID NO:119, SEQ ID NO:121, or SEQ ID NO:123, and wherein the second polynucleotide adapter comprises the sequence of SEQ ID NO:7, SEQ ID NO:86, SEQ ID NO:87, SEQ ID NO:89, SEQ ID NO:91, SEQ ID NO:118, SEQ ID NO:120, SEQ ID NO:122, or SEQ ID NO:124.

Embodiment 29. The kit of Embodiment 26 or 27, wherein the first polynucleotide adapter comprises the sequence of SEQ ID NO:2, SEQ ID NO:109, SEQ ID NO:111, SEQ ID NO:113, SEQ ID NO:115, SEQ ID NO:141, SEQ ID NO:143, SEQ ID NO:145, or SEQ ID NO:147, and wherein the second polynucleotide adapter comprises the sequence of SEQ ID NO:7, SEQ ID NO:86, SEQ ID NO:87, SEQ ID NO:89, SEQ ID NO:91, SEQ ID NO:118, SEQ ID NO:120, SEQ ID NO:122, or SEQ ID NO:124.

Embodiment 30. The kit of Embodiment 26 or 27, wherein the first polynucleotide adapter comprises the sequence of SEQ ID NO:5, SEQ ID NO:85, SEQ ID NO:88, SEQ ID NO:90, SEQ ID NO:92, SEQ ID NO:117, SEQ ID NO:119, SEQ ID NO:121, or SEQ ID NO:123, and wherein the second polynucleotide adapter comprises the sequence of SEQ ID NO:6, SEQ ID NO:110, SEQ ID NO:112, SEQ ID NO:114, SEQ ID NO:116, SEQ ID NO:142, SEQ ID NO:144, SEQ ID NO:146, or SEQ ID NO:148.

Embodiment 31. A solid support comprising a first plurality of immobilized oligonucleotides, and a second plurality of immobilized oligonucleotides, wherein the immobilized oligonucleotides of the first plurality comprise a sequence selected from SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123, and the immobilized oligonucleotides of the second plurality comprise a sequence selected from SEQ ID NO:7, SEQ ID NO:30, SEQ ID NO:87, SEQ ID NO:89, SEQ ID NO:91, SEQ ID NO:86, SEQ ID NO:118, SEQ ID NO:120, SEQ ID NO:122, or SEQ ID NO:124.

Embodiment 32. The solid support of Embodiment 31, wherein the immobilized oligonucleotides of the first plurality are covalently attached to a polymer on the solid support via a first linker.

Embodiment 33. The solid support of Embodiment 31 or 32, wherein the immobilized oligonucleotides of the second plurality are covalently attached to a polymer on the solid support via a second linker.

Embodiment 34. The solid support of Embodiment 32 or 33, wherein the first linker, the second linker, or both the first linker and the second linker comprises 8 to 16 thymine nucleotides, and wherein the linker is at the 5' end of the immobilized oligonucleotides.

Embodiment 35. The solid support of any one of Embodiments 32 to 34, wherein the first linker, the second linker, or both the first linker and the second linker comprises a cleavable site.

Embodiment 36. The solid support of Embodiment 35, wherein the cleavable site comprises a diol linker, disulfide linker, photocleavable linker, abasic site, deoxyuracil triphosphate (dUTP), deoxy-8-Oxo-guanine triphosphate (d-8-oxoG), methylated nucleotide, ribonucleotide, or a sequence containing a modified or unmodified nucleotide that is specifically recognized by a cleaving agent.

Embodiment 37. The solid support of any one of Embodiments 32 to 36, wherein the first linker, the second linker, or both the first linker and the second linker comprises 1 to 5 uracil nucleotides.

Embodiment 38. The solid support of any one of Embodiments 31 to 37, wherein the solid support is a flow cell, particle, chip, slide, multi-well container, or unpatterned solid support.

Embodiment 39. The solid support of any one of Embodiments 31 to 38, wherein the solid support further comprises a polymer, resist, and/or hydrogel.

Embodiment 40. The solid support of any one of Embodiments 31 to 37, or 39, wherein said solid support comprises two or more wells, wherein each well comprises the first plurality of immobilized oligonucleotides and the second plurality of immobilized oligonucleotides.

Embodiment 41. The solid support of claim 40, wherein the first plurality of immobilized oligonucleotides and the second plurality of immobilized oligonucleotides are covalently attached to a polymer within the wells.

Embodiment 42. The solid support of Embodiments 40 or 41, wherein each well of the solid support is separated by an interstitial region.

Embodiment 43. The solid support of Embodiment 42, wherein the interstitial region is substantially free of said polymer.

Embodiment 44. The solid support of any one of Embodiments 40 to 43, wherein the solid support comprises about 0.2 wells to about 4.0 wells per $\mu m^2$.

Embodiment 45. The solid support of any one of Embodiments 40 to 44, wherein each of the wells are separated from each other by about 0.2 µm to about 2.0 µm.

Embodiment 46. The solid support of any one of Embodiments 31 to 45, comprising about 100 oligonucleotides per $\mu m^2$ to about 1,000,000 oligonucleotides per $\mu m^2$ of said first plurality of immobilized oligonucleotides.

Embodiment 47. The solid support of any one of Embodiments 31 to 45, comprising about 100 oligonucleotides per $\mu m^2$ to about 1,000,000 oligonucleotides per $\mu m^2$ of said second plurality of immobilized oligonucleotides.

Embodiment 48. A kit comprising the solid support of any one of Embodiments 31 to 47.

Embodiment 49. The kit of Embodiment 48, further comprising a polymerase and a plurality of deoxynucleotides (dNTPs).

Embodiment 50. A microfluidic device comprising the solid support of any one of Embodiments 31 to 47.

Embodiment 51. A method of immobilizing a polynucleotide, the method comprising: contacting the solid support of any one of Embodiments 31 to 47 with a polynucleotide comprising a primer binding sequence; hybridizing said primer binding sequence to a first immobilized oligonucleotide of the second plurality of immobilized oligonucleotides; and extending the first immobilized oligonucleotide with a polymerase to form a first immobilized polynucleotide.

Embodiment 52. The method of Embodiment 51, wherein said polynucleotide further comprises a primer sequence, and said first immobilized polynucleotide comprises a complement of the primer sequence.

Embodiment 53. The method of Embodiment 52, comprising hybridizing the complement of the primer sequence to a second immobilized oligonucleotide of the first plurality of immobilized oligonucleotides, and extending the second immobilized oligonucleotide with a polymerase to form a second immobilized polynucleotide.

Embodiment 54. The method of Embodiment 53, further comprising amplifying the first and second immobilized polynucleotides to form amplification products.

Embodiment 55. The method of Embodiment 54, wherein amplifying comprises 1 to 100 bridge-PCR amplification cycles.

Embodiment 56. The method of Embodiment 54, wherein the amplifying comprises about 5 minutes to about 4 hours of solid-phase rolling circle amplification (RCA), solid-phase exponential rolling circle amplification (eRCA), solid-phase recombinase polymerase amplification (RPA), solid-phase helicase dependent amplification (HDA), or template walking amplification.

Embodiment 57. The method of any one of Embodiments 54 to 56, further comprising sequencing the amplification products.

Embodiment 58. The method of Embodiment 57, wherein sequencing comprises hybridizing a sequencing primer to an amplification product, or a complement thereof, and contacting the sequencing primer with a sequencing solution comprising one or more modified nucleotides comprising a reversible terminator, and monitoring the sequential incorporation of complementary nucleotides to generate one or more sequencing reads, wherein the reversible terminator is removed prior to the introduction of the next complementary nucleotide.

Embodiment 59. The method of Embodiment 57, wherein sequencing comprises hybridizing a sequencing primer to an amplification product, or a complement thereof, incorporating one or more modified nucleotides into the sequencing primer with a polymerase to create an extension strand, and detecting the one or more incorporated nucleotides.

Embodiment 60. The method of any one of Embodiments 51 to 59, wherein the first immobilized oligonucleotide comprises a cleavable site.

Embodiment 61. The method of any one of Embodiments 51 to 60, wherein the second immobilized oligonucleotide comprises a cleavable site.

Embodiment 62. The method of Embodiments 60 or 61, further comprising cleaving the cleavable site and removing the immobilized polynucleotide from said solid support.

Embodiment 63. The method of Embodiment 62, wherein cleaving the cleavable site comprises contacting said cleavable site with a cleaving agent.

Embodiment 64. The method of Embodiment 63, wherein the cleaving agent is selected from sodium periodate, RNase, formamidopyrimidine DNA glycosylase (Fpg), endonuclease, uracil DNA glycosylase (UDG), TCEP, THPP, sodium dithionite ($Na_2S_2O_4$), hydrazine ($N_2H_4$), Pd(0), or ultraviolet radiation.

Embodiment 65. A plurality of nucleic acid molecules, wherein each nucleic acid molecule comprises a first end, a target sequence, and a second end, wherein the first end comprises a sequence selected from SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123, wherein the target sequence of said plurality of nucleic acid molecules are different from each other.

Embodiment 66. The plurality of Embodiment 65, wherein the second end comprises a sequence selected from SEQ ID NO:4, SEQ ID NO:102, SEQ ID NO:104, SEQ ID NO:106, SEQ ID NO:108, SEQ ID NO:134, SEQ ID NO:136, SEQ ID NO:138, or SEQ ID NO:140.

Embodiment 67. The plurality of Embodiments 65 or 66, wherein the target sequence comprises genomic DNA.

Embodiment 68. The plurality of any one of Embodiments 65 to 68, wherein the target sequence comprises a cancer-associated gene, or fragment thereof.

Embodiment 69. The plurality of any one of Embodiments 65 to 68 wherein the nucleic acid molecule comprises 50 to 1000 nucleotides.

Embodiment 70. The plurality of any one of Embodiments 65 to 68, wherein the nucleic acid molecule comprises 100 to 500 nucleotides.

Embodiment 71. The plurality of any one of Embodiments 65 to 68, wherein the nucleic acid molecule consists of 50 to 1000 nucleotides.

Embodiment 72. A plurality of oligonucleotides, wherein each oligonucleotide is capable of hybridizing to SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123.

125

Embodiment 73. The plurality of Embodiment 72, wherein each oligonucleotide comprises the sequence of SEQ ID NO:2, SEQ ID NO:28, SEQ ID NO:109, SEQ ID NO:111, SEQ ID NO:113, SEQ ID NO:115, SEQ ID NO:141, SEQ ID NO:143, SEQ ID NO: 145, or SEQ ID NO:147.

Embodiment 74. A plurality of oligonucleotides, wherein each oligonucleotide is capable of hybridizing to SEQ ID NO:7, SEQ ID NO:30, SEQ ID NO:87, SEQ ID NO:89, SEQ ID NO:91, SEQ ID NO:86, SEQ ID NO:118, SEQ ID NO:120, SEQ ID NO:122, or SEQ ID NO:124.

Embodiment 75. The plurality of Embodiment 74, wherein each oligonucleotide comprises the sequence of SEQ ID NO:6, SEQ ID NO:11, SEQ ID NO:110, SEQ ID NO:112, SEQ ID NO:114, SEQ ID NO:116, SEQ ID NO:142, SEQ ID NO:144, SEQ ID NO:146, or SEQ ID NO:148.

Embodiment 76. The plurality of any one of Embodiments 65 to 75, wherein capable of hybridizing comprises hybridization at 5×SSC and 40° C.

Embodiment 77. The plurality of any one of Embodiments 65 to 75, wherein the oligonucleotide is a linear oligonucleotide comprising a 5' end and a 3' end.

Embodiment 78. The plurality of any one of Embodiments 65 to 75, wherein the oligonucleotide is a circular oligonucleotide.

Embodiment 79. A kit comprising an oligonucleotide, wherein the oligonucleotide comprises a first sequencing primer sequence, a platform primer sequence, a platform primer binding sequence, and a second sequencing primer binding sequence, wherein said platform primer sequence comprises a sequence selected from SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123; and said platform primer binding sequence comprises a sequence selected from SEQ ID NO:4, SEQ ID NO:102, SEQ ID NO:104, SEQ ID NO:106, SEQ ID NO:108, SEQ ID NO:134, SEQ ID NO:136, SEQ ID NO:138, or SEQ ID NO:140.

Embodiment 80. The kit of Embodiment 79, further comprising a second plurality of second oligonucleotides, wherein the second oligonucleotides of the second plurality comprise the same platform primer sequence.

Embodiment 81. The kit of Embodiment 80, wherein the oligonucleotides of the plurality of oligonucleotides include an index sequence.

126

Embodiment 82. A kit comprising a first oligonucleotide comprising a first sequencing primer sequence and a second sequencing primer binding sequence; a second oligonucleotide comprising from 5' to 3', a first platform primer sequence and a sequence complementary to the first sequencing primer sequence; a third oligonucleotide comprising from 5' to 3', a second platform primer sequence and a sequence complementary to the second sequencing primer binding sequence; wherein said first platform primer sequence comprises a sequence selected from SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123; and said second platform primer sequence comprise a sequence selected from SEQ ID NO:7, SEQ ID NO:30, SEQ ID NO:87, SEQ ID NO:89, SEQ ID NO:91, SEQ ID NO:86, SEQ ID NO:118, SEQ ID NO:120, SEQ ID NO:122, or SEQ ID NO:124.

Embodiment 83. A polynucleotide adapter, comprising a first strand comprising a first binding sequence and a first tail sequence; and a second strand comprising a second binding sequence and a second tail sequence, wherein at least a portion of the first binding sequence is hybridized to a portion of the second binding sequence; wherein the first tail sequence comprises SEQ ID NO:5, SEQ ID NO:9, SEQ ID NO:85, SEQ ID NO:92, SEQ ID NO:90, SEQ ID NO:88, SEQ ID NO:117, SEQ ID NO:119, SEQ ID NO:121, or SEQ ID NO:123 and the second tail sequence comprises SEQ ID NO:4, SEQ ID NO:102, SEQ ID NO:104, SEQ ID NO:106, SEQ ID NO:108, SEQ ID NO:134, SEQ ID NO:136, SEQ ID NO:138, or SEQ ID NO:140, and the first binding sequence comprises SEQ ID NO:152 and the second binding sequence comprises SEQ ID NO:178.

Embodiment 84. The polynucleotide adapter of Embodiment 83, wherein the polynucleotide adapter is a Y polynucleotide adapter.

Embodiment 85. The polynucleotide adapter of Embodiment 83, wherein the polynucleotide adapter is a hairpin adapter.

Embodiment 86. The polynucleotide adapter of Embodiment 85, wherein the hairpin adapter comprises a cleavable site.

Embodiment 87. The polynucleotide adapter of Embodiment 85, wherein the first tail sequence is covalently attached to the second tail sequence.

What is claimed is:

1. A solid support comprising a first plurality of immobilized oligonucleotides, and a second plurality of immobilized oligonucleotides, wherein each oligonucleotide of the first plurality of immobilized oligonucleotides comprises SEQ ID NO:92, and wherein each oligonucleotide of the second plurality of immobilized oligonucleotides comprises SEQ ID NO:89.

2. The solid support of claim 1, wherein each oligonucleotide of the first plurality of immobilized oligonucleotides is covalently attached to a polymer on the solid support via a first linker.

3. The solid support of claim 1, wherein each oligonucleotide of the second plurality of immobilized oligonucleotides is covalently attached to a polymer on the solid support via a second linker.

4. The solid support of claim 1, wherein the solid support is a multi-well container, flow cell, particle, chip, slide, or unpatterned solid support.

5. The solid support of claim 1, wherein the solid support further comprises a polymer, resist, and/or hydrogel.

6. The solid support of claim 1, wherein said solid support comprises two or more wells, wherein each well comprises the first plurality of immobilized oligonucleotides and the second plurality of immobilized oligonucleotides.

7. The solid support of claim 6, wherein each oligonucleotide of the first plurality of immobilized oligonucleotides and each oligonucleotide of the second plurality of immobilized oligonucleotides is covalently attached to a polymer within the wells.

8. A kit comprising the solid support of claim 7.

9. The kit of claim 8, further comprising a polymerase and a plurality of deoxynucleotides (dNTPs).

10. A microfluidic device comprising the solid support of claim 7.

11. The solid support of claim 6, wherein the solid support comprises about 0.2 wells to about 4.0 wells per µm².

12. The solid support of claim 6, wherein each of the wells is separated from each other by about 0.2 µm to about 2.0 µm.

13. The solid support of claim 1, comprising about 100 oligonucleotides per µm² to about 1,000,000 oligonucleotides per µm² of said first plurality of immobilized oligonucleotides.

14. The solid support of claim 1, comprising about 100 oligonucleotides per µm² to about 1,000,000 oligonucleotides per µm² of said second plurality of immobilized oligonucleotides.

15. The solid support of claim 1, wherein each oligonucleotide of the first plurality of immobilized oligonucleotides is covalently attached to a polymer on the solid support via a first linker, and wherein each oligonucleotide of the second plurality of immobilized oligonucleotides is covalently attached to said polymer on the solid support via a second linker.

16. The solid support of claim 15, wherein the first linker, the second linker, or both the first linker and the second linker comprise 8 to 16 thymine nucleotides, and wherein each linker is at the 5' end of the immobilized oligonucleotides.

17. The solid support of claim 15, wherein the first linker, the second linker, or both the first linker and the second linker comprises a cleavable site.

18. The solid support of claim 17, wherein the cleavable site comprises a deoxyuracil triphosphate (dUTP), diol linker, disulfide linker, photocleavable linker, abasic site, deoxy-8-Oxo-guanine triphosphate (d-8-oxoG), methylated nucleotide, ribonucleotide, or a sequence containing a modified or unmodified nucleotide that is specifically recognized by a cleaving agent.

19. The solid support of claim 15, wherein the first linker, the second linker, or both the first linker and the second linker comprises 1 to 5 uracil nucleotides.

20. A solid support comprising:
a first immobilized oligonucleotide comprising SEQ ID NO:92, and
a second immobilized oligonucleotide comprising SEQ ID NO:89.

21. The solid support of claim 20, wherein the first immobilized oligonucleotide further comprises a first index sequence, and the second immobilized oligonucleotide further comprises a second index sequence.

22. The solid support of claim 20, wherein the first immobilized oligonucleotide is covalently attached to a polymer on the solid support via a first linker, and the second immobilized oligonucleotide is covalently attached to said polymer on the solid support via a second linker.

\* \* \* \* \*

SEQUENCE LISTING

```
Sequence total quantity: 185
SEQ ID NO: 1            moltype = DNA  length = 28
FEATURE                 Location/Qualifiers
source                  1..28
                        mol_type = other DNA
                        organism = synthetic construct
SEQUENCE: 1
cagggaagga gtgcgtggct gcctttgt                                            28

SEQ ID NO: 2            moltype = DNA  length = 28
FEATURE                 Location/Qualifiers
source                  1..28
                        mol_type = other DNA
                        organism = synthetic construct
SEQUENCE: 2
tgtttccgtc ggtgcgtgag gaagggac                                            28

SEQ ID NO: 3            moltype = DNA  length = 28
FEATURE                 Location/Qualifiers
source                  1..28
```

```
                            mol_type = other DNA
                            organism = synthetic construct
SEQUENCE: 3
gtcccttcct cacgcaccga cggaaaca                                              28

SEQ ID NO: 4               moltype = DNA   length = 28
FEATURE                    Location/Qualifiers
source                     1..28
                           mol_type = other DNA
                           organism = synthetic construct
SEQUENCE: 4
gtggttggtg agggtcatct cgctggag                                              28

SEQ ID NO: 5               moltype = DNA   length = 28
FEATURE                    Location/Qualifiers
source                     1..28
                           mol_type = other DNA
                           organism = synthetic construct
SEQUENCE: 5
acaaaggcag ccacgcactc cttccctg                                              28

SEQ ID NO: 6               moltype = DNA   length = 28
FEATURE                    Location/Qualifiers
source                     1..28
                           mol_type = other DNA
                           organism = synthetic construct
SEQUENCE: 6
gaggtcgctc tactgggagt ggttggtg                                              28

SEQ ID NO: 7               moltype = DNA   length = 28
FEATURE                    Location/Qualifiers
source                     1..28
                           mol_type = other DNA
                           organism = synthetic construct
SEQUENCE: 7
ctccagcgag atgaccctca ccaaccac                                              28

SEQ ID NO: 8               moltype = DNA   length = 28
FEATURE                    Location/Qualifiers
source                     1..28
                           mol_type = other DNA
                           organism = synthetic construct
SEQUENCE: 8
caccaaccac tcccagtaga gcgacctc                                              28

SEQ ID NO: 9               moltype = DNA   length = 41
FEATURE                    Location/Qualifiers
source                     1..41
                           mol_type = other DNA
                           organism = synthetic construct
SEQUENCE: 9
acaaaggcag ccacgcactc cttccctgaa ggccggaatc t                               41

SEQ ID NO: 10              moltype = DNA   length = 41
FEATURE                    Location/Qualifiers
source                     1..41
                           mol_type = other DNA
                           organism = synthetic construct
SEQUENCE: 10
gctgccgcca ctagccatct tactgctgag gactcttcgc t                               41

SEQ ID NO: 11              moltype = DNA   length = 40
FEATURE                    Location/Qualifiers
source                     1..40
                           mol_type = other DNA
                           organism = synthetic construct
SEQUENCE: 11
gattccggcc ttgtggttgg tgagggtcat ctcgctggag                                 40

SEQ ID NO: 12              moltype = DNA   length = 40
FEATURE                    Location/Qualifiers
source                     1..40
                           mol_type = other DNA
                           organism = synthetic construct
SEQUENCE: 12
gcgaagagtc ctggagtgcc gccaatgtat gcgagggtga                                 40

SEQ ID NO: 13              moltype = DNA   length = 71
FEATURE                    Location/Qualifiers
```

```
                        source          1..71
                                        mol_type = other DNA
                                        organism = synthetic construct
SEQUENCE: 13
gcgcgcgttt tttttgcttg cgtctcctgc cagccatatc cggtctacgt gatccttttt          60
tttcgcgcgc t                                                               71

SEQ ID NO: 14           moltype = DNA   length = 83
FEATURE                 Location/Qualifiers
source                  1..83
                        mol_type = other DNA
                        organism = synthetic construct
SEQUENCE: 14
gcgcgcgttt tttttttttt tgcttgcgtc tcctgccagc catatccggt ctacgtgatc          60
cttttttttt tttttcgcgc gct                                                  83

SEQ ID NO: 15           moltype = DNA   length = 62
FEATURE                 Location/Qualifiers
source                  1..62
                        mol_type = other DNA
                        organism = synthetic construct
SEQUENCE: 15
ggatcacgta gattttgctt gcgtctcctg ccagccatat ccggttttt tacgtgattc          60
ct                                                                         62

SEQ ID NO: 16           moltype = DNA   length = 81
FEATURE                 Location/Qualifiers
source                  1..81
                        mol_type = other DNA
                        organism = synthetic construct
SEQUENCE: 16
gcgaagagtc ctggagtgcc gccaatgtat gcgagggtga gctgccgcca ctagccatct          60
tactgctgag gactcttcgc t                                                    81

SEQ ID NO: 17           moltype = DNA   length = 93
FEATURE                 Location/Qualifiers
source                  1..93
                        mol_type = other DNA
                        organism = synthetic construct
SEQUENCE: 17
gcgaagagtc cttttttttgg agtgccgcca atgtatgcga gggtgagctg ccgccactag          60
ccatcttact gctgtttttt aggactcttc gct                                       93

SEQ ID NO: 18           moltype = DNA   length = 100
FEATURE                 Location/Qualifiers
source                  1..100
                        mol_type = other DNA
                        organism = synthetic construct
SEQUENCE: 18
gcgaagagtc cttttttttgg agtgccgcca atgtatgcga gggtgatttt tttgctgccg          60
ccactagcca tcttactgct gttttttagg actcttcgct                                100

SEQ ID NO: 19           moltype = DNA   length = 81
FEATURE                 Location/Qualifiers
source                  1..81
                        mol_type = other DNA
                        organism = synthetic construct
SEQUENCE: 19
gattccggcc ttgtggttgg tgagggtcat ctcgctggag acaaaggcag ccacgcactc          60
cttccctgaa ggccggaatc t                                                    81

SEQ ID NO: 20           moltype = DNA   length = 93
FEATURE                 Location/Qualifiers
source                  1..93
                        mol_type = other DNA
                        organism = synthetic construct
SEQUENCE: 20
gattccggcc ttttttttgt ggttggtgag ggtcatctcg ctggagacaa aggcagccac          60
gcactccttc cctgttttttt aaggccggaa tct                                      93

SEQ ID NO: 21           moltype = DNA   length = 100
FEATURE                 Location/Qualifiers
source                  1..100
                        mol_type = other DNA
                        organism = synthetic construct
SEQUENCE: 21
gattccggcc ttttttttgt ggttggtgag ggtcatctcg ctggagtttt tttacaaagg          60
cagccacgca ctccttccct gttttttaag gccggaatct                                100
```

```
SEQ ID NO: 22            moltype = DNA   length = 61
FEATURE                  Location/Qualifiers
source                   1..61
                         mol_type = other DNA
                         organism = synthetic construct
SEQUENCE: 22
ggatcacgta gattttgctt gcgtctcctg ccagccatat ccggttttc tacgtgatcc    60
t                                                                    61

SEQ ID NO: 23            moltype = DNA   length = 77
FEATURE                  Location/Qualifiers
source                   1..77
                         mol_type = other DNA
                         organism = synthetic construct
SEQUENCE: 23
ggatcacgta gatttttttt ttttgcttgc gtctcctgcc agccatatcc ggtttttttt    60
tttttctacg tgatcct                                                   77

SEQ ID NO: 24            moltype = DNA   length = 101
FEATURE                  Location/Qualifiers
source                   1..101
                         mol_type = other DNA
                         organism = synthetic construct
SEQUENCE: 24
ggatcacgta gatttttttt tttttttttt tttttgcttg cgtctcctg ccagccatat     60
ccggtttttt tttttttttt ttttttttc tacgtgatcc t                        101

SEQ ID NO: 25            moltype = DNA   length = 103
FEATURE                  Location/Qualifiers
source                   1..103
                         mol_type = other DNA
                         organism = synthetic construct
SEQUENCE: 25
ggatcacgta gatttttttt tttttttttt tttttttttt tttttttttt ttgcttgcgt    60
ctcctgccag ccatatccgg tttttttttt tctacgtgat cct                     103

SEQ ID NO: 26            moltype = DNA   length = 67
FEATURE                  Location/Qualifiers
source                   1..67
                         mol_type = other DNA
                         organism = synthetic construct
SEQUENCE: 26
ggatcacgta gattttagat ctgcttgcgt ctcctgccag ccatatccgg tttttctacg    60
tgatcct                                                              67

SEQ ID NO: 27            moltype = DNA   length = 82
FEATURE                  Location/Qualifiers
source                   1..82
                         mol_type = other DNA
                         organism = synthetic construct
SEQUENCE: 27
ggatcacgta gatttttttt ttttagatct gcttgcgtct cctgccagcc atatccggtt    60
tttttttttt ctacgtgatc ct                                             82

SEQ ID NO: 28            moltype = DNA   length = 41
FEATURE                  Location/Qualifiers
source                   1..41
                         mol_type = other DNA
                         organism = synthetic construct
SEQUENCE: 28
tgtttccgtc ggtgcgtgag gaagggactt ccggccttag a                        41

SEQ ID NO: 29            moltype = DNA   length = 41
FEATURE                  Location/Qualifiers
source                   1..41
                         mol_type = other DNA
                         organism = synthetic construct
SEQUENCE: 29
cgacggcggt gatcggtaga atgacgactc ctgagaagcg a                        41

SEQ ID NO: 30            moltype = DNA   length = 40
FEATURE                  Location/Qualifiers
source                   1..40
                         mol_type = other DNA
                         organism = synthetic construct
SEQUENCE: 30
ctaaggccgg aacaccaacc actcccagta gagcgacctc                          40
```

```
SEQ ID NO: 31          moltype = DNA   length = 40
FEATURE                Location/Qualifiers
source                 1..40
                       mol_type = other DNA
                       organism = synthetic construct
SEQUENCE: 31
cgcttctcag gacctcacgg cggttacata cgctcccact                              40

SEQ ID NO: 32          moltype = DNA   length = 71
FEATURE                Location/Qualifiers
source                 1..71
                       mol_type = other DNA
                       organism = synthetic construct
SEQUENCE: 32
cgcgcgcaaa aaaaacgaac gcagaggacg gtcggtatag ccagatgca ctaggaaaaa         60
aaagcgcgcg a                                                            71

SEQ ID NO: 33          moltype = DNA   length = 83
FEATURE                Location/Qualifiers
source                 1..83
                       mol_type = other DNA
                       organism = synthetic construct
SEQUENCE: 33
cgcgcgcaaa aaaaaaaaa acgaacgcag aggacggtcg gtataggcca gatgcactag         60
gaaaaaaaaa aaaagcgcg cga                                                83

SEQ ID NO: 34          moltype = DNA   length = 62
FEATURE                Location/Qualifiers
source                 1..62
                       mol_type = other DNA
                       organism = synthetic construct
SEQUENCE: 34
cctagtgcat ctaaaacgaa cgcagaggac ggtcggtata ggccaaaaag atgcactaag        60
ga                                                                      62

SEQ ID NO: 35          moltype = DNA   length = 81
FEATURE                Location/Qualifiers
source                 1..81
                       mol_type = other DNA
                       organism = synthetic construct
SEQUENCE: 35
cgcttctcag gacctcacgg cggttacata cgctcccact cgacggcggt gatcggtaga        60
atgacgactc ctgagaagcg a                                                 81

SEQ ID NO: 36          moltype = DNA   length = 93
FEATURE                Location/Qualifiers
source                 1..93
                       mol_type = other DNA
                       organism = synthetic construct
SEQUENCE: 36
cgcttctcag gaaaaaaacc tcacggcggt tacatacgct cccactcgac ggcggtgatc        60
ggtagaatga cgacaaaaaa tcctgagaag cga                                    93

SEQ ID NO: 37          moltype = DNA   length = 100
FEATURE                Location/Qualifiers
source                 1..100
                       mol_type = other DNA
                       organism = synthetic construct
SEQUENCE: 37
cgcttctcag gaaaaaaacc tcacggcggt tacatacgct cccactaaaa aaacgacggc        60
ggtgatcggt agaatgacga caaaaaatcc tgagaagcga                            100

SEQ ID NO: 38          moltype = DNA   length = 81
FEATURE                Location/Qualifiers
source                 1..81
                       mol_type = other DNA
                       organism = synthetic construct
SEQUENCE: 38
ctaaggccgg aacaccaacc actcccagta gagcgacctc tgtttccgtc ggtgcgtgag        60
gaagggactt ccggccttag a                                                 81

SEQ ID NO: 39          moltype = DNA   length = 93
FEATURE                Location/Qualifiers
source                 1..93
                       mol_type = other DNA
                       organism = synthetic construct
```

```
SEQUENCE: 39
ctaaggccgg aaaaaaaaca ccaaccactc ccagtagagc gacctctgtt tccgtcggtg    60
cgtgaggaag ggacaaaaaa ttccggcctt aga                                 93

SEQ ID NO: 40           moltype = DNA   length = 100
FEATURE                 Location/Qualifiers
source                  1..100
                        mol_type = other DNA
                        organism = synthetic construct
SEQUENCE: 40
ctaaggccgg aaaaaaaaca ccaaccactc ccagtagagc gacctcaaaa aaatgtttcc    60
gtcggtgcgt gaggaaggga caaaaaattc cggccttaga                         100

SEQ ID NO: 41           moltype = DNA   length = 61
FEATURE                 Location/Qualifiers
source                  1..61
                        mol_type = other DNA
                        organism = synthetic construct
SEQUENCE: 41
cctagtgcat ctaaaacgaa cgcagaggac ggtcggtata ggccaaaaag atgcactagg    60
a                                                                    61

SEQ ID NO: 42           moltype = DNA   length = 77
FEATURE                 Location/Qualifiers
source                  1..77
                        mol_type = other DNA
                        organism = synthetic construct
SEQUENCE: 42
cctagtgcat ctaaaaaaaa aaaacgaacg cagaggacgg tcggtatagg ccaaaaaaaa    60
aaaaagatgc actagga                                                   77

SEQ ID NO: 43           moltype = DNA   length = 101
FEATURE                 Location/Qualifiers
source                  1..101
                        mol_type = other DNA
                        organism = synthetic construct
SEQUENCE: 43
cctagtgcat ctaaaaaaaa aaaaaaaaaa aaaaacgaa cgcagaggac ggtcggtata    60
ggccaaaaaa aaaaaaaaaa aaaaaaaag atgcactagg a                        101

SEQ ID NO: 44           moltype = DNA   length = 103
FEATURE                 Location/Qualifiers
source                  1..103
                        mol_type = other DNA
                        organism = synthetic construct
SEQUENCE: 44
cctagtgcat ctaaaaaaaa aaaaaaaaaa aaaaaaaaaa aaaaaaaaa aacgaacgca    60
gaggacggtc ggtataggcc aaaaaaaaaa agatgcacta gga                     103

SEQ ID NO: 45           moltype = DNA   length = 67
FEATURE                 Location/Qualifiers
source                  1..67
                        mol_type = other DNA
                        organism = synthetic construct
SEQUENCE: 45
cctagtgcat ctaaaatcta gacgaacgca gaggacggtc ggtataggcc aaaaagatgc    60
actagga                                                              67

SEQ ID NO: 46           moltype = DNA   length = 82
FEATURE                 Location/Qualifiers
source                  1..82
                        mol_type = other DNA
                        organism = synthetic construct
SEQUENCE: 46
cctagtgcat ctaaaaaaaa aaaatctaga cgaacgcaga ggacggtcgg tataggccaa    60
aaaaaaaaaa gatgcactag ga                                             82

SEQ ID NO: 47           moltype = DNA   length = 41
FEATURE                 Location/Qualifiers
source                  1..41
                        mol_type = other DNA
                        organism = synthetic construct
SEQUENCE: 47
agattccggc cttcagggaa ggagtgcgtg gctgcctttg t                        41
```

```
SEQ ID NO: 48           moltype = DNA   length = 41
FEATURE                 Location/Qualifiers
source                  1..41
                        mol_type = other DNA
                        organism = synthetic construct
SEQUENCE: 48
agcgaagagt cctcagcagt aagatggcta gtggcggcag c                            41

SEQ ID NO: 49           moltype = DNA   length = 40
FEATURE                 Location/Qualifiers
source                  1..40
                        mol_type = other DNA
                        organism = synthetic construct
SEQUENCE: 49
tcaccctcgc atacattggc ggcactccag gactcttcgc                              40

SEQ ID NO: 50           moltype = DNA   length = 40
FEATURE                 Location/Qualifiers
source                  1..40
                        mol_type = other DNA
                        organism = synthetic construct
SEQUENCE: 50
ctccagcgag atgaccctca ccaaccacaa ggccggaatc                              40

SEQ ID NO: 51           moltype = DNA   length = 71
FEATURE                 Location/Qualifiers
source                  1..71
                        mol_type = other DNA
                        organism = synthetic construct
SEQUENCE: 51
agcgcgcgaa aaaaaggat cacgtagacc ggatatggct ggcaggagac gcaagcaaaa         60
aaaacgcgcg c                                                             71

SEQ ID NO: 52           moltype = DNA   length = 62
FEATURE                 Location/Qualifiers
source                  1..62
                        mol_type = other DNA
                        organism = synthetic construct
SEQUENCE: 52
aggaatcacg tagaaaaacc ggatatggct ggcaggagac gcaagcaaaa tctacgtgat        60
cc                                                                       62

SEQ ID NO: 53           moltype = DNA   length = 83
FEATURE                 Location/Qualifiers
source                  1..83
                        mol_type = other DNA
                        organism = synthetic construct
SEQUENCE: 53
agcgcgcgaa aaaaaaaaa aaggatcacg tagaccggat atggctggca ggagacgcaa         60
gcaaaaaaaa aaaaacgcg cgc                                                 83

SEQ ID NO: 54           moltype = DNA   length = 81
FEATURE                 Location/Qualifiers
source                  1..81
                        mol_type = other DNA
                        organism = synthetic construct
SEQUENCE: 54
agcgaagagt cctcagcagt aagatggcta gtggcggcag ctcaccctcg catacattgg        60
cggcactcca ggactcttcg c                                                  81

SEQ ID NO: 55           moltype = DNA   length = 93
FEATURE                 Location/Qualifiers
source                  1..93
                        mol_type = other DNA
                        organism = synthetic construct
SEQUENCE: 55
agcgaagagt cctaaaaaac agcagtaaga tggctagtgg cggcagctca ccctcgcata        60
cattggcggc actccaaaaa aaggactctt cgc                                     93

SEQ ID NO: 56           moltype = DNA   length = 100
FEATURE                 Location/Qualifiers
source                  1..100
                        mol_type = other DNA
                        organism = synthetic construct
SEQUENCE: 56
agcgaagagt cctaaaaaac agcagtaaga tggctagtgg cggcagcaaa aaatcaccc         60
tcgcatacat tggcggcact ccaaaaaaag gactcttcgc                             100
```

| | | |
|---|---|---|
| SEQ ID NO: 57 | moltype = DNA   length = 81 | |
| FEATURE | Location/Qualifiers | |
| source | 1..81 | |
| | mol_type = other DNA | |
| | organism = synthetic construct | |
| SEQUENCE: 57 | | |
| agattccggc cttcagggaa ggagtgcgtg gctgcctttg tctccagcga gatgaccctc | | 60 |
| accaaccaca aggccggaat c | | 81 |

| | | |
|---|---|---|
| SEQ ID NO: 58 | moltype = DNA   length = 93 | |
| FEATURE | Location/Qualifiers | |
| source | 1..93 | |
| | mol_type = other DNA | |
| | organism = synthetic construct | |
| SEQUENCE: 58 | | |
| agattccggc cttaaaaaac agggaaggag tgcgtggctg cctttgtctc cagcgagatg | | 60 |
| accctcacca accacaaaaa aaaggccgga atc | | 93 |

| | | |
|---|---|---|
| SEQ ID NO: 59 | moltype = DNA   length = 100 | |
| FEATURE | Location/Qualifiers | |
| source | 1..100 | |
| | mol_type = other DNA | |
| | organism = synthetic construct | |
| SEQUENCE: 59 | | |
| agattccggc cttaaaaaac agggaaggag tgcgtggctg cctttgtaaa aaaactccag | | 60 |
| cgagatgacc ctcaccaacc acaaaaaaaa ggccggaatc | | 100 |

| | | |
|---|---|---|
| SEQ ID NO: 60 | moltype = DNA   length = 61 | |
| FEATURE | Location/Qualifiers | |
| source | 1..61 | |
| | mol_type = other DNA | |
| | organism = synthetic construct | |
| SEQUENCE: 60 | | |
| aggatcacgt agaaaaaccg gatatggctg gcaggagacg caagcaaaat ctacgtgatc | | 60 |
| c | | 61 |

| | | |
|---|---|---|
| SEQ ID NO: 61 | moltype = DNA   length = 77 | |
| FEATURE | Location/Qualifiers | |
| source | 1..77 | |
| | mol_type = other DNA | |
| | organism = synthetic construct | |
| SEQUENCE: 61 | | |
| aggatcacgt agaaaaaaaa aaaaccgga tatggctggc aggagacgca agcaaaaaaa | | 60 |
| aaaaatctac gtgatcc | | 77 |

| | | |
|---|---|---|
| SEQ ID NO: 62 | moltype = DNA   length = 101 | |
| FEATURE | Location/Qualifiers | |
| source | 1..101 | |
| | mol_type = other DNA | |
| | organism = synthetic construct | |
| SEQUENCE: 62 | | |
| aggatcacgt agaaaaaaaa aaaaaaaaaa aaaaaaccg gatatggctg gcaggagacg | | 60 |
| caagcaaaaa aaaaaaaaaa aaaaaaaat ctacgtgatc c | | 101 |

| | | |
|---|---|---|
| SEQ ID NO: 63 | moltype = DNA   length = 82 | |
| FEATURE | Location/Qualifiers | |
| source | 1..82 | |
| | mol_type = other DNA | |
| | organism = synthetic construct | |
| SEQUENCE: 63 | | |
| aggatcacgt agaaaaaaaa aaaaccggat atggctggca ggagacgcaa gcagatctaa | | 60 |
| aaaaaaaaaa tctacgtgat cc | | 82 |

| | | |
|---|---|---|
| SEQ ID NO: 64 | moltype = DNA   length = 67 | |
| FEATURE | Location/Qualifiers | |
| source | 1..67 | |
| | mol_type = other DNA | |
| | organism = synthetic construct | |
| SEQUENCE: 64 | | |
| aggatcacgt agaaaaaccg gatatggctg gcaggagacg caagcagatc taaaatctac | | 60 |
| gtgatcc | | 67 |

| | | |
|---|---|---|
| SEQ ID NO: 65 | moltype = DNA   length = 103 | |
| FEATURE | Location/Qualifiers | |
| source | 1..103 | |
| | mol_type = other DNA | |
| | organism = synthetic construct | |

SEQUENCE: 65
aggatcacgt agaaaaaaaa aaaccggata tggctggcag gagacgcaag caaaaaaaaa    60
aaaaaaaaaa aaaaaaaaaa aaaaaaaaaa atctacgtga tcc                     103

SEQ ID NO: 66          moltype = DNA   length = 40
FEATURE                Location/Qualifiers
source                 1..40
                       mol_type = other DNA
                       organism = synthetic construct
SEQUENCE: 66
agtgggagcg tatgtaaccg ccgtgaggtc ctgagaagcg                          40

SEQ ID NO: 67          moltype = DNA   length = 40
FEATURE                Location/Qualifiers
source                 1..40
                       mol_type = other DNA
                       organism = synthetic construct
SEQUENCE: 67
gaggtcgctc tactgggagt ggttggtgtt ccggccttag                          40

SEQ ID NO: 68          moltype = DNA   length = 41
FEATURE                Location/Qualifiers
source                 1..41
                       mol_type = other DNA
                       organism = synthetic construct
SEQUENCE: 68
tcgcttctca ggagtcgtca ttctaccgat caccgccgtc g                        41

SEQ ID NO: 69          moltype = DNA   length = 41
FEATURE                Location/Qualifiers
source                 1..41
                       mol_type = other DNA
                       organism = synthetic construct
SEQUENCE: 69
tctaaggccg gaagtcccctt cctcacgcac cgacggaaac a                       41

SEQ ID NO: 70          moltype = DNA   length = 62
FEATURE                Location/Qualifiers
source                 1..62
                       mol_type = other DNA
                       organism = synthetic construct
SEQUENCE: 70
tccttagtgc atcttttttgg cctataccga ccgtcctctg cgttcgtttt agatgcacta   60
gg                                                                  62

SEQ ID NO: 71          moltype = DNA   length = 83
FEATURE                Location/Qualifiers
source                 1..83
                       mol_type = other DNA
                       organism = synthetic construct
SEQUENCE: 71
tcgcgcgctt tttttttttt ttcctagtgc atctggccta taccgaccgt cctctgcgtt   60
cgtttttttt ttttttgcgc gcg                                            83

SEQ ID NO: 72          moltype = DNA   length = 71
FEATURE                Location/Qualifiers
source                 1..71
                       mol_type = other DNA
                       organism = synthetic construct
SEQUENCE: 72
tcgcgcgctt tttttcctta gtgcatctgg cctataccga ccgtcctctg cgttcgtttt   60
ttttgcgcgc g                                                        71

SEQ ID NO: 73          moltype = DNA   length = 81
FEATURE                Location/Qualifiers
source                 1..81
                       mol_type = other DNA
                       organism = synthetic construct
SEQUENCE: 73
tcgcttctca ggagtcgtca ttctaccgat caccgccgtc gagtgggagc gtatgtaacc   60
gccgtgaggt cctgagaagc g                                             81

SEQ ID NO: 74          moltype = DNA   length = 100
FEATURE                Location/Qualifiers
source                 1..100
                       mol_type = other DNA
                       organism = synthetic construct

```
SEQUENCE: 74
tcgcttctca ggattttttg tcgtcattct accgatcacc gccgtcgttt ttttagtggg    60
agcgtatgta accgccgtga ggttttttc ctgagaagcg                           100

SEQ ID NO: 75           moltype = DNA   length = 93
FEATURE                 Location/Qualifiers
source                  1..93
                        mol_type = other DNA
                        organism = synthetic construct
SEQUENCE: 75
tcgcttctca ggattttttg tcgtcattct accgatcacc gccgtcgagt gggagcgtat    60
gtaaccgccg tgaggttttt ttcctgagaa gcg                                 93

SEQ ID NO: 76           moltype = DNA   length = 100
FEATURE                 Location/Qualifiers
source                  1..100
                        mol_type = other DNA
                        organism = synthetic construct
SEQUENCE: 76
tctaaggccg gaattttttg tcccttcctc acgcaccgac ggaaacattt ttttgaggtc    60
gctctactgg gagtggttgg tgttttttt ccggccttag                           100

SEQ ID NO: 77           moltype = DNA   length = 93
FEATURE                 Location/Qualifiers
source                  1..93
                        mol_type = other DNA
                        organism = synthetic construct
SEQUENCE: 77
tctaaggccg gaattttttg tcccttcctc acgcaccgac ggaaacagag gtcgctctac    60
tgggagtggt tggtgttttt tttccggcct tag                                 93

SEQ ID NO: 78           moltype = DNA   length = 81
FEATURE                 Location/Qualifiers
source                  1..81
                        mol_type = other DNA
                        organism = synthetic construct
SEQUENCE: 78
tctaaggccg gaagtccctt cctcacgcac cgacggaaac agaggtcgct ctactgggag    60
tggttggtgt tccggcctta g                                              81

SEQ ID NO: 79           moltype = DNA   length = 101
FEATURE                 Location/Qualifiers
source                  1..101
                        mol_type = other DNA
                        organism = synthetic construct
SEQUENCE: 79
tcctagtgca tctttttttt ttttttttt tttttttggc ctataccgac cgtcctctgc     60
gttcgttttt tttttttttt ttttttta gatgcactag g                          101

SEQ ID NO: 80           moltype = DNA   length = 77
FEATURE                 Location/Qualifiers
source                  1..77
                        mol_type = other DNA
                        organism = synthetic construct
SEQUENCE: 80
tcctagtgca tctttttttt tttttggcct ataccgaccg tcctctgcgt tcgtttttt     60
tttttagatg cactagg                                                   77

SEQ ID NO: 81           moltype = DNA   length = 61
FEATURE                 Location/Qualifiers
source                  1..61
                        mol_type = other DNA
                        organism = synthetic construct
SEQUENCE: 81
tcctagtgca tcttttttggc ctataccgac cgtcctctgc gttcgtttta gatgcactag   60
g                                                                    61

SEQ ID NO: 82           moltype = DNA   length = 82
FEATURE                 Location/Qualifiers
source                  1..82
                        mol_type = other DNA
                        organism = synthetic construct
SEQUENCE: 82
tcctagtgca tctttttttt ttttggccta taccgaccgt cctctgcgtt cgtctagatt    60
tttttttttt agatgcacta gg                                             82

SEQ ID NO: 83           moltype = DNA   length = 67
FEATURE                 Location/Qualifiers
source                  1..67
```

```
                        mol_type = other DNA
                        organism = synthetic construct
SEQUENCE: 83
tcctagtgca tcttttggc ctataccgac cgtcctctgc gttcgtctag attttagatg    60
cactagg                                                             67

SEQ ID NO: 84           moltype = DNA   length = 103
FEATURE                 Location/Qualifiers
source                  1..103
                        mol_type = other DNA
                        organism = synthetic construct
SEQUENCE: 84
tcctagtgca tctttttttt tttggcctat accgaccgtc ctctgcgttc gtttttttt     60
tttttttttt tttttttttt tttttttttt tagatgcact agg                    103

SEQ ID NO: 85           moltype = DNA   length = 25
FEATURE                 Location/Qualifiers
source                  1..25
                        mol_type = other DNA
                        organism = synthetic construct
SEQUENCE: 85
acaaaggcag ccacgcactc cttcc                                         25

SEQ ID NO: 86           moltype = DNA   length = 16
FEATURE                 Location/Qualifiers
source                  1..16
                        mol_type = other DNA
                        organism = synthetic construct
SEQUENCE: 86
ctccagcgag atgacc                                                   16

SEQ ID NO: 87           moltype = DNA   length = 25
FEATURE                 Location/Qualifiers
source                  1..25
                        mol_type = other DNA
                        organism = synthetic construct
SEQUENCE: 87
ctccagcgag atgaccctca ccaac                                         25

SEQ ID NO: 88           moltype = DNA   length = 16
FEATURE                 Location/Qualifiers
source                  1..16
                        mol_type = other DNA
                        organism = synthetic construct
SEQUENCE: 88
acaaaggcag ccacgc                                                   16

SEQ ID NO: 89           moltype = DNA   length = 22
FEATURE                 Location/Qualifiers
source                  1..22
                        mol_type = other DNA
                        organism = synthetic construct
SEQUENCE: 89
ctccagcgag atgaccctca cc                                            22

SEQ ID NO: 90           moltype = DNA   length = 19
FEATURE                 Location/Qualifiers
source                  1..19
                        mol_type = other DNA
                        organism = synthetic construct
SEQUENCE: 90
acaaaggcag ccacgcact                                                19

SEQ ID NO: 91           moltype = DNA   length = 19
FEATURE                 Location/Qualifiers
source                  1..19
                        mol_type = other DNA
                        organism = synthetic construct
SEQUENCE: 91
ctccagcgag atgaccctc                                                19

SEQ ID NO: 92           moltype = DNA   length = 22
FEATURE                 Location/Qualifiers
source                  1..22
                        mol_type = other DNA
                        organism = synthetic construct
SEQUENCE: 92
acaaaggcag ccacgcactc ct                                            22
```

| | | |
|---|---|---|
| SEQ ID NO: 93<br>FEATURE<br>source | moltype = DNA   length = 25<br>Location/Qualifiers<br>1..25<br>mol_type = other DNA<br>organism = synthetic construct | |
| SEQUENCE: 93<br>ccttcctcac gcaccgacgg aaaca | | 25 |
| SEQ ID NO: 94<br>FEATURE<br>source | moltype = DNA   length = 25<br>Location/Qualifiers<br>1..25<br>mol_type = other DNA<br>organism = synthetic construct | |
| SEQUENCE: 94<br>caaccactcc cagtagagcg acctc | | 25 |
| SEQ ID NO: 95<br>FEATURE<br>source | moltype = DNA   length = 22<br>Location/Qualifiers<br>1..22<br>mol_type = other DNA<br>organism = synthetic construct | |
| SEQUENCE: 95<br>tcctcacgca ccgacggaaa ca | | 22 |
| SEQ ID NO: 96<br>FEATURE<br>source | moltype = DNA   length = 22<br>Location/Qualifiers<br>1..22<br>mol_type = other DNA<br>organism = synthetic construct | |
| SEQUENCE: 96<br>ccactcccag tagagcgacc tc | | 22 |
| SEQ ID NO: 97<br>FEATURE<br>source | moltype = DNA   length = 19<br>Location/Qualifiers<br>1..19<br>mol_type = other DNA<br>organism = synthetic construct | |
| SEQUENCE: 97<br>tcacgcaccg acggaaaca | | 19 |
| SEQ ID NO: 98<br>FEATURE<br>source | moltype = DNA   length = 19<br>Location/Qualifiers<br>1..19<br>mol_type = other DNA<br>organism = synthetic construct | |
| SEQUENCE: 98<br>ctcccagtag agcgacctc | | 19 |
| SEQ ID NO: 99<br>FEATURE<br>source | moltype = DNA   length = 16<br>Location/Qualifiers<br>1..16<br>mol_type = other DNA<br>organism = synthetic construct | |
| SEQUENCE: 99<br>cgcaccgacg gaaaca | | 16 |
| SEQ ID NO: 100<br>FEATURE<br>source | moltype = DNA   length = 16<br>Location/Qualifiers<br>1..16<br>mol_type = other DNA<br>organism = synthetic construct | |
| SEQUENCE: 100<br>ccagtagagc gacctc | | 16 |
| SEQ ID NO: 101<br>FEATURE<br>source | moltype = DNA   length = 25<br>Location/Qualifiers<br>1..25<br>mol_type = other DNA<br>organism = synthetic construct | |
| SEQUENCE: 101<br>ggaaggagtg cgtggctgcc tttgt | | 25 |
| SEQ ID NO: 102<br>FEATURE<br>source | moltype = DNA   length = 25<br>Location/Qualifiers<br>1..25<br>mol_type = other DNA<br>organism = synthetic construct | |
| SEQUENCE: 102<br>gttggtgagg gtcatctcgc tggag | | 25 |

```
SEQ ID NO: 103          moltype = DNA   length = 22
FEATURE                 Location/Qualifiers
source                  1..22
                        mol_type = other DNA
                        organism = synthetic construct
SEQUENCE: 103
aggagtgcgt ggctgccttt gt                                              22

SEQ ID NO: 104          moltype = DNA   length = 22
FEATURE                 Location/Qualifiers
source                  1..22
                        mol_type = other DNA
                        organism = synthetic construct
SEQUENCE: 104
ggtgagggtc atctcgctgg ag                                              22

SEQ ID NO: 105          moltype = DNA   length = 19
FEATURE                 Location/Qualifiers
source                  1..19
                        mol_type = other DNA
                        organism = synthetic construct
SEQUENCE: 105
agtgcgtggc tgcctttgt                                                  19

SEQ ID NO: 106          moltype = DNA   length = 19
FEATURE                 Location/Qualifiers
source                  1..19
                        mol_type = other DNA
                        organism = synthetic construct
SEQUENCE: 106
gagggtcatc tcgctggag                                                  19

SEQ ID NO: 107          moltype = DNA   length = 16
FEATURE                 Location/Qualifiers
source                  1..16
                        mol_type = other DNA
                        organism = synthetic construct
SEQUENCE: 107
gcgtggctgc ctttgt                                                     16

SEQ ID NO: 108          moltype = DNA   length = 16
FEATURE                 Location/Qualifiers
source                  1..16
                        mol_type = other DNA
                        organism = synthetic construct
SEQUENCE: 108
ggtcatctcg ctggag                                                     16

SEQ ID NO: 109          moltype = DNA   length = 25
FEATURE                 Location/Qualifiers
source                  1..25
                        mol_type = other DNA
                        organism = synthetic construct
SEQUENCE: 109
tgtttccgtc ggtgcgtgag gaagg                                           25

SEQ ID NO: 110          moltype = DNA   length = 25
FEATURE                 Location/Qualifiers
source                  1..25
                        mol_type = other DNA
                        organism = synthetic construct
SEQUENCE: 110
gaggtcgctc tactgggagt ggttg                                           25

SEQ ID NO: 111          moltype = DNA   length = 22
FEATURE                 Location/Qualifiers
source                  1..22
                        mol_type = other DNA
                        organism = synthetic construct
SEQUENCE: 111
tgtttccgtc ggtgcgtgag ga                                              22

SEQ ID NO: 112          moltype = DNA   length = 22
FEATURE                 Location/Qualifiers
source                  1..22
                        mol_type = other DNA
                        organism = synthetic construct
```

-continued

```
SEQUENCE: 112
gaggtcgctc tactgggagt gg                                              22

SEQ ID NO: 113            moltype = DNA  length = 19
FEATURE                   Location/Qualifiers
source                    1..19
                          mol_type = other DNA
                          organism = synthetic construct
SEQUENCE: 113
tgtttccgtc ggtgcgtga                                                  19

SEQ ID NO: 114            moltype = DNA  length = 19
FEATURE                   Location/Qualifiers
source                    1..19
                          mol_type = other DNA
                          organism = synthetic construct
SEQUENCE: 114
gaggtcgctc tactgggag                                                  19

SEQ ID NO: 115            moltype = DNA  length = 16
FEATURE                   Location/Qualifiers
source                    1..16
                          mol_type = other DNA
                          organism = synthetic construct
SEQUENCE: 115
tgtttccgtc ggtgcg                                                     16

SEQ ID NO: 116            moltype = DNA  length = 16
FEATURE                   Location/Qualifiers
source                    1..16
                          mol_type = other DNA
                          organism = synthetic construct
SEQUENCE: 116
gaggtcgctc tactgg                                                     16

SEQ ID NO: 117            moltype = DNA  length = 25
FEATURE                   Location/Qualifiers
source                    1..25
                          mol_type = other DNA
                          organism = synthetic construct
SEQUENCE: 117
aaggcagcca cgcactcctt ccctg                                           25

SEQ ID NO: 118            moltype = DNA  length = 25
FEATURE                   Location/Qualifiers
source                    1..25
                          mol_type = other DNA
                          organism = synthetic construct
SEQUENCE: 118
cagcgagatg accctcacca accac                                           25

SEQ ID NO: 119            moltype = DNA  length = 22
FEATURE                   Location/Qualifiers
source                    1..22
                          mol_type = other DNA
                          organism = synthetic construct
SEQUENCE: 119
gcagccacgc actccttccc tg                                              22

SEQ ID NO: 120            moltype = DNA  length = 22
FEATURE                   Location/Qualifiers
source                    1..22
                          mol_type = other DNA
                          organism = synthetic construct
SEQUENCE: 120
cgagatgacc ctcaccaacc ac                                              22

SEQ ID NO: 121            moltype = DNA  length = 19
FEATURE                   Location/Qualifiers
source                    1..19
                          mol_type = other DNA
                          organism = synthetic construct
SEQUENCE: 121
gccacgcact ccttccctg                                                  19
```

```
SEQ ID NO: 122           moltype = DNA  length = 19
FEATURE                  Location/Qualifiers
source                   1..19
                         mol_type = other DNA
                         organism = synthetic construct
SEQUENCE: 122
gatgaccctc accaaccac                                                      19

SEQ ID NO: 123           moltype = DNA  length = 16
FEATURE                  Location/Qualifiers
source                   1..16
                         mol_type = other DNA
                         organism = synthetic construct
SEQUENCE: 123
acgcactcct tccctg                                                         16

SEQ ID NO: 124           moltype = DNA  length = 16
FEATURE                  Location/Qualifiers
source                   1..16
                         mol_type = other DNA
                         organism = synthetic construct
SEQUENCE: 124
gaccctcacc aaccac                                                         16

SEQ ID NO: 125           moltype = DNA  length = 25
FEATURE                  Location/Qualifiers
source                   1..25
                         mol_type = other DNA
                         organism = synthetic construct
SEQUENCE: 125
gtcccttcct cacgcaccga cggaa                                               25

SEQ ID NO: 126           moltype = DNA  length = 25
FEATURE                  Location/Qualifiers
source                   1..25
                         mol_type = other DNA
                         organism = synthetic construct
SEQUENCE: 126
caccaaccac tcccagtaga gcgac                                               25

SEQ ID NO: 127           moltype = DNA  length = 22
FEATURE                  Location/Qualifiers
source                   1..22
                         mol_type = other DNA
                         organism = synthetic construct
SEQUENCE: 127
gtcccttcct cacgcaccga cg                                                  22

SEQ ID NO: 128           moltype = DNA  length = 22
FEATURE                  Location/Qualifiers
source                   1..22
                         mol_type = other DNA
                         organism = synthetic construct
SEQUENCE: 128
caccaaccac tcccagtaga gc                                                  22

SEQ ID NO: 129           moltype = DNA  length = 19
FEATURE                  Location/Qualifiers
source                   1..19
                         mol_type = other DNA
                         organism = synthetic construct
SEQUENCE: 129
gtcccttcct cacgcaccg                                                      19

SEQ ID NO: 130           moltype = DNA  length = 19
FEATURE                  Location/Qualifiers
source                   1..19
                         mol_type = other DNA
                         organism = synthetic construct
SEQUENCE: 130
caccaaccac tcccagtag                                                      19

SEQ ID NO: 131           moltype = DNA  length = 16
FEATURE                  Location/Qualifiers
source                   1..16
                         mol_type = other DNA
                         organism = synthetic construct
```

```
SEQUENCE: 131
gtcccttcct cacgca                                                       16

SEQ ID NO: 132          moltype = DNA   length = 16
FEATURE                 Location/Qualifiers
source                  1..16
                        mol_type = other DNA
                        organism = synthetic construct
SEQUENCE: 132
caccaaccac tcccag                                                       16

SEQ ID NO: 133          moltype = DNA   length = 25
FEATURE                 Location/Qualifiers
source                  1..25
                        mol_type = other DNA
                        organism = synthetic construct
SEQUENCE: 133
cagggaagga gtgcgtggct gcctt                                             25

SEQ ID NO: 134          moltype = DNA   length = 25
FEATURE                 Location/Qualifiers
source                  1..25
                        mol_type = other DNA
                        organism = synthetic construct
SEQUENCE: 134
gtggttggtg agggtcatct cgctg                                             25

SEQ ID NO: 135          moltype = DNA   length = 22
FEATURE                 Location/Qualifiers
source                  1..22
                        mol_type = other DNA
                        organism = synthetic construct
SEQUENCE: 135
cagggaagga gtgcgtggct gc                                                22

SEQ ID NO: 136          moltype = DNA   length = 22
FEATURE                 Location/Qualifiers
source                  1..22
                        mol_type = other DNA
                        organism = synthetic construct
SEQUENCE: 136
gtggttggtg agggtcatct cg                                                22

SEQ ID NO: 137          moltype = DNA   length = 19
FEATURE                 Location/Qualifiers
source                  1..19
                        mol_type = other DNA
                        organism = synthetic construct
SEQUENCE: 137
cagggaagga gtgcgtggc                                                    19

SEQ ID NO: 138          moltype = DNA   length = 19
FEATURE                 Location/Qualifiers
source                  1..19
                        mol_type = other DNA
                        organism = synthetic construct
SEQUENCE: 138
gtggttggtg agggtcatc                                                    19

SEQ ID NO: 139          moltype = DNA   length = 16
FEATURE                 Location/Qualifiers
source                  1..16
                        mol_type = other DNA
                        organism = synthetic construct
SEQUENCE: 139
cagggaagga gtgcgt                                                       16

SEQ ID NO: 140          moltype = DNA   length = 16
FEATURE                 Location/Qualifiers
source                  1..16
                        mol_type = other DNA
                        organism = synthetic construct
SEQUENCE: 140
gtggttggtg agggtc                                                       16
```

```
SEQ ID NO: 141          moltype = DNA  length = 25
FEATURE                 Location/Qualifiers
source                  1..25
                        mol_type = other DNA
                        organism = synthetic construct
SEQUENCE: 141
ttccgtcggt gcgtgaggaa gggac                                              25

SEQ ID NO: 142          moltype = DNA  length = 25
FEATURE                 Location/Qualifiers
source                  1..25
                        mol_type = other DNA
                        organism = synthetic construct
SEQUENCE: 142
gtcgctctac tgggagtggt tggtg                                              25

SEQ ID NO: 143          moltype = DNA  length = 22
FEATURE                 Location/Qualifiers
source                  1..22
                        mol_type = other DNA
                        organism = synthetic construct
SEQUENCE: 143
cgtcggtgcg tgaggaaggg ac                                                 22

SEQ ID NO: 144          moltype = DNA  length = 22
FEATURE                 Location/Qualifiers
source                  1..22
                        mol_type = other DNA
                        organism = synthetic construct
SEQUENCE: 144
gctctactgg gagtggttgg tg                                                 22

SEQ ID NO: 145          moltype = DNA  length = 19
FEATURE                 Location/Qualifiers
source                  1..19
                        mol_type = other DNA
                        organism = synthetic construct
SEQUENCE: 145
cggtgcgtga ggaagggac                                                     19

SEQ ID NO: 146          moltype = DNA  length = 19
FEATURE                 Location/Qualifiers
source                  1..19
                        mol_type = other DNA
                        organism = synthetic construct
SEQUENCE: 146
ctactgggag tggttggtg                                                     19

SEQ ID NO: 147          moltype = DNA  length = 16
FEATURE                 Location/Qualifiers
source                  1..16
                        mol_type = other DNA
                        organism = synthetic construct
SEQUENCE: 147
tgcgtgagga agggac                                                        16

SEQ ID NO: 148          moltype = DNA  length = 16
FEATURE                 Location/Qualifiers
source                  1..16
                        mol_type = other DNA
                        organism = synthetic construct
SEQUENCE: 148
ctgggagtgg ttggtg                                                        16

SEQ ID NO: 149          moltype = DNA  length = 33
FEATURE                 Location/Qualifiers
source                  1..33
                        mol_type = other DNA
                        organism = synthetic construct
SEQUENCE: 149
agatcggaag agcacacgtc tgaactccag tca                                     33

SEQ ID NO: 150          moltype = DNA  length = 33
FEATURE                 Location/Qualifiers
source                  1..33
                        mol_type = other DNA
                        organism = synthetic construct
```

-continued

```
SEQUENCE: 150
agatcggaag agcgtcgtgt agggaaagag tgt                              33

SEQ ID NO: 151          moltype = DNA   length = 22
FEATURE                 Location/Qualifiers
source                  1..22
                        mol_type = other DNA
                        organism = synthetic construct
SEQUENCE: 151
gccttggcac ccgagaattc ca                                         22

SEQ ID NO: 152          moltype = DNA   length = 33
FEATURE                 Location/Qualifiers
source                  1..33
                        mol_type = other DNA
                        organism = synthetic construct
SEQUENCE: 152
acactctttc cctacacgac gctcttccga tct                              33

SEQ ID NO: 153          moltype = DNA   length = 32
FEATURE                 Location/Qualifiers
source                  1..32
                        mol_type = other DNA
                        organism = synthetic construct
SEQUENCE: 153
cactctttcc ctacacgacg ctcttccgat ct                               32

SEQ ID NO: 154          moltype = DNA   length = 37
FEATURE                 Location/Qualifiers
source                  1..37
                        mol_type = other DNA
                        organism = synthetic construct
SEQUENCE: 154
cggtctcggc attcctgctg aaccgctctt ccgatct                          37

SEQ ID NO: 155          moltype = DNA   length = 31
FEATURE                 Location/Qualifiers
source                  1..31
                        mol_type = other DNA
                        organism = synthetic construct
SEQUENCE: 155
actctttccc tacacgacgc tcttccgatc t                                31

SEQ ID NO: 156          moltype = DNA   length = 34
FEATURE                 Location/Qualifiers
source                  1..34
                        mol_type = other DNA
                        organism = synthetic construct
SEQUENCE: 156
gtgactggag ttcagacgtg tgctcttccg atct                             34

SEQ ID NO: 157          moltype = DNA   length = 21
FEATURE                 Location/Qualifiers
source                  1..21
                        mol_type = other DNA
                        organism = synthetic construct
SEQUENCE: 157
caagcagaag acggcatacg a                                           21

SEQ ID NO: 158          moltype = DNA   length = 23
FEATURE                 Location/Qualifiers
source                  1..23
                        mol_type = other DNA
                        organism = synthetic construct
SEQUENCE: 158
cgactcacta tagggagagc ggc                                         23

SEQ ID NO: 159          moltype = DNA   length = 24
FEATURE                 Location/Qualifiers
source                  1..24
                        mol_type = other DNA
                        organism = synthetic construct
SEQUENCE: 159
aagaacatcg attttccatg gcag                                        24
```

| | | |
|---|---|---|
| SEQ ID NO: 160 | moltype = DNA length = 33 | |
| FEATURE | Location/Qualifiers | |
| source | 1..33 | |
| | mol_type = other DNA | |
| | organism = synthetic construct | |
| SEQUENCE: 160 | | |
| aacgccaaac ctacggcttt acttcctgtg gct | | 33 |

| | | |
|---|---|---|
| SEQ ID NO: 161 | moltype = DNA length = 33 | |
| FEATURE | Location/Qualifiers | |
| source | 1..33 | |
| | mol_type = other DNA | |
| | organism = synthetic construct | |
| SEQUENCE: 161 | | |
| tcttgagtca ttcgcagggc atgtgccaga cct | | 33 |

| | | |
|---|---|---|
| SEQ ID NO: 162 | moltype = DNA length = 33 | |
| FEATURE | Location/Qualifiers | |
| source | 1..33 | |
| | mol_type = other DNA | |
| | organism = synthetic construct | |
| SEQUENCE: 162 | | |
| tcggcgttgt ctgctatcgt tcttggcact cct | | 33 |

| | | |
|---|---|---|
| SEQ ID NO: 163 | moltype = DNA length = 33 | |
| FEATURE | Location/Qualifiers | |
| source | 1..33 | |
| | mol_type = other DNA | |
| | organism = synthetic construct | |
| SEQUENCE: 163 | | |
| ggagcaataa ccataaggcc gttgacaagc cct | | 33 |

| | | |
|---|---|---|
| SEQ ID NO: 164 | moltype = DNA length = 33 | |
| FEATURE | Location/Qualifiers | |
| source | 1..33 | |
| | mol_type = other DNA | |
| | organism = synthetic construct | |
| SEQUENCE: 164 | | |
| ggcgtattgc cttggttctg gcagcctcat tgt | | 33 |

| | | |
|---|---|---|
| SEQ ID NO: 165 | moltype = DNA length = 33 | |
| FEATURE | Location/Qualifiers | |
| source | 1..33 | |
| | mol_type = other DNA | |
| | organism = synthetic construct | |
| SEQUENCE: 165 | | |
| cagcagaggg aacgatttca acttcctgtg gct | | 33 |

| | | |
|---|---|---|
| SEQ ID NO: 166 | moltype = DNA length = 33 | |
| FEATURE | Location/Qualifiers | |
| source | 1..33 | |
| | mol_type = other DNA | |
| | organism = synthetic construct | |
| SEQUENCE: 166 | | |
| ctactgcaag ggtgtctaga atgtgccaga cct | | 33 |

| | | |
|---|---|---|
| SEQ ID NO: 167 | moltype = DNA length = 33 | |
| FEATURE | Location/Qualifiers | |
| source | 1..33 | |
| | mol_type = other DNA | |
| | organism = synthetic construct | |
| SEQUENCE: 167 | | |
| gaccgactcg tgaaacgtaa tcttggcact cct | | 33 |

| | | |
|---|---|---|
| SEQ ID NO: 168 | moltype = DNA length = 33 | |
| FEATURE | Location/Qualifiers | |
| source | 1..33 | |
| | mol_type = other DNA | |
| | organism = synthetic construct | |
| SEQUENCE: 168 | | |
| acacattctt tgcgcccaga gttgacaagc cct | | 33 |

| | | |
|---|---|---|
| SEQ ID NO: 169 | moltype = DNA length = 33 | |
| FEATURE | Location/Qualifiers | |
| source | 1..33 | |
| | mol_type = other DNA | |
| | organism = synthetic construct | |

```
SEQUENCE: 169
atttcattcg acacccggtc gcagcctcat tgt                                33

SEQ ID NO: 170          moltype = DNA   length = 25
FEATURE                 Location/Qualifiers
source                  1..25
                        mol_type = other DNA
                        organism = synthetic construct
SEQUENCE: 170
acgaccttct tgtagtcctt acggc                                         25

SEQ ID NO: 171          moltype = DNA   length = 25
FEATURE                 Location/Qualifiers
source                  1..25
                        mol_type = other DNA
                        organism = synthetic construct
SEQUENCE: 171
acagtttagg tccactctcc accac                                         25

SEQ ID NO: 172          moltype = DNA   length = 25
FEATURE                 Location/Qualifiers
source                  1..25
                        mol_type = other DNA
                        organism = synthetic construct
SEQUENCE: 172
tgatagctga aactagcctc accgc                                         25

SEQ ID NO: 173          moltype = DNA   length = 25
FEATURE                 Location/Qualifiers
source                  1..25
                        mol_type = other DNA
                        organism = synthetic construct
SEQUENCE: 173
acccatatcg aggagtcaag ttggc                                         25

SEQ ID NO: 174          moltype = DNA   length = 25
FEATURE                 Location/Qualifiers
source                  1..25
                        mol_type = other DNA
                        organism = synthetic construct
SEQUENCE: 174
atgggctgcc tatgccgtaa tatcc                                         25

SEQ ID NO: 175          moltype = DNA   length = 25
FEATURE                 Location/Qualifiers
source                  1..25
                        mol_type = other DNA
                        organism = synthetic construct
SEQUENCE: 175
agtaatgaac agcgcgtggt cacac                                         25

SEQ ID NO: 176          moltype = DNA   length = 29
FEATURE                 Location/Qualifiers
source                  1..29
                        mol_type = other DNA
                        organism = synthetic construct
SEQUENCE: 176
acaaaggcag ccacgcactc cttccctgt                                     29

SEQ ID NO: 177          moltype = DNA   length = 29
FEATURE                 Location/Qualifiers
source                  1..29
                        mol_type = other DNA
                        organism = synthetic construct
SEQUENCE: 177
ctccagcgag atgaccctca ccaaccact                                     29

SEQ ID NO: 178          moltype = DNA   length = 31
FEATURE                 Location/Qualifiers
source                  1..31
                        mol_type = other DNA
                        organism = synthetic construct
SEQUENCE: 178
gatcggaaga gcacacgtct gaactccagt c                                  31
```

```
SEQ ID NO: 179          moltype = DNA  length = 29
FEATURE                 Location/Qualifiers
source                  1..29
                        mol_type = other DNA
                        organism = synthetic construct
SEQUENCE: 179
agtggttggt gagggtcatc tcgctggag                                       29

SEQ ID NO: 180          moltype = DNA  length = 63
FEATURE                 Location/Qualifiers
source                  1..63
                        mol_type = other DNA
                        organism = synthetic construct
SEQUENCE: 180
acaaaggcag ccacgcactc cttccctgtn nnnnnnnnnn nacactctttt ccctacacga    60
cgc                                                                   63

SEQ ID NO: 181          moltype = DNA  length = 62
FEATURE                 Location/Qualifiers
source                  1..62
                        mol_type = other DNA
                        organism = synthetic construct
SEQUENCE: 181
ctccagcgag atgaccctca ccaaccactn nnnnnnnnnn ngtgactgga gttcagacgt    60
gt                                                                    62

SEQ ID NO: 182          moltype = DNA  length = 51
FEATURE                 Location/Qualifiers
source                  1..51
                        mol_type = other DNA
                        organism = synthetic construct
SEQUENCE: 182
acaaaggcag ccacgcactc cttccctgta cactctttcc ctacacgacg c              51

SEQ ID NO: 183          moltype = DNA  length = 50
FEATURE                 Location/Qualifiers
source                  1..50
                        mol_type = other DNA
                        organism = synthetic construct
SEQUENCE: 183
ctccagcgag atgaccctca ccaaccactg tgactggagt tcagacgtgt                50

SEQ ID NO: 184          moltype = DNA  length = 59
FEATURE                 Location/Qualifiers
source                  1..59
                        mol_type = other DNA
                        organism = synthetic construct
SEQUENCE: 184
acaaaggcag ccacgcactc cttccctgtn nnnnnnaca ctctttccct acacgacgc       59

SEQ ID NO: 185          moltype = DNA  length = 58
FEATURE                 Location/Qualifiers
source                  1..58
                        mol_type = other DNA
                        organism = synthetic construct
SEQUENCE: 185
ctccagcgag atgaccctca ccaaccactn nnnnnngtg actggagttc agacgtgt        58
```